(12) United States Patent
Peterson et al.

(10) Patent No.: US 11,186,876 B2
(45) Date of Patent: *Nov. 30, 2021

(54) METHOD FOR PREDICTING RESPONSE TO BREAST CANCER THERAPEUTIC AGENTS AND METHOD OF TREATMENT OF BREAST CANCER

(71) Applicant: Medivation Prostate Therapeutics LLC, New York, NY (US)

(72) Inventors: Amy Christian Peterson, San Francisco, CA (US); Hirdesh Uppal, San Ramon, CA (US)

(73) Assignee: Medivation Prostate Therapeutics LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/215,340

(22) Filed: Dec. 10, 2018

(65) Prior Publication Data

US 2019/0169697 A1   Jun. 6, 2019

Related U.S. Application Data

(63) Continuation of application No. 14/962,864, filed on Dec. 8, 2015, now Pat. No. 10,196,693.

(60) Provisional application No. 62/167,110, filed on May 27, 2015, provisional application No. 62/142,504, filed on Apr. 3, 2015, provisional application No. 62/091,195, filed on Dec. 12, 2014.

(51) Int. Cl.
| | | |
|---|---|---|
| *A61K 31/4164* | (2006.01) |
| *C12Q 1/6886* | (2018.01) |
| *A61K 31/337* | (2006.01) |
| *A61K 31/4166* | (2006.01) |
| *A61K 45/06* | (2006.01) |

(52) U.S. Cl.
CPC .......... *C12Q 1/6886* (2013.01); *A61K 31/337* (2013.01); *A61K 31/4166* (2013.01); *A61K 45/06* (2013.01); *C12Q 2600/106* (2013.01); *C12Q 2600/112* (2013.01); *C12Q 2600/158* (2013.01)

(58) Field of Classification Search
CPC .... C07D 233/76; A61K 31/4164; A61P 35/00
USPC ....................................................... 514/389
See application file for complete search history.

(56) References Cited

U.S. PATENT DOCUMENTS

| | | |
|---|---|---|
| 8,110,594 B2 | 2/2012 | Jung et al. |
| 8,183,274 B2 | 5/2012 | Sawyers et al. |
| 8,648,105 B2 | 2/2014 | Jung et al. |
| 9,126,941 B2 | 9/2015 | Sawyers et al. |
| 9,517,229 B2 | 12/2016 | Protter et al. |
| 10,111,861 B2 | 10/2018 | Protter et al. |
| 10,196,693 B2 * | 2/2019 | Peterson .............. A61K 31/337 |
| 2003/0219767 A1 | 11/2003 | Ayers et al. |
| 2007/0004753 A1 | 1/2007 | Sawyers et al. |
| 2007/0059720 A9 | 3/2007 | Fuqua et al. |
| 2007/0192880 A1 | 8/2007 | Muyan et al. |
| 2008/0139634 A2 | 6/2008 | Jung et al. |
| 2009/0111864 A1 | 4/2009 | Jung et al. |
| 2009/0299640 A1 | 12/2009 | Ellis et al. |
| 2010/0172975 A1 | 7/2010 | Sawyers et al. |
| 2010/0210665 A1 | 8/2010 | Sawyers et al. |
| 2011/0003839 A1 | 1/2011 | Jung et al. |
| 2011/0130296 A1 | 6/2011 | Benz et al. |
| 2011/0145176 A1 | 6/2011 | Perou et al. |
| 2011/0152348 A1 | 6/2011 | Worm et al. |
| 2012/0214864 A1 | 8/2012 | Richer et al. |
| 2013/0004482 A1 | 1/2013 | Perou et al. |
| 2013/0345161 A1 | 12/2013 | Perou et al. |
| 2014/0107180 A1 | 4/2014 | Macleod et al. |
| 2014/0154681 A1 | 6/2014 | Wallden |
| 2015/0253329 A1 | 9/2015 | Mouchantat |
| 2016/0078167 A1 | 3/2016 | Rosner et al. |
| 2016/0168646 A1 | 6/2016 | Peterson et al. |
| 2017/0087132 A1 | 3/2017 | Protter et al. |

FOREIGN PATENT DOCUMENTS

| | | |
|---|---|---|
| WO | WO-2006124118 A1 | 11/2006 |
| WO | WO-2007126765 A2 | 11/2007 |
| WO | WO-2010099238 A1 | 9/2010 |
| WO | WO-2010118354 A1 | 10/2010 |
| WO | WO-2010125117 A2 | 11/2010 |
| WO | WO-2011028905 A1 | 3/2011 |
| WO | WO-2011044327 A1 | 4/2011 |
| WO | WO-2012125828 A2 | 9/2012 |
| WO | WO-2012125858 A1 | 9/2012 |
| WO | WO-2013066440 A1 | 5/2013 |
| WO | WO-2014031164 A1 | 2/2014 |
| WO | WO-2016094408 A1 | 6/2016 |

OTHER PUBLICATIONS

Perou, C., et al., "Molecular portraits of human breast tumours," Nature, 2000, 406:747-752.
Sorlie, T., et al., "Gene expression patterns of breast carcinomas distinguish tumor subclasses with clinical implications," PNAS, 2001, 98(19):10869-10874.
Bertucci, F., et al., "How basal are triple-negative breast cancers?," Int. J. Cancer, 2008, 123:236-240.
Ogawa, Y., et al., "Androgen receptor expression in breast cancer: relationship with clinicopathological factors and biomarkers," Int. J. Clin. Oncol., 2008, 13:431-435.

(Continued)

*Primary Examiner* — Raymond J Henley, III
(74) *Attorney, Agent, or Firm* — Faegre Drinker Biddle & Reath LLP

(57) ABSTRACT

Methods for treating triple negative breast cancer with an androgen receptor inhibitor are provided, as well as methods for screening for the likelihood of the effectiveness of such treatment.

37 Claims, 29 Drawing Sheets

Specification includes a Sequence Listing.

(56) References Cited

OTHER PUBLICATIONS

Wang, X., et al., "Increased expression of osteopontin in patients with triple-negative breast cancer," Eur. J. Clin. Invest., 2008, 38:438-446.
Parker, J., et al., "Supervised Risk Predictor of Breast Cancer Based on Intrinsic Subtypes," J. Clin. Oncol., 2009, 27(8):1160-1167.
Choo, J., et al., "Biomarkers for Basal-like Breast Cancer," Cancers, 2010, 2:1040-1065.
Collins, L., et al., "Androgen receptor expression in breast cancer in relation to molecular phenotype: results from the Nurses' Health Study," Mod. Pathol., 2011, 24(7):924-931.
Garay, J., et al., "Androgen receptor as a targeted therapy for breast cancer," Am. J. Cancer Res., 2012, 2(4):434-445.
Kelly, C., et al., "Agreement in Risk Prediction Between the 21-Gene Recurrence Score Assay (Oncotype DX) and the PAM50 Breast Cancer Intrinsic Classifier™ in Early-Stage Estrogen Receptor-Positive Breast Cancer," The Oncologist, 2012, 17:492-498.
Gucalp, A., et al., "Phase II Trial of Bicalutamide in Patients with Androgen Receptor-Positive, Estrogen Receptor-Negative Metastatic Breast Cancer," Clin. Cancer Res., 2013, 19(19):5505-5512.
Nielsen, T., et al., "Immunohistochemical and clinical characterization of the basal-like subtype of invasive breast carcinoma," Clinical Cancer Research, 2004, 10:5367-5374.
Prat, A., et al., "Predicting response and survival in chemotherapy-treated triple-negative breast cancer," British Journal of Cancer, 2014, 111:1532-1541.
Traina, T.A., et al., "A Phase 1 Open-Label Study Evaluating the Safety, Tolerability, and Pharmacokinetics of Enzalutamide Alone or Combined With an Aromatase Inhibitor in Women With Advanced Breast Cancer," Ann. Oncol., 2014, 25:i4. doi: 10.1093/annonc/mdu064.1.
IMPAKT 2014 News: "Enzalutamide With or Without an Aromatase Inhibitor for Advanced Breast Cancer," 2014 Breast Cancer Conference (May 8-10, 2014, Brussels, Belgium), available at: https://www.esmo.org/Conferences/Past-Conferences/IMPAKT-2014-Breast-Cancer/News/Enzalutamide-With-or-Without-an-Aromatase-Inhibitor-for-Advanced-Breast-Cancer.
Notice of Allowance in U.S. Appl. No. 14/236,036, dated Mar. 24, 2016.
Office Action in U.S. Appl. No. 14/236,036, dated May 20, 2015.
International Search Report and Written Opinion for PCT/US2012/048471, dated Apr. 1, 2013.
International Preliminary Report on Patentability for PCT/US2012/048471, dated Feb. 4, 2014.
Supplemental Search Report and Search Opinion for EP 12 84 6720, dated Feb. 9, 2015.
De Amicis, F., et al., "Androgen Receptor Overexpression Induces Tamoxifen Resistance in Human Breast Cancer Cells," Breast Cancer Res. Treat., 2010, 121:1-11.
"Tamoxifen" Dec. 2004 [online]: Wikipedia [retrieved on May 5, 2015], available at: http://en.wikipedia.org/wiki/Tamoxifen.
Cochrane, D., et al., "Role of the androgen receptor in breast cancer and preclinical analysis of enzalutamide," Breast Cancer Research, 2014, 16(1):R7.
Doane, A., et al., "An estrogen receptor-negative breast cancer subset characterized by a hormonally regulated transcriptional program and response to androgen," Oncogene, 2006, 25(28):3994-4008.
Graham, T., et al., "Reciprocal regulation of ZEB1 and AR in triple negative breast cancer cells," Breast Cancer Research and Treatment, 2009, 123(1):139-147.
Ni, M., et al., "Targeting Androgen Receptor in Estrogen Receptor-Negative Breast Cancer," Cancer Cell, 2011, 20(1):119-131.
Robinson, J., et al., "Androgen receptor driven transcription in molecular apocrine breast cancer is mediated by FoxA1," The EMBO Journal, 2011, 31(6):3019-3027.
Santana-Davila, R., et al., "Treatment options for patients with triple-negative breast cancer," Journal of Hematology & Oncology, 2010, 3(1):1-11.
Parker, J., et al., "A novel biomarker to predict sensitivity to enzalutamide (ENZA) in TNBC," Journal of Clinical Oncology, 2015, 33(15):1083.
Traina, T., et al., "Results from a phase 2 study of enzalutamide (ENZA), an androgen receptor (AR) inhibitor, in advanced AR+triple-negative breast cancer (TNBC)," Journal of Clinical Oncology, 2015, 33(15):1003.
Zhao, T., et al., "A Phase II Clinical Trial of Flutamide in the Treatment of Advanced Breast Cancer," Tumori, 1988, 74:53-56.
Perrault, D., et al. "Phase II study of flutamide in patients with metastatic breast cancer. A National Cancer Instiute of Canada Clinical Trials Group Study," Investigational New Drugs, 1988, 6:207-210.
Barton, V., et al., "Multiple Molecular Subtypes of Triple-Negative Breast Cancer Critically Rely on Androgen Receptor and Respond to Enzalutamide In Vivo," Mol. Cancer Ther., 2015, 14(3):769-778.
Cochrane, D., et al., "Abstract P2-14-02: Preclinical Evaluation of Enzalutamide in Breast Cancer Models," Cancer Res., 2012, 72(24 Suppl):Abstract nr P2-14-02. doi: 10.1158/0008-5472.SABCS12-P2-14-02.
Hudis, C., et al., "Triple-Negative Breast Cancer: An Unmet Medical Need," The Oncologist, 2011, 16(1 Suppl): 1-11.
Gucalp, A., et al., "Triple-Negative Breast Cancer Role of the Androgen Receptor," The Cancer Journal, 2010, 16(1):62-65.
Park, S., et al., "Expression of androgen receptors in primary breast cancer," Annals of Oncology, 2010, 21(3):488-492. doi: 10.1093/annonc/mdp510.
Venkitaraman, R., "Triple-negative/basal-like breast cancer: clinical, pathologic and molecular features," Expert Rev. Anticancer Ther., 2010, 10(2):199-207. doi: 10.1586/era.09.189.
Ogawa, Y., et al., "Androgen receptor expression in breast cancer: relationship with clinicopathological factors and biomarkers," Int. J. Clin. Oncol., 2008, 13:431-435. doi: 10.1007/s10147-008-0770-6.
Tan, A., et al., "Therapeutic Strategies for Triple-Negative Breast Cancer," The Cancer Journal, 2008, 14(6):343-351.
Nahleh, Z., "Androgen receptor as a target for the treatment of hormone receptor-negative breast cancer: an unchartered territory," Future Oncol., 2008, 4(1):15-21.
Loibl, S., et al., "Androgen-Receptor Expression in Triple Negative Breast Cancer: Results from the Neoadjuvant Gepartrio Trial," Annals of Oncology, 2009, 20(2 Suppl):ii45. doi: 10.1093/annonc/mdp103.
Cimino-Mathews, A., et al., "Androgen Receptor Expression Is Usually Maintained in Initial Surgically-Resected Breast Cancer Metastases, but Often Lost in Terminal Metastases Found at Autopsy," Annual Meeting Abstracts, 33A.
Cimino-Mathews, A., et al., "Androgen receptor expression is usually maintained in initial surgically resected breast cancer metastases but is often lost in end-stage metastases found at autopsy," Human Pathology, 2012, 43:1003-1011.
Minami, C., et al., "Management Options in Triple-Negative Breast Cancer," Breast Cancer: Basic and Clinical Research, 2011, 5:175-179. doi: 10.4137/BCBCR.S6562.
Chen, J., et al., "Expression of androgen receptor in breast carcinoma and its relationship with estrogen receptor, progesterone receptor and HER2 status," Chin. J. Pathol., 2010, 39(11):743-746. doi: 10.3760/cma.j.issn.0529-5807.2010.11.007.
Richer, J.K., et al., "P2.22 MDV3100, An Androgen Receptor Signaling Inhibitor, Abrogates Breast Cancer Proliferation and Tumor Growth in Preclinical Models," Annals of Oncology, 2012, 23(1 Suppl):i31. doi: 10.1093/annonc/mds018.
Elias, A., et al., "MDV3100-08: A phase I open-label, dose-escalation study evaluating the safety, tolerability, and pharmacokinetics of MDV3100 in women with incurable breast cancer," Journal of Clinical Oncology, 2012, 30(15 Suppl):TPS668. doi: 10.1200/jco.2012.30.15_suppl.tps668.
D'Amato, N., et al., "Abstract 4756: Elucidating the role of AR in breast cancer," Cancer Research, 2013, 73(8 Suppl):Abstract nr 4756. doi: 10.1158/1538-7445.AM2013-4756.
Barton, V., et al., "Abstract A047: Targeting androgen receptor decreases proliferation of triple-negative breast cancer," Molecular Cancer Research, 2013, 11(10 Suppl):Abstract nr A047.

(56) References Cited

OTHER PUBLICATIONS

Barton, V., et al., "Abstract OR38-2: Targeting Androgen Receptor Decreases Proliferation and Invasion in Preclinical Models of Triple Negative Breast Cancer," Therapies for Cancer, Endocrine Society's 96th Annual Meeting and Expo, Jun. 21-24, 2014, Chicago.
Barton, V., et al., "Androgen Receptor Biology in Triple Negative Breast Cancer: a Case for Classification as AR+ or Quadruple Negative Disease," Horm. Canc., 2015, 6:206-213. doi: 10.1007/s12672-015-0232-3.
Barton, V., et al., "Abstract P3-04-02: Multiple subtypes of triple negative breast cancer are dependent on androgen receptor," Cancer Res., 2015, 75(9 Suppl):Abstract nr P3-04-02.
Gordon, M., et al., "Abstract P6-03-07: Targeting multiple pathways in breast cancer: Androgen receptor, HER2, and mTOR," Cancer Research, 2015, 75(9 Suppl):Abstract nr P6-03-07, available at: http://cancerres.aacrjournals.org/content/75/9_Supplement/P6-03-07.
Gordon, M., et al., "Abstract SAT-312: The Anti-Androgen Enzalutamide Synergizes with Trastuzumab and Everolimus to Inhibit Breast Cancer Growth Via Distinct Mechanisms," Biomarkers and Hormone-Dependent Cancers, Endocrine Society's 97th Annual Meeting and Expo, Mar. 5-8, 2015, San Diego, 2 pgs.
Barton, V., et al., "Anti-androgen therapy in triple-negative breast cancer," Ther. Adv. Med. Oncol., 2016, 8(4):305-308. doi: 10.1177/1758834016646735.
Notice of Allowance and Notice of Allowability, including Reasons for Allowance, for U.S. Appl. No. 15/373,914, dated Aug. 16, 2017.
Original and Allowed Claims from U.S. Appl. No. 15/373,914, filed Dec. 9, 2016.
Tibshirani, R., et al., "Diagnosis of multiple cancer types by shrunken centroids of gene expression," PNAS, 2002, 99(10):6567-6572.
Amendment Accompanying Request for Continued Examination filed Jun. 24, 2016 in U.S. Appl. No. 14/236,036 now U.S. Pat. No. 9,517,229.
Notice of Allowance and Notice of Allowability, including Reasons for Allowance, for U.S. Appl. No. 14/236,036, now U.S. Pat. No. 9,517,229, dated Aug. 19, 2016.
Richer, J., et al., "The Role of Androgen Receptors in Postmenopausal Breast Cancer" [Abstract], presented at the Department of Defense Era of Hope Conference, Aug. 2-5, 2011, available online Jul. 26, 2011.
Preliminary Amendment filed Jan. 29, 2014 in U.S. Appl. No. 14/236,036, now U.S. Pat. No. 9,517,229.
Response to Office Action filed Nov. 20, 2015 in U.S. Appl. No. 14/236,036, now U.S. Pat. No. 9,517,229.
Chacón, R., et al., "Triple-negative breast cancer," Breast Cancer Research, 2010, 12(2 Suppl):S3.
The Cancer Genome Atlas Network, "Comprehensive molecular portraits of human breast tumours," Nature, 2012, 490:61-70.
Bullard, J., et al., "Evaluation of statistical methods for normalization and differential expression in mRNA-Seq experiments," BMC Bioinformatics, 2010, 11:94.
Wang, K., et al., "MapSplice: Accurate mapping of RNA-seq reads for splice junction discovery," Nucleic Acids Research, 2010, 38(18). doi: 10.1093/nar/gkq622.
Carey, L., et al., "TBCRC 001: Randonmized Phase II Study of Cetuximab in Combination with Carboplatin in Stage IV Triple-Negative Breast Cancer," Journal of Clinical Oncology, 2012, 30(21):2615-2623.
Von Minckwitz, G., et al., "Bevacizumab plus chemotherapy versus chemotherapy alone as second-line treatment for patients with HER2-negative locally recurrent or metastatic breast cancer after first-line treatment with bevacizumab plus chemotherapy (TANIA): an open-label, randomised phase 3 trial," Lancet Oncology, 2014, 15:1269-1278.
Carey, L. A., et al., "TBCRC 001: EGFR inhibition with cetuximab added to carboplatin in metastatic triple-negative (basal-like) breast cancer," Journal of Clinical Oncology, 2008, 26(15 Suppl):1009.

Gerratana, L., et al., "Pattern of metastasis and outcome in patients with breast cancer," Clin. Exp. Metastasis, 2015, 32:125-133.
Hänzelmann, S., et al., "GSVA: gene set variation analysis for microarray and RNA-Seq data," BMC Bioinformatics, 2013, 14:7.
Hatzis, C., et al., "Effects of Tissue Handling on RNA Integrity and Microarray Measurements From Resected Breast Cancers," J. Nat'l Cancer Inst., 2011, 103(24):1871-1883.
Hoadley, K., et al., "Multiplatform Analysis of 12 Cancer Types Reveals Molecular Classification within and across Tissues of Origin," Cell, 2014, 158:929-944.
Kassam, F., et al., "Survival Outcomes for Patients with Metastatic Triple-Negative Breast Cancer: Implications for Clinical Practice and Trial Design," Clinical Breast Cancer, 2009, 9(1):29-33.
Kast, K., et al., "Impact of breast cancer subtypes and patterns of metastasis on outcome," Breast Cancer Res. Treat., 2015, 150:621-629.
Loibl, S., et al., "Androgen receptor expression in primary breast cancer and its predictive and prognostic value in patients treated with neoadjuvant chemotherapy," Breast Cancer Res. Treat., 2011, 130:477-487.
Miller, K., et al., "Abstract P3-07-25: Improved clinical outcomes on enzalutamide observed in patients with Predict AR+ triple-negative breast cancer: prognosis or prediction?," Cancer Research, 2016, 76(4 Suppl):Abstract nr P3-07-25.
Twelves, C., et al., "Clinical Roundtable Monograph: Effective Management of Quality of Life in Metastatic Breast Cancer," Clinical Advances in Hematology & Oncology, 2014, 12(2 Suppl 4):1-16.
Prat, A., et al., "A PAM50-Based Chemoendocrine Score for Hormone Receptor-Positive Breast Cancer with an Intermediate Risk of Relapse," Clin. Cancer Res., 2017, 23(12):3035-3045.
Schneider, B., et al., "Triple-Negative Breast Cancer: Risk Factors to Potential Targets," Clin. Cancer Res., 2008, 14(24):8010-8018.
Nielsen, T., et al., "A Comparison of PAM50 Intrinsic Subtyping with Immunohistochemistry and Clinical Prognostic Factors in Tamoxifen-Treated Estrogen Receptor-Positive Breast Cancer," Clin. Cancer Res., 2010, 16(21):5222-5232.
O'Shaughnessy, J., et al., "Iniparib plus Chemotherapy in Metastatic Triple-Negative Breast Cancer," The New England Journal of Medicine, 2011, 364(3):205-214.
Prat, A., et al., "Molecular Characterization of Basal-Like and Non-Basal-Like Triple-Negative Breast Cancer," The Oncologist, 2013, 18:123-133.
Rodriguez, A., et al., "A randomized, parallel-arm, phase II trial to assess the efficacy of preoperative ixabepilone with or without cetuximab in patients with triple-negative breast cancer (TNBC)," Journal of Clinical Oncology, 2014, 32(15 Suppl):1133.
Storey, J., et al., "Statistical significance for genomewide studies," PNAS, 2003, 100(16):9440-9445.
Thomas, E., et al., "Ixabepilone Plus Capecitabine for Metastatic Breast Cancer Progressing After Anthracycline and Taxane Treatment," Journal of Clinical Oncology, 2007, 25(33):5210-5217.
Traina, T., et al., "Enzalutamide for the Treatment of Androgen Receptor-Expressing Triple-Negative Breast Cancer," Journal of Clinical Oncology, 2018, 36:1-9.
U.S. Office Action that issued in U.S. Appl. No. 15/373,914, dated Feb. 16, 2018.
Zhang, J., et al., "Novel therapeutic strategies for patients with triple-negative breast cancer," OncoTargets and Therapy, 2016, 9:6519-6528.
Wu, Y., et al., "Androgen Receptor-mTor Crosstalk is Regulated by Testosterone Availability: Implication for Prostate Cancer Cell Survival," Anticancer Res., 2010, 30(10):3895-3901.
Thakkar, A., et al., "Vitamin D and androgen receptor-targeted therapy for triple-negative breast cancer," Breast Cancer Res. Treat., 2016, 157:77-90.
Tentler, J., et al., "Patient-derived tumour xenografts as models for oncology drug development," Nat. Rev. Clin. Oncol., 2012, 9(6):338-350.
Takayama, K., et al., "TET2 repression by androgen hormone regulates global hydroxymethylation status and prostate cancer progression," Nature Comm., 2015, 6(8219).

(56) References Cited

OTHER PUBLICATIONS

Lehmann, B., et al., "Identification of human triple-negative breast cancer subtypes and preclinical models for selection of targeted therapies," Journal of Clinical Investigation, 2011, 121(7):2750-2767.

Sun, T., et al., "The role of microRNA-221 and -222 in Androgen-independent Prostate Cancer Cell lines," Cancer Res., 2009, 69(8):3356-3363.

Saha, P., et al., "Concepts and targets in triple-negative breast cancer: recent results and clinical implications," Therapeutic Advances in Medical Oncology, 2016, 8(5):351-359.

Ricciardi, G., et al., "Androgen Receptor (AR), E-Cadherin, and Ki-67 as Emerging Targets and Novel Prognostic Markers in Triple-Negative Breast Cancer (TNBC) Patients," PLOS One, 2015, 10(6).

Rampurwala, M., et al., "Role of the Androgen Receptor in Triple-Negative Breast Cancer," Clinical Advances in Hematology and Oncology, 2016, 14(3):186-193.

Phipps, A., et al., "Body size and risk of luminal, HER2-overexpressing, and triple-negative breast cancer in postmenopausal women," Cancer Epidemiol. Biomarkers Prev., 2008, 17(8):2078-2086.

Palma, G., et al., "Triple negative breast cancer: looking for the missing link between biology and treatments," Oncotarget, 2015, 6(29):26560-26574.

Niemeier, L., et al., "Androgen receptor in breast cancer: expression in estrogen receptor-positive tumors and in estrogen receptor-negative tumors with apocrine differentiation," Modern Pathology, 2010, 23:205-212.

Narayanan, R., et al., "Androgen Receptor: A Complex Therapeutic Target for Breast Cancer," Cancers, 2016, 8(12):108.

Mizokami, A., et al., "Prostate cancer stromal cells and LNCaP cells coordinately activate the androgen receptor through synthesis of testosterone and dihydrotestosterone from dehydroepiandrosterone," Endocrine-Related Cancer, 2009, 16:1139-1155.

Masiello, D., et al., "Bicalutamide Functions as an Androgen Receptor Antagonist by Assembly of a Transcriptionally Inactive Receptor," Journal of Biological Chemistry, 2002, 277(29):26321-26326.

Mancini, P., et al., "Standard of Care and Promising New Agents for Triple Negative Metastatic Breast Cancer," Cancers, 2014, 6:2187-2223.

Levine, D., et al., "A phase II evaluation of goserelin and bicalutamide in patients with ovarian cancer in second or higher complete clinical disease remission," Cancer, 2007, 110(11):2448-2456. Abstract Only.

Jiang, H., et al., "Androgen receptor expression predicts different clinical outcomes for breast cancer patients stratified by hormone receptor status," Oncotarget, 2016, 7(27):41285-41293.

Isakoff, S., "Triple Negative Breast Cancer: Role of Specific Chemotherapy Agents," Cancer J., 2010, 16(1):53-61.

Ieni, A., et al., "Prognostic value of androgen receptor expression in triple negative breast carcinomas: personal experience and comments on a review about 'Triple-negative breast cancer: treatment challenges and solutions' by Collignon et al," Breast Cancer—Targets and Therapy, 2016, 8:157-159.

Gonzalez-Angulo, A., et al., "Metformin: A Therapeutic Opportunity in Breast Cancer," Clin. Cancer Res., 2010, 16(6):1695-1700.

Foulkes, W., et al., "Triple-Negative Breast Cancer," The New England Journal of Medicine, 2010, 363(20):1938-1948.

Farla, P., et al., "Antiandrogens prevent stable DNA-binding of the androgen receptor," Journal of Cell Science, 2005, 118:4187-4198.

De Ruijter, T., et al., "Characteristics of triple-negative breast cancer," J. Cancer Res. Clin. Oncol., 2011, 137:183-192.

De Leon, J., et al., "Targeting the regulation of androgen receptor signaling by the heat shock protein 90 cochaperone FKBP52 in prostate cancer cells," Proc. Nat'l Academy of Science, 2011, 108(29):11878-11883.

Davis, S. L., et al., "Triple-negative breast cancer: bridging the gap from cancer genomics to predictive biomarkers," Ther. Adv. Med. Oncol., 2014, 6(3):88-100.

Cummings, S., et al., "Serum Estradiol Level and Risk of Breast Cancer During Treatment with Raloxifene," JAMA, 2002, 287(2):216-220.

Collignon, J., et al., "Triple-negative breast cancer: treatment challenges and solutions," Breast Cancer Targets and Therapy, 2016, 8:93-107.

Choi, Y., et al., "Triple-negative, basal-like, and quintuple-negative breast cancers: better prediction model for survival," BMC Cancer, 2010, 10:507.

Carey, L., et al., "Triple-negative breast cancer: disease entity or title of convenience?," Nat. Rev. Clin. Oncol., 2010, 7(12):683-692. Abstract only.

Asano, Y., et al., "Expression and Clinical Significance of Androgen Receptor in Triple-Negative Breast Cancer," Cancers, 2017, 9(1), 4.

"Different subtypes of triple-negative breast cancer respond to different therapies," eScience News, 2011, 2 pages.

Anders, C., et al., "Understanding and Treating Triple-Negative Breast Cancer," Oncology (Williston Park), 2008, 22(11):1233-1243.

Anders, C., et al., "Biology, Metastatic Patterns, and Treatment of Patients with Triple-Negative Breast Cancer," Clin. Breast Cancer, 2009, 9(2 Suppl):S73-S81.

Adam, R., et al., "Heparin-Binding Epidermal Growth Factor-Like Growth Factor Stimulates Androgen-Independent Prostate Tumor Growth and Antagonizes Androgen Receptor Function," Endocrinology, 2002, 143(12):4599-4608.

Abstracts, Royal College of Radiologists Breast Group Annual Scientific Meeting, Brighton, UK, Nov. 1-2, 2010, Breast Cancer Research, 2010, 12(3 Suppl):S1-S16.

Abramson, V., et al., "Subtyping of triple-negative breast cancer: implications for therapy," Cancer, 2015, 121(1):8-16.

Amiri-Kordestani, L., et al., "Association of clinical benefit rate (CBR) with survival: A pooled-analysis of metastatic breast cancer (MBC) trials submitted to the U.S. Food and Drug Administration (FDA)," J. Clin. Oncol., 2016, 34(15 Suppl):Abstract.

Vera-Badillo, F., et al., "Androgen Receptor Expression and Outcomes in Early Breast Cancer: A Systematic Review and Meta-Analysis," J. Nat'l Cancer Inst., 2014, 106(1):djt319.

Krop, I., et al., "Abstract GS4-07: Results from a randomized placebo-controlled phase 2 trial evaluating exemestane ± enzalutamide in patients with hormone receptor-positive breast cancer," Proceedings of the 2017 San Antonio Breast Cancer Symposium, Dec. 5-9, 2017, San Antonio, TX; Cancer Res., 2018, 78(4 Suppl):Abstract nr GS4-07.

Ramos, C., et al., "Androgen receptor (AR) activation in breast cancer (BC) liver metastases," J. Clin. Oncol., 2017, 35(15 Suppl):11619.

Kumar, V., et al., "Androgen Receptor Immunohistochemistry as a Companion Diagnostic Approach to Predict Clinical Response to Enzalutamide in Triple-Negative Breast Cancer," JCO Precision Oncology, 2017, 1:1-19. doi: 10.1200/P.O.17.00075.

Hammond, M. E., et al., "American Society of Clinical Oncology/College of American Pathologists Guideline Recommendations for Immunohistochemical Testing of Estrogen and Progesterone Receptors in Breast Cancer," J. Clin. Oncol., 2010, 28(16):2784-2795.

Traina, T., et al., "Overall survival (OS) in patients (Pts) with diagnostic positive (Dx+) breast cancer: Subgroup analysis from a phase 2 study of enzalutamide (ENZA), an androgen receptor (AR) inhibitor, in Ar+ triple-negative breast cancer (TNBC) treated with 0-1 prior lines of therapy," J. Clin. Oncol., 2017, 35(15 Suppl):1089.

European Office Action for EP Patent Application No. 15 831 013.6-1111, dated Apr. 4, 2018.

Farmer, P., et al., "Identification of molecular apocrine breast tumours by microarray analysis," Oncogene, 2005, 24:4660-4671.

International Search Report and Written Opinion from the EPO in PCT/US2015/064500 dated Apr. 26, 2016, 13 pages.

Traina, T., et al., "Stage 1 results from MDV3100-11: A 2-stage study of enzalutamide (ENZA), an androgen receptor (AR) inhibitor, in advanced AR+ triple-negative breast cancer (TNBC)," SABCS

(56) References Cited

OTHER PUBLICATIONS

2014 San Antonio Breast Cancer Symposium, P5-19-09, p. 1130, retrieved from: https://www.sabcs.org/Portals/SABCS2016/Documents/2014SABCSCall4Abstracts.pdf.
Mrklic, I., et al., "Expression of androgen receptors in triple negative breast carcinomas," ACTA Histochemica, 2013, 115(4):344-348.
Fioretti, F., et al., "Revising the role of the androgen receptor in breast cancer," Journal of Molecular Endocrinology, 2014, 52(3):R257-R265.
Sundem, G., "Study Shows Anti-Androgen Receptor Therapy for Triple-Negative Breast Cancer May Benefit More Than Just High-Androgen Receptor Tumors," Colorado Cancer Blogs, Jun. 23, 2014, retrieved from: http://www.coloradocancerblogs.org/study-shows-anti-androgen-receptor-therapy-triple-negative-breast-cancer-may-benefit-just-high-androgen-receptor-tumors/ [retrieved on Mar. 24, 2016].
Thike, A., et al., "Loss of androgen receptor expression predicts early recurrence in triple-negative and basal-like breast cancer," Modern Pathology, 2014, 27(3):352-360.
Cheang, M., et al., "Basal-Like Breast Cancer Defined by Five Biomarkers Has Superior Prognostic Value than Triple-Negative Phenotype," Clinical Cancer Research, 2008, 14(5):1368-1376.
Notice of Opposition filed against European Patent No. 2739153, dated May 21, 2019.
Cochrane, D.R., et al., "The Role of Androgen Receptor in Postmenopausal Breast Cancer," Endocrine Reviews, 2011, 32(Suppl.): Abstract No. P1-47. doi: 10.1093/edrv/32.supp.1.
Higano, C., et al., "Antitumor Activity of MDV3100 in Pre- and Post-Docetaxel Advanced Prostate Cancer: Long-Term Follow-Up of the Phase 1-2 Study," American Society of Clinical Oncology Genitourinary Cancers Symposium, Feb. 17-19, 2011.
Jung, M., et al., "Structure-Activity Relationship for Thiohydantoin Androgen Receptor Antagonists for Castration-Resistant Prostate Cancer (CRPC)," J. Med. Chem., 2010, 53(7):2779-2796.
Naderi, A., et al., "Synergy between inhibitors of androgen receptor and MEK has therapeutic implications in estrogen receptor-negative breast cancer," Breast Cancer Research, 2011, 13:R36.
Risbridger, G., et al., "Breast and prostate cancer: more similar than different," Nature Reviews, 2010, 10:205-212.
Tran, C., et al., "Development of a Second-Generation Antiandrogen for Treatment of Advanced Prostate Cancer," Science, 2009, 324(5928):787-790.
U.S. Appl. No. 16/168,896, Peterson et al.
Japanese Office Action for JP Patent Application No. 2017-531209, dated Jan. 27, 2020.
Ahmad, N., et al., "Steroid hormone receptors in cancer development: A target for cancer therapeutics," Cancer Letters, 2011, 300: 1-9.
"Bicalutamide for the Treatment of Androgen Receptor Positive (AR(+)), Estrogen Receptor Negative, Progesterone Receptor Negative (ER(−)/PR(−)) Metastatic Breast Cancer Patients: A Phase II Feasibility Study," available at: http://abstract.asco.org/AbstView_114_94715.html, 11 pages, last full review May 25, 2012.
Badve, S., et al., "Basal-like and triple-negative breast cancers: a critical review with an emphasis on the implications for pathologists and oncologists," Modern Pathology, 2011, 24: 157-167.
Barton, V., et al., "Androgen Receptor Supports an Anchorage-Independent, Cancer Stem Cell-like Population in Triple-Negative Breast Cancer," Cancer Res., 2017, 77(13): 3455-3466.
Belikov, S., et al., FoxA1 corrupts the antiandrogenic effect of bicalutamide but only weakly attenuates the effect of MDV3100 (Enzalutamide™), Mol. Cell. Endocrinol., 2013, 365: 95-107.
Bernales, S., et al., "Effect of MDV3100, a novel androgen receptor signaling inhibitor, on cell proliferation and tumor size in an apocrine breast cancer xenograft model," J. Clin. Oncol., 2012, 30(15 Suppl): 3072. Abstract.
Berrada, N., et al., "Treatment of triple-negative metastatic breast cancer: toward individualized targeted treatments or chemosensitization," Annals Oncol., 2010, 21(7 Suppl): vii30-vii35.

Bertucci, F., "Basal Breast Cancer," Cancer & Chemotherapy Rev., 2010, 5: 3-10.
Bhattacharya, S., et al., "Development of enzalutamide for metastatic castration-resistant prostate cancer," Ann. N.Y. Acad. Sci., 2015, 1358: 13-27.
Bosch, A., et al., "Triple-negative breast cancer: Molecular features, pathogenesis, treatment and current lines of research," Cancer Treatment Reviews, 2010, 36: 206-215.
Bouchalova, K., et al., "Triple Negative Breast Cancer—Current Status and Prospective Targeted Treatment Based on HER1 (EGFR), TOP2A and C-MYC Gene Assessment," Biomed. Pap. Med. Fac. Univ. Palacky Olomouc Czech Repub., 2009, 153(1): 13-18.
Burness, M., et al., "Epidermal Growth Factor Receptor in Triple-Negative and Basal-Like Breast Cancer: Promising Clinical Target or Only a Marker?" Cancer J., 2010, 16(1): 23-32.
Cadoo, K., et al., "Advances in Molecular and Clinical Subtyping of Breast Cancer and Their Implications for Therapy," Surg. Oncol. Clin. N. Am., 2013, 22: 823-840.
Carotenuto, P., et al., "Triple Negative Breast Cancer: From Molecular Portrait to Therapeutic Intervention," Critical Reviews™ in Eukaryotic Gene Expression, 2010, 20(1): 17-34.
Carvalho, F., et al., "Triple-negative breast carcinomas are a heterogeneous entity that differs between young and old patients," Clinics, 2010, 65(10): 1033-1036.
Castan, J. C., et al., "Stage 1 results from MDV3100-11: A 2-stage study of enzalutamide (ENZA), an androgen receptor (AR) inhibitor, in advanced Ar+ triple-negative breast cancer (TNBC)," Annals of Oncology, 2015, 26(3 Suppl): iii6-iii9.
Chacón, R., et al., "Triple-negative breast cancer," Breast Cancer Res., 2010, 12(2 Suppl): S3.
Chen, Y., et al., "Anti-androgens and androgen-deleting therapies in prostate cancer: new agents for an established target," Lancet Oncol., 2009, 10: 981-991.
Chia, K., et al., "Non-canonical AR activity facilitates endocrine resistance in breast cancer," Endocrine-Related Cancer, 2019, 26(2): 251-264.
Christenson, J., et al., "MMTV-PyMT and Derived Met-1 Mouse Mammary Tumor Cells as Models for Studying the Role of the Androgen Receptor in Triple-Negative Breast Cancer Progression," Horm. Canc., 2017, 8: 69-77.
Clarke, B., et al., "Modulators of Androgen and Estrogen Receptor Activity," Crit. Rev. in Eukaryotic Gene Expression, 2010, 20(4): 275-294.
Clarke, B., et al.,"New selective estrogen and androgen receptor modulators," Curr. Opinion in Rheumatology, 2009, 21: 374-379.
Cleere, D., "Triple-negative breast cancer: a clinical update," Commun. Oncol., 2010, 7(5): 203-211.
Cochrane, D., et al., "Abstract LB-109: MDV3100, an androgen receptor signaling inhibitor, inhibits tumor growth in breast cancer preclinical models regardless of estrogen receptor status," Proceedings: AACR 103rd Annual Meeting, Mar. 31-Apr. 4, 2012, Chicago, IL; Cancer Res., 2012, 72(8 Suppl): Abstract nr LB-109.
Constantinidou, A., et al., "Beyond triple-negative breast cancer: the need to define new subtypes," Expert Rev. Anticancer Ther., 2010, 10(8): 1197-1213.
Conzen, S., "Nuclear Receptors and Breast Cancer," Mol. Endocrinol., 2008, 22(10): 2215-2228.
Cortes, J., et al., "Overall survival (OS) from the phase 2 study of enzalutamide (ENZA), an androgen receptor (AR) signaling inhibitor, in AR+ advanced triple-negative breast cancer (aTNBC)," Eur. J. Cancer, 2015, 51(3 Suppl): S265.
D'Amato, N., et al., "Cooperative Dynamics of AR and ER Activity in Breast Cancer," Mol. Cancer Res., 2016, 14(11): 1054-1067.
D'Amato, N., et al., "Targeting Androgen Receptor in Her2-Driven Breast Cancer," Presentation OR07-4, Jun. 15, 2013.
Dawood, S., "Triple-Negative Breast Cancer: Epidemiology and Management Options," Drugs, 2010, 70(17): 2247-2258.
Dawson, S.J., et al., "Triple negative breast cancers: Clinical and prognostic implications," Eur. J. Cancer, 2009, 45(1 Suppl): 27-40.
De Laurentiis, M., et al., "Treatment of triple negative breast cancer (TNBC): current options and future perspectives," Cancer Treatment Reviews, 2010, 36S3: S80-S86.

(56) References Cited

OTHER PUBLICATIONS

Dimitrakakis, C., "Androgens and Breast Cancer in Men and Women," *Endocrinol. Metab. Clin. N. Am.*, 2011, 40: 533-547.

Dizdar, O., et al., "Current and emerging treatment options in triple-negative breast cancer," *Oncol. Rev.*, 2010, 4: 5-13.

Elias, A., et al., "Effect of MDV3100, an androgen receptor signaling inhibitor, on tumor growth of estrogen and androgen receptor-positive (ER+/AR+) breast cancer xenografts," *J. Clin. Oncol.*, 2012, 30(15 Suppl): 564-564.

Elias, A.D., et al., "Abstract P1-16-05: MDV3100-08: A phase 1 study evaluating the safety and pharmacokinetics of enzalutamide plus fulvestrant in women with advanced hormone receptor-positive breast cancer," Proceedings of the Thirty-Eighth Annual CTRC-AACR San Antonio Breast Cancer Symposium, Dec. 8-12, 2015, San Antonio, TX; *Cancer Res.*, 2016, 76(4 Suppl): Abstract nr P1-16-05.

Elias, A., "Triple-Negative Breast Cancer: A Short Review," *Am. J. Clin. Oncol.*, 2010, 33(6): 637-645.

Ellis, P., "Recent advances in systemic therapy for breast cancer: new technologies for a new era," *Breast Cancer Res.*, 2009, 11(4): 107.

Elsawaf, Z., et al., "Triple-Negative Breast Cancer: Clinical and Histological Correlations," *Breast Care*, 2011, 6: 273-278.

Feng, J., et al., "Androgen and AR contribute to breast cancer development and metastasis: an insight of mechanisms," *Oncogene*, 2017, 36: 2775-2790.

Folkerd, E., et al., "Influence of Sex Hormones on Cancer Progression," *J. Clin. Oncol.*, 2010, 28: 4038-4044.

Further Submissions, Opposition to EP 2739153, dated Dec. 16, 2019, 10 pages.

Garay, J., et al., "The growth response to androgen receptor signaling in Erα-negative human breast cells is dependent on p21 and mediated by MAPK activation," *Breast Cancer Research*, 2012, 14: R27.

Gluz, O., et al., "Triple-negative breast cancer—current status and future directions," *Annals of Oncol.*, 2009, 20(12): 1913-1927.

Goetz, M., et al., "Gene-Expression-Based Predictors for Breast Cancer," *N. Engl. J. Med.*, 2007, 356: 752-753.

Gordon, M., et al., "Synergy between Androgen Receptor Antagonism and Inhibition of mTOR and HER2 in Breast Cancer," *Mol. Cancer Ther.*, 2017, 16(7): 1389-1400.

Greenberg, S., et al., "Triple-Negative Breast Cancer: Role of Antiangiogenic Agents," *Cancer J.*, 2010, 16(1): 33-38.

Gucalp, A., et al., "Androgen Receptor-Positive, Triple-Negative Breast Cancer," *Cancer*, 2017, 123(10): 1686-1688.

Gucalp, A., et al., "Targeting the androgen receptor in triple-negative breast cancer," *Curr. Probl. Cancer*, 2016, 40: 141-50.

Gucalp, A., et al., "The Androgen Receptor in Breast Cancer: Biology and Treatment Considerations," *Curr. Breast Cancer Rep.*, 2012, 4: 56-65.

History of Changes for Study NCT00468715, "Bicalutamide in Treating Patients with Metastatic Breast Cancer," ClinicalTrials.gov archive, Apr. 3, 2019, 1-10.

Honma, N., et al., "Clinical importance of androgen receptor in breast cancer patients treated with adjuvant tamoxifen monotherapy," *Breast Cancer*, 2013, 20: 323-330.

Hurvitz, S., et al., "What's positive about 'triple-negative' breast cancer?" *Future Oncol.*, 2009, 5(7): 1015-1025.

Irshad, S., et al., "Molecular heterogeneity of triple-negative breast cancer and its clinical implications," *Curr. Op. Oncol.*, 2011, 23: 566-577.

Ismail-Khan, R., et al., "A Review of Triple-Negative Breast Cancer," *Cancer Control*, 2010, 17(3): 173-176.

Jordan, V.C., "A Century of Deciphering the Control Mechanisms of Sex Steroid Action in Breast and Prostate Cancer: The Origins of Targeted Therapy and Chemoprevention," *Cancer Res.*, 2009, 69: 1243-1254.

Kemppainen, J., et al., "Agonist and Antagonist Activities of Hydroxyflutamide and Casodex Relate to Androgen Receptor Stabilization," *Urology*, 1996, 48(1): 157-163.

Lee, S., et al., "Male Breast Cancer During Finasteride Therapy," *J. Natl. Cancer Inst.*, 2004, 96(4): 338-339.

Lehmann, B., et al., "PIK3CA mutations in androgen receptor-positive triple negative breast cancer confer sensitivity to the combination of PI3K and androgen receptor inhibitors," *Breast Cancer Res.*, 2014, 16: 406, 14 pages.

Lerma, E., et al., "Triple Negative Breast Carcinomas: Similarities and Differences With Basal Like Carcinomas," *Appl. Immunohistochem. Mol. Morphol.*, 2009, 17(6): 483-494.

Leung, J., et al., "Non-Genomic Actions of the Androgen Receptor in Prostate Cancer," *Frontiers in Endocrinology*, 2017, vol. 8, Article 2, 8 pages.

Liedtke, C., et al., "Current Issues of Targeted Therapy in Metastatic Triple-Negative Breast Cancer," *Breast Care*, 2011, 6: 234-239.

Ligresti, G., et al., "Breast cancer: Molecular basis and therapeutic strategies (Review)," *Mol. Med. Reports*, 2008, 1: 451-458.

Lu, H., et al., "Research progress in triple-negative breast cancer," *Chinese-German J. Clin. Oncol.*, 2010, 9(4): 239-242.

Lundin, K.B., et al., "Androgen receptor genotypes predict response to endocrine treatment in breast cancer patients," *Br. J. Cancer*, 2011, 105(11): 1676-1683 [Abstract only].

Lyons, T., et al., "Androgen Receptor-Targeted Therapy for Breast Cancer," *Curr. Breast Cancer Rep.*, 2017, 9: 242-250.

Ma, X., et al., "A two-gene expression ratio predicts clinical outcome in breast cancer patients treated with tamoxifen," *Cancer Cell*, 2004, 5: 607-616.

Maegawa, R., et al., "Triple-Negative Breast Cancer: Unique Biology and Its Management," *Cancer Investigation*, 2010, 28: 878-883.

Mina, A., et al., "Targeting the androgen receptor in triple-negative breast cancer: current perspectives," *OncoTargets and Therapy*, 2017, 10: 4675-4685.

O'Shaughnessy, J., "Improving Quality of Life in Patients With Metastatic Breast Cancer," *Clin. Adv. Hematol. Oncol.*, 2014, 12(2)(4 Suppl): 10-12.

Pal, S.K., et al., "Triple-negative breast cancer: Novel therapies and new directions," *Maturitas*, 2009, 63: 269-274.

Pal, S.K., et al., "Triple negative breast cancer: unmet medical needs," *Breast Cancer Res. Treat.*, 2011, 125: 627-636.

Park, S., et al., "Androgen receptor expression is significantly associated with better outcomes in estrogen receptor-positive breast cancers," *Annals of Oncol.*, 2011, 22(8): 1755-1762.

Response to Office Action filed Dec. 19, 2017, in U.S. Appl. No. 14/962,864, now U.S. Pat. No. 10,196,693.

Allowed Claims filed Dec. 8, 2015, in U.S. Appl. No. 14/962,864, now U.S. Pat. No. 10,196,693.

Non-Final Office Action dated Oct. 13, 2017, in U.S. Appl. No. 14/962,864, now U.S. Pat. No. 10,196,693.

Notice of Allowance dated Feb. 5, 2018, in U.S. Appl. No. 14/962,864, now U.S. Pat. No. 10,196,693.

Notice of Allowance dated Mar. 30, 2018, in U.S. Appl. No. 14/962,864, now U.S. Pat. No. 10,196,693.

Phan, V.T., et al., "Abstract P2-07-04: A novel diagnostic androgen receptor gene signature links clinical outcomes and preclinical response to enzalutamide, paclitaxel or the combination in triple-negative breast cancer," Proceedings of the Thirty-Eighth Annual CTRC-AACR San Antonio Breast Cancer Symposium, Dec. 8-12, 2015, San Antonio, TX; *Cancer Res.*, 2016, 76(4 Suppl): Abstract nr P2-07-04.

Proverbs-Singh, T., et al., "Targeting the androgen receptor in prostate and breast cancer: several new agents in development," *Endocrine-Related Cancer*, 2015, 22: R87-R106.

Response to Opposition filed Oct. 14, 2019, in EP 2739153.

Cochrane, D., et al., "The Role of Androgen Receptors in Postmenopausal Breast Cancer," poster presented at the Department of Defense Era of Hope Conference, Aug. 2-5, 2011.

Schwartzberg, L., et al., "A Phase I/Ib Study of Enzalutamide Alone and in Combination with Endocrine Therapies in Women with Advanced Breast Cancer," *Clin. Cancer Res.*, 2017, 23(15): 4046-4054.

Schwartzberg, L., et al., "Enzalutamide plus exemestane: A pilot study to assess safety, pharmacokinetics, and effects on circulating estrogens in women with advanced hormone-positive breast cancer," *J. Clin. Oncol.*, 2014, 32(15 Suppl): 545-545.

(56) References Cited

OTHER PUBLICATIONS

Schwartzberg, L., et al., "Enzalutamide plus exemestane: A pilot study to assess safety, pharmacokinetics, and effects on circulating estrogens in women with advanced hormone-positive breast cancer," poster presented May 30-Jun. 3, 2014.
Sgroi, D., et al., "RE: A two-gene expression ratio predicts clinical outcome in breast cancer patients treated with tamoxifen," *Cancer Cell*, 2004, 6: 445.
Shah, P., et al., "The role of the androgen receptor in triple-negative breast cancer," *Women's Health*, 2013, 9(4): 351-360.
Summons to Attend Oral Proceedings and Preliminary Opinion in Opposition to EP 2739153, dated Jan. 13, 2020.
Traina, T.A., et al., "Abstract OT3-2-08: A phase 2 single-arm study of the clinical activity and safety of enzalutamide in patients with advanced androgen receptor-positive triple-negative breast cancer," Proceedings of the Thirty-Sixth Annual CTRC-AACR San Antonio Breast Cancer Symposium, Dec. 10-14, 2013, San Antonio, TX; *Cancer Res.*, 2013, 73(24 Suppl): Abstract nr OT3-2-08.
Traina, T.A., et al., "Androgen Receptor Inhibition Can Stabilize Disease in Patients with AR(+), ER(−)/PR(−) Metastatic Breast Cancer," *Annals of Oncol.*, 2009, 20(2 Suppl): ii63-ii64.
Trudeau, M., et al., "A phase 2 single-arm study to assess clinical activity, efficacy and safety of enzalutamide (ENZA) with trastuzumab in HER2+ AR+ metastatic or locally advanced breast cancer," *J. Clin. Oncol.*, 2017, 33(15 Suppl). doi: 10.1200/jco.2015.33.15_suppl.tps640.
Wellberg, E., et al., "The Androgen Receptor Supports Tumor Progression After the Loss of Ovarian Function in a Preclinical Model of Obesity and Breast Cancer," *Horm. Canc.*, 2017, 8(5-6): 269-285. doi: 10.1007/s12672-017-0302-9.
Yanagita, Y., et al., "Astellas' Drug Discovery Strategy: Focus on Oncology," *Jpn. J. Clin. Oncol.*, 2012, 42(4): 241-246.
Yardley, D.A., et al., "Abstract OT3-2-01: A phase 2 randomized, double-blind, placebo-controlled multicenter trial evaluating the efficacy and safety of enzalutamide in combination with exemestane in estrogen or progesterone receptor-positive and HER2 non-amplified advanced breast cancer," Proceedings of the Thirty-Sixth Annual CTRC-AACR San Antonio Breast Cancer Symposium Dec. 10-14, 2013, San Antonio, TX; *Cancer Res.*, 2013, 73(24 Suppl): Abstract nr OT3-2-01.
Zarif, J., et al., "The Importance of Non-Nuclear AR Signaling in Prostate Cancer Progression and Therapeutic Resistance," *Cell Signal*, 2016, 28(5): 348-356.
Extended European Search Report for EP 18190012.7, dated Dec. 20, 2018.
Extended European Search Report for EP 19187649.9, dated Jan. 16, 2020.
European Search Report for EP Patent Application No. 19192143.6, dated Dec. 18, 2019.
Bianchini, G., et al., "Triple-negative breast cancer: challenges and opportunities of a heterogeneous disease," *Nature Reviews Clinical Oncology*, 2016, 13: 674-690.
Caiazza, F., et al., "Preclinical evaluation of the AR inhibitor enzalutamide in triple-negative breast cancer cells," *Endocrine-Related Cancer*, 2016, 23: 323-334.
Giovannelli, P., et al., "The Androgen Receptor in Breast Cancer," *Frontiers in Endocrinology*, 2018, 9, Article 492.
Huang, R., et al., "Androgen Receptor Expression and Bicalutamide Antagonize Androgen Receptor Inhibit p-Catenin Transcription Complex in Estrogen Receptor-Negative Breast Cancer," *Cellular Physiol. Biochem.*, 2017, 43: 2212-2225.
Lehmann, B., et al., "Identification of human triple-negative breast cancer subtypes and preclinical models for selection of targeted therapies," *Journal of Clinical Investigation*, 2011, 121 (7): 2750-2767 [Data Included].
European Office Action for EP Patent Application No. 19192143.6, dated Apr. 26, 2021.

\* cited by examiner

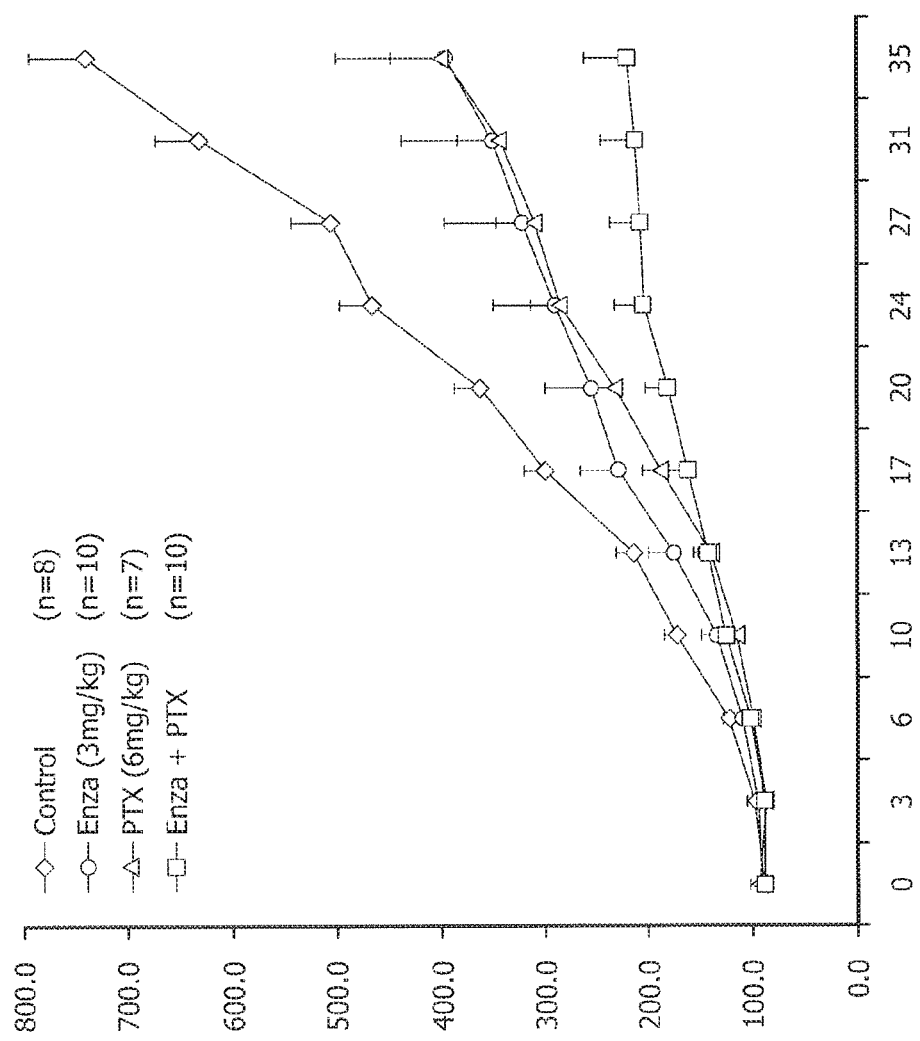

SEQUENCE LISTING

```
<160> NUMBER OF SEQ ID NOS: 151

<210> SEQ ID NO 1
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 1
aaagattcct gggacctga                                                   19

<210> SEQ ID NO 2
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 2
acagccactt tcagaagcaa g                                                21

<210> SEQ ID NO 3
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 3
ctggaagagt tgaataaaga gc                                               22
```

```
<210> SEQ ID NO 4
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 4
tacctgaacc ggcacctg                                                 18

<210> SEQ ID NO 5
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 5
gcacaaagcc attctaagtc                                               20

<210> SEQ ID NO 6
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 6
gctggctgag cagaaag                                                  17

<210> SEQ ID NO 7
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 7
ctttcgcctg agcctattt                                                19

<210> SEQ ID NO 8
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 8
ggccaaaatc gacaggac                                                 18

<210> SEQ ID NO 9
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 9
ctgtctgagt gccgtggat                                                19

<210> SEQ ID NO 10
<211> LENGTH: 20
<212> TYPE: DNA
<213> ORGANISM: Artificial Sequence
<220> FEATURE:
<223> OTHER INFORMATION: Chemically synthesized primer
```

```
<400> SEQUENCE: 10
gtaaatcacc ttctgagcct                                          20

<210> SEQ ID NO 11
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 11
ggaggcggaa gaaaccag                                            18

<210> SEQ ID NO 12
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 12
gacaaggaga atcaaaagat cagc                                     24

<210> SEQ ID NO 13
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 13
gtggcagcag atcacaa                                             17

<210> SEQ ID NO 14
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 14
cctcacgaat tgctgaactt                                          20

<210> SEQ ID NO 15
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 15
catgaaatag tgcatagttt gcc                                      23

<210> SEQ ID NO 16
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 16
acacagaatc tatcccacc agagt                                     25

<210> SEQ ID NO 17
```

-continued

<210> SEQ ID NO 17
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 17
gctggctctc acactgatag                                               20

<210> SEQ ID NO 18
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 18
gcagggagag gagtttgt                                                 18

<210> SEQ ID NO 19
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 19
cccatccatg tgaggaagta taa                                           23

<210> SEQ ID NO 20
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 20
cttcttggac cttggcg                                                  17

<210> SEQ ID NO 21
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 21
gctactacgc agacacg                                                  17

<210> SEQ ID NO 22
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 22
gatgttcgag tcacagagg                                                19

<210> SEQ ID NO 23
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 23
ttcggctgga aggaacc                                                 17

<210> SEQ ID NO 24
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 24
cgtggcagat gtgaacga                                                18

<210> SEQ ID NO 25
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 25
ggagatccgt caactccaaa                                              20

<210> SEQ ID NO 26
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 26
tgggtcgtgt caggaaac                                                18

<210> SEQ ID NO 27
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 27
cgcagtcatc cagagatgtg                                              20

<210> SEQ ID NO 28
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 28
actcagtaca agaaagaacc g                                            21

<210> SEQ ID NO 29
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 29
gttggaccag tcaacatctc tg                                           22

<210> SEQ ID NO 30
<211> LENGTH: 18
<212> TYPE: DNA

```
<213> ORGANISM: Artificial Sequence
<220> FEATURE:
<223> OTHER INFORMATION: Chemically synthesized primer

<400> SEQUENCE: 30
tgtggctcat taggcaac                                                      18

<210> SEQ ID NO 31
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 31
gactccaagc gcgaaaac                                                      18

<210> SEQ ID NO 32
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 32
ccaacaaaat attcatggtt cttg                                               24

<210> SEQ ID NO 33
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 33
ccagtagcat tgtccgag                                                      18

<210> SEQ ID NO 34
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 34
gtctctggta atgcacact                                                     19

<210> SEQ ID NO 35
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 35
gtggaatgcc tgctgacc                                                      18

<210> SEQ ID NO 36
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 36
aggggtgccc tctgagat                                                      18
```

<210> SEQ ID NO 37
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 37
cgagatcgcc aagatgtt                                                 18

<210> SEQ ID NO 38
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 38
aggcgaacac acaacgtc                                                 18

<210> SEQ ID NO 39
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 39
agcctcgaac aattgaaga                                                19

<210> SEQ ID NO 40
<211> LENGTH: 27
<212> TYPE: DNA
<213> ORGANISM: Artificial Sequence
<220> FEATURE:
<223> OTHER INFORMATION: Chemically synthesized primer

<400> SEQUENCE: 40
atcgactgtg taaacaacta gagaaga                                       27

<210> SEQ ID NO 41
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 41
tttaagaggg caatggaagg                                               20

<210> SEQ ID NO 42
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 42
tgccgcagaa ctcacttg                                                 18

<210> SEQ ID NO 43
<211> LENGTH: 20
<212> TYPE: DNA
<213> ORGANISM: Artificial Sequence
<220> FEATURE:

<223> OTHER INFORMATION: Chemically synthesized primer

<400> SEQUENCE: 43
cctcagatga tgcctatcca                                               20

<210> SEQ ID NO 44
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 44
cagcaagcga tggcatagt                                                19

<210> SEQ ID NO 45
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 45
aatgccaccg aagcctc                                                  17

<210> SEQ ID NO 46
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 46
tcgaactgaa ggctatttac gag                                           23

<210> SEQ ID NO 47
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 47
gtcgaagccg caattagg                                                 18

<210> SEQ ID NO 48
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 48
caaacgtgtg ttctggaagg                                               20

<210> SEQ ID NO 49
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 49
tgccctgtat gatgtcagga                                               20

```
<210> SEQ ID NO 50
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 50
gtgaggggtg tcagctcagt                                               20

<210> SEQ ID NO 51
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 51
tggggcagtt ctgtattact tc                                            22

<210> SEQ ID NO 52
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 52
cgatggtttt gtacaagatt tctc                                          24

<210> SEQ ID NO 53
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 53
gcaaatcctt gggcaga                                                  17

<210> SEQ ID NO 54
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 54
gccgtacagt tccacaaagg                                               20

<210> SEQ ID NO 55
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 55
gacgcttcct atcactctat tc                                            22

<210> SEQ ID NO 56
<211> LENGTH: 22
<212> TYPE: DNA
<213> ORGANISM: Artificial Sequence
<220> FEATURE:
<223> OTHER INFORMATION: Chemically synthesized primer
```

<400> SEQUENCE: 56
ttcctccatc aagagttcaa ca                                              22

<210> SEQ ID NO 57
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 57
gggcacatcc agatgttt                                                    18

<210> SEQ ID NO 58
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 58
gggtctgcac agactgcat                                                   19

<210> SEQ ID NO 59
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 59
tccttgtaat ggggagacca                                                  20

<210> SEQ ID NO 60
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 60
acttgggata tgtgaataag acc                                              23

<210> SEQ ID NO 61
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 61
ggggaaagac aaagtttcca                                                  20

<210> SEQ ID NO 62
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 62
actgtctggg tccatggcta                                                  20

<210> SEQ ID NO 63
<211> LENGTH: 18

```
<212> TYPE: DNA
<213> ORGANISM: Artificial Sequence
<220> FEATURE:
<223> OTHER INFORMATION: Chemically synthesized primer

<400> SEQUENCE: 63
ggatttcgtg gtgggttc                                                       18

<210> SEQ ID NO 64
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 64
ccacagtctg tgataaacgg                                                     20

<210> SEQ ID NO 65
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 65
ccatcaacat tctctttatg aacg                                                24

<210> SEQ ID NO 66
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 66
atcaactccc aaacggtcac                                                     20

<210> SEQ ID NO 67
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 67
gcccttacac atcggagaac                                                     20

<210> SEQ ID NO 68
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 68
gacttcaggg tgctggac                                                       18

<210> SEQ ID NO 69
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 69
```

-continued

```
tgtgaagcca gcaatatgta tc                                            22

<210> SEQ ID NO 70
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 70
tattgggagg caggaggttt a                                             21

<210> SEQ ID NO 71
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 71
ctgagttcat gttgctgacc                                               20

<210> SEQ ID NO 72
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 72
gacagctact attcccgtt                                                19

<210> SEQ ID NO 73
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 73
tatgtgagta agctcggaga c                                             21

<210> SEQ ID NO 74
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 74
agtgggcatc ccgtaga                                                  17

<210> SEQ ID NO 75
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 75
agtggacatg cgagtggag                                                19

<210> SEQ ID NO 76
<211> LENGTH: 18
<212> TYPE: DNA
<213> ORGANISM: Artificial Sequence
```

<220> FEATURE:
<223> OTHER INFORMATION: Chemically synthesized primer

<400> SEQUENCE: 76
caccgctgga aactgaac                                            18

<210> SEQ ID NO 77
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 77
cgtgcacatc catgacctt                                           19

<210> SEQ ID NO 78
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 78
gaggagatga ccttgcc                                             17

<210> SEQ ID NO 79
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 79
gccatagcca ctgccact                                            18

<210> SEQ ID NO 80
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 80
cttcgactgg actctgt                                             17

<210> SEQ ID NO 81
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 81
cagacatgtt ggtattgcac att                                      23

<210> SEQ ID NO 82
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 82
aggcgatcct gggaaattat                                          20

```
<210> SEQ ID NO 83
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 83
cccatttgtc tgtcttcac                                                  19

<210> SEQ ID NO 84
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 84
ctgatggttg aggctgtt                                                   18

<210> SEQ ID NO 85
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 85
cgcactccag cacctagac                                                  19

<210> SEQ ID NO 86
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 86
tcacagggtc aaacttccag t                                               21

<210> SEQ ID NO 87
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 87
gatggtagag ttccagtgat t                                               21

<210> SEQ ID NO 88
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 88
tctggtcacg cagggcaa                                                   18

<210> SEQ ID NO 89
<211> LENGTH: 20
<212> TYPE: DNA
<213> ORGANISM: Artificial Sequence
<220> FEATURE:
<223> OTHER INFORMATION: Chemically synthesized primer
```

<400> SEQUENCE: 89
acacagatga tggagatgtc                                              20

<210> SEQ ID NO 90
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 90
agtagctaca tctccaggtt ctctg                                        25

<210> SEQ ID NO 91
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 91
cggattttat caacgatgca g                                            21

<210> SEQ ID NO 92
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 92
catttgccgt ccttcatcg                                               19

<210> SEQ ID NO 93
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 93
gcaggtcaaa actctcaaag                                              20

<210> SEQ ID NO 94
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 94
agcgggcttc tgtaatctga                                              20

<210> SEQ ID NO 95
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 95
gcctcagatt tcaactcgt                                               19

<210> SEQ ID NO 96

```
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 96
ctgctgagaa tcaaagtggg a                                                 21

<210> SEQ ID NO 97
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 97
ggaacaaact gctctgcca                                                    19

<210> SEQ ID NO 98
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 98
acagctcttt agcatttgtg ga                                                22

<210> SEQ ID NO 99
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 99
gggactatca atgttgggtt ctc                                               23

<210> SEQ ID NO 100
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 100
cacacagttc actgctccac a                                                 21

<210> SEQ ID NO 101
<211> LENGTH: 2199
<212> TYPE: DNA
<213> ORGANISM: Homo sapiens

<400> SEQUENCE: 101
cagcggcgct gcggcggctc gcgggagacg ctgcgcgcgg ggctagcggg cggcggagcg        60
gacggcgacg gggcgctctc gggctgccgg cggggccgag cgccgcgcgt cccgagcatg       120
gcaggctccc tgcctcccctg cgtggtggac tgtggcaccg gtataccaa gcttggctac       180 gcaggcaaca ctgagcccca gttcattatt ccttcatgta ttgccatcag agagtcagca       240
aaggtagttg accaagctca aaggagagtg ttgaggggag ttgatgacct tgactttttc       300
ataggagatg aagccatcga taaacctaca tatgctacaa agtggccgat acgacatgga       360
atcattgaag actgggatct tatggaaagg ttcatggagc aagtggtttt taaatatcttt      420
```

```
cgagctgaac ctgaggacca ttattttta atgacagaac ctccactcaa tacaccagaa    480
aacagagagt atcttgcaga aattatgttt gaatcattta acgtaccagg actctacatt    540
gcagttcagg cagtgctggc cttggcggca tcttggacat ctcgacaagt gggtgaacgt    600
acgttaacgg ggatagtcat tgacagcgga gatggagtca cccatgttat cccagtggca    660
gaaggttatg taattggaag ctgcatcaaa cacatcccga ttgcaggtag agatattacg    720
tatttcattc aacagctgct aagggagagg gaggtgggaa tccctcctga gcagtcactg    780
gagaccgcaa aagccattaa ggagaaatac tgttacattt gccccgatat agtcaaggaa    840
tttgccaagt atgatgtgga tccccggaag tggatcaaac agtacacggg tatcaatgcg    900
atcaaccaga agaagtttgt tatagacgtt ggttacgaaa gattcctggg acctgaaata    960
ttctttcacc cggagtttgc caacccagac tttatggagt ccatctcaga tgttgttgat   1020
gaagtaatac agaactgccc catcgatgtg cggcgcccgc tgtataagaa tgtcgtactc   1080
tcaggaggct ccaccatgtt cagggatttc ggacgccgac tgcagaggga tttgaagaga   1140
gtggtggatg ctaggctgag gctcagcgag gagctcagcg gcgggaggat caagccgaag   1200 cctgtgtgagg tccaggtggt cacgcatcac atgcagcgct acgccgtgtg gttcggaggc   1260
tccatgctgg cctcgactcc cgagttcttt caggtctgcc acaccaagaa ggactatgaa   1320
gagtacgggc ccagcatctg ccgccacaac cccgtctttg gagtcatgtc ctagtgtctg   1380
cctgaacgcg tcgttcgatg gtgtcacgtt ggggaacaag tgtccttcag aacccagaga   1440
aggccgccgt tctgtaaata gcgacgtcgg tgttgctgcc cagcagcgtg cttgcattgc   1500
cggtgcatga ggcgcggcgc gggcccttca gtaaaagcca tttatccgtg tgccgaccgc   1560
tgtctgccag cctcctcctt ctcccgcccct cctcaccctc gctctcccctc ctcctcctcc   1620 tccgagctgc tagctgacaa atacaattct gaaggaatcc aaatgtgact ttgaaaattg   1680
ttagagaaaa caacattaga aaatggcgca aaatcgttag gtcccaggag agaatgtggg   1740
ggcgcaaacc cttttcctcc cagcctattt ttgtaaataa aatgtttaaa cttgaaatac   1800
aaatcgatgt ttatatttcc tatcattttg tattttatgg tatttggtac aactggctga   1860
tactaagcac gaatagatat tgatgttatg gagtgctgta atccaaagtt tttaattgtg   1920
aggcatgttc tgatatgttt ataggcaaac aaataaaaca gcaaactttt ttgccacatg   1980
tttgctagaa aatgattata ctttattgga gtgacatgaa gtttgaacac taaacagtaa   2040
tgtatgagaa ttactacaga tacatgtatc ttttagtttt ttttgtttga actttctgga   2100
gctgttttat agaagatgat ggtttgttgt cggtgagtgt tggatgaaat acttccttgc   2160
accattgtaa taaaagctgt tagaatattt gtaaatatc                          2199
```

<210> SEQ ID NO 102
<211> LENGTH: 1989
<212> TYPE: DNA
<213> ORGANISM: Homo sapiens

<400> SEQUENCE: 102

```
cagcggcgct gcggcggctc gcgggagacg ctgcgcgcgg ggctagcggg cggcggagcg     60
gacggcgacg gggcgctctc gggctgccgg cggggccgag cgccgcgcgt cccgagcatg    120
gcaggctccc tgcctccctg cgtggtggac tgtggcaccg ggtataccaa gcttggctac    180
gcaggcaaca ctgagcccca gttcattatt ccttcatgta ttgccatcag agagtcagca    240
aaggtagttg accaagctca aaggagagtg ttgagggag ttgatgacct tgacttttc    300
```

-continued

| | |
|---|---|
| ataggagatg aagccatcga taaacctaca tatgctacaa agtggccgat acgacatgga | 360 |
| atcattgaag actgggatct tatggaaagg ttcatggagc aagtggtttt taaatatctt | 420 |
| cgagctgaac ctgaggacca ttatttttta atgacagaac ctccactcaa tacaccagaa | 480 |
| aacagagagt atcttgcaga aattatgttt gaatcattta acgtaccagg actctacatt | 540 |
| gcagttcagg cagtgctggc cttggcggca tcttggacat ctcgacaagt gggtgaacgt | 600 |
| acgttaacgg ggatagtcat tgacagcgga gatggagtca cccatgttat cccagtggca | 660 |
| gaaggttatg taattggaag ctgcatcaaa cacatcccga ttgcaggtag agatattacg | 720 |
| tatttcattc aacagctgct aagggagagg gaggtgggaa tccctcctga gcagtcactg | 780 |
| gagaccgcaa aagccattaa ggagaaatac tgttacattt gccccgatat agtcaaggaa | 840 |
| tttgccaagt atgatgtgga tccccggaag tggatcaaac agtacacggg tatcaatgcg | 900 |
| atcaaccaga agaagtttgt tatagacgtt ggttacgaaa gattcctggg acctgaaata | 960 |
| ttctttcacc cggagtttgc caacccagac tttatggagt ccatctcaga tgttgttgat | 1020 |
| gaagtaatac agaactgccc catcgatgtg cggcgcccgc tgtataagcc cgagttcttt | 1080 |
| caggtctgcc acaccaagaa ggactatgaa gagtacgggc cagcatctg ccgccacaac | 1140 |
| cccgtctttg gagtcatgtc ctagtgtctg cctgaacgcg tcgttcgatg gtgtcacgtt | 1200 |
| ggggaacaag tgtccttcag aacccagaga aggccgccgt tctgtaaata gcgacgtcgg | 1260 |
| tgttgctgcc cagcagcgtg cttgcattgc cggtgcatga ggcgcggcgc gggcccttca | 1320 |
| gtaaaagcca tttatccgtg tgccgaccgc tgtctgccag cctcctcctt ctcccgccct | 1380 |
| cctcacccte gctctccctc ctcctcctcc tccgagctgc tagctgacaa atacaattct | 1440 |
| gaaggaatcc aaatgtgact ttgaaaattg ttagagaaaa caacattaga aaatggcgca | 1500 |
| aaatcgttag gtcccaggag agaatgtggg ggcgcaaacc ctttttcctcc cagcctattt | 1560 |
| ttgtaaataa aatgtttaaa cttgaaatac aaatcgatgt ttatatttcc tatcattttg | 1620 |
| tattttatgg tatttggtac aactggctga tactaagcac gaatagatat tgatgttatg | 1680 |
| gagtgctgta atccaaagtt tttaattgtg aggcatgttc tgatatgttt ataggcaaac | 1740 |
| aaataaaaca gcaaacttt ttgccacatg tttgctagaa aatgattata ctttattgga | 1800 |
| gtgacatgaa gtttgaacac taaacagtaa tgtatgagaa ttactacaga tacatgtatc | 1860 |
| ttttagtttt ttttgtttga actttctgga gctgttttat agaagatgat ggtttgttgt | 1920 |
| cggtgagtgt tggatgaaat acttccttgc accattgtaa taaaagctgt tagaatattt | 1980 |
| gtaaatatc | 1989 |

<210> SEQ ID NO 103
<211> LENGTH: 4786
<212> TYPE: DNA
<213> ORGANISM: Homo sapiens

<400> SEQUENCE: 103

| | |
|---|---|
| ctcggcgctg aaattcaaat ttgaacggct gcagaggccg agtccgtcac tggaagccga | 60 |
| gaggagagga cagctggttg tgggagagtt ccccgcctc agactcctgg ttttttccag | 120 |
| gagacacact gagctgagac tcactttct cttcctgaat ttgaaccacc gtttccatcg | 180 |
| tctcgtagtc cgacgcctgg ggcgatggat ccgtttacgg agaaactgct ggagcgaacc | 240 |
| cgtgccaggc gagagaatct tcagagaaaa atggctgaga ggcccacagc agctccaagg | 300 |
| tctatgactc atgctaagcg agctagacag ccacttttcag aagcaagtaa ccagcagccc | 360 |
| ctctctggtg gtgaagagaa atcttgtaca aaaccatcgc catcaaaaaa acgctgttct | 420 |

```
gacaacactg aagtagaagt ttctaacttg gaaaataaac aaccagttga gtcgacatct    480
gcaaaatctt gttctccaag tcctgtgtct cctcaggtgc agccacaagc agcagatacc    540
atcagtgatt ctgttgctgt cccggcatca ctgctgggca tgaggagagg gctgaactca    600
agattggaag caactgcagc ctcctcagtt aaaacacgta tgcaaaaact tgcagagcaa    660
cggcgccgtt gggataatga tgatatgaca gatgacattc ctgaaagctc actcttctca    720
ccaatgccat cagaggaaaa ggctgcttcc cctcccagac ctctgctttc aaatgcctcg    780
gcaactccag ttggcagaag gggccgtctg gccaatcttg ctgcaactat tgctcctgg     840 gaagatgatg taaatcactc atttgcaaaa caaaacagtg tacaagaaca gcctggtacc    900
gcttgtttat ccaaattttc ctctgcaagt ggagcatctg ctaggatcaa tagcagcagt    960
gttaagcagg aagctacatt ctgttcccaa agggatggcg atgcctcttt gaataaagcc   1020
ctatcctcaa gtgctgatga tgcgtctttg gttaatgcct caatttccag ctctgtgaaa   1080
gctacttctc cagtgaaatc tactacatct atcactgatg ctaaaagttg tgagggacaa   1140
aatcctgagc tacttccaaa aactcctatt agtcctctga aaacgggggt atcgaaacca   1200
attgtgaagt caacttatc ccagacagtt ccatccaagg gagaattaag tagagaaatt   1260
tgtctgcaat ctcaatctaa agacaaatct acgacaccag gaggaacagg aattaagcct   1320
ttcctggaac gctttggaga gcgttgtcaa gaacatagca agaaagtcc agctcgtagc   1380 acaccccaca gaaccccat tattactcca aatacaaagg ccatccaaga aagattattc   1440
aagcaagaca catcttcatc tactacccat ttagcacaac agctcaagca ggaacgtcaa   1500
aaagaactag catgtcttcg tggccgattt gacaagggca atatatggag tgcagaaaaa   1560
ggcggaaact caaaaagcaa acaactagaa accaaacagg aaactcactg tcagagcact   1620
cccctcaaaa acaccaagg tgtttcaaaa actcagtcac ttccagtaac agaaaaggtg   1680
accgaaaacc agataccagc caaaaattct agtacagaac ctaaaggttt cactgaatgc   1740
gaaatgacga atctagccc tttgaaaata acattgtttt tagaagagga caaatcctta   1800
aaagtaacat cagacccaaa ggttgagcag aaaattgaag tgatacgtga aattgagatg   1860
agtgtggatg atgatgatat caatagttcg aaagtaatta atgacctctt cagtgatgtc   1920
ctagaggaag gtgaactaga tatggagaag agccaagagg agatggatca agcattagca   1980
gaaagcagcg aagaacagga agatgcactg aatatctcct caatgtcttt acttgcacca   2040
ttggcacaaa cagttggtgt ggtaagtcca gagagtttag tgtccacacc tagactggaa   2100
ttgaaagaca ccagcagaag tgatgaaagt ccaaaaccag gaaaattcca agaactcgt    2160 gtccctcgag ctgaatctgg tgatagcctt ggttctgaag atcgtgatct tctttacagc   2220
attgatgcat atagatctca aagattcaaa gaaacagaac gtccatcaat aaagcaggtg   2280
attgttcgga aggaagatgt tacttcaaaa ctggatgaaa aaaataatgc ctttccttgt   2340
caagttaata tcaaacagaa aatgcaggaa ctcaataacg aaataaatat gcaacagaca   2400
gtgatctatc aagctagcca ggctcttaac tgctgtgttg atgaagaaca tggaaaaggg   2460
tccctagaag aagctgaagc agaaagactt cttctaattg caactgggaa gagaacactt   2520
ttgattgatg aattgaataa attgaagaac gaaggacctc agaggaagaa taaggctagt   2580
ccccaaagtg aatttatgcc atccaaagga tcagttactt tgtcagaaat ccgcttgcct   2640
ctaaaagcag attttgtctg cagtacggtt cagaaaccag atgcagcaaa ttactattac   2700
ttaattatac taaaagcagg agctgaaaat atggtagcca caccattagc aagtacttca   2760
```

-continued

```
aactctctta acggtgatgc tctgacattc actactacat ttactctgca agatgtatcc    2820
aatgactttg aaataaatat tgaagtttac agcttggtgc aaaagaaaga tccctcaggc    2880
cttgataaga agaaaaaaac atccaagtcc aaggctatta ctccaaagcg actcctcaca    2940
tctataacca caaaaagcaa cattcattct tcagtcatgg ccagtccagg aggtcttagt    3000
gctgtgcgaa ccagcaactt cgcccttgtt ggatcttaca cattatcatt gtcttcagta    3060
ggaaatacta agtttgttct ggacaaggtc ccctttttat cttctttgga aggtcatatt    3120
tatttaaaaa taaaatgtca agtgaattcc agtgttgaag aaagaggttt tctaaccata    3180
tttgaagatg ttagtggttt tggtgcctgg catcgaagat ggtgtgttct ttctggaaac    3240
tgtatatctt attggactta tccagatgat gagaaacgca agaatcccat aggaaggata    3300
aatctggcta attgtaccag tcgtcagata gaaccagcca acagagaatt ttgtgcaaga    3360
cgcaacactt ttgaattaat tactgtccga ccacaaagag aagatgaccg agagactctt    3420
gtcagccaat gcagggacac actctgtgtt accaagaact ggctgtctgc agatactaaa    3480
gaagagcggg atctctggat gcaaaaactc aatcaagttc ttgttgatat tcgcctctgg    3540
caacctgatg cttgctacaa acctattgga aagccttaaa ccgggaaatt tccatgctat    3600
ctagaggttt ttgatgtcat cttaagaaac acacttaaga gcatcagatt tactgattgc    3660
attttatgct ttaagtacga aagggtttgt gccaatattc actacgtatt atgcagtatt    3720
tatatctttt gtatgtaaaa cttttaactga tttctgtcat tcatcaatga gtagaagtaa    3780
atacattata gttgattttg ctaaatctta atttaaaagc ctcatttttcc tagaaatcta    3840 attattcagt tattcatgac aatatttttt taaaagtaag aaattctgag ttgtcttctt    3900
ggagctgtag gtcttgaagc agcaacgtct ttcagggggtt ggagacagaa acccattctc    3960
caatctcagt agttttttcg aaaggctgtg atcatttatt gatcgtgata tgacttgtta    4020
ctagggtact gaaaaaaatg tctaaggcct ttacagaaac attttttagta atgaggatga    4080 gaacttttttc aaatagcaaa tatatattgg cttaaagcat gaggctgtct tcagaaaagt    4140
gatgtggaca taggaggcaa tgtgtgagac ttggggggttc aatatttttat atagaagagt    4200 taataagcac atggtttaca tttactcagc tactatatat gcagtgtggt gcacattttc    4260
acagaattct ggcttcatta agatcattat ttttgctgcg tagcttacag acttagcata    4320
ttagtttttt ctactcctac aagtgtaaat tgaaaaatct ttatattaaa aaagtaaact    4380
gttatgaagc tgctatgtac taataatact ttgcttgcca aagtgtttgg gttttgttgt    4440
tgtttgtttg tttgtttgtt tttggttcat gaacaacagt gtctagaaac ccattttgaa    4500
agtggaaaat tattaagtca cctatcacct ttaaacgcct tttttttaaaa ttataaaata    4560 ttgtaaagca gggtctcaac ttttaaatac actttgaact tcttctctga attattaaag    4620
ttctttatga cctcatttat aaacactaaa ttctgtcacc tcctgtcatt ttattttta    4680 ttcattcaaa tgtattttttt cttgtgcata ttataaaaat atattttatg agctcttact    4740
caaataaata cctgtaaatg tctaaaggaa aaaaaaaaaa aaaaa                    4786
```

<210> SEQ ID NO 104
<211> LENGTH: 3885
<212> TYPE: DNA
<213> ORGANISM: Homo sapiens

<400> SEQUENCE: 104

```
aggccgggggc ggggctggga agtagtcggg cggggttgtg agacgccgcg ctcagcttcc      60
atcgctgggc ggtcaacaag tgcgggcctg gctcagcgcg ggggggcgcg gagaccgcga     120
```

-continued

| | |
|---|---|
| ggcgaccggg agcggctggg ttcccggctg cgcgcccttc ggccaggccg ggagccgcgc | 180 |
| cagtcggagc ccccggccca gcgtggtccg cctccctctc ggcgtccacc tgcccggagt | 240 |
| actgccagcg ggcatgaccg acccaccagg ggcgccgccg ccggcgctcg caggccgcgg | 300 |
| atgaagaaga aaacccggcg ccgctcgacc cggagcgagg agttgacccg gagcgaggag | 360 |
| ttgaccctga gtgaggaagc gacctggagt gaagaggcga cccagagtga ggaggcgacc | 420 |
| cagggcgaag agatgaatcg gagccaggag gtgacccggg acgaggagtc gacccggagc | 480 |
| gaggaggtga ccagggagga aatggcggca gctgggctca ccgtgactgt cacccacagc | 540 |
| aatgagaagc acgaccttca tgttacctcc cagcagggca gcagtgaacc agttgtccaa | 600 |
| gacctggccc aggttgttga agaggtcata ggggttccac agtcttttca gaaactcata | 660 |
| tttaagggaa aatctctgaa ggaaatggaa acaccgttgt cagcacttgg aatacaagat | 720 |
| ggttgccggg tcatgttaat tgggaaaaag aacagtccac aggaagaggt tgaactaaag | 780 |
| aagttgaaac atttggagaa gtctgtggag aagatagctg accagctgga agagttgaat | 840 |
| aaagagctta ctggaatcca gcagggtttt ctgcccaagg atttgcaagc tgaagctctc | 900 |
| tgcaaacttg ataggagagt aaaagccaca atagagcagt ttatgaagat cttggaggag | 960 |
| attgacacac tgatcctgcc agaaaatttc aaagacagta gattgaaaag gaaaggcttg | 1020 |
| gtaaaaaagg ttcaggcatt cctagccgag tgtgacacag tggagcagaa catctgccag | 1080 |
| gagactgagc ggctgcagtc tacaaacttt gccctggccg agtgaggtgt agcagaaaaa | 1140 |
| ggctgtgctg ccctgaagaa tggcgccacc agctctgccg tctctggagc ggaatttacc | 1200 |
| tgatttcttc agggctgctg ggggcaactg gccatttgcc aattttccta ctctcacact | 1260 |
| ggttctcaat gaaaaatagt gtcttgtgtga ttttgagtaa agctcctatc tgttttctcc | 1320 |
| ttctgtctct gtggttgtac tgtccagcaa tccaccttttt ctggagaggg ccacctctgc | 1380 |
| ccaaattttc ccagctgttt ggacctctgg gtgctttctt tgggctggtg agagctctaa | 1440 |
| tttgccttgg gccagtttca ggtttatagg cccctcagt cttcagatac atgagggctt | 1500 |
| cttgctctt tgatcgtgt agtcccatag ctgtaaaacc agaatcacca ggaggttgca | 1560 |
| cctagtcagg aatattggga atggcctaga acaaggtgtt tggcacataa gtagaccact | 1620 |
| tatccctcat tgtgacctaa ttccagagca tctggctggg ttgttgggtt ctagactttg | 1680 |
| tcctcacctc ccagtgaccc tgactagcca caggccatga gataccaggg ggccgttcct | 1740 |
| tggatggagc ctgtggttga tgcaaggctt ccttgtcccc aagcaagtct tcagaaggtt | 1800 |
| agaacccagt gttgactgag tctgtgcttg aaaccaggcc agagccatgg attaggaagg | 1860 |
| gcaaagagaa ggcaccagaa tgagtaaagc aggcaggtgg tgaagccaac cataaacttc | 1920 |
| tcaggagtga catgtgcttc cttcaaaggc attttttgtta accatatcct tctgagttct | 1980 |
| atgtttcctt cacagctgtt ctatccattt tgtggactgt cccccacccc caccccatca | 2040 |
| ttgttttttaa aaaattaagg cctggcgcag cagctcatgc ctataatccc agcactttgg | 2100 |
| gaggctgagg cgggcggatc acttgaggcc aggagtttga ccagcccca gcaacatag | 2160 |
| caaaaccccca ttctgcttta aaaaaaaaaa aaaaaaaaat tagcttggcg tagtggcatg | 2220 |
| tgcctataat cccagctact ggggaggctg aggcacaaga atcatttgaa cctgggaggt | 2280 |
| agaggttgct gtgagccgag attacgcccc tgcactccag cctgggtcac agagtgagac | 2340 |
| tccatctcag aaaaaaaaaa aattgagtca ggtgcagtag ctccttcctg tagtcccagc | 2400 |
| tacttgggag gctgaggcta gaggatcact tgagcccagg agtttgagtc tagtctgggc | 2460 |

| | | | | |
|---|---|---|---|---|
| aacatagcaa | gaccccatct | ctaaaattta | agtaagtaaa | agtagataaa taaaaagaaa | 2520 |
| aaaaaactgt | ttatgtgctc | atcataaagt | agaagagtgg | tttgcttttt ttttttttt | 2580 |
| tggattaatg | aggaaatcat | tctgtggctc | tagtcataat | ttatgcttaa taacattgat | 2640 |
| agtagccctt | tgcgctataa | ctctacctaa | agactcacat | catttggcag agagagagtc | 2700 |
| gttgaagtcc | caggaattca | ggactgggca | ggttaagacc | tcagacaagg tagtagaggt | 2760 |
| agacttgtgg | acaaggctcg | gtcccagcc | caccgcaccc | caactttaat cagagtggtt | 2820 |
| cactattgat | ctattttgt | gtgatagctg | tgtggcgtgg | gccacaacat ttaatgagaa | 2880 |
| gttactgtgc | accaaactgc | cgaacaccat | tctaaactat | tcatatatat tagtcattta | 2940 |
| attcttacat | aacttgagag | gtagacagat | atccttattt | tagagatgag gaaaccaaga | 3000 |
| gaacttaggt | cattagcgca | aggttgtaga | gtaagcggca | aagccaagac acaaagctgg | 3060 |
| gtggtttggt | ttcagagcca | gtgcttttcc | cctctactgt | actgcctctc aaccaacaca | 3120 |
| gggttgcaca | ggcccattct | ctgattttt | tcctcttgtc | ctctgcctct ccctctagct | 3180 |
| cccacttcct | ctctgctcta | gttcattttc | tttagagcag | cccgagtgat catgaagtgc | 3240 |
| aaatcttgcc | atgtcagtcc | cctgcttaga | accctccaat | ggctcacttt ctctttaggc | 3300 |
| aaaagtcttt | accccatgcc | ttctcccatc | tcatctcaac | cccctcattt gttggctgtc | 3360 |
| tgctgtcagc | cactcttctt | tcaggtcctc | agatgcactg | caccctctcc tgcctggggg | 3420 |
| tctttgctcc | tgctactacc | tctgcttgaa | cagctcctca | ccttccttcc tccaacccta | 3480 |
| cccttgtata | ggtgactttt | gttcatcctt | cagaattcaa | ctcacatgtc tcttgcatgg | 3540 |
| agaaccctca | cctactgtgt | tgagaccctg | tccagccccc | aggtgggatc ctctctcgac | 3600 |
| ttcccataca | tttctttcac | agcatttaca | tagtccatga | tagtttactt gtgggattat | 3660 |
| ttggttaatc | tttgccttta | acaccagggt | tccttgggtg | aaggagcttc tttatccttgg | 3720 |
| taacagcatt | atttcaagca | taacttgtaa | tatagttata | ttacatatat aacatatata | 3780 |
| tatataacat | aacatatata | acatatataa | caagcataac | ttgttatata gtcttgtata | 3840 |
| tagtaagacc | tcaataaata | tttggagaac | aaaaaaaaaa | aaaaa | 3885 |

```
<210> SEQ ID NO 105
<211> LENGTH: 6492
<212> TYPE: DNA
<213> ORGANISM: Homo sapiens

<400> SEQUENCE: 105
```

| | | | | |
|---|---|---|---|---|
| tttctgtgaa | gcagaagtct | gggaatcgat | ctggaaatcc | tcctaatttt tactccctct | 60 |
| ccccgcgact | cctgattcat | tgggaagttt | caaatcagct | ataactggag agtgctgaag | 120 |
| attgatggga | tcgttgcctt | atgcatttgt | tttggttta | caaaaggaa acttgacaga | 180 |
| ggatcatgct | gtacttaaaa | aatacaacat | cacagaggaa | gtagactgat attaacaata | 240 |
| cttactaata | ataacgtgcc | tcatgaaata | aagatccgaa | aggaattgga ataaaaattt | 300 |
| cctgcatctc | atgccaaggg | ggaaacacca | gaatcaagtg | ttccgcgtga ttgaagacac | 360 |
| cccctcgtcc | aagaatgcaa | agcacatcca | ataaaatagc | tggattataa ctcctcttct | 420 |
| ttctctgggg | gccgtggggt | gggagctggg | gcgagaggtg | ccgttggccc cgttgctttt | 480 |
| tcctctggga | aggatggcgc | acgctgggag | aacagggtac | gataaccggg agatagtgat | 540 |
| gaagtacatc | cattataagc | tgtcgcagag | gggctacgag | tgggatgcgg gagatgtggg | 600 |
| cgccgcgccc | ccggggccg | ccccgcacc | gggcatcttc | tcctcccagc ccgggcacac | 660 |
| gccccatcca | gccgcatccc | gggacccggt | cgccaggacc | tcgccgctgc agaccccggc | 720 |

```
tgccccggc gccgccgcgg ggcctgcgct cagcccggtg ccacctgtgg tccacctgac    780
cctccgccag gccggcgacg acttctcccg ccgctaccgc cgcgacttcg ccagagatgtc    840 cagccagctg cacctgacgc ccttcaccgc gcggggacgc tttgccacgg tggtggagga    900
gctcttcagg gacggggtga actggggggag gattgtggcc ttctttgagt tcggtggggt    960
catgtgtgtg gagagcgtca accgggagat gtcgccctg gtggacaaca tcgccctgtg   1020
gatgactgag tacctgaacc ggcacctgca cacctggatc caggataacg gaggctggga   1080
tgcctttgtg gaactgtacg gccccagcat gcggcctctg tttgatttct cctggctgtc   1140
tctgaagact ctgctcagtt tggccctggt gggagcttgc atcaccctgg gtgcctatct   1200
gggccacaag tgaagtcaac atgcctgccc caaacaaata tgcaaaaggt tcactaaagc   1260
agtagaaata atatgcattg tcagtgatgt accatgaaac aaagctgcag gctgtttaag   1320
aaaaaataac acacatataa acatcacaca cacagacaga cacacacaca caacaatt   1380 aacagtcttc aggcaaaacg tcgaatcagc tatttactgc caaagggaaa tatcatttat   1440 ttttttacatt attaagaaaa aaagatttat ttatttaaga cagtcccatc aaaactcctg   1500
tctttggaaa tccgaccact aattgccaag caccgcttcg tgtggctcca cctggatgtt   1560
ctgtgcctgt aaacatagat tcgctttcca tgttgttggc cggatcacca tctgaagagc   1620
agacggatgg aaaaaggacc tgatcattgg ggaagctggc tttctggctg ctggaggctg   1680
gggagaaggt gttcattcac ttgcatttct ttgccctggg ggctgtgata ttaacagagg   1740
gagggttcct gtggggggaa gtccatgcct ccctggcctg aagaagagac tctttgcata   1800
tgactcacat gatgcatacc tggtgggagg aaaagagttg ggaacttcag atggacctag   1860
tacccactga gatttccacg ccgaaggaca gcgatgggaa aaatgcccctt aaatcatagg   1920 aaagtatttt tttaagctac caattgtgcc gagaaaagca ttttagcaat ttatacaata   1980
tcatccagta ccttaagccc tgattgtgta tattcatata ttttggatac gcacccccca   2040
actcccaata ctggctctgt ctgagtaaga aacagaatcc tctggaactt gaggaagtga   2100
acatttcggt gacttccgca tcaggaaggc tagagttacc cagagcatca ggccgccaca   2160
agtgcctgct tttaggagac cgaagtccgc agaacctgcc tgtgtcccag cttggaggcc   2220
tggtcctgga actgagccgg ggccctcact ggcctcctcc agggatgatc aacagggcag   2280
tgtggtctcc gaatgtctgg aagctgatgg agctcagaat tccactgtca agaaagagca   2340 gtagagggt gtggctgggc ctgtcaccct ggggccctcc aggtaggccc gttttcacgt   2400
ggagcatggg agccacgacc cttcttaaga catgtatcac tgtagaggga aggaacagag   2460
gccctgggcc cttcctatca gaaggacatg gtgaaggctg gaacgtgag gagaggcaat   2520 ggccacggcc cattttggct gtagcacatg gcacgttggc tgtgtggcct ggcccacct   2580 gtgagtttaa agcaaggctt taaatgactt tggagagggt cacaaatcct aaaagaagca   2640
ttgaagtgag gtgtcatgga ttaattgacc cctgtctatg gaattacatg taaaacatta   2700
tcttgtcact gtagtttggt tttatttgaa aacctgacaa aaaaaaagtt ccaggtgtgg   2760
aatatggggg ttatctgtac atcctggggc attaaaaaaa aaatcaatgg tggggaacta   2820
taaagaagta acaaaagaag tgacatcttc agcaaataaa ctaggaaatt ttttttttctt   2880 ccagtttaga atcagccttg aaacattgat ggaataactc tgtggcatta ttgcattata   2940 taccattat ctgtattaac tttggaatgt actctgttca atgtttaatg ctgtggttga   3000
tatttcgaaa gctgctttaa aaaaatacat gcatctcagc gttttttgt ttttaattgt   3060
```

```
atttagttat ggcctataca ctatttgtga gcaaaggtga tcgttttctg tttgagattt    3120
ttatctcttg attcttcaaa agcattctga gaaggtgaga taagccctga gtctcagcta    3180
cctaagaaaa acctggatgt cactggccac tgaggagctt tgtttcaacc aagtcatgtg    3240
catttccacg tcaacagaat tgtttattgt gacagttata tctgttgtcc ctttgacctt    3300
gtttcttgaa ggtttcctcg tccctgggca attccgcatt taattcatgg tattcaggat    3360
tacatgcatg tttggttaaa cccatgagat tcattcagtt aaaaatccag atggcaaatg    3420
accagcagat tcaaatctat ggtggtttga cctttagaga gttgctttac gtggcctgtt    3480
tcaacacaga cccacccaga gccctcctgc cctccttccg cggggggcttt ctcatggctg    3540 tccttcaggg tcttcctgaa atgcagtggt gcttacgctc caccaagaaa gcaggaaacc    3600
tgtggtatga agccagacct ccccggcggg cctcagggaa cagaatgatc agacctttga    3660
atgattctaa ttttttaagca aaatattatt ttatgaaagg tttacattgt caaagtgatg    3720
aatatggaat atccaatcct gtgctgctat cctgccaaaa tcattttaat ggagtcagtt    3780
tgcagtatgc tccacgtggt aagatcctcc aagctgcttt agaagtaaca atgaagaacg    3840
tggacgtttt taatataaag cctgttttgt cttttgttgt tgttcaaacg ggattcacag    3900
agtatttgaa aaatgtatat atattaagag gtcacggggg ctaattgctg gctggctgcc    3960
ttttgctgtg gggttttgtt acctggtttt aataacagta aatgtgccca gcctcttggc    4020
cccagaactg tacagtattg tggctgcact tgctctaaga gtagttgatg ttgcattttc    4080
cttattgtta aaaacatgtt agaagcaatg aatgtatata aagcctcaa ctagtcattt    4140 ttttctcctc ttcttttttt tcattatatc taattatttt gcagttgggc aacagagaac    4200
catccctatt ttgtattgaa gagggattca catctgcatc ttaactgctc tttatgaatg    4260
aaaaaacagt cctctgtatg tactcctctt tacactggcc agggtcagag ttaaatagag    4320
tatatgcact ttccaaattg gggacaaggg ctctaaaaaa agccccaaaa ggagaagaac    4380
atctgagaac ctcctcggcc ctcccagtcc ctcgctgcac aaatactccg caagagaggc    4440
cagaatgaca gctgacaggg tctatggcca tcgggtcgtc tccgaagatt tggcaggggc    4500
agaaaactct ggcaggctta agatttggaa taaagtcaca gaattaagga agcacctcaa    4560
tttagttcaa acaagacgcc aacattctct ccacagctca cttacctctc tgtgttcaga    4620
tgtggccttc catttatatg tgatctttgt tttattagta aatgcttatc atctaaagat    4680
gtagctctgg cccagtggga aaaattagga agtgattata atcgagagg agttataata    4740 atcaagatta aatgtaaata atcagggcaa tcccaacaca tgtctagctt tcacctccag    4800
gatctattga gtgaacagaa ttgcaaatag tctctatttg taattgaact tatcctaaaa    4860
caaatagttt ataaatgtga acttaaactc taattaattc caactgtact tttaaggcag    4920
tggctgtttt tagactttct tatcacttat agttagtaat gtacacctac tctatcagag    4980
aaaaacagga aaggctcgaa atacaagcca ttctaaggaa attagggagt cagttgaaat    5040
tctattctga tcttattctg tggtgtcttt tgcagcccag acaaatgtgg ttacacactt    5100
tttaagaaat acaattctac attgtcaagc ttatgaaggt tccaatcaga tctttattgt    5160
tattcaattt ggatctttca gggattttt ttttaaatta ttatgggaca aaggacattt    5220
gttggagggg tgggagggag gaagaatttt taaatgtaaa acattcccaa gtttggatca    5280
gggagttgga agttttcaga ataaccagaa ctaagggtat gaaggacctg tattggggtc    5340
gatgtgatgc ctctgcgaag aaccttgtgt gacaaatgag aaacattttg aagtttgtgg    5400
tacgaccttt agattccaga gacatcagca tggctcaaag tgcagctccg tttggcagtg    5460
```

```
caatggtata aatttcaagc tggatatgtc taatgggtat ttaaacaata aatgtgcagt    5520
tttaactaac aggatattta atgacaacct tctggttggt agggacatct gtttctaaat    5580
gtttattatg tacaatacag aaaaaaattt tataaaatta agcaatgtga aactgaattg    5640
gagagtgata atacaagtcc tttagtctta cccagtgaat cattctgttc catgtctttg    5700
gacaaccatg accttggaca atcatgaaat atgcatctca ctggatgcaa agaaaatcag    5760
atggagcatg aatggtactg taccggttca tctggactgc cccagaaaaa taacttcaag    5820
caaacatcct atcaacaaca aggttgttct gcataccaag ctgagcacag aagatgggaa    5880
cactggtgga ggatggaaag gctcgctcaa tcaagaaaat tctgagacta ttaataaata    5940
agactgtagt gtagatactg agtaaatcca tgcacctaaa ccttttggaa atctgccgt     6000 gggccctcca gatagctcat ttcattaagt ttttccctcc aaggtagaat ttgcaagagt    6060
gacagtggat tgcatttctt ttggggaagc tttcttttgg tggttttgtt tattatacct    6120
tcttaagttt tcaaccaagg tttgcttttg ttttgagtta ctggggttat ttttgtttta    6180
aataaaaata agtgtacaat aagtgttttt gtattgaaag cttttgttat caagattttc    6240
atacttttac cttccatggc tcttttttaag attgatactt ttaagaggtg gctgatattc    6300
tgcaacactg tacacataaa aaatacggta aggatacttt acatggttaa ggtaaagtaa    6360
gtctccagtt ggccaccatt agctataatg gcactttgtt tgtgttgttg gaaaaagtca    6420
cattgccatt aaactttcct tgtctgtcta gttaatattg tgaagaaaaa taaagtacag    6480
tgtgagatac tg                                                       6492

<210> SEQ ID NO 106
<211> LENGTH: 2724
<212> TYPE: DNA
<213> ORGANISM: Homo sapiens

<400> SEQUENCE: 106
cccagaaggc cgcgggggt ggaccgccta agagggcgtg cgctcccgac atgccccgcg      60
gcgcgccatt aaccgccaga tttgaatcgc gggacccgtt ggcagaggtg gcggcggcgg    120
catgggtgcc ccgacgttgc cccctgcctg gcagcccttt ctcaaggacc accgcatctc    180
tacattcaag aactggccct tcttggaggg ctgcgcctgc accccggagc ggatggccga    240
ggctggcttc atccactgcc ccactgagaa cgagccagac ttggcccagt gtttcttctg    300
cttcaaggag ctggaaggct gggagccaga tgacgacccc attgggccgg gcacggtggc    360
ttacgcctgt aataccagca cttttgggagg ccgaggcggg cggatcacga gagaggaaca    420
taaaaagcat tcgtccggtt gcgctttcct ttctgtcaag aagcagtttg aagaattaac    480
ccttggtgaa tttttgaaac tggacagaga aagagccaag aacaaaattg caaggaaac     540 caacaataag aagaaagaat ttgaggaaac tgcggagaaa gtgcgccgtg ccatcgagca    600
gctggctgcc atggattgag gcctctggcc ggagctgcct ggtcccagag tggctgcacc    660
acttccaggg tttattccct ggtgccacca gccttcctgt gggcccctta gcaatgtctt    720
aggaaaggag atcaacattt tcaaattaga tgtttcaact gtgctcttgt tttgtcttga    780
aagtggcacc agaggtgctt ctgcctgtgc agcgggtgct gctggtaaca gtggctgctt    840
ctctctctct ctctcttttt tgggggctca ttttttgctgt tttgattccc gggcttacca    900
ggtgagaagt gagggaggaa gaaggcagtg tccccttttgc tagagctgac agcttttgttc    960 gcgtgggcag agccttccac agtgaatgtg tctggacctc atgttgttga ggctgtcaca   1020
```

```
gtcctgagtg tggacttggc aggtgcctgt tgaatctgag ctgcaggttc cttatctgtc    1080
acacctgtgc ctcctcagag gacagttttt ttgttgttgt gttttttttgt tttttttttt    1140 ttggtagatg catgacttgt gtgtgatgag agaatggaga cagagtccct ggctcctcta    1200
ctgtttaaca acatggcttt cttattttgt ttgaattgtt aattcacaga atagcacaaa    1260
ctacaattaa aactaagcac aaagccattc taagtcattg gggaaacggg gtgaacttca    1320
ggtggatgag gagacagaat agagtgatag gaagcgtctg gcagatactc cttttgccac    1380
tgctgtgtga ttagacaggc ccagtgagcc gcggggcaca tgctggccgc tcctccctca    1440
gaaaaaggca gtggcctaaa tcctttttaa atgacttggc tcgatgctgt gggggactgg    1500
ctgggctgct gcaggccgtg tgtctgtcag cccaaccttc acatctgtca cgttctccac    1560
acggggagga gacgcagtcc gcccaggtcc ccgctttctt tggaggcagc agctcccgca    1620
gggctgaagt ctggcgtaag atgatggatt tgattcgccc tcctccctgt catagagctg    1680
cagggtggat tgttacagct tcgctggaaa cctctggagg tcatctcggc tgttcctgag    1740
aaataaaaag cctgtcattt caaacactgc tgtggaccct actgggtttt taaaatattg    1800 tcagttttc atcgtcgtcc ctagcctgcc aacagccatc tgcccagaca gccgcagtga    1860
ggatgagcgt cctggcagag acgcagttgt ctctgggcgc ttgccagagc cacgaacccc    1920
agacctgttt gtatcatccg ggctccttcc gggcagaaac aactgaaaat gcacttcaga    1980
cccacttatt tctgccacat ctgagtcggc ctgagataga cttttccctc taaactggga    2040
gaatatcaca gtggttttg ttagcagaaa atgcactcca gcctctgtac tcatctaagc    2100
tgcttatttt tgatatttgt gtcagtctgt aaatggatac ttcactttaa taactgttgc    2160
ttagtaattg gctttgtaga gaagctggaa aaaatggtt ttgtcttcaa ctccttttgca    2220 tgccaggcgg tgatgtggat ctcggcttct gtgagcctgt gctgtgggca gggctgagct    2280
ggagccgccc ctctcagccc gcctgccacg gcctttcctt aaaggccatc cttaaaacca    2340 gacccctcatg gctaccagca cctgaaagct tcctcgacat ctgttaataa agccgtaggc    2400
ccttgtctaa gtgcaaccgc ctagactttc tttcagatac atgtccacat gtccattttt    2460
caggttctct aagttggagt ggagtctggg aagggttgtg aatgaggctt ctgggctatg    2520
ggtgaggttc caatggcagg ttagagcccc tcgggccaac tgccatcctg gaaagtagag    2580
acagcagtgc ccgctgccca gaagagacca gcaagccaaa ctggagcccc cattgcaggc    2640
tgtcgccatg tggaaagagt aactcacaat tgccaataaa gtctcatgtg gttttatcta    2700
aaaaaaaaaa aaaaaaaaaa aaaa                                           2724
```

<210> SEQ ID NO 107
<211> LENGTH: 4934
<212> TYPE: DNA
<213> ORGANISM: Homo sapiens

<400> SEQUENCE: 107

```
aatgagggta tttataaact acttaaatta taaaagaat gagacatcag acttacagtt      60
ttggatacta atttttttca cttaacgttc attatgtgat aggagttttc catcctatta    120
taccgctgtg cgatctgatc ttgggcacgt taaccaacct cttgttgcct cgattttctc    180
acctgtaaaa gtgggggtaa tcataatgct tacttagtag gatagccctg aagaataagt    240
gacttagcga acataaatag cttacaatag ggttttcagc atgggaagga ttcagtaaat    300
gttagctgtc atcatcacca cctacaaagg aagcaatact gtgctgaaag ttttttccatc    360 attaatgtaa tttctatagt acgattccca agaagatatt aaaattatgg aaataaaggt    420
```

```
attggtatat tcctaattat ttcctaaaag attgtattga taaatatgct catccttccc      480
ttaacgggat gcattccaga aaaacaagtc aaatgttaga caaagtatca gaagggaaat      540
tctgtagcca gagagctaaa aattacaata gggtctctaa ttatacttca acttttttag      600
gaataattct cagtgtgttt tcccacattt catatgtaat tttttttttt tttttttttt      660
gagacagagc ctcgccctgt caccaggctg gagtacagtg gcgcgatctc ggctcactgc      720
aacttccacc tgctgggttc aagcaattct tctgacctca ggtgatccac ccgcctcggc      780
ctcccaaagt gctgggatta acaggcgt ggcatgagtc accgcgcccg gccgatcttt       840
acttttttat tctttgtacc ccctgcctat ccagttagca tgtgattaaa gtcaaagatt      900
tgccactttg ggccacatct attaattttc atctttgtta taattgtatt tagttttttga     960 tctacactgc ttattactcc cagtcatttt ttatagaact gaaaatctgg taaaatactc     1020
aaaattgcac tgacttctat gtagaggcga cactccatca gaaccgtggg ctgacaggga     1080
atcccactgt gcaggagctg cgcgcatttt catttctgat tctctttggc gtatccagga     1140
ctctgatgac atgatcatat atttatcagt agtaacaggt tgggccattt gtttttttgtg    1200 gtaaatcata tatttaagat tttagaaata agttgatagc catgtatttt ggaatttgaa     1260
aaagacattg cattactcag cttcaaatta agctttaatc aaatagtgaa acttccatt      1320 aatggacagt gtatcccttt ttgtgtattt aaaaaaaaaa acactgaata tagtgccttt     1380
gtgacagggg agcttggttc ctgacaatgt cctcttgagc cttttttttt tttttgagat     1440
ggagtctcac tgtgtcaccc aggctggagt gcagtggcgc catcttggct cactgcaacc     1500 tccgcccct gggttcaagt gattctcatt cctcagcttc ctaagtagct gggattacag      1560
gcacgcacca ccatgaccag ctaatttta ctttttagt agagacaggg ttttgccatg       1620
ttggctaggt tggtctcgaa ctcctgacct caagtaatcc acccaccatg gcctccccaa     1680
agtgctggga ttacaggcgt gagccatttc acccggcctc tcttccgtct ttgagctgtg    1740
aggaaatagc tacattacat gagctgctag atctgcctta tggtcagaaa tgaaggttga     1800
actctcagga acagtgacat atatacacac tgatatttcc aaagtacaat gccccaaatt     1860
gatccacaaa ggaattaagg tcatttgcaa caaaatcaca gaatagtaac aaataaatag     1920
aagataaata tggccaggga tgctgcaaac tgatatactg ccaagtttat cagttgggaa     1980
tcccaacagt gaaaagcata aaatgaaag gaattttaag gagactttt atagaagagt       2040 gggaaggatt ggaggagcca acaagtgatg gtgaggcaca cagggaagag cttcagtggg     2100
caccatcccc tctctggttt gaaggggtag ggaggggacc agagctggga ggaggggct      2160 ggaatactgc tggaggagcc actcccttcc agacctgctg tggccatcac agaatgcagc     2220
cactgccaga gcagcagccc gaggaaccag gcaggggag cacaagtacc ctagcctctc      2280
tctttctgtt tcttgcctgc cgatctcctc cactggctaa acccagctgg atgctaagag     2340
tacagtcagc ctgcctgctg aggagggacc accaggacc accatcagca agggatccaa     2400
tgtctttctg cctctgcaga atgaaggttg gggcgcgggg ggcgctctac ttcttaggga    2460
tattgtggga ataaaaggaa ataggcaaaa aatgttttg aaaacaaag cacatactgc      2520 gcacccgtgg gccactactg cttttgaccc ctggctctgt ttcatgaagt aatgtcgtgt     2580
cattctcttt ttaggtgcta caggatttct ttaggtttgt tttctgtcca ccatatttca     2640
actcatgtgt gctgtttgtt gtgctaaaac aaatatttgc tgatgcctga gtgaatagtt     2700
gaatatttta tataagtcaa atttatacgt aatgattttt cttgtaactt agccgtttct    2760
```

```
cttttacaaa ctcagaaaac ctcagacttt gaaaaggcct tgaagttcct cacctgaaat    2820
ctgagaactt ggagcgcctt aaaaaatcta aggaaaaca aaacagtgaa agaacatgat    2880
atagtcagtg tagagaataa aattatttat gtaattaata ttgaggatgc agataacaca    2940
ttgtgaaatc ttgcttgtaa aaaatctcga tctgctgaag aaagatgttc tctctagaga    3000
tctttgaaag cataattatt gagcttttaa aatgttagaa acaaaagtta gacccacaca    3060
tattctggcg tgtggaagat ttgcattcct tcccctgccc gccccgcccc cacacttgtg    3120
agttgtgcct gtgtacgcag ttcctgtagc actcggctgg gcagaaatca tctttcagca    3180
ctaagggaac atagttatga tctggaccct ctgggagtgg tcagtgccca agaacaggta    3240
tgggactcca gaaagttctg ctctcaaccc tattttgaaa tagagttaca cattgttcta    3300
caattatttg agttaataag cagctctttt caaacgtgat tatgcccttc caagtttaaa    3360
tacactagac tttagtgaaa gtaattgacc tcatctcatt tctctcctgt tatattaaga    3420
tcactttcag taaaaggtag aagcttttga agtggtgagg aggaggtaga ggagggacat    3480
agagcagata ggggctggaa agtggggtga ggaagagagt ggcttctctt tggcagagta    3540
ccaaggaaaa gccctatctg tacagaacct ttgtgcctgg gaacttgatg gctgcaacct    3600
gagcctcaac ctagtttgct tgcggagcca gaagagaagc taaaaacctt cagttaacca    3660
agccagacac caagaaagtt aaaccgaaag agaaccccc accccccgca aaaaaagaa    3720 gtaaagtggg ttaaagtgat atcatgttag cacagaaaga gaacataagg gtcatctaag    3780
ttcatctgcc ccctcttcta tttcaaggtg cagaaactaa ggcacaaggg accccgtgtc    3840
ctgctcttga tcacatagct agtgggtgcc aagccaggtc tagaactctg ttctctgggg    3900
tcacaggctg gctcttcatc cctctagaga gatagctcat ctgtgtgcac ctgagcccgt    3960
tgtgtttcgg agtcaaagca aataaaggct caaactccaa gactgttttg cagaccggct    4020
gcagtagata tgggggagg agaaacctgc tttaaattgc ttcaagcaag ttgtttctgc    4080
aaaggtgttg actttttct ttcaactttc tagtgagtca ctgcagcctg agctgttatt    4140
tgtcattatg caataattca ggaactaact caagattctt cttttaaat tatttgttta    4200 tttagagaca gagtcttgct ctgttgccca ggctggagtg cagtggtgtg atctcggctc    4260
actgcagcct ctgcctcctg ggttcaagca attctcatgt ctcagcctcc cgaatagctg    4320
gtattgcagg ctcgtgccac cacccctgc taattttgt aatttagtg gagacacggt    4380 ttcgccatgt tggccgggct cgtcttgagc tcctggcctc aggtgatccg cccgcctcgg    4440
cctcccaaag tgctgggatt gcagccgtga gcctccacac ccggcctatt tatttatttt    4500
taaattggct gctcttagaa aggcatacca tgtttctgga tgggaaggct tattaattca    4560
ccctaattta atgtataaat ttgatgcaat catagtcaca gtcccagtgg aattttttaa    4620
cttggtaaga tgttctaaaa ttaatgagag aacttgaatt accaggtatt gaaacactgt    4680
aaagccacaa tcatgtaaac agtatgttat aaccatggga atagaggtct gtgatacagc    4740 agaaaaagt gaaaaaaga ataactgtat tcataaaaat ttaaatgtgg agtcactggg    4800
ggaaaggatt aaatattcga taatgtagaa acaactcaac tatttggaga aatgtaaatt    4860
tagagcctta tctcatgcca tataccaaaa tactatttag atttgattaa aaaataaaaa    4920
aaaaaaaaaa aaaa                                                    4934
```

<210> SEQ ID NO 108
<211> LENGTH: 2177
<212> TYPE: DNA
<213> ORGANISM: Homo sapiens

<400> SEQUENCE: 108

```
cgaacgcctt cgcgcgatcg ccctggaaac gcattctctg cgaccggcag ccgccaatgg      60
gaagggagtg agtgccacga acaggccaat aaggagggag cagtgcgggg tttaaatctg     120
aggctaggct ggctcttctc ggcgtgctgc ggcggaacgg ctgttggttt ctgctgggtg     180
taggtccttg gctggtcggg cctccggtgt tctgcttctc cccgctgagc tgctgcctgg     240
tgaagaggaa gccatggcgc tccgagtcac caggaactcg aaaattaatg ctgaaaataa     300
ggcgaagatc aacatggcag gcgcaaagcg cgttcctacg gccccctgctg caacctccaa    360
gcccggactg aggccaagaa cagctcttgg ggacattggt aacaaagtca gtgaacaact     420
gcaggccaaa atgcctatga agaaggaagc aaaaccttca gctactggaa aagtcattga     480
taaaaaacta ccaaaacctc ttgaaaaggt acctatgctg gtgccagtgc cagtgtctga     540
gccagtgcca gagccagaac ctgagccaga acctgagcct gttaaagaag aaaaactttc     600
gcctgagcct attttggttg atactgcctc tccaagccca atggaaacat ctggatgtgc     660
ccctgcagaa gaagacctgt gtcaggcttt ctctgatgta attcttgcag taaatgatgt     720
ggatgcagaa gatggagctg atccaaacct ttgtagtgaa tatgtgaaag atatttatgc     780
ttatctgaga caacttgagg aagagcaagc agtcagacca aaatacctac tgggtcggga     840
agtcactgga aacatgagag ccatcctaat tgactggcta gtacaggttc aaatgaaatt     900
caggttgttg caggagacca tgtacatgac tgtctccatt attgatcggt tcatgcagaa     960
taattgtgtg cccaagaaga tgctgcagct ggttggtgtc actgccatgt ttattgcaag    1020
caaatatgaa gaaatgtacc ctccagaaat tggtgacttt gcttttgtga ctgacaacac    1080
ttatactaag caccaaatca gacagatgga aatgaagatt ctaagagctt aaactttgg     1140
tctgggtcgg cctctacctt tgcacttcct tcggagagca tctaagattg agaggttga    1200
tgtcgagcaa catactttgg ccaaataacct gatggaacta actatgttgg actatgacat    1260
ggtgcacttt cctccttctc aaattgcagc aggagctttt tgcttagcac tgaaaattct    1320
ggataatggt gaatggacac caactctaca acattacctg tcatatactg aagaatctct    1380
tcttccagtt atgcagcacc tggctaagaa tgtagtcatg gtaaatcaag gacttacaaa    1440
gcacatgact gtcaagaaca agtatgccac atcgaagcat gctaagatca gcactctacc    1500
acagctgaat tctgcactag ttcaagattt agccaaggct gtggcaaagg tgtaacttgt    1560
aaacttgagt tggagtacta tatttacaaa taaaattggc accatgtgcc atctgtacat    1620
attactgttg catttacttt taataaagct tgtggcccct tttacttttt tatagcttaa    1680
ctaatttgaa tgtggttact tcctactgta gggtagcgga aaagttgtct taaaaggtat    1740
ggtggggata tttttaaaaa ctccttttgg tttacctggg gatccaattg atgtatatgt    1800
ttatatactg ggttcttgtt ttatataccct ggcttttact ttattaatat gagttactga   1860
aggtgatgga ggtatttgaa aattttactt ccataggaca tactgcatgt aagccaagtc    1920
atggagaatc tgctgcatag ctctatttta aagtaaaagt ctaccaccga atccctagtc    1980
cccctgtttt ctgtttcttc ttgtgattgc tgccataatt ctaagttatt tacttttacc    2040
actatttaag ttatcaactt tagctagtat cttcaaactt tcactttgaa aaatgagaat    2100
tttatattct aagccagttt tcattttggt tttgtgtttt ggttaataaa acaatactca    2160
aatacaaaaa aaaaaaa                                                   2177
```

<210> SEQ ID NO 109

<211> LENGTH: 2011
<212> TYPE: DNA
<213> ORGANISM: Homo sapiens

<400> SEQUENCE: 109

| | | | | | |
|---|---|---|---|---|---|
| gcggccgcca | gcgcggtgta | ggggcaggc | gcggatcccg | ccaccgccgc | gcgctcggcc | 60 |
| cgccgactcc | cggcgccgcc | gccgccactg | ccgtcgccgc | cgccgcctgc | cgggactgga | 120 |
| gcgcgccgtc | cgccgcggac | aagaccctgg | cctcaggccg | gagcagcccc | atcatgccga | 180 |
| gggagcgcag | ggagcgggat | gcgaaggagc | gggacaccat | gaaggaggac | ggcggcgcgg | 240 |
| agttctcggc | tcgctccagg | aagaggaagg | caaacgtgac | cgttttttg | caggatccag | 300 |
| atgaagaaat | ggccaaaatc | gacaggacgg | cgagggacca | gtgtgggagc | cagccttggg | 360 |
| acaataatgc | agtctgtgca | gacccctgct | ccctgatccc | cacacctgac | aagaagatg | 420 |
| atgaccgggt | ttacccaaac | tcaacgtgca | agcctcggat | tattgcacca | tccagaggct | 480 |
| ccccgctgcc | tgtactgagc | tgggcaaata | gagaggaagt | ctggaaaatc | atgttaaaca | 540 |
| aggaaaagac | atacttaagg | gatcagcact | ttcttgagca | cacccctctt | ctgcagccaa | 600 |
| aaatgcgagc | aattcttctg | gattggttaa | tggaggtgtg | tgaagtctat | aaacttcaca | 660 |
| gggagacctt | ttacttggca | caagatttct | ttgaccggta | tatggcgaca | aagaaaatg | 720 |
| ttgtaaaaac | tcttttacag | cttattggga | tttcatcttt | atttattgca | gccaaacttg | 780 |
| aggaaatcta | tcctccaaag | ttgcaccagt | ttgcgtatgt | gacagatgga | gcttgttcag | 840 |
| gagatgaaat | tctcaccatg | gaattaatga | ttatgaaggc | ccttaagtgg | cgtttaagtc | 900 |
| ccctgactat | tgtgtcctgg | ctgaatgtat | acatgcaggt | tgcatatcta | aatgacttac | 960 |
| atgaagtgct | actgccgcag | tatccccagc | aaatctttat | acagattgca | gagctgttgg | 1020 |
| atctctgtgt | cctggatgtt | gactgccttg | aatttcctta | tggtatactt | gctgcttcgg | 1080 |
| ccttgtatca | tttctcgtca | tctgaattga | tgcaaaaggt | ttcagggtat | cagtggtgcg | 1140 |
| acatagagaa | ctgtgtcaag | tggatggttc | catttgccat | ggttataagg | gagacgggga | 1200 |
| gctcaaaact | gaagcacttc | aggggcgtcg | ctgatgaaga | tgcacacaac | atacagaccc | 1260 |
| acagagacag | cttggatttg | ctggacaaag | cccgagcaaa | gaaagccatg | ttgtctgaac | 1320 |
| aaaatagggc | ttctcctctc | cccagtgggc | tcctcacccc | gccacagagc | ggtaagaagc | 1380 |
| agagcagcgg | gccggaaatg | gcgtgaccac | cccatccttc | tccaccaaag | acagttgcgc | 1440 |
| gcctgctcca | cgttctcttc | tgtctgttgc | agcggaggcg | tgcgtttgct | tttacagata | 1500 |
| tctgaatgga | agagtgtttc | ttccacaaca | gaagtatttc | tgtggatggc | atcaaacagg | 1560 |
| gcaaagtgtt | ttttattgaa | tgcttatagg | ttttttttaa | ataagtgggt | caagtacacc | 1620 |
| agccacctcc | agacaccagt | gcgtgctccc | gatgctgcta | tggaaggtgc | tacttgacct | 1680 |
| aagggactcc | cacaacaaca | aaagcttgaa | gctgtggagg | gccacggtgg | cgtggctctc | 1740 |
| ctcgcaggtg | ttctgggctc | cgttgtacca | agtggagcag | gtggttgcgg | gcaagcgttg | 1800 |
| tgcagagccc | atagccagct | gggcaggggg | ctgccctctc | cacattatca | gttgacagtg | 1860 |
| tacaatgcct | ttgatgaact | gttttgtaag | tgctgctata | tctatccatt | ttttaataaa | 1920 |
| gataatactg | tttttgaaaa | aaaaaaaaaa | aaaaaaaaaa | aaaaaaaaaa | aaaaaaaaaa | 1980 |
| aaaaaaaaaa | aaaaaaaaaa | aaaaaaaaaa | a | | | 2011 |

<210> SEQ ID NO 110
<211> LENGTH: 1737
<212> TYPE: DNA
<213> ORGANISM: Homo sapiens

<400> SEQUENCE: 110

```
gagggcacgg gctccgtagg caccaactgc aaggacccct ccccctgcgg gcgctcccat     60
ggcacagttc gcgttcgaga gtgacctgca ctcgctgctt cagctggatg cacccatccc    120
caatgcaccc cctgcgcgct ggcagcgcaa agccaaggaa gccgcaggcc cggccccctc    180
acccatgcgg gccgccaacc gatcccacag cgccggcagg actccgggcc gaactcctgg    240
caaatccagt tccaaggttc agaccactcc tagcaaacct ggcggtgacc gctatatccc    300
ccatcgcagt gctgcccaga tggaggtggc cagcttcctc ctgagcaagg agaaccagcc    360
tgaaaacagc cagacgccca ccaagaagga acatcagaaa gcctgggctt tgaacctgaa    420
cggttttgat gtagaggaag ccaagatcct tcggctcagt ggaaaaacca caaaaatgcg    480
ccagagggtt atcacgaaca gactgaaagt actctacagc caaaaggcca ctcctggctc    540
cagccggaag acctgccgtt tacattcctt ccctgccaag accgtatcct ggatgcgcct    600
gaaatcgaat gactattaac tgaacctgtg ggactggcag tccggggaat gtccgggccg    660
ggccacggcc acgaggtgtt ccgtgtggag tgcaagctgg acacaccgt gccgcttgtg     720
cacagggcca cgcggggaaa taatcccggg gcgcgcaaag cggcactggc gagagccgca    780
cgggccggtg ctggggtgg tacaacaggc caaaacaaca cacaaggcca acaagacata     840
cgcgcgctga caccacggtg caaagcgctc agacgagtag taaccggcac tgtggttgct    900
gcctccccac ctctcccgct ctcagcgtaa gataaaagaa agaagagcaa aaagcaaaga    960
aagaagacga gacgagacac acaggaacga acagtaaagc aagctaaagc aaacgcaaga   1020
ccagacaaca gaaatagaaa gaaccaacag agaggagaca gaacaggacg ccagcaacat   1080
agcaacaaac gaacagaaga gagcactaaa caaaagcagc agcaagacga gacaggagag   1140
aaggaggaag gagggccgag cgagcaggga gcgcgagcag cgaggcgaag cagcagacaa   1200
gggcaggcga agggcaacga gaggaggcac cacacaaaaa ggagagggga caggagaagc   1260
agcgagagaa gcggaggagc aacaagagga agaaaaggag agggagagga gggagagagc   1320
ggaaggagga agaaacagca cgaggcgacg aaggggggag acgcggggc aggaaaagac    1380
acaggaaggc agcgcggagg aggagaaggg gaagcaggaa ggagacggaa ggagaagagg   1440
gagaggacag cgcaagagag cgcgcgcggc gacagcgagg gacggagcga gagagaggaa   1500
acggaaagcg agagggaaga ggagaggcaa cgcagcgaac caaccgaaaa cagcagaaag   1560
agaggagaag gacgcgcaaa gaggcaagcg caagacgaca ggaaacgaag cgagagacga   1620
gaagccggtg acgagcagga gaaagggaag gcaggagaca ggacaggcgg aagagagaca   1680
cgcgagacgc aaagagtgag cagaacgaag cgaagagcaa cgcacgagag aaacgac      1737
```

<210> SEQ ID NO 111
<211> LENGTH: 3053
<212> TYPE: DNA
<213> ORGANISM: Homo sapiens

<400> SEQUENCE: 111

```
gagcgcggct ggagtttgct gctgccgctg tgcagtttgt tcagggg ctt gtggtggtga     60
gtccgagagg ctgcgtgtga gagacgtgag aaggatcctg cactgaggag gtggaaagaa    120
gaggattgct cgaggaggcc tggggtctgt gaggcagcgg agctgggtga aggctgcggg    180
ttccggcgag gcctgagctg tgctgtcgtc atgcctcaaa cccgatccca ggcacaggct    240
acaatcagtt ttccaaaaag gaagctgtct cgggcattga acaaagctaa aaactccagt    300
```

```
gatgccaaac tagaaccaac aaatgtccaa accgtaacct gttctcctcg tgtaaaagcc      360
ctgcctctca gccccaggaa acgtctgggc gatgacaacc tatgcaacac tccccattta      420
cctccttgtt ctccaccaaa gcaaggcaag aaagagaatg gtccccctca ctcacataca      480
cttaagggac gaagattggt atttgacaat cagctgacaa ttaagtctcc tagcaaaaga      540
gaactagcca aagttcacca aaacaaaata cttcttcag ttagaaaaag tcaagagatc      600
acaacaaatt ctgagcagag atgtccactg aagaaagaat ctgcatgtgt gagactattc      660
aagcaagaag gcacttgcta ccagcaagca aagctggtcc tgaacacagc tgtcccagat      720
cggctgcctg ccagggaaag ggagatggat gtcatcagga atttcttgag gaacacatc      780 tgtgggaaaa aagctggaag ccttaccctt tctggtgctc ctggaactgg aaaaactgcc      840
tgcttaagcc ggattctgca agacctcaag aaggaactga aaggctttaa aactatcatg      900
ctgaattgca tgtccttgag gactgcccag gctgtattcc cagctattgc tcaggagatt      960
tgtcaggaag aggtatccag gccagctggg aaggacatga tgaggaaatt ggaaaaacat     1020
atgactgcag agaagggccc catgattgtg ttggtattgg acgagatgga tcaactggac     1080
agcaaaggcc aggatgtatt gtacacgcta tttgaatggc catggctaag caattctcac     1140
ttggtgctga ttggtattgc taatacctg gatctcacag atagaattct acctaggctt     1200
caagctagag aaaaatgtaa gccacagctg ttgaacttcc caccttatac cagaaatcag     1260
atagtcacta ttttgcaaga tcgacttaat caggtatcta gagatcaggt tctggacaat     1320
gctgcagttc aattctgtgc ccgcaaagtc tctgctgttt caggagatgt tcgcaaagca     1380
ctggatgttt gcaggagagc tattgaaatt gtagagtcag atgtcaaaag ccagactatt     1440
ctcaaaccac tgtctgaatg taaatcacct tctgagcctc tgattcccaa gagggttggt     1500
cttattcaca tatcccaagt catctcagaa gttgatggta acaggatgac cttgagccaa     1560
gaaggagcac aagattcctt ccctcttcag cagaagatct tggtttgctc tttgatgctc     1620
ttgatcaggc agttgaaaat caagaggtc actctgggga agttatatga agcctacagt     1680
aaagtctgtc gcaaacagca ggtggcggct gtggaccagt cagagtgttt gtcactttca     1740
gggctcttgg aagccagggg cattttagga ttaaagagaa acaaggaaac ccgtttgaca     1800
aaggtgtttt tcaagattga agagaaagaa atagaacatg ctctgaaaga taaagcttta     1860
attggaaata tcttagctac tggattgcct taaattcttc tcttacaccc caccccgaaag    1920 tattcagctg gcatttagag agctacagtc ttcattttag tgctttacac attcgggcct     1980
gaaaacaaat atgaccttt ttacttgaag ccaatgaatt ttaatctata gattctttaa      2040
tattagcaca gaataatatc tttgggtctt actattttta cccataaaag tgaccaggta     2100
gacccttttt aattacattc actacttcta ccacttgtgt atctctagcc aatgtgcttg     2160
caagtgtaca gatctgtgta gaggaatgtg tgtatattta cctcttcgtt tgctcaaaca     2220
tgagtgggta ttttttttgtt tgttttttt gttgttgttg ttttgaggc gcgtctcacc      2280 ctgttgccca ggctggagtg caatggcgcg ttctctgctc actacagcac ccgcttccca     2340
ggttgaagtg attctcttgc ctcagcctcc cgagtagctg ggattacagg tgccaccac      2400 cgcgcccagc taatttttta attttttagta gagacagggt tttaccatgt tggccaggct    2460
ggtcttgaac tcctgaccct caagtgatct gcccaccttg gcctcctaa gtgctgggat      2520 tataggcgtg agccaccatg ctcagccatt aaggtatttt gttaagaact ttaagtttag     2580
ggtaagaaga atgaaaatga tccagaaaaa tgcaagcaag tccacatgga gatttggagg    2640
acactggtta aagaatttat ttctttgtat agtatactat gttcatggtg cagatactac     2700
```

| aacattgtgg cattttagac tcgttgagtt tcttgggcac tcccaagggc gttggggtca | 2760 |
| taaggagact ataactctac agattgtgaa tatatttatt ttcaagttgc attctttgtc | 2820 |
| tttttaagca atcagatttc aagagagctc aagctttcag aagtcaatgt gaaaattcct | 2880 |
| tcctaggctg tcccacagtc tttgctgccc ttagatgaag ccacttgttt caagatgact | 2940 |
| actttggggt tgggttttca tctaaacaca ttttccagt cttattagat aaattagtcc | 3000 |
| atatggttgg ttaatcaaga gccttctggg tttggtttgg tggcattaaa tgg | 3053 |

<210> SEQ ID NO 112
<211> LENGTH: 1843
<212> TYPE: DNA
<213> ORGANISM: Homo sapiens

<400> SEQUENCE: 112

| gcggaatggg gcgggacttc cagtaggagg cggcaagttt gaaaagtgat gacggttgac | 60 |
| gtttgctgat ttttgacttt gcttgtagct gctccccgaa ctcgccgtct tcctgtcggc | 120 |
| ggccggcact gtagattaac aggaaacttc caagatggaa actttgtctt tccccagata | 180 |
| taatgtagct gagattgtga ttcatattcg caataagatc ttaacaggag ctgatggtaa | 240 |
| aaacctcacc aagaatgatc tttatccaaa tccaaagcct gaagtcttgc acatgatcta | 300 |
| catgagagcc ttacaaatag tatatggaat tcgactggaa catttttaca tgatgccagt | 360 |
| gaactctgaa gtcatgtatc cacatttaat ggaaggcttc ttaccattca gcaatttagt | 420 |
| tactcatctg gactcatttt tgcctatctg ccgggtgaat gactttgaga ctgctgatat | 480 |
| tctatgtcca aaagcaaaac ggacaagtcg ttttttaagt ggcattatca actttattca | 540 |
| cttcagagaa gcatgccgtg aaacgtatat ggaatttctt tggcaatata atcctctgc | 600 |
| ggacaaaatg caacagttaa acgccgcaca ccaggaggca ttaatgaaac tggagagact | 660 |
| tgattctgtt ccagttgaag agcaagaaga gttcaagcag cttttcagatg gaattcagga | 720 |
| gctacaacaa tcactaaatc aggattttca tcaaaaaacg atagtgctgc aagagggaaa | 780 |
| ttcccaaaag aagtcaaata tttcagagaa accaagcgt ttgaatgaac taaaattgtc | 840 |
| ggtggttct ttgaaagaaa tacaagagag tttgaaaaca aaaattgtgg attctccaga | 900 |
| gaagttaaag aattataaag aaaaaatgaa agatacggtc cagaagctta aaaatgccag | 960 |
| acaagaagtg gtggagaaat atgaaatcta tggagactca gttgactgcc tgccttcatg | 1020 |
| tcagttggaa gtgcagttat atcaaaagaa aatacaggac ctttcagata taggaaaa | 1080 |
| attagccagt atcttaaagg agagcctgaa cttggaggac caaattgaga gtgatgagtc | 1140 |
| agaactgaag aaattgaaga ctgaagaaaa ttcgttcaaa agactgatga ttgtgaagaa | 1200 |
| ggaaaaactt gccacagcac aattcaaaat aaataagaag catgaagatg ttaagcaata | 1260 |
| caaacgcaca gtaattgagg attgcaataa agttcaagaa aaagaggtg ctgtctatga | 1320 |
| acgagtaacc acaattaatc aagaaatcca aaaaattaaa cttggaattc aacaactaaa | 1380 |
| agatgctgct gaaagggaga aactgaagtc ccaggaaata tttctaaact gaaaactgc | 1440 |
| tttggagaaa taccacgacg gtattgaaaa ggcagcagag gactcctatg ctaagataga | 1500 |
| tgagaagaca gctgaactga gaggaagat gttcaaaatg tcaacctgat taacaaaatt | 1560 |
| acatgtcttt ttgtaaatgg cttgccatct tttaattttc tatttagaaa gaaaagttga | 1620 |
| agcgaatgga agtatcagaa gtaccaaata atgttggctt catcagttt tatacactct | 1680 |
| cataagtagt taataagatg aatttaatgt aggctttat taatttataa ttaaaataac | 1740 |

```
ttgtgcagct attcatgtct ctactctgcc ccttgttgta aatagtttga gtaaaacaaa    1800
actagttacc tttgaaatat atatatttt ttctgttact atc                       1843

<210> SEQ ID NO 113
<211> LENGTH: 3686
<212> TYPE: DNA
<213> ORGANISM: Homo sapiens

<400> SEQUENCE: 113
ggctagcgcg ggaggtggag aaagaggctt gggcggcccc gctgtagccg cgtgtgggag      60
gacgcacggg cctgcttcaa agctttggga taacagcgcc tccgggggat aatgaatgcg     120
gagcctccgt tttcagtcga cttcagatgt gtctccactt ttttccgctg tagccgcaag     180
gcaaggaaac atttctcttc ccgtactgag gaggctgagg agtgcactgg gtgttctttt     240
ctcctctaac ccagaactgc gagacagagg ctgagtccct gtaaagaaca gctccagaaa     300
agccaggaga gcgcaggagg gcatccggga ggccaggagg ggttcgctgg ggcctcaacc     360
gcacccacat cggtcccacc tgcgaggggg cgggacctcg tggcgctgga ccaatcagca     420
cccacctgcg ctcacctggc ctcctcccgc tggctcccgg gggctgcggt gctcaaaggg     480
gcaagagctg agcggaacac cggcccgccg tcgcggcagc tgcttcaccc ctctctctgc     540
agccatgggg ctccctcgtg gacctctcgc gtctctcctc cttctccagg tttgctggct     600
gcagtgcgcg gcctccgagc cgtgccgggc ggtcttcagg gaggctgaag tgaccttgga     660
ggcgggaggc gcggagcagg agcccggcca ggcgctgggg aaagtattca tgggctgccc     720
tgggcaagag ccagctctgt ttagcactga taatgatgac ttcactgtgc ggaatggcga     780
gacagtccag gaaagaaggt cactgaagga aggaatcca ttgaagatct tcccatccaa     840
acgtatctta cgaagacaca agagagattg ggtggttgct ccaatatctg tccctgaaaa     900
tggcaagggt cccttccccc agagactgaa tcagctcaag tctaataaag atagagacac     960
caagattttc tacagcatca cggggccggg gcagacagc cccctgagg gtgtcttcgc    1020 tgtagagaag gagacaggct ggttgttgtt gaataagcca ctggaccggg aggagattgc    1080
caagtatgag ctctttggcc acgctgtgtc agagaatggt gcctcagtgg aggacccat    1140 gaacatctcc atcatagtga ccgaccagaa tgaccacaag cccaagttta cccaggacac    1200
cttccgaggg agtgtcttag ggagtcct accaggtact tctgtgatgc agatgacagc    1260
cacagatgag gatgatgcca tctacaccta caatggggtg gttgcttact ccatccatag    1320
ccaagaacca aaggacccac acgacctcat gttcacaatt caccggagca caggcaccat    1380
cagcgtcatc tccagtggcc tggaccggga aaaagtccct gagtacacac tgaccatcca    1440
ggccacagac atggatgggg acggctccac caccacggca gtggcagtag tggagatcct    1500
tgatgccaat gacaatgctc ccatgtttga cccccagaag tacgaggccc atgtgcctga    1560
gaatgcagtg ggccatgagg tgcagaggct gacggtcact gatctggacg cccccaactc    1620
accagcgtgg cgtgccacct accttatcat gggcggtgac gacgggggacc attttaccat    1680 caccacccac cctgagagca accagggcat cctgacaacc aggaagggtt tggattttga    1740
ggccaaaaac cagcacaccc tgtacgttga agtgaccaac gaggcccctt ttgtgctgaa    1800
gctcccaacc tccacagcca catagtggt ccacgtggag gatgtgaatg aggcacctgt    1860
gtttgtccca ccctccaaag tcgttgaggt ccaggagggc atcccactg ggagcctgt    1920 gtgtgtctac actgcagaag accctgacaa ggagaatcaa aagatcagct accgcatcct    1980
gagagaccca gcagggtggc tagccatgga cccagacagt gggcaggtca cagctgtggg    2040
```

```
caccctcgac cgtgaggatg agcagtttgt gaggaacaac atctatgaag tcatggtctt    2100
ggccatggaa aatggaagcc ctcccaccac tggcacggga acccttctgc taacactgat    2160
tgatgtcaac gaccatggcc cagtccctga gccccgtcag atcaccatct gcaaccaaag    2220
ccctgtgcgc caggtgctga acatcacgga caaggacctg tctccccaca cctccccttt    2280
ccaggcccag ctcacagatg actcagacat ctactggacg gcagaggtca acgaggaagg    2340
tgacacagtg gtcttgtccc tgaagaagtt cctgaagcag gatacatatg acgtgcacct    2400
ttctctgtct gaccatggca acaaagagca gctgacggtg atcagggcca ctgtgtgcga    2460
ctgccatggc catgtcgaaa cctgccctgg accctggaaa ggaggtttca tcctcccctgt  2520
```
(approximate — see image)
```
gctgggggct gtcctggctc tgctgttcct cctgctggtg ctgcttttgt tggtgagaaa    2580
gaagcggaag atcaaggagc ccctcctact cccagaagat gacacccgtg acaacgtctt    2640
ctactatggc gaagaggggg gtggcgaaga ggaccaggac tatgacatca cccagctcca    2700
ccgaggtctg gaggccaggc cggaggtggt tctccgcaat gacgtggcac caaccatcat    2760
cccgacaccc atgtaccgtc ctaggccagc caacccagat gaaatcggca ctttataat     2820 tgagaacctg aaggcggcta acacagaccc cacagccccg ccctacgaca ccctcttggt    2880
gttcgactat gagggcagcg gctccgacgc cgcgtccctg agctccctca cctcctccgc    2940
ctccgaccaa gaccaagatt acgattatct gaacgagtgg ggcagccgct tcaagaagct    3000
ggcagacatg tacggtggcg gggaggacga ctaggcggcc tgcctgcagg gctggggacc    3060
aaacgtcagg ccacagagca tctccaaggg gtctcagttc cccttcagc tgaggacttc     3120 ggagcttgtc aggaagtggc cgtagcaact tggcggagac aggctatgag tctgacgtta    3180
gagtggttgc ttccttagcc tttcaggatg gaggaatgtg ggcagtttga cttcagcact    3240
gaaaacctct ccacctgggc cagggttgcc tcagaggcca gtttccaga agcctcttac      3300 ctgccgtaaa atgctcaacc ctgtgtcctg ggcctgggcc tgctgtgact gacctacagt    3360
ggactttctc tctggaatgg aaccttctta ggcctcctgg tgcaacttaa tttttttttt    3420
taatgctatc ttcaaaacgt tagagaaagt tcttcaaaag tgcagccag agctgctggg     3480 cccactggcc gtcctgcatt tctggttttcc agaccccaat gcctcccatt cggatggatc   3540
tctgcgtttt tatactgagt gtgcctaggt tgcccttat tttttatttt ccctgttgcg      3600
ttgctataga tgaagggtga ggacaatcgt gtatatgtac tagaacttt ttattaaaga     3660 aactttccc aaaaaaaaaa aaaaaa                                          3686

<210> SEQ ID NO 114
<211> LENGTH: 10316
<212> TYPE: DNA
<213> ORGANISM: Homo sapiens

<400> SEQUENCE: 114
gagaccagaa gcgggcgaat tgggcaccgg tggcggctgc gggcagtttg aattagactc       60
tgggctccag cccgccgaag ccgcgccaga actgtactct ccgagaggtc gttttcccgt      120
ccccgagagc aagtttattt acaaatgttg gagtaataaa gaaggcagaa caaaatgagc      180
tgggctttgg aagaatggaa agaagggctg cctacaagag ctcttcagaa aattcaagag      240
cttgaaggac agcttgacaa actgaagaag gaaaagcagc aaaggcagtt tcagcttgac      300
agtctcgagg ctgcgctgca gaagcaaaaa cagaaggttg aaaatgaaaa aaccgagggt      360
acaaacctga aagggagaa tcaaagattg atggaaatat gtgaaagtct ggagaaaact      420
```

```
aagcagaaga tttctcatga acttcaagtc aaggagtcac aagtgaattt ccaggaagga    480
caactgaatt caggcaaaaa acaaatagaa aaactggaac aggaacttaa aaggtgtaaa    540
tctgagcttg aaagaagcca acaagctgcg cagtctgcag atgtctctct gaatccatgc    600
aatacaccac aaaaaatttt tacaactcca ctaacaccaa gtcaatatta tagtggttcc    660
aagtatgaag atctaaaaga aaaatataat aaagaggttg aagaacgaaa aagattagag    720
gcagaggtta aagccttgca ggctaaaaaa gcaagccaga ctcttccaca agccaccatg    780
aatcaccgcg acattgcccg gcatcaggct tcatcatctg tgttctcatg gcagcaagag    840
aagaccccaa gtcatctttc atctaattct caaagaactc caattaggag agatttctct    900
gcatcttact tttctgggga acaagaggtg actccaagtc gatcaacttt gcaaataggg    960
aaaagagatg ctaatagcag tttctttgac aattctagca gtcctcatct tttggatcaa   1020
ttaaaagcgc agaatcaaga gctaagaaac aagattaatg agttggaact acgcctgcaa   1080
ggacatgaaa aagaaatgaa aggccaagtg aataagtttc aagaactcca actccaactg   1140
gagaaagcaa agtggaatt aattgaaaaa gagaaagttt tgaacaaatg tagggatgaa    1200
ctagtgagaa caacagcaca atacgaccag gcgtcaacca agtatactgc attggaacaa   1260
aaactgaaaa aattgacgga agatttgagt tgtcagcgac aaaatgcaga aagtgccaga   1320
tgttctctgg aacagaaaat taaggaaaaa gaaaaggagt ttcaagagga gctctcccgt   1380
caacagcgtt ctttccaaac actggaccag gagtgcatcc agatgaaggc cagactcacc   1440
caggagttac agcaagccaa gaatatgcac aacgtcctgc aggctgaact ggataaactc   1500
acatcagtaa agcaacagct agaaaacaat ttggaagagt ttaagcaaaa gttgtgcaga   1560
gctgaacagg cgttccaggc gagtcagatc aaggagaatg agctgaggag aagcatggag   1620
gaaatgaaga aggaaaacaa cctccttaag agtcactctg agcaaaaggc cagagaagtc   1680
tgccacctgg aggcagaact caagaacatc aaacagtgtt taaatcagag ccagaatttt   1740
gcagaagaaa tgaaagcgaa gaatacctct caggaaacca tgttaagaga tcttcaagaa   1800
aaaataaatc agcaagaaaa ctccttgact ttagaaaaac tgaagcttgc tgtggctgat   1860
ctggaaaagc agcgagattg ttctcaagac cttttgaaga aaagagaaca tcacattgaa   1920
caacttaatg ataagttaag caagacagag aaagagtcca agccttgct gagtgcttta   1980 gagttaaaaa agaaagaata tgaagaattg aagaagagaa aaactctgtt ttcttgttgg   2040
aaaagtgaaa acgaaaaact tttaactcag atggaatcag aaaaggaaaa cttgcagagt   2100
aaaattaatc acttggaaac ttgtctgaag acacagcaaa taaaaagtca tgaatacaac   2160
gagagagtaa gaacgctgga gatggacaga gaaaacctaa gtgtcgagat cagaaacctt   2220
cacaacgtgt tagacagtaa gtcagtggag gtagagaccc agaaactagc ttatatggag   2280
ctacagcaga aagctgagtt ctcagatcag aaacatcaga aggaaataga aatatgtgt   2340 ttgaagactt ctcagcttac tgggcaagtt gaagatctag aacacaagct tcagttactg   2400
tcaaatgaaa taatggacaa agaccggtgt taccaagact tgcatgccga atatgagagc   2460
ctcagggatc tgctaaaatc caaagatgct tctctggtga caaatgaaga tcatcagaga   2520
agtcttttgg cttttgatca gcagcctgcc atgcatcatt cctttgcaaa tataattgga   2580
gaacaaggaa gcatgccttc agagaggagt gaatgtcgtt tagaagcaga ccaaagtccg   2640
aaaaattctg ccatcctaca aaatagagtt gattcacttg aattttcatt agagtctcaa   2700
aaacagatga actcagacct gcaaaagcag tgtgaagagt tggtgcaaat caaaggagaa   2760
atagaagaaa atctcatgaa agcagaacag atgcatcaaa gttttgtggc tgaaacaagt   2820
```

```
cagcgcatta gtaagttaca ggaagacact tctgctcacc agaatgttgt tgctgaaacc    2880
ttaagtgccc ttgagaacaa ggaaaaagag ctgcaacttt taaatgataa ggtagaaact    2940
gagcaggcag agattcaaga attaaaaaag agcaaccatc tacttgaaga ctctctaaag    3000
gagctacaac ttttatccga aaccctaagc ttggagaaga aagaaatgag ttccatcatt    3060
tctctaaata aaagggaaat tgaagagctg acccaagaga atgggactct taaggaaatt    3120
aatgcatcct taaatcaaga gaagatgaac ttaatccaga aaagtgagag ttttgcaaac    3180
tatatagatg aaagggagaa aagcatttca gagttatctg atcagtacaa gcaagaaaaa    3240
cttattttac tacaaagatg tgaagaaacc ggaaatgcat atgaggatct tagtcaaaaa    3300
tacaaagcag cacaggaaaa gaattctaaa ttagaatgct tgctaaatga atgcactagt    3360
ctttgtgaaa ataggaaaaa tgagttggaa cagctaaagg aagcatttgc aaaggaacac    3420
caagaattct taacaaaatt agcatttgct gaagaaagaa atcagaatct gatgctagag    3480
ttggagacag tgcagcaagc tctgagatct gagatgacag ataaccaaaa caattctaag    3540
agcgaggctg gtggtttaaa gcaagaaatc atgactttaa aggaagaaca aaacaaaatg    3600
caaaaggaag ttaatgactt attacaagag aatgaacagc tgatgaaggt aatgaagact    3660
aaacatgaat gtcaaaatct agaatcagaa ccaattagga actctgtgaa agaaagagag    3720
agtgagagaa atcaatgtaa ttttaaacct cagatggatc ttgaagttaa agaaatttct    3780
ctagatagtt ataatgcgca gttggtgcaa ttagaagcta tgctaagaaa taaggaatta    3840
aaacttcagg aaagtgagaa ggagaaggag tgcctgcagc atgaattaca gacaattaga    3900
ggagatcttg aaaccagcaa tttgcaagac atgcagtcac aagaaattag tggccttaaa    3960
gactgtgaaa tagatgcgga agaaaagtat atttcagggc ctcatgagtt gtcaacaagt    4020
caaaacgaca atgcacacct tcagtgctct ctgcaaacaa caatgaacaa gctgaatgag    4080
ctagagaaaa tatgtgaaat actgcaggct gaaaagtatg aactcgtaac tgagctgaat    4140
gattcaaggt cagaatgtat cacagcaact aggaaaatgg cagaagaggt agggaaacta    4200
ctaaatgaag ttaaaatatt aaatgatgac agtggtcttc tccatggtga gttagtggaa    4260
gacataccag gaggtgaatt tggtgaacaa ccaaatgaac agcaccctgt gtctttggct    4320
ccattggacg agagtaattc ctacgagcac ttgacattgt cagacaaaga agttcaaatg    4380
cactttgccg aattgcaaga gaaattctta tctttacaaa gtgaacacaa aattttacat    4440
gatcagcact gtcagatgag ctctaaaatg tcagagctgc agacctatgt tgactcatta    4500
aaggccgaaa atttggtctt gtcaacgaat ctgagaaact ttcaaggtga cttggtgaag    4560
gagatgcagc tgggcttgga ggaggggctc gttccatccc tgtcatcctc ttgtgtgcct    4620
gacagctcta gtcttagcag tttgggagac tcctcctttt acagagctct tttagaacag    4680
acaggagata tgtctctttt gagtaattta gaaggggctg tttcagcaaa ccagtgcagt    4740
gtagatgaag tattttgcag cagtctgcag gaggagaatc tgaccaggaa agaaacccct    4800
tcggccccag cgaagggtgt tgaagagctt gagtccctct gtgaggtgta ccggcagtcc    4860
ctcgagaagc tagaagagaa aatggaaagt caagggatta tgaaaaataa ggaaattcaa    4920
gagctcgagc agttattaag ttctgaaagg caagagcttg actgccttag gaagcagtat    4980
ttgtcagaaa atgaacagtg gcaacagaag ctgacaagcg tgactctgga gatggagtcc    5040
aagttggcgg cagaaaagaa acagacggaa caactgtcac ttgagctgga agtagcacga    5100
ctccagctac aaggtctgga cttaagttct cggtctttgc ttggcatcga cacagaagat    5160
```

```
gctattcaag gccgaaatga gagctgtgac atatcaaaag aacatacttc agaaactaca    5220
gaaagaacac caaagcatga tgttcatcag atttgtgata agatgctca gcaggacctc     5280
aatctagaca ttgagaaaat aactgagact ggtgcagtga aacccacagg agagtgctct    5340
ggggaacagt ccccagatac caattatgag cctccagggg aagataaaac ccagggctct    5400
tcagaatgca tttctgaatt gtcatttttct ggtcctaatg ctttggtacc tatggatttc   5460
ctggggaatc aggaagatat ccataatctt caactgcggg taaaagagac atcaaatgag    5520
aatttgagat tacttcatgt gatagaggac cgtgacagaa agttgaaag tttgctaaat     5580
gaaatgaaag aattagactc aaaactccat ttacaggagg tacaactaat gaccaaaatt    5640
gaagcatgca tagaattgga aaaaatagtt ggggaactta agaagaaaa ctcagattta     5700
agtgaaaaat tggaatattt ttcttgtgat caccaggagt tactccagag agtgaaaact    5760
tctgaaggcc tcaattctga tttagaaatg catgcagata aatcatcacg tgaagatatt    5820
ggagataatg tggccaaggt gaatgacagc tggaaggaga gatttcttga tgtgaaaaat   5880
gagctgagta ggatcagatc ggagaaagct agcattgagc atgaagccct ctacctggag    5940
gctgacttag aggtagttca aacagagaag ctatgtttag aaaaagacaa tgaaaataag    6000
cagaaggtta ttgtctgcct tgaagaagaa ctctcagtgg tcacaagtga gagaaaccag    6060
cttcgtggag aattagatac tatgtcaaaa aaaccacgg cactggatca gttgtctgaa    6120
aaaatgaagg agaaaacaca agagcttgag tctcatcaaa gtgagtgtct ccattgcatt    6180
caggtggcag aggcagaggt gaaggaaaag acggaactcc ttcagacttt gtcctctgat    6240
gtgagtgagc tgtaaaaga caaaactcat ctccaggaaa agctgcagag tttggaaaag    6300
gactcacagg cactgtcttt gacaaaatgt gagctggaaa accaaattgc acaactgaat    6360
aaagagaaag aattgcttgt caaggaatct gaaagcctgc aggccagact gagtgaatca    6420
gattatgaaa agctgaatgt ctccaaggcc ttggaggccg cactggtgga gaaaggtgag    6480
ttcgcattga ggctgagctc aacacaggag gaagtgcatc agctgagaag aggcatcgag    6540
aaactgagag ttcgcattga ggccgatgaa agaagcagc tgcacatcgc agagaaactg     6600
aaagaacgcg agcgggagaa tgattcactt aaggataaag ttgagaacct tgaaagggaa    6660
ttgcagatgt cagaagaaaa ccaggagcta gtgattcttg atgccgagaa ttccaaagca    6720
gaagtagaga ctctaaaaac acaaatagaa gagatggcca aagcctgaa agtttttgaa    6780
ttagaccttg tcacgttaag gtctgaaaaa gaaaatctga caaacaaat acaagaaaaa    6840
caaggtcagt tgtcagaact agacaagtta ctctcttcat ttaaaagtct gttagaagaa    6900
aaggagcaag cagagataca gatcaaagaa gaatctaaaa ctgcagtgga gatgcttcag    6960
aatcagttaa aggagctaaa tgaggcagta gcagccttgt gtggtgacca agaaattatg    7020
aaggccacag aacagagtct agacccacca atagaggaag agcatcagct gagaaatagc    7080
attgaaaagc tgagagcccg cctagaagct gatgaaaaga agcagctctg tgtcttacaa    7140
caactgaagg aaagtgagca tcatgcagat ttacttaagg gtagagtgga gaaccttgaa    7200
agagagctag agatagccag gacaaaccaa gagcatgcag ctcttgaggc agagaattcc    7260
aaaggagagg tagagaccct aaaagcaaaa atagaaggga tgacccaaag tctgagaggt    7320
ctggaattag atgttgttac tataaggtca gaaaaagaaa atctgacaaa tgaattacaa    7380
aaagagcaag agcgaatatc tgaattagaa ataataaatt catcatttga aaatattttg    7440
caagaaaaag agcaagagaa agtacagatg aaagaaaaat caagcactgc catggagatg    7500
cttcaaacac aattaaaaga gctcaatgag agagtggcag ccctgcataa tgaccaagaa    7560
```

```
gcctgtaagg ccaaagagca gaatcttagt agtcaagtag agtgtcttga acttgagaag    7620
gctcagttgc tacaaggcct tgatgaggcc aaaataatt atattgtttt gcaatcttca     7680
gtgaatggcc tcattcaaga agtagaagat ggcaagcaga aactggagaa aaggatgaa     7740 gaaatcagta gactgaaaaa tcaaattcaa gaccaagagc agcttgtctc taaactgtcc    7800
caggtggaag gagagcacca actttggaag gagcaaaact tagaactgag aaatctgaca    7860
gtggaattgg agcagaagat ccaagtgcta caatccaaaa atgcctcttt gcaggacaca    7920
ttagaagtgc tgcagagttc ttacaagaat ctagagaatg agcttgaatt gacaaaaatg    7980
gacaaaatgt cctttgttga aaagtaaac aaaatgactg caaaggaaac tgagctgcag     8040
agggaaatgc atgagatggc acagaaaaca gcagagctgc aagaagaact cagtggagag    8100
aaaaataggc tagctggaga gttgcagtta ctgttggaag aaataaagag cagcaaagat    8160
caattgaagg agctcacact agaaaatagt gaattgaaga gagcctaga ttgcatgcac     8220 aaagaccagg tggaaaagga agggaaagtg agagaggaaa tagctgaata tcagctacgg    8280
cttcatgaag ctgaaaagaa acaccaggct ttgctttgg acacaaacaa acagtatgaa     8340
gtagaaatcc agacataccg agagaaattg acttctaaag aagaatgtct cagttcacag    8400
aagctggaga tagacctttt aaagtctagt aaagaagagc tcaataattc attgaaagct    8460
actactcaga ttttggaaga attgaagaaa ccaagatgg acaatctaaa atatgtaaat     8520
cagttgaaga aggaaaatga acgtgcccag gggaaaatga agttgttgat caaatcctgt    8580
aaacagctgg aagaggaaaa ggagatactg cagaaagaac tctctcaact tcaagctgca    8640
caggagaagc agaaaacagg tactgttatg gataccaagg tcgatgaatt aacaactgag    8700
atcaaagaac tgaaagaaac tcttgaagaa aaaaccaagg aggcagatga atacttggat    8760
aagtactgtt ccttgcttat aagccatgaa agttagaga aagctaaaga gatgttagag     8820
acacaagtgg cccatctgtg ttcacagcaa tctaaacaag attcccgagg gtctcctttg    8880
ctaggtccag ttgttccagg accatctcca atcccttctg ttactgaaaa gaggttatca    8940
tctggccaaa ataaagcttc aggcaagagg caaagatcca gtggaatatg ggagaatggt    9000
agaggaccaa cacctgctac cccagagagc ttttctaaaa aaagcaagaa agcagtcatg    9060
agtggtattc accctgcaga agacacggaa ggtactgagt ttgagccaga gggacttcca    9120
gaagttgtaa agaaagggtt tgctgacatc ccgacaggaa agactagccc atatatcctg    9180
cgaagaacaa ccatggcaac tcggaccagc ccccgcctgg ctgcacagaa gttagcgcta    9240
tccccactga gtctcggcaa agaaaatctt gcagagtcct ccaaaccaac agctggtggc    9300
agcagatcac aaaaggtcaa agttgctcag cggagcccag tagattcagg caccatcctc    9360
cgagaaccca ccacgaaatc cgtcccagtc aataatcttc ctgagagaag tccgactgac    9420
agccccagag agggcctgag ggtcaagcga ggccgacttg tccccagccc caaagctgga    9480
ctggagtcca acggcagtga gaactgtaag gtccagtgaa ggcactttgt gtgtcagtac    9540
ccctgggagg tgccagtcat tgaatagata aggctgtgcc tacaggactt ctctttagtc    9600
agggcatgct ttattagtga ggagaaaaca attccttaga agtcttaaat atattgtact    9660
ctttagatct cccatgtgta ggtattgaaa agtttggaa gcactgatca cctgttagca     9720
ttgccattcc tctactgcaa tgtaaatagt ataaagctat gtatataaag ctttttggta    9780
atatgttaca attaaaatga caagcactat atcacaatct ctgtttgtat gtgggtttta    9840
cactaaaaaa atgcaaaaca cattttattc ttctaattaa cagctcctag gaaaatgtag    9900
```

```
acttttgctt tatgatattc tatctgtagt atgaggcatg gaatagtttt gtatcgggaa    9960
tttctcagag ctgagtaaaa tgaaggaaaa gcatgttatg tgttttaag gaaaatgtgc    10020 acacatatac atgtaggagt gtttatcttt ctcttacaat ctgttttaga catctttgct    10080
tatgaaacct gtacatatgt gtgtgtgggt atgtgtttat ttccagtgag ggctgcaggc    10140
ttcctagagg tgtgctatac catgcgtctg tcgttgtgct ttttctgtt tttagaccaa     10200 tttttacag ttcttggta agcattgtcg tatctggtga tggattaaca tatagccttt      10260
gttttctaat aaaatagtcg ccttcgtttt ctgtaaaaaa aaaaaaaaaa aaaaaa        10316

<210> SEQ ID NO 115
<211> LENGTH: 2639
<212> TYPE: DNA
<213> ORGANISM: Homo sapiens

<400> SEQUENCE: 115
ggcacgaggg gccgacgcga gcgccgcgct tcgcttcagc tgctagctgg cccaagggag     60
gcgaccgcga agggtggcga ggggcggcca ggacccgcag ccccgggggcc gggccggtcc    120 ggaccgccag ggagggcagg tcagtgggca gatcgcgtcc gcgggattca atctctgccc    180
gctctgataa cagtccttt ccctggcgct cacttcgtgc ctggcacccg gctgggcgcc     240
tcaagaccgt tgtctcttcg atcgcttctt tggacttggc gaccatttca gagatgtctt    300
ccagaagtac caaagattta attaaaagta agtggggatc gaagcctagt aactccaaat    360
ccgaaactac attagaaaaa ttaaagggag aaattgcaca cttaaagaca tcagtggatg    420
aaatcacaag tgggaaagga aagctgactg ataaagagag acacagactt ttggagaaaa    480
ttcgagtcct tgaggctgag aaggagaaga atgcttatca actcacagag aaggacaaag    540
aaatacagcg actgagagac caactgaagg ccagatatag tactaccgca ttgcttgaac    600
agctggaaga gacaacgaga gaaggagaaa ggagggagca ggtgttgaaa gccttatctg    660
aagagaaaga cgtattgaaa caacagttgt ctgctgcaac ctcacgaatt gctgaacttg    720
aaagcaaaac caatacactc cgtttatcac agactgtggc tccaaactgc ttcaactcat    780
caataaataa tattcatgaa atggaaatac agctgaaaga tgctctggag aaaaatcagc    840
agtggctcgt gtatgatcag cagcgggaag tctatgtaaa aggacttta gcaaagatct     900 ttgagttgga aaagaaaacg gaaacagctg ctcattcact cccacagcag acaaaaaagc    960
ctgaatcaga aggttatctt caagaagaga agcagaaatg ttacaacgat ctcttggcaa    1020
gtgcaaaaaa agatcttgag gttgaacgac aaaccataac tcagctgagt tttgaactga    1080
gtgaatttcg aagaaaatat gaagaaccc aaaagaagt tcacaattta aatcagctgt      1140
tgtattcaca agaagggca gatgtgcaac atctggaaga tgataggcat aaaacagaga     1200
agatacaaaa actcagggaa gagaatgata ttgctagggg aaaacttgaa gagagaaga    1260 agagatccga agagctctta tctcaggtcc agtttcttta cacatctctg ctaaagcagc   1320
aagaagaaca acaagggta gctctgttgg aacaacagat gcaggcatgt actttagact     1380
ttgaaaatga aaaactcgac cgtcaacatg tgcagcatca attgcatgta attcttaagg   1440
agctccgaaa agcaagaaat caaataacac agttggaatc cttgaaacag cttcatgagt   1500
ttgccatcac agagccatta gtcactttcc aaggagagac tgaaaacaga gaaaaagttg   1560
ccgcctcacc aaaaagtccc actgctgcac tcaatgaaag cctggtggaa tgtcccaagt   1620
gcaatataca gtatccagcc actgagcatc gcgatctgct tgtccatgtg gaatactgtt   1680
caaagtagca aaataagtat ttgttttgat attaaaagat tcaatactgt attttctgtt   1740
```

| | | |
|---|---|---|
| agcttgtggg cattttgaat tatatatttc acattttgca taaaactgcc tatctacctt | 1800 |
| tgacactcca gcatgctagt gaatcatgta tcttttaggc tgctgtgcat ttctcttggc | 1860 |
| agtgatacct ccctgacatg gttcatcatc aggctgcaat gacagaatgt ggtgagcagc | 1920 |
| gtctactgag actactaaca ttttgcactg tcaaaatact tggtgaggaa agatagctc | 1980 |
| aggttattgc taatgggtta atgcaccagc aagcaaaata ttttatgttt tgggggtttg | 2040 |
| aaaaatcaaa gataattaac caaggatctt aactgtgttc gcatttttta tccaagcact | 2100 |
| tagaaaacct acaatcctaa ttttgatgtc cattgttaag aggtggtgat agatactatt | 2160 |
| tttttttttca tattgtatag cggttattag aaaagttggg gattttcttg atctttattg | 2220 |
| ctgcttacca ttgaaactta acccagctgt gttccccaac tctgttctgc gcacgaaaca | 2280 |
| gtatctgttt gaggcataat cttaagtggc cacacacaat gttttctctt atgttatctg | 2340 |
| gcagtaactg taacttgaat tacattagca cattctgctt agctaaaatt gttaaaataa | 2400 |
| actttaataa acccatgtag ccctctcatt tgattgacag tattttagtt atttttggca | 2460 |
| ttcttaaagc tgggcaatgt aatgatcaga tctttgtttg tctgaacagg tattttttata | 2520 |
| catgcttttt gtaaaccaaa aacttttaaa tttcttcagg ttttctaaca tgcttaccac | 2580 |
| tgggctactg taaatgagaa aagaataaaa ttatttaatg ttttaaaaaa aaaaaaaaa | 2639 |

<210> SEQ ID NO 116
<211> LENGTH: 2632
<212> TYPE: DNA
<213> ORGANISM: Homo sapiens

<400> SEQUENCE: 116

| | | |
|---|---|---|
| ggcggctgag cctgagcggg gatgtagagg cggcggcagc agaggcggca ctggcggcaa | 60 |
| gagcagacgc ccgagccgag cgagaagagc ggcagagcct tatcccctga agccgggccc | 120 |
| cgcgtcccag ccctgcccag cccgcgccca gccatgcgcg ccgcctgctg agtccgggcg | 180 |
| ccgcacgctg agccctccgc ccgcgagccg cgctcagctc gggggtgatt agttgctttt | 240 |
| tgttgttttt taatttgggc cgcggggagg gggaggaggg gcaggtgctg caggctcccc | 300 |
| cccctccccg cctcgggcca gccgcggcgg cgcgactcgg gctccggacc cgggcactgc | 360 |
| tggcggctgg agcggagcgc accgcggcgg tggtgcccag agcggagcgc agctccctgc | 420 |
| cccgccccctc cccctcggcc tcgcggcgac ggcggcggtg gcggcttgga cgactcggag | 480 |
| agccgagtga agacatttcc acctggacac ctgaccatgt gcctgccctg agcagcgagg | 540 |
| cccaccagge atctctgttg tgggcagcag ggccaggtcc tggtctgtgg accctcggca | 600 |
| gttggcaggc tccctctgca gtggggtctg ggcctcggcc ccaccatgtc gagcctcggc | 660 |
| ggtggctccc aggatgccgg cggcagtagc agcagcagca ccaatggcag cggtggcagt | 720 |
| ggcagcagtg gcccaaaggc aggagcagca gacaagagtg cagtggtggc tgccgccgca | 780 |
| ccagcctcag tggcagatga cacaccaccc ccgagcgtc ggaacaagag cggtatcatc | 840 |
| agtgagcccc tcaacaagag cctgcgccgc tcccgcccgc tctcccacta ctcttctttt | 900 |
| ggcagcagtg gtggtagtgg cggtggcagc atgatgggcg gagagtctgc tgacaaggcc | 960 |
| actgcggctg cagccgctgc ctccctgttg gccaatggga tgacctggc ggcggccatg | 1020 |
| gcggtggaca aaagcaaccc tacctcaaag cacaaaagtg gtgctgtggc cagcctgctg | 1080 |
| agcaaggcag agcgggccac ggagctggca gccgagggac agctgacgct gcagcagttt | 1140 |
| gcgcagtcca cagagatgct gaagcgcgtg gtgcaggagc atctcccgct gatgagcgag | 1200 |

```
gcgggtgctg gcctgcctga catggaggct gtggcaggtg ccgaagccct caatggccag    1260
tccgacttcc cctacctggg cgctttcccc atcaacccag gcctcttcat tatgaccccg    1320
gcaggtgtgt tcctggccga gagcgcgctg cacatggcgg gcctggctga gtaccccatg    1380
cagggagagc tggcctctgc catcagctcc ggcaagaaga agcggaaacg ctgcggcatg    1440
tgcgcgccct gccggcggcg catcaactgc gagcagtgca gcagttgtag gaatcgaaag    1500
actggccatc agatttgcaa attcagaaaa tgtgaggaac tcaaaaagaa gccttccgct    1560
gctctggaga aggtgatgct tccgacggga gccgccttcc ggtggtttca gtgacggcgg    1620
cggaacccaa agctgccctc tccgtgcaat gtcactgctc gtgtggtctc cagcaaggga    1680
ttcgggcgaa gacaaacgga tgcacccgtc tttagaacca aaaatattct ctcacagatt    1740
tcattcctgt ttttatatat atattttttg ttgtcgtttt aacatctcca cgtccctagc    1800
ataaaaagaa aaagaaaaaa atttaaactg cttttcgga agaacaacaa caaaaaagag     1860
gtaaagacga atctataaag taccgagact tcctgggcaa agaatggaca atcagtttcc    1920
ttcctgtgtc gatgtcgatg ttgtctgtgc aggagatgca gttttgtgt  agagaatgta    1980 aattttctgt aaccttttga aatctagtta ctaataagca ctactgtaat ttagcacagt    2040
ttaactccac cctcatttaa acttcctttg attctttccg accatgaaat agtgcatagt    2100
ttgcctggag aatccactca cgttcataaa gagaatgttg atggcgccgt gtagaagccg    2160
ctctgtatcc atccacgcgt gcagagctgc agcagggag  ctcacagaag gggagggagc    2220
accaggccag ctgagctgca cccacagtcc cgagactggg atcccccacc caacagtga    2280 ttttggaaaa aaaaatgaaa gttctgttcg tttatccatt gcgatctggg gagccccatc    2340
tcgatatttc caatcctggc tactttttctt agagaaaata agtcctttt  ttctggcctt    2400 gctaatggca acagaagaaa gggcttcttt gcgtggtccc ctgctggtgg gggtgggtcc    2460 ccaggggggcc cctgcggcc  tgggcccccc tgcccacggc cagcttcctg ctgatgaaca    2520
tgctgtttgt attgttttag gaaccaggc  tgttttgtga ataaaacgaa tgcatgtttg    2580
tgtcacgaaa aaaaaaaaa  aaaaaaaaa  aaaaaaaaa  aaaaaaaaa  aa            2632
```

```
<210> SEQ ID NO 117
<211> LENGTH: 5616
<212> TYPE: DNA
<213> ORGANISM: Homo sapiens

<400> SEQUENCE: 117
```

```
cccggcgca gcgcggccgc agcagcctcc gcccccgca cggtgtgagc gcccgacgcg       60
gccgaggcgg ccggagtccc gagctagccc cggcggccgc cgccgcccag accggacgac    120
aggccacctc gtcggcgtcc gcccgagtcc ccgcctcgcc gccaacgcca caaccaccgc    180
gcacggcccc ctgactccgt ccagtattga tcgggagagc cggagcgagc tcttcgggga    240
gcagcgatgc gaccctccgg gacggccggg gcagcgctcc tggcgctgct ggctgcgctc    300
tgcccggcga gtcgggctct ggaggaaaag aaagtttgcc aaggcacgag taacaagctc    360
acgcagttgg gcactttga  agatcatttt ctcagcctcc agaggatgtt caataactgt    420
gaggtggtcc ttgggaattt ggaaattacc tatgtgcaga ggaattatga tctttccttc    480
ttaaagacca tccaggaggt ggctggttat gtcctcattg ccctcaacac agtggagcga    540
attcctttgg aaaacctgca gatcatcaga ggaaatatgt actacgaaaa ttcctatgcc    600
ttagcagtct tatctaacta tgatgcaaat aaaaccggac tgaaggagct gcccatgaga    660
aatttacagg aaatcctgca tggcgccgtg cggttcagca acaaccctgc cctgtgcaac    720
```

```
gtggagagca tccagtggcg ggacatagtc agcagtgact ttctcagcaa catgtcgatg    780
gacttccaga accacctggg cagctgccaa aagtgtgatc caagctgtcc caatgggagc    840
tgctggggtg caggagagga gaactgccag aaactgacca aaatcatctg tgcccagcag    900
tgctccgggc gctgccgtgg caagtccccc agtgactgct gccacaacca gtgtgctgca    960
ggctgcacag gcccccggga gagcgactgc ctggtctgcc gcaaattccg agacgaagcc   1020
acgtgcaagg acacctgccc cccactcatg ctctacaacc ccaccacgta ccagatggat   1080 gtgaacccg agggcaaata cagctttggt gccacctgcg tgaagaagtg tccccgtaat   1140
tatgtggtga cagatcacgg ctcgtgcgtc cgagcctgtg gggccgacag ctatgagatg   1200
gaggaagacg gcgtccgcaa gtgtaagaag tgcgaagggc cttgccgcaa agtgtgtaac   1260
ggaataggta ttggtgaatt taaagactca ctctccataa atgctacgaa tattaaacac   1320
ttcaaaaact gcacctccat cagtggcgat ctccacatcc tgccggtggc atttaggggt   1380
gactccttca cacatactcc tcctctggat ccacaggaac tggatattct gaaaaccgta   1440
aaggaaatca cagggttttt gctgattcag gcttggcctg aaaacaggac ggacctccat   1500
gcctttgaga acctagaaat catacgcggc aggaccaagc aacatggtca gttttctctt   1560
gcagtcgtca gcctgaacat aacatccttg ggattacgct ccctcaagga gataagtgat   1620
ggagatgtga taatttcagg aaacaaaaat ttgtgctatg caaatacaat aaactggaaa   1680
aaactgtttg gacctccgg tcagaaaacc aaaattataa gcaacagagg tgaaaacagc   1740
tgcaaggcca caggccaggt ctgccatgcc ttgtgctccc ccgagggctg ctggggcccg   1800
gagcccaggg actgcgtctc ttgccggaat gtcagccgag cagggaatg cgtggacaag   1860 tgcaaccttc tggagggtga gccaaggag tttgtggaga actctgagtg catacagtgc   1920
cacccagagt gcctgcctca ggccatgaac atcacctgca caggacgggg accagacaac   1980
tgtatccagt gtgcccacta cattgacggc ccccactgcg tcaagacctg cccggcagga   2040
gtcatgggag aaaacaacac cctggtctgg aagtacgcag acgccggcca tgtgtgccac   2100
ctgtgccatc caaactgcac ctacggatgc actgggccag tcttgaagg ctgtccaacg   2160 aatgggccta agatcccgtc catcgccact gggatggtgg gggcctcct cttgctgctg   2220 gtggtggccc tggggatcgg cctcttcatg cgaaggcgcc acatcgttcg gaagcgcacg   2280
ctgcggaggc tgctgcagga gagggagctt gtggagcctc ttacacccag tggagaagct   2340
cccaaccaag ctctcttgag gatcttgaag gaaactgaat tcaaaaagat caaagtgctg   2400
ggctccggtg cgttcggcac ggtgtataag ggactctgga tcccagaagg tgagaaagtt   2460
aaaattcccg tcgctatcaa ggaattaaga gaagcaacat ctccgaaagc caacaaggaa   2520
atcctcgatg aagcctacgt gatggccagc gtggacaacc ccacgtgtg ccgcctgctg   2580 ggcatctgcc tcacctccac cgtgcagctc atcacgcagc tcatgccctt cggctgcctc   2640
ctggactatg tccgggaaca caaagacaat attggctccc agtacctgct caactggtgt   2700
gtgcagatcg caaagggcat gaactacttg gaggaccgtc gcttggtgca ccgcgacctg   2760
gcagccagga acgtactggt gaaaacaccg cagcatgtca agatcacaga tttggctg   2820 gccaaactgc tgggtgcgga agagaaagaa taccatgcag aaggaggcaa agtgcctatc   2880
aagtggatgg cattggaatc aattttacac agaatctata cccaccagag tgatgtctgg   2940
agctacgggg tgaccgtttg ggagttgatg acctttggat ccaagccata tgacggaatc   3000
cctgccagcg agatctcctc catcctggag aaaggagaac gcctccctca gccacccata   3060
```

```
tgtaccatcg atgtctacat gatcatggtc aagtgctgga tgatagacgc agatagtcgc   3120
ccaaagttcc gtgagttgat catcgaattc tccaaaatgg cccgagaccc ccagcgctac   3180
cttgtcattc aggggggatga aagaatgcat ttgccaagtc ctacagactc caacttctac   3240
cgtgccctga tggatgaaga agacatggac gacgtggtgg atgccgacga gtacctcatc   3300
ccacagcagg gcttcttcag cagcccctcc acgtcacgga ctcccctcct gagctctctg   3360
agtgcaacca gcaacaattc caccgtggct tgcattgata gaaatgggct gcaaagctgt   3420
cccatcaagg aagacagctt cttgcagcga tacagctcag accccacagg cgccttgact   3480
gaggacagca tagacgacac cttcctccca gtgcctgaat acataaacca gtccgttccc   3540
aaaaggcccg ctggctctgt gcagaatcct gtctatcaca atcagcctct gaaccccgcg   3600
cccagcagag acccacacta ccaggacccc cacagcactg cagtgggcaa ccccgagtat   3660
ctcaacactg tccagcccac ctgtgtcaac agcacattcg acagccctgc ccactgggcc   3720
cagaaaggca gccaccaaat tagcctggac aaccctgact accagcagga cttcttttccc   3780 aaggaagcca agccaaatgg catctttaag ggctccacag ctgaaaatgc agaataccta   3840
agggtcgcgc cacaaagcag tgaatttatt ggagcatgac cacggaggat agtatgagcc   3900
ctaaaaatcc agactctttc gatacccagg accaagccac agcaggtcct ccatcccaac   3960
agccatgccc gcattagctc ttagacccac agactggttt tgcaacgttt acaccgacta   4020
gccaggaagt acttccacct cgggcacatt ttgggaagtt gcattccttt gtcttcaaac   4080
tgtgaagcat ttacagaaac gcatccagca agaatattgt cccttgagc agaaatttat   4140 cttttcaaaga ggtatatttg aaaaaaaaaa aagtatatg tgaggatttt tattgattgg   4200
ggatcttgga gttttttcatt gtcgctattg attttttactt caatgggctc ttccaacaag   4260
gaagaagctt gctggtagca cttgctaccc tgagttcatc caggcccaac tgtgagcaag   4320
gagcacaagc cacaagtctt ccagaggatg cttgattcca gtggttctgc ttcaaggctt   4380
ccactgcaaa acactaaaga tccaagaagg ccttcatggc cccagcaggc cggatcggta   4440
ctgtatcaag tcatggcagg tacagtagga taagccactc tgtcccttcc tgggcaaaga   4500
agaaacggag gggatggaat tcttccttag acttactttt gtaaaaatgt ccccacggta   4560
cttactcccc actgatggac cagtggtttc cagtcatgag cgttagactg acttgtttgt   4620
cttccattcc attgttttga aactcagtat gctgccctg tcttgctgtc atgaaatcag   4680
caagagagga tgacacatca ataataact cggattccag cccacattgg attcatcagc   4740
atttggacca ataagcccaca gctgagaatg tggaatacct aaggatagca ccgcttttgt   4800
tctcgcaaaa acgtatctcc taatttgagg ctcagatgaa atgcatcagg tcctttgggg   4860
catagatcag aagactacaa aaatgaagct gctctgaaat ctcctttagc catcacccca   4920 acccccaaa attagtttgt gttacttatg gaagatagtt ttctccttttt acttcacttc   4980 aaaagctttt tactcaaaga gtatatgttc cctccaggtc agctgccccc aaaccccctc   5040
cttacgcttt gtcacacaaa aagtgtctct gccttgagtc atctattcaa gcacttacag   5100
ctctggccac aacagggcat tttacaggtg cgaatgacag tagcattatg agtagtgtgg   5160
aattcaggta gtaaatatga aactagggtt tgaaattgat aatgcttca caacatttgc   5220 agatgtttta gaaggaaaaa agttccttcc taaaataatt tctctacaat ggaagattg   5280 gaagattcag ctagttagga gcccaccttt tttcctaatc tgtgtgtgcc ctgtaacctg   5340
actggttaac agcagtcctt tgtaaacagt gttttaaact ctcctagtca atatccaccc   5400
catccaattt atcaaggaag aaatggttca gaaaatattt tcagcctaca gttatgttca   5460
```

```
gtcacacaca catacaaaat gttcctttg ctttttaaagt aatttttgac tcccagatca    5520
gtcagagccc ctacagcatt gttaagaaag tatttgattt ttgtctcaat gaaaataaaa    5580
ctatattcat ttccactcta aaaaaaaaaa aaaaaa                              5616

<210> SEQ ID NO 118
<211> LENGTH: 4816
<212> TYPE: DNA
<213> ORGANISM: Homo sapiens

<400> SEQUENCE: 118
gttcccggat ttttgtgggc gcctgccccg cccctcgtcc cctgctgtg tccatatatc      60 gaggcgatag ggttaaggga aggcggacgc ctgatgggtt aatgagcaaa ctgaagtgtt    120
ttccatgatc ttttttgagt cgcaattgaa gtaccactc ccgagggtga ttgcttcccc    180
atgcggggta gaacctttgc tgtcctgttc accactctac ctccagcaca gaatttggct    240
tatgcctact caatgtgaag atgatgagga tgaaaacctt tgtgatgatc cacttccact    300
taatgaatgg tggcaaagca agctatatt caagaccaca tgcaaagcta ctccctgagc    360
aaagagtcac agataaaacg ggggcaccag tagaatggcc aggacaaacg cagtgcagca    420
cagagactca gaccctggca gccatgcctg cgcaggcagt gatgagagtg acatgtactg    480
ttgtggacat gcacaaaagt gagtgtgcac cggcacagac atgaagctgc ggctccctgc    540
cagtcccgag acccacctgg acatgctccg ccacctctac cagggctgcc aggtggtgca    600
gggaaacctg gaactcacct acctgcccac caatgccagc ctgtccttcc tgcaggatat    660
ccaggaggtg cagggctacg tgctcatcgc tcacaaccaa gtgaggcagg tcccactgca    720
gaggctgcgg attgtgcgag gcacccagct ctttgaggac aactatgccc tggccgtgct    780
agacaatgga gacccgctga caataccac ccctgtcaca ggggcctccc caggaggcct    840
gcgggagctg cagcttcgaa gcctcacaga gatcttgaaa ggagggggtct tgatccagcg    900 gaacccccag ctctgctacc aggacacgat tttgtggaag acatcttcc acaagaacaa    960 ccagctggct ctcacactga tagacaccaa ccgctctcgg gcctgccacc cctgttctcc    1020
gatgtgtaag ggctcccgct gctggggaga gagttctgag gattgtcaga gcctgacgcg    1080
cactgtctgt gccggtggct gtgcccgctg caaggggcca ctgcccactg actgctgcca    1140
tgagcagtgt gctgccggct gcacgggccc caagcactct gactgcctgg cctgcctcca    1200
cttcaaccac agtggcatct gtgagctgca ctgcccagcc ctggtcacct acaacacaga    1260
cacgtttgag tccatgccca tcccgagggg ccggtataca ttcggcgcca gctgtgtgac    1320
tgcctgtccc tacaactacc tttctacgga cgtgggatcc tgcaccctcg tctgccccct    1380
gcacaaccaa gaggtgacag cagaggatgg aacacagcgg tgtgagaagt gcagcaagcc    1440
ctgtgcccga gtgtgctatg gtctgggcat ggagcacttg cgagaggtga gggcagttac    1500
cagtgccaat atccaggagt ttgctggctg caagaagatc tttgggagcc tggcatttct    1560
gccggagagc tttgatgggg acccagcctc caacactgcc ccgctccagc cagagcagct    1620
ccaagtgttt gagactctgg aagagatcac aggttaccta tacatctcag catggccgga    1680
cagcctgcct gacctcagcg tcttccagaa cctgcaagta atccggggac gaattctgca    1740
caatggcgcc tactcgctga cctgcaagg gctgggcatc agctggctgg ggctgcgctc    1800
actgagggaa ctgggcagtg actggccct catccaccat aacacccacc tctgcttcgt    1860
gcacacggtg ccctgggacc agctctttcg gaacccgcac caagctctgc tccacactgc    1920
```

```
caaccggcca gaggacgagt gtgtgggcga gggcctggcc tgccaccagc tgtgcgcccg    1980
agggcactgc tggggtccag ggcccaccca gtgtgtcaac tgcagccagt tccttcgggg    2040
ccaggagtgc gtggaggaat gccgagtact gcaggggctc cccagggagt atgtgaatgc    2100
caggcactgt ttgccgtgcc accctgagtg tcagccccag aatggctcag tgacctgttt    2160
tggaccggag gctgaccagt gtgtggcctg tgcccactat aaggaccctc ccttctgcgt    2220
ggcccgctgc cccagcggtg tgaaacctga cctctcctac atgcccatct ggaagtttcc    2280
agatgaggag ggcgcatgcc agccttgccc catcaactgc acccactcct gtgtggacct    2340
ggatgacaag ggctgccccg ccgagcagag agccagccct ctgacgtcca tcatctctgc    2400
ggtggttggc attctgctgg tcgtggtctt gggggtggtc tttgggatcc tcatcaagcg    2460
acggcagcag aagatccgga agtacacgat gcggagactg ctgcaggaaa cggagctggt    2520
ggagccgctg acacctagcg gagcgatgcc caaccaggcg cagatgcgga tcctgaaaga    2580
gacggagctg aggaaggtga aggtgcttgg atcggcgct tttggcacag tctacaaggg    2640
catctggatc cctgatgggg agaatgtgaa aattccagtg gccatcaaag tgttgaggga    2700
aaacacatcc cccaaagcca caaagaaat cttagacgaa gcatacgtga tggctggtgt    2760
gggctcccca tatgtctccc gccttctggg catctgcctg acatccacgg tgcagctggt    2820
gacacagctt atgccctatg gctgcctctt agaccatgtc cgggaaaacc gcggacgcct    2880
gggctcccag gacctgctga actggtgtat gcagattgcc aaggggatga gctacctgga    2940
ggatgtgcgg ctcgtacaca gggacttggc cgctcggaac gtgctggtca agagtcccaa    3000
ccatgtcaaa attacagact cgggctggc tcggctgctg acattgacg agacagagta    3060
ccatgcagat ggggcaagg tgcccatcaa gtggatggcg ctggagtcca ttctccgccg    3120
gcggttcacc caccagagtg atgtgtgag ttatggtgtg actgtgtggg agctgatgac    3180
ttttggggcc aaaccttacg atgggatccc agcccgggag atccctgacc tgctggaaaa    3240
gggggagcgg ctgccccagc ccccatctg caccattgat gtctacatga tcatggtcaa    3300
atgttggatg attgactctg aatgtcggcc aagattccgg gagttggtgt ctgaattctc    3360
ccgcatggcc agggacccc agcgctttgt ggtcatccag aatgaggact gggcccagc    3420
cagtcccttg gacagcacct tctaccgctc actgctggag gacgatgaca tgggggacct    3480
ggtggatgct gaggagtatc tggtacccca gcagggcttc ttctgtccag accctgcccc    3540
gggcgctggg ggcatggtcc accacaggca ccgcagctca tctaccagga gtggcggtgg    3600
ggacctgaca ctagggctgg agccctctga agaggaggcc cccaggtctc cactggcacc    3660
ctccgaaggg gctggctccg atgtatttga tggtgacctg ggaatggggg cagccaaggg    3720
gctgcaaagc ctcccacac atgacccag ccctctacag cggtacagtg aggaccccac    3780
agtaccctg ccctctgaga ctgatggcta cgttgccccc ctgacctgca gcccccagcc    3840
tgaatatgtg aaccagccag atgttcggcc ccagcccct tcgccccgag agggccctct    3900
gcctgctgcc cgacctgctg gtgccactct ggaaaggccc aagactctct ccccagggaa    3960
gaatggggtc gtcaaagacg ttttttgcctt tgggggtgcc gtggagaacc ccgagtactt    4020
gacaccccag gaggagctg cccctcagcc ccacctcct cctgccttca gcccagcctt    4080
cgacaacctc tattactggg accaggaccc accagagcgg gggctccac ccagcacctt    4140
caaagggaca cctacggcag agaacccaga gtacctgggt ctggacgtgc agtgtgaac    4200
cagaaggcca agtccgcaga agccctgatg tgtcctcagg gagcagggaa ggcctgactt    4260
ctgctggcat caagaggtgg gagggccctc cgaccactc caggggaacc tgccatgcca    4320
```

| | |
|---|---:|
| ggaacctgtc ctaaggaacc ttccttcctg cttgagttcc cagatggctg aagggggtcc | 4380 |
| agcctcgttg aagaggaac agcactgggg agtctttgtg gattctgagg ccctgcccaa | 4440 |
| tgagactcta gggtccagtg gatgccacag cccagcttgg ccctttcctt ccagatcctg | 4500 |
| ggtactgaaa gccttaggga agctggcctg agagggaag cggccctaag ggagtgtcta | 4560 |
| agaacaaaag cgacccattc agagactgtc cctgaaacct agtactgccc cccatgagga | 4620 |
| aggaacagca atggtgtcag tatccaggct ttgtacagag tgcttttctg tttagttttt | 4680 |
| actttttttg ttttgttttt ttaaagatga aataaagacc caggggggaga atgggtgttg | 4740 |
| tatggggagg caagtgtggg gggtccttct ccacacccac tttgtccatt tgcaaatata | 4800 |
| ttttggaaaa cagcta | 4816 |

<210> SEQ ID NO 119
<211> LENGTH: 6466
<212> TYPE: DNA
<213> ORGANISM: Homo sapiens

<400> SEQUENCE: 119

| | |
|---|---:|
| atggtcataa cagcctcctg tctaccgact cagaacggat tttaccaaaa ctgaaaatgc | 60 |
| aggctccatg ctcagaagct cttttaacagg ctcgaaaggt ccatgctcct ttctcctgcc | 120 |
| cattctatag cataagaaga cagtctctga gtgataatct tctcttcaag aagaagaaaa | 180 |
| ctaggaagga gtaagcacaa agatctcttc acattctccg ggactgcggt accaaatatc | 240 |
| agcacagcac ttcttgaaaa aggatgtaga ttttaatctg aactttgaac catcactgag | 300 |
| gtggcccgcc ggtttctgag ccttctgccc tgcggggaca cggtctgcac cctgcccgcg | 360 |
| gccacggacc atgaccatga ccctccacac caaagcatct gggatggccc tactgcatca | 420 |
| gatccaaggg aacgagctgg agcccctgaa ccgtccgcag ctcaagatcc ccctggagcg | 480 |
| gccccctggc gaggtgtacc tggacagcag caagcccgcc gtgtacaact ccccgagggg | 540 |
| cgccgcctac gagttcaacg ccgcggccgc cgccaacgcg caggtctacg gtcagaccgg | 600 |
| cctcccctac ggccccgggt ctgaggctgc ggcgttcggc tccaacggcc tgggggggttt | 660 |
| cccccccactc aacagcgtgt ctccgagccc gctgatgcta ctgcacccgc cgccgcagct | 720 |
| gtcgcctttc ctgcagcccc acggccagca ggtgccctac tacctggaga acgagcccag | 780 |
| cggctacacg gtgcgcgagg ccggcccgcc ggcattctac aggccaaatt cagataatcg | 840 |
| acgccagggt ggcagagaaa gattggccag taccaatgac aagggaagta tggctatgga | 900 |
| atctgccaag gagactcgct actgtgcagt gtgcaatgac tatgcttcag gctaccatta | 960 |
| tggagtctgg tcctgtgagg gctgcaaggc cttcttcaag agaagtattc aaggacataa | 1020 |
| cgactatatg tgtccagcca ccaaccagtg caccattgat aaaaacagga ggaagagctg | 1080 |
| ccaggcctgc cggctccgca atgctacga agtgggaatg atgaaaggtg ggatacgaaa | 1140 |
| agaccgaaga ggagggagaa tgttgaaaca caagcgccag agagatgatg gggagggcag | 1200 |
| gggtgaagtg gggtctgctg gagacatgag agctgccaac ctttggccaa gcccgctcat | 1260 |
| gatcaaacgc tctaagaaga acagcctggc cttgtccctg acggccgacc agatggtcag | 1320 |
| tgccttgttg gatgctgagc cccccatact ctattccgag tatgatccta ccagaccctt | 1380 |
| cagtgaagct tcgatgatgg gcttactgac caacctggca gacagggagc tggttcacat | 1440 |
| gatcaactgg gcgaagaggg tgccaggctt tgtggatttg acccctccatg atcaggtcca | 1500 |
| ccttctagaa tgtgcctggc tagagatcct gatgattggt ctcgtctggc gctccatgga | 1560 |

```
gcacccaggg aagctactgt tgctcctaa cttgctcttg gacaggaacc agggaaaatg    1620
tgtagagggc atggtggaga tcttcgacat gctgctggct acatcatctc ggttccgcat    1680
gatgaatctg cagggagagg agtttgtgtg cctcaaatct attattttgc ttaattctgg    1740
agtgtacaca tttctgtcca gcaccctgaa gtctctggaa gagaaggacc atatccaccg    1800
agtcctggac aagatcacag acactttgat ccacctgatg gccaaggcag gcctgaccct    1860
gcagcagcag caccagcggc tggcccagct cctcctcatc ctctcccaca tcaggcacat    1920
gagtaacaaa ggcatggagc atctgtacag catgaagtgc aagaacgtgg tgcccctcta    1980
tgacctgctg ctggagatgc tggacgccca ccgcctacat gcgcccacta gccgtggagg    2040
ggcatccgtg gaggagacgg accaaagcca cttggccact gcgggctcta cttcatcgca    2100
ttccttgcaa aagtattaca tcacgggga ggcagagggt ttccctgcca cggtctgaga    2160
gctccctggc tcccacacgg ttcagataat ccctgctgca ttttaccctc atcatgcacc    2220
actttagcca aattctgtct cctgcataca ctccggcatg catccaacac caatggcttt    2280
ctagatgagt ggccattcat ttgcttgctc agttcttagt ggcacatctt ctgtcttctg    2340
ttgggaacag ccaaagggat tccaaggcta atctttgta acagctctct ttcccccttg    2400
ctatgttact aagcgtgagg attcccgtag ctcttcacag ctgaactcag tctatggtt    2460 ggggctcaga taactctgtg catttaagct acttgtagag acccaggcct ggagagtaga    2520 catttgcct ctgataagca cttttaaat ggctctaaga ataagccaca gcaaagaatt    2580
taaagtggct cctttaattg gtgacttgga gaaagctagg tcaagggttt attatagcac    2640
cctcttgtat tccatggca atgcatcctt ttatgaaagt ggtacacctt aaagctttta    2700
tatgactgta gcagagtatc tggtgattgt caattcattc cccctatagg aatacaaggg    2760
gcacacaggg aaggcagatc ccctagttgg caagactatt ttaacttgat acactgcaga    2820
ttcagatgtg ctgaaagctc tgcctctggc tttccggtca tgggttccag ttaattcatg    2880
cctcccatgg acctatggag agcagcaagt tgatcttagt taagtctccc tatatgaggg    2940
ataagttcct gattttgtt tttatttttg tgttacaaaa gaaagccctc cctccctgaa    3000
cttgcagtaa ggtcagcttc aggacctgtt ccagtgggca ctgtacttgg atcttcccgg    3060
cgtgtgtgtg ccttacacag gggtgaactg ttcactgtgg tgatgcatga tgagggtaaa    3120
tggtagttga aaggagcagg ggccctggtg ttgcatttag ccctgggca tggagctgaa    3180 cagtacttgt gcaggattgt tgtggctact agagaacaag agggaaagta gggcagaaac    3240
tggatacagt tctgaggcac agccagactt gctcagggtg gccctgccac aggctgcagc    3300
tacctaggaa cattccttgc agaccccgca ttgcccttg ggggtgccct gggatccctg    3360
gggtagtcca gctcttcttc atttcccagc gtggccctgg ttggaagaag cagctgtcac    3420
agctgctgta gacagctgtg ttcctacaat tggcccagca ccctggggca cgggagaagg    3480
gtggggaccg ttgctgtcac tactcaggct gactggggcc tggtcagatt acgtatgccc    3540
ttggtggttt agagataatc caaaatcagg gtttggtttg gggaagaaaa tcctcccct    3600 tcctccccg ccccgttccc taccgcctcc actcctgcca gctcatttcc ttcaatttcc    3660
tttgacctat aggctaaaaa agaaaggctc attccagcca cagggcagcc ttccctgggc    3720
ctttgcttct ctagcacaat tatgggttac ttccttttc ttaacaaaaa agaatgtttg    3780
atttcctctg ggtgacctta ttgtctgtaa ttgaaaccct attgagaggt gatgtctgtg    3840
ttagccaatg acccaggtga gctgctcggg cttctcttgg tatgtcttgt ttggaaaagt    3900
ggatttcatt catttctgat tgtccagtta agtgatcacc aaaggactga gaatctggga    3960
```

```
gggcaaaaaa aaaaaaaaag ttttatgtg cacttaaatt tggggacaat tttatgtatc    4020
tgtgttaagg atatgtttaa gaacataatt cttttgttgc tgtttgttta agaagcacct    4080
tagtttgttt aagaagcacc ttatatagta taatatatat tttttgaaa ttacattgct     4140 tgtttatcag acaattgaat gtagtaattc tgttctggat ttaatttgac tgggttaaca    4200
tgcaaaaacc aaggaaaaat atttagtttt tttttttttt tttgtatact tttcaagcta    4260
ccttgtcatg tatacagtca tttatgccta aagcctggtg attattcatt taaatgaaga    4320
tcacatttca tatcaacttt tgtatccaca gtagacaaaa tagcactaat ccagatgcct    4380
attgttggat actgaatgac agacaatctt atgtagcaaa gattatgcct gaaaaggaaa    4440
attattcagg gcagctaatt ttgcttttac caaaatatca gtagtaatat ttttggacag    4500
tagctaatgg gtcagtgggt tcttttaat gtttatactt agattttctt ttaaaaaaat      4560
taaaataaaa caaaaaaaaa tttctaggac tagacgatgt aataccagct aaagccaaac    4620
aattatacag tggaaggttt tacattattc atccaatgtg tttctattca tgttaagata    4680
ctactacatt tgaagtgggc agagaacatc agatgattga aatgttcgcc cagggtctc     4740 cagcaacttt ggaaatctct ttgtattttt acttgaagtg ccactaatgg acagcagata    4800
ttttctggct gatgttggta ttgggtgtag gaacatgatt taaaaaaaaa ctcttgcctc    4860
tgctttcccc cactctgagg caagttaaaa tgtaaaagat gtgatttatc tgggggctc     4920 aggtatggtg gggaagtgga ttcaggaatc tggggaatgg caaatatatt aagaagagta    4980
ttgaaagtat ttggaggaaa atggttaatt ctgggtgtgc accagggttc agtagagtcc    5040
acttctgccc tggagaccac aaatcaacta gctccattta cagccatttc taaaatggca    5100
gcttcagttc tagagaagaa agaacaacat cagcagtaaa gtccatggaa tagctagtgg    5160
tctgtgtttc ttttcgccat tgcctagctt gccgtaatga ttctataatg ccatcatgca    5220
gcaattatga gaggctaggt catccaaaga gaagaccta tcaatgtagg ttgcaaaatc       5280
taacccctaa ggaagtgcag tcttttgattt gatttcccta gtaaccttgc agatatgttt    5340
aaccaagcca tagcccatgc cttttgaggg ctgaacaaat aagggactta ctgataattt    5400
acttttgatc acattaaggt gttctcacct tgaaatctta tacactgaaa tggccattga    5460
tttaggccac tggcttagag tactccttcc cctgcatgac actgattaca aatactttcc    5520
tattcatact ttccaattat gagatggact gtgggtactg ggagtgatca ctaacaccat    5580
agtaatgtct aatattcaca ggcagatctg cttggggaag ctagttatgt gaaaggcaaa    5640
tagagtcata cagtagctca aaaggcaacc ataattctct ttggtgcagg tcttgggagc    5700
gtgatctaga ttacactgca ccattcccaa gttaatcccc tgaaaactta ctctcaactg    5760
gagcaaatga actttggtcc caaatatcca tcttttcagt agcgttaatt atgctctgtt    5820
tccaactgca tttcctttcc aattgaatta aagtgtggcc tcgttttag tcatttaaaa      5880 ttgttttcta agtaattgct gcctctatta tggcacttca atttgcact gtcttttgag      5940 attcaagaaa aatttctatt cttttttttg catccaattg tgcctgaact tttaaaatat    6000
gtaaatgctg ccatgttcca aacccatcgt cagtgtgtgt gtttagagct gtgcaccta     6060 gaaacaacat attgtcccat gagcaggtgc ctgagacaca gaccccttg cattcacaga     6120 gaggtcattg gttatagaga cttgaattaa taagtgacat tatgccagtt tctgttctct    6180
cacaggtgat aaacaatgct ttttgtgcac tacatactct tcagtgtaga gctcttgttt    6240
tatgggaaaa ggctcaaatg ccaaattgtg tttgatggat taatatgccc ttttgccgat    6300
```

```
gcatactatt actgatgtga ctcggttttg tcgcagcttt gctttgttta atgaaacaca   6360
cttgtaaacc tcttttgcac tttgaaaaag aatccagcgg gatgctcgag cacctgtaaa   6420
caattttctc aacctatttg atgttcaaat aaagaattaa actaaa                  6466
```

<210> SEQ ID NO 120
<211> LENGTH: 3478
<212> TYPE: DNA
<213> ORGANISM: Homo sapiens

<400> SEQUENCE: 120

```
aaattgaaag gtcagccttt cgcgcgctgt gtaggcaagt tacccgtgtt ctgcgttgcc     60
ggccgtgggt gctctggcca cagtgagtta ggggcgtcgg agcgggtttc tccaaccgca    120
atcggctccg ctcaagggga ggaggagagt cccttctcgg aaggcctaag gaaacgtgtc    180
gtctggaatg ggcttggggg ccacgcctgc acatctccgc gagacagagg gataaagtga    240
agatggtgct gttattgtta cctcgagtgc cacatgcgac ctctgagata tgtacacagt    300
cattcttact atcgcactca gccattctta ctacgctaaa aagaaataa  ttattcgagg    360 atatttgcct ggcccagaag aaacttatgt aaatttcatg aactattata tccgttttcc    420
tcggagtgag agaaaactct ttttagatat catctgagag aactagtgaa tcccagtcac    480
tgagtggagt tgagagtcta agaacctctg aaatttgaga actgctggac cagagccttt    540
agagctctga taaggtgtca acagggtagt taatttggca ccatggggat acagggattg    600
ctacaattta tcaaagaagc ttcagaaccc atccatgtga ggaagtataa agggcaggta    660
gtagctgtgg atacatattg ctggcttcac aaaggagcta ttgcttgtgc tgaaaaacta    720
gccaaaggtg aacctactga taggtatgta ggattttgta tgaaatttgt aaatatgtta    780
ctatctcatg ggatcaagcc tattctcgta tttgatggat gtactttacc ttctaaaaag    840
gaagtagaga gatctagaag agaaagacga caagccaatc ttcttaaggg aaagcaactt    900
cttcgtgagg ggaaagtctc ggaagctcga gagtgtttca cccggtctat caatatcaca    960
catgccatgg cccacaaagt aattaaagct gcccggtctc aggggggtaga ttgcctcgtg   1020 gctccctatg aagctgatgc gcagttggcc tatcttaaca aagcgggaat tgtgcaagcc   1080
ataattacag aggactcgga tctcctagct tttggctgta aaaaggtaat tttaaagatg   1140
gaccagtttg gaaatggact tgaaattgat caagctcggc taggaatgtg cagacagctt   1200
ggggatgtat tcacggaaga gaagtttcgt tacatgtgta ttctttcagg ttgtgactac   1260
ctgtcatcac tgcgtgggat tggattagca aaggcatgca aagtcctaag actagccaat   1320
aatccagata tagtaaaggt tatcaagaaa attggacatt atctcaagat gaatatcacg   1380
gtaccagagg attacatcaa cgggtttatt cgggccaaca ataccttcct ctatcagcta   1440 gttttttgatc ccatcaaaag gaaacttatt cctctgaacg cctatgaaga tgatgttgat   1500
cctgaaacac taagctacgc tgggcaatat gttgatgatt ccatagctct tcaaatagca   1560
cttggaaata agatataaaa acttttgaa cagatcgatg actacaatcc agacactgct   1620
atgcctgccc attcaagaag tcatagttgg gatgacaaaa catgtcaaaa gtcagctaat   1680
gttagcagca tttggcatag gaattactct cccagaccag agtcgggtac tgtttcagat   1740
gccccacaat tgaaggaaaa tccaagtact gtgggagtgg aacgagtgat tagtactaaa   1800
gggttaaatc tcccaaggaa atcatccatt gtgaaaagac caagaagtgc agagctgtca   1860
gaagatgacc tgttgagtca gtattctctt tcatttacga agaagaccaa gaaaaatagc   1920
tctgaaggca ataaatcatt gagctttttct gaagtgtttg tgcctgacct ggtaaatgga   1980
```

```
cctactaaca aaaagagtgt aagcactcca cctaggacga gaaataaatt tgcaacattt   2040
ttacaaagga aaaatgaaga aagtggtgca gttgtggttc cagggaccag aagcaggttt   2100
ttttgcagtt cagattctac tgactgtgta tcaaacaaag tgagcatcca gcctctggat   2160
gaaactgctg tcacagataa agagaacaat ctgcatgaat cagagtatgg agaccaagaa   2220
ggcaagagac tggttgacac agatgtagca cgtaattcaa gtgatgacat tccgaataat   2280
catattccag gtgatcatat tccagacaag gcaacagtgt ttacagatga agagtcctac   2340
tcttttgaga gcagcaaatt tacaaggacc atttcaccac ccactttggg aacactaaga   2400
agttgtttta gttggtctgg aggtcttgga gattttttcaa gaacgccgag ccctctccaa   2460
agcacagcat tgcagcagtt ccgaagaaag agcgattccc ccacctcttt gcctgagaat   2520
aatatgtctg atgtgtcgca gttaaagagc gaggagtcca gtgacgatga gtctcatccc   2580
ttacgagaag aggcatgttc ttcacagtcc caggaaagtg gagaattctc actgcagagt   2640
tcaaatgcat caaagctttc tcagtgctct agtaaggact ctgattcaga ggaatctgat   2700
tgcaatatta agttacttga cagtcaaagt gaccagacct ccaagctacg tttatctcat   2760
ttctcaaaaa aagacacacc tctaaggaac aaggttcctg ggctatataa gtccagttct   2820
gcagactctc tttctacaac caagatcaaa cctctaggac ctgccagagc cagtgggctg   2880
agcaagaagc cggcaagcat ccagaagaga aagcatcata atgccgagaa caagccgggg   2940
ttacagatca aactcaatga gctctggaaa aactttggat ttaaaaaaga ttctgaaaag   3000
cttcctcctt gtaagaaacc cctgtcccca gtcagagata acatccaact aactccagaa   3060
gcggaagagg atatatttaa caaacctgaa tgtggccgtg ttcaagagc aatattccag   3120 taaatgcaga ctgctgcaaa gcttttgcct gcaagagaat ctgatcaatt tgaagtccct   3180
gtttgggaat gaggcactta tcagcatgaa gaatttttc tcattctgtg ccattttaaa   3240
aatagaatac attttgtata ttaactttat aattggggttg tggtttttt gctcagcttt   3300 ttatattttt ataagaagct aaatagaaga ataattgtat ctctgacagg ttttttggagg   3360 ttttagtgtt aattgggaaa atcctctgga gtttataaaa gtctactcta aatatttctg   3420
taatgttgtc aagtagaaag atagtaaatg gagaaactac aaaaaaaaaa aaaaaaaa    3478
```

<210> SEQ ID NO 121
<211> LENGTH: 5192
<212> TYPE: DNA
<213> ORGANISM: Homo sapiens

<400> SEQUENCE: 121

```
ccatgacctg ccttgagaag gggcaggga agccagatgg actggaagtg gagtggcagt     60
gaccaaggag gaggaggtgt gataggcttc ccacgcaggg tagatccaga gacaccagtg    120
ccacccatag gccctagga ctgcagtggt cacccgattc ctttgtccca gctgagactc      180
agttctgagt gttctatttt ggggaacaga ggcgtccttg gtagcatttg aagaggata      240 gccagctggg gtgtgtgtac atcacagcct gacagtaaca gcatccgaac cagaggtgac    300
tggctaaggg cagacccagg gcaacaggtt aaccgttcta gggccgggca cagggaggag    360
aacattccaa cactctgtgt gcccagtgcc gacgcacgtt ctctctttta tcctcaaaac    420
agtcctatga ggatataagc cagagagaga cagagacaag gaattacaag ttggtgagag    480
tcaggatttg aacttggctc tggcagatgg aaaattaggg tctgtattct ttacaaaacc    540
gtgtgtgcct cagatggagt tggtgcataa caagcagagg tatccagggt cgcggtcctg    600
```

```
cttgccacgg aagggccgc cttgtcagtt gtgaccaccc agccctggaa atgtcagtaa    660
tgctgtaagg agtggggatc ggatcagatg ccatccagat gctgaagttt gaccttgtgt    720
cattttttcac tttctttttt ggctcttctg caatcaattc atttatttag caaaaaagaa    780
attatgtgtg ccgagagcat gcagaagata tgtctccgtt ctctgcttcc ctccaaaaaa    840
gaatcccaaa actgctttct gtgaacgtgt gccagggtcc cagcaggact cagggagagc    900
aggaagccca gcccagaccc cttgcacaac ctaccgtggg gaggccttag gctctggcta    960
ctacagagct ggttccagtc tgcactgcca cagcctggcc agggacttgg acacatctgc   1020
tggccacttc ctgtctcagt ttccttatct gcaaaataag ggaaaagccc ccacaaaggt   1080
gcacgtgtag caggagctct tttccctccc tattttagga aggcagttgg tgggaagtcc   1140
agcttgggtc cctgagagct gtgagaagga gatgcggctg ctgctggccc tgttgggggt   1200
cctgctgagt gtgcctgggc ctccagtctt gtccctggag gcctctgagg aagtggagct   1260
tggtatggct tctgaggtgg agagggtgg caggggtggg aagagtgggc accaggaggg   1320
ggctgctggg ctgagcaaag ctggaaagga tccttgccca ggccctgaga aggtggcggc   1380
agggcagggc tcaaccactg agactcagtc agtgcctggc ttccagcaag cattcatcta   1440
tcactgtgtc tgcgagagag gactggcctt gcagggcgca gggccctaag ctgggctgca   1500
gagctggtgg tgagctcctt gcctgggtgt gtgtgcgtgt gtgtgtgtgt tctgtgcact   1560
gggtgtgtga cctaggaggt ccaggcagca tgtgtggtat aagcattatg agggtgatat   1620
gccccggtgc agcatgaccc tgtatgtggc accaacagca tgtgccttgt gtgtgtgtgt   1680
gtccgtatgt gtgtgtgtgt atgcgtgtgt gtgtgtgtgt gtgtgtgtct tggccactgt   1740
catgtgcact aaatgctgtg tgtgtgacat gccccaagag tgtggcattt gccctgggtg   1800
tggcatccgc agcatgtggc tgtgtgggtg tcaaggagtg gtggctcctt cagcatgcgt   1860
tgcgaagtgc ttgtgccctg catgtgcggt gtgttctctg tacacaggag gctgcctcag   1920
atggggctgc ggggtctgct gacctctgcc ctctgcccac agagccctgc ctggctccca   1980
gcctggagca gcaagagcag gagctgacag tagcccttgg gcagcctgtg cggctgtgct   2040
gtgggcgggc tgagcgtggt ggccactggt acaaggaggg cagtcgcctg cacctgctg    2100
gccgtgtacg gggctggagg ggccgcctag agattgccag cttcctacct gaggatgctg   2160
gccgctacct ctgcctggca cgaggctcca tgatcgtcct gcagaatctc accttgatta   2220
caggtgactc cttgacctcc agcaacgatg atgaggaccc caagtcccat agggacctct   2280
cgaataggca cagttacccc cagcaaggtc agtaggtctc caaggacttg tgtccccgct   2340
gctgctcatc tgatcactga agaggagg cctgtgtggg aacacacggt cattctaggg   2400
gccttcccct gccctccagc accctactgg acacacccc agcgcatgga gaagaaactg   2460
catgcagtac ctgcggggaa caccgtcaag ttccgctgtc cagctgcagg caaccccacg   2520
cccaccatcc gctggcttaa ggatggacag gcctttcatg gggagaaccg cattggaggc   2580
attcggctgc gccatcagca ctggagtctc gtgatggaga gcgtggtgcc ctcggaccgc   2640
ggcacataca cctgcctggt agagaacgct gtgggcagca tccgttataa ctacctgcta   2700
gatgtgctgg agcggtcccc gcaccggccc atcctgcagg ccgggctccc ggccaacacc   2760
acagccgtgg tgggcagcga cgtggagctg ctgtgcaagg tgtacagcga tgcccagccc   2820
cacatccagt ggctgaagca catcgtcatc aacggcagca gcttcggagc cgacggtttc   2880
ccctatgtgc aagtcctaaa gactgcagac atcaatagct cagaggtgga ggtcctgtac   2940
ctgcggaacg tgtcagccga ggacgcaggc gagtacacct gcctcgcagg caattccatc   3000
```

```
ggcctctcct accagtctgc ctggctcacg gtgctgccag gtgagcacct gaagggccag    3060
gagatgctgc gagatgcccc tctgggccag cagtgggggc tgtggcctgt tgggtggtca    3120
gtctctgttg gcctgtgggg tctggcctgg ggggcagtgt gtggatttgt gggtttgagc    3180
tgtatgacag cccctctgtg cctctccaca cgtggccgtc catgtgaccg tctgctgagg    3240
tgtgggtgcc tgggactggg cataactaca gcttcctccg tgtgtgtccc cacatatgtt    3300
gggagctggg agggactgag ttagggtgca cggggcggcc agtctcacca ctgaccagtt    3360
tgtctgtctg tgtgtgtcca tgtgcgaggg cagaggagga ccccacatgg accgcagcag    3420
cgcccgaggc caggtatacg acatcatcc tgtacgcgtc gggctccctg gccttggctg    3480
tgctcctgct gctggccagg ctgtatcgag gcaggcgct ccacggccgg caccccgcc     3540 cgcccgccac tgtgcagaag ctctcccgct ccctctggc ccgacagttc tccctggagt    3600
caggctcttc cggcaagtca agctcatccc tggtacgagg cgtgcgtctc tcctccagcg    3660
gccccgcctt gctcgccggc ctcgtgagtc tagatctacc tctcgaccca ctatgggagt    3720
tcccccggga caggctggtg cttgggaagc ccctaggcga gggctgcttt ggccaggtag    3780
tacgtgcaga ggccttttggc atggaccctg cccggcctga ccaagccagc actgtggccg    3840
tcaagatgct caaagacaac gcctctgaca aggacctggc cgacctggtc tcggagatgg    3900
aggtgatgaa gctgatcggc cgacacaaga acatcatcaa cctgcttggt gtctgcaccc    3960
aggaagggcc cctgtacgtg atcgtggagt gcgccgccaa gggaaacctg cgggagttcc    4020
tgcgggcccg gcgccccca ggccccgacc tcagccccga cggtcctcgg agcagtgagg    4080
ggccgctctc cttcccagtc ctggtctcct gcgcctacca ggtggcccga ggcatgcagt    4140
atctggagtc ccggaagtgt atccaccggg acctggctgc ccgcaatgtg ctggtgactg    4200
aggacaatgt gatgaagatt gctgactttg gctggcccg cggcgtccac acattgact     4260 actataagaa aaccagcaac ggccgcctgc ctgtgaagtg gatggcgccc gaggccttgt    4320
ttgaccgggt gtacacacac cagagtgacg tgtggtcttt gggatcctg ctatgggaga    4380 tcttcaccct cggggggctcc ccgtatcctg gcatcccggt ggaggagctg ttctcgctgc    4440
tgcgggaggg acatcggatg gaccgacccc cacactgccc cccagagctg tacgggctga    4500
tgcgtgagtg ctggcacgca gcgccctccc agaggcctac cttcaagcag ctggtggagg    4560
cgctggacaa ggtcctgctg gccgtctctg aggagtacct cgacctccgc ctgacccttg    4620
gaccctattc cccctctggt ggggacgcca gcagcacctg ctcctccagc gattctgtct    4680
tcagccacga ccccctgcca ttgggatcca gctccttccc cttcgggtct ggggtgcaga    4740
catgagcaag gctcaaggct gtgcaggcac ataggctggt ggccttgggc cttgggctc    4800 agccacagcc tgacacagtg ctcgaccttg atagcatggg gccctggcc cagagttgct    4860 gtgccgtgtc caagggccgt gcccttgccc ttggagctgc cgtgcctgtg tcctgatggc    4920
ccaaatgtca gggttctgct cggcttcttg gaccttggcg cttagtcccc atcccgggtt    4980
tggctgagcc tggctggaga gctgctatgc taaacctcct gcctcccaat accagcagga    5040
ggttctgggc ctctgaaccc cctttcccca cacctccccc tgctgctgct gccccagcgt    5100
cttgacggga gcattggccc ctgagcccag agaagctgga agcctgccga aaacaggagc    5160
aaatggcgtt ttataaatta ttttttttgaa at                                 5192
```

<210> SEQ ID NO 122
<211> LENGTH: 3124
<212> TYPE: DNA

<213> ORGANISM: Homo sapiens

<400> SEQUENCE: 122

```
taagatccac atcagctcaa ctgcacttgc ctcgcagagg cagcccgctc acttcccgcg      60
gaggcgctcc ccggcgccgc gctccgcggc agccgcctgc ccccgcgct gccccgccc      120
gccgcgccgc cgccgccgcc gcgcacgccg cgcccgcag ctctgggctt cctcttcgcc     180
cgggtggcgt tgggcccgcg cgggcgctcg ggtgactgca gctgctcagc tcccctcccc    240
cgccccgcgc cgcgcggccg cccgtcgctt cgcacagggc tggatggttg tattgggcag    300
ggtggctcca ggatgttagg aactgtgaag atggaagggc atgaaaccag cgactggaac    360
agctactacg cagacacgca ggaggcctac tcctccgtcc cggtcagcaa catgaactca    420
ggcctgggct ccatgaactc catgaacacc tacatgacca tgaacaccat gactacgagc    480
ggcaacatga ccccggcgtc cttcaacatg tcctatgcca cccgggcct aggggccggc    540
ctgagtcccg gcgcagtagc cggcatgccg ggggctcgg cgggcgccat gaacagcatg    600
actgcggccg gcgtgacggc catgggtacg gcgctgagcc cgagcggcat gggcgccatg    660
ggtgcgcagc aggcggcctc catgaatggc ctgggccct acgcggccgc catgaacccg    720
tgcatgagcc ccatggcgta cgcgccgtcc aacctgggcc gcagccgcgc gggcggcggc    780
ggcgacgcca agacgttcaa gcgcagctac ccgcacgcca agccgcccta ctcgtacatc    840
tcgctcatca ccatggccat ccagcaggcg cccagcaaga tgctcacgct gagcgagatc    900
taccagtgga tcatggacct cttcccctat taccggcaga accagcagcg ctggcagaac    960
tccatccgcc actcgctgtc cttcaatgac tgcttcgtca aggtggcacg ctccccggac   1020
aagccgggca agggctccta ctggacgctg cacccggact ccggcaacat gttcgagaac   1080
ggctgctact gccgccgcca gaagcgcttc aagtgcgaga gcagccgggg ggccggcggc   1140
gggggcggga gcggaagcgg gggcagcggc gccaagggcg gccctgagag ccgcaaggac   1200
ccctctggcg cctctaaccc cagcgccgac tcgcccctcc atcggggtgt gcacgggaag   1260
accggccagc tagagggcgc gccggccccc gggcccgccg ccagccccca gactctggac   1320
cacagtgggg cgacgcgac aggggcgcc tcggagttga agactccagc ctcctcaact   1380
gcgcccccca taagctccgg gccggggcg ctggcctctg tgcccgcctc tcacccggca   1440
cacggcttgg caccccacga gtcccagctg cacctgaaag gggaccccca ctactccttc   1500
aaccacccgt tctccatcaa caacctcatg tcctcctcgg agcagcagca taagctggac   1560
ttcaaggcat acgaacaggc actgcaatac tcgccttacg gctctacgtt gcccgccagc   1620
ctgcctctag gcagcgcctc ggtgaccacc aggagcccca tcgagccctc agccctggag   1680
ccggcgtact accaaggtgt gtattccaga cccgtcctaa acacttccta gctcccggga   1740
ctgggggtt tgtctggcat agccatgctg gtagcaagag agaaaaaatc aacagcaaac    1800
aaaaccacac aaaccaaacc gtcaacagca taataaaatc ccaacaacta ttttttatttc   1860
attttttcatg cacaacccttt ccccagtgc aaaagactgt tactttatta ttgtattcaa    1920
aattcattgt gtatattact acaaagacaa ccccaaaacca attttttttcc tgcgaagttt   1980
aatgatccac aagtgtatat atgaaattct cctccttcct tgccccctc tctttcttcc    2040
ctctttcccc tccagacatt ctagtttgtg gagggttatt taaaaaaaca aaaaggaag    2100
atggtcaagt ttgtaaaata tttgtttgtg cttttttcccc ctccttacct gaccccctac   2160
gagtttacag gtctgtggca atactcttaa ccataagaat tgaaatggtg aagaaacaag    2220
tatacactag aggctcttaa aagtattgaa agacaatact gctgttatat agcaagacat    2280
```

```
aaacagatta taaacatcag agccatttgc ttctcagttt acatttctga tacatgcaga    2340
tagcagatgt ctttaaatga aatacatgta tattgtgtat ggacttaatt atgcacatgc    2400
tcagatgtgt agacatcctc cgtatattta cataacatat agaggtaata gataggtgat    2460
atacatgata cattctcaag agttgcttga ccgaaagtta caaggacccc aaccccttg     2520
tcctctctac ccacagatgg ccctgggaat caattcctca ggaattgccc tcaagaactc    2580
tgcttcttgc tttgcagagt gccatggtca tgtcattctg aggtcacata acacataaaa    2640
ttagtttcta tgagtgtata ccatttaaag aattttttt tcagtaaaag ggaatattac     2700
aatgttggag gagagataag ttatagggag ctggatttca aaacgtggtc caagattcaa    2760
aaatcctatt gatagtggcc attttaatca ttgccatcgt gtgcttgttt catccagtgt    2820
tatgcacttt ccacagttgg acatggtgtt agtatagcca gacgggtttc attattattt    2880
ctctttgctt tctcaatgtt aatttattgc atggtttatt ctttttcttt acagctgaaa    2940
ttgctttaaa tgatggttaa aattacaaat taaattgtta attttttatca atgtgattgt   3000
aattaaaaat attttgattt aaataacaaa aataatacca gatttttaagc cgtggaaaat  3060
gttcttgatc atttgcagtt aaggacttta aataaatcaa atgttaacaa aaaaaaaaa    3120
aaaa                                                                 3124

<210> SEQ ID NO 123
<211> LENGTH: 3452
<212> TYPE: DNA
<213> ORGANISM: Homo sapiens

<400> SEQUENCE: 123
atgcaggcgc gctactccgt gtccagcccc aactccctgg gagtggtgcc ctacctcggc     60
ggcgagcaga gctactaccg cgcggcggcc gcggcggccg gggcggctta caccgccatg    120
ccggccccca tgagcgtgta ctcgcaccct gcgcacgccg agcagtaccc gggcggcatg    180
gcccgcgcct acgggcccta cacgccgcag ccgcagccca aggacatggt gaagccgccc    240
tatagctaca tcgcgctcat caccatggcc atccagaacg ccccggacaa gaagatcacc    300
ctgaacggca tctaccagtt catcatggac cgcttcccct tctaccggga caacaagcag    360
ggctggcaga acagcatccg ccacaacctc tcgctcaacg agtgcttcgt caaggtgccg    420
cgcgacgaca agaagccggg caagggcagc tactggacgc tggaccccga ctcctacaac    480
atgttcgaga acggcagctt cctgcggcgg cggcggcgct tcaagaagaa ggacgcggtg    540
aaggacaagg aggagaagga caggctgcac ctcaaggagc cgccccgcc cggccgccag    600
ccccgcccg cgccgccgga gcaggccgac ggcaacgcgc ccggtccgca gccgccgccc     660
gtgcgcatcc aggacatcaa gaccgagaac ggtacgtgcc cctcgccgcc ccagcccctg    720
tccccggccg ccgccctggg cagcggcagc gccgccgcgg tgcccaagat cgagagcccc    780
gacagcagca gcagcagcct gtccagcggg agcagccccc cgggcagcct gccgtcggcg    840
cggccgctca gcctggacgg tgcggattcc gcgccgccgc cgcccgcgcc ctccgccccg    900
ccgccgcacc atagccaggg cttcagcgtg gacaacatca tgacgtcgct gcggggtcg    960
ccgcagagcg cggccgcgga gctcagctcc ggccttctgg cctcggcggc cgcgtcctcg    1020
cgcgcgggga tcgcacccc gctggcgctc ggcgcctact cgcccggcca gagctccctc   1080
tacagctccc cctgcagcca gacctccagc gcgggcagct cggcggcgg cggcggcggc   1140
gcggggccg cggggggcgc gggcggcgcc gggacctacc actgcaacct gcaagccatg    1200
```

```
agcctgtacg cggccggcga gcgcggggc cacttgcagg gcgcgcccgg gggcgcgggc    1260
ggctcggccg tggacgaccc cctgcccgac tactctctgc ctccggtcac cagcagcagc    1320
tcgtcgtccc tgagtcacgg cggcggcggc ggcggcggcg ggggaggcca ggaggccggc    1380
caccaccctg cggcccacca aggccgcctc acctcgtggt acctgaacca ggcgggcgga    1440
gacctgggcc acttggcgag cgcggcggcg gcggcggcg ccgcaggcta cccgggccag    1500
cagcagaact tccactcggt gcgggagatg ttcgagtcac agaggatcgg cttgaacaac    1560
tctccagtga acgggaatag tagctgtcaa atggccttcc cttccagcca gtctctgtac    1620
cgcacgtccg gagctttcgt ctacgactgt agcaagtttt gacacaccct caaagccgaa    1680
ctaaatcgaa ccccaaagca ggaaaagcta aggaaccca tcaaggcaaa atcgaaacta    1740
aaaaaaaaaa atccaattaa aaaaaacccc tgagaatatt caccacacca gcgaacagaa    1800
tatccctcca aaaattcagc tcaccagcac cagcacgaag aaaactctat tttcttaacc    1860
gattaattca gagccacctc cactttgcct tgtctaaata aacaaacccg taaactgttt    1920
tatacagaga cagcaaaatc ttggtttatt aaaggacagt gttactccag ataacacgta    1980
agtttcttct tgcttttcag agacctgctt tcccctcctc ccgtctcccc tctcttgcct    2040
tcttccttgc ctctcacctg taagatatta ttttatccta tgttgaaggg aggggggaaag   2100 tccccgttta tgaaagtcgc tttcttttta ttcatggact tgttttaaaa tgtaaattgc    2160
aacatagtaa tttatttta atttgtagtt ggatgtcgtg gaccaaacgc cagaaagtgt    2220
tcccaaaacc tgacgttaaa ttgcctgaaa ctttaaattg tgctttttt ctcattataa    2280 aaagggaaac tgtattaatc ttattctatc ctcttttctt tcttttttgtt gaacatattc    2340 attgtttgtt tattaataaa ttaccattca gtttgaatga gacctatatg tctggatact    2400
ttaatagagc tttaattatt acgaaaaaag atttcagaga taaaacacta gaagttacct    2460
attctccacc taaatctctg aaaaatggag aaaccctctg actagtccat gtcaaatttt    2520
actaaaagtc tttttgttta gatttatttt cctgcagcat cttctgcaaa atgtactata    2580
tagtcagctt gctttgaggc tagtaaaaag atattttct aaacagattg gagttggcat    2640
ataaacaaat acgttttctc actaatgaca gtccatgatt cggaaatttt aagcccatga    2700
atcagccgcg gtcttaccac ggtgatgcct gtgtgccgag agatgggact gtgcggccag    2760
atatgcacag ataaatattt ggcttgtgta ttccatataa aattgcagtg catattatac    2820
atccctgtga gccagatgct gaatagatat tttcctatta tttcagtcct ttataaaagg    2880
aaaaataaac cagttttttaa atgtatgtat ataattctcc cccatttaca atccttcatg    2940
tattacatag aaggattgct tttttaaaaa tatactgcgg gttggaaagg gatatttaat    3000
ctttgagaaa ctattttaga aaatatgttt gtagaacaat tattttttgaa aaagatttaa    3060 agcaataaca agaaggaagg cgagaggagc agaacatttt ggtctagggt ggtttcttt    3120 taaaccattt tttcttgtta atttacagtt aaacctaggg gacaatccgg attggcctc    3180 ccccttttgt aaataaccca ggaaatgtaa taaattcatt atcttagggt gatctgccct    3240
gccaatcaga ctttggggag atggcgattt gattacagac gttcggggg gtgggggct    3300 tgcagtttgt tttggagata atacagtttc ctgctatctg ccgctcctat ctagaggcaa    3360
cacttaagca gtaattgctg ttgcttgttg tcaaatttg atcattgtta aaggattgct    3420
gcaaataaat acactttaat ttcagtcaaa aa                                    3452

<210> SEQ ID NO 124
<211> LENGTH: 1749
```

<212> TYPE: DNA
<213> ORGANISM: Homo sapiens

<400> SEQUENCE: 124

```
gtggcctcga ggtggtggca gggccgcccc ctgcagtccg gagacgaacg cacggaccgg      60
gcctccggag gcaggttcgg ctggaaggaa ccgctctcgc ttcgtcctac acttgcgcaa     120
atgtctccga gcttactcac atagcatatt ggtatatcaa aatgaaatgc aaggaaccaa     180
aaataacata attgaaggca gtaaaagtga aattaaatag gaagatcatc agtcaaggaa     240
gacccactgg agaggacaga aaatgaagca gtgttttatc atgtgtattt cagcaggtct     300
tcttgaaatt taactaaaaa tatgactgct ctctcttcag agaactgctc ttttcagtac     360
cagttacgtc aaacaaacca gcccctagac gttaactatc tgctattctt gatcatactt     420
gggaaaatat tattaaatat ccttacacta ggaatgagaa gaaaaaacac ctgtcaaaat     480
tttatggaat attttttgcat tcactagca ttcgttgatc ttttacttt ggtaaacatt     540
tccattatat tgtatttcag ggattttgta cttttaagca ttaggttcac taaataccac     600
atctgcctat ttactcaaat tatttccttt acttatggct ttttgcatta ccagttttc     660
ctgacagctt gtatagatta ttgcctgaat ttctctaaaa caaccaagct ttcatttaag     720
tgtcaaaaat tattttattt cttttacagta attttaattt ggatttcagt ccttgcttat     780
gttttgggag acccagccat ctaccaaagc ctgaaggcac agaatgctta ttctcgtcac     840
tgtcctttct atgtcagcat tcagagttac tggctgtcat ttttcatggt gatgatttta     900
tttgtagctt tcataacctg ttgggaagaa gttactactt tggtacaggc tatcaggata     960
acttcctata tgaatgaaac tatcttatat tttccttttt catcccactc cagttatact    1020
gtgagatcta aaaaaatatt cttatccaag ctcattgtct gttttctcag tacctggtta    1080
ccatttgtac tacttcaggt aatcattgtt ttacttaaag ttcagattcc agcatatatt    1140
gagatgaata ttccctggtt atactttgtc aatagttttc tcattgctac agtgtattgg    1200
tttaattgtc acaagcttaa tttaaaagac attggattac ctttggatcc atttgtcaac    1260
tggaagtgct gcttcattcc acttacaatt cctaatcttg agcaaattga aaagcctata    1320
tcaataatga tttgttaata ttattaatta aaagttacag ctgtcataag atcataattt    1380
tatgaacaga aagaactcag gacatattaa aaaataaact gaactaaaac aacttttgcc    1440
ccctgactga tagcatttca gaatgtgtct tttgaagggc tataccagtt attaaatagt    1500
gttttatttt aaaaacaaaa taattccaag aagtttttat agttattcag ggacactata    1560
ttacaaatat tactttgtta ttaacacaaa aagtgataag agttaacatt tggctatact    1620
gatgtttgtg ttactcaaaa aaactactgg atgcaaactg ttatgtaaat ctgagatttc    1680
actgacaact ttaagatatc aacctaaaca tttttattaa atgttcaaat gtaagcaaga    1740
aaaaaaaaa                                                            1749
```

<210> SEQ ID NO 125
<211> LENGTH: 2285
<212> TYPE: DNA
<213> ORGANISM: Homo sapiens

<400> SEQUENCE: 125

```
acccgccccc atctgcccaa gataatttta gtttccttgg gcctggaatc tggacacaca      60
gggctccccc ccgcctctga cttctctgtc cgaagtcggg acaccctcct accacctgta     120
gagaagcggg agtggatctg aaataaaatc caggaatctg ggggttccta gacggagcca     180
```

| | |
|---|---|
| gacttcggaa cgggtgtcct gctactcctg ctggggctcc tccaggacaa gggcacacaa | 240 |
| ctggttccgt taagcccctc tctcgctcag acgccatgga gctggatctg tctccacctc | 300 |
| atcttagcag ctctccggaa gacctttgcc cagcccctgg gacccctcct gggactcccc | 360 |
| ggcccctga taccctctg cctgaggagg taaagaggtc ccagcctctc ctcatcccaa | 420 |
| ccaccggcag gaaacttcga gaggaggaga ggcgtgccac ctccctcccc tctatcccca | 480 |
| acccttccc tgagctctgc agtcctccct cacagagccc aattctcggg gcccctcca | 540 |
| gtgcaagggg gctgctcccc cgcgatgcca gccgccccca tgtagtaaag gtgtacagtg | 600 |
| aggatgggc ctgcaggtct gtggaggtgg cagcaggtgc cacagctcgc cacgtgtgtg | 660 |
| aaatgctggt gcagcgagct cacgccttga gcgacgagac ctggggctg gtggagtgcc | 720 |
| accccacct agcactggag cggggttttgg aggaccacga gtccgtggtg gaagtgcagg | 780 |
| ctgcctggcc cgtgggcgga gatagccgct tcgtcttccg gaaaaacttc gccaagtacg | 840 |
| aactgttcaa gagctcccca cactccctgt cccagaaaaa aatggtctcc agctgtctcg | 900 |
| atgcacacac tggtatatcc catgaagacc tcatccagaa cttcctgaat gctggcagct | 960 |
| tcctgagat ccagggcttt ctgcagctgc ggggttcagg acggaagctt tggaaacgct | 1020 |
| ttttctgctt cttgcgccga tctggcctct attactccac caagggcacc tctaaggatc | 1080 |
| cgaggcacct gcagtacgtg gcagatgtga acgagtccaa cgtgtacgtg gtgacgcagg | 1140 |
| gccgcaagct ctacgggatg cccactgact tcggtttctg tgtcaagccc aacaagcttc | 1200 |
| gaaatggcca aaggggcctt cggatcttct gcagtgaaga tgagcagagc cgcacctgct | 1260 |
| ggctggctgc cttccgcctc ttcaagtacg gggtgcagct gtacaagaat taccagcagg | 1320 |
| cacagtctcg ccatctgcat ccatcttgtt tgggctcccc acccttgaga agtgcctcag | 1380 |
| ataatacccct ggtggccatg gacttctctg gccatgctgg gcgtgtcatt gagaaccccc | 1440 |
| gggaggctct gagtgtggcc ctggaggagg cccaggcctg gaggaagaag acaaaccacc | 1500 |
| gcctcagcct gccatgcca gcctccggca cgagcctcag tgcagccatc caccgcaccc | 1560 |
| aactctggtt ccacgggcgc atttcccgtg aggagagcca gcggcttatt ggacagcagg | 1620 |
| gcttggtaga cggcctgttc ctggtccggg agagtcagcg gaaccccag ggctttgtcc | 1680 |
| tctctttgtg ccacctgcag aaagtgaagc attatctcat cctgccgagc gaggaggagg | 1740 |
| gccgcctgta cttcagcatg gatgatggcc agacccgctt cactgacctg ctgcagctcg | 1800 |
| tggagttcca ccagctgaac cgcggcatcc tgccgtgctt gctgcgccat tgctgcacgc | 1860 |
| gggtggcccct ctgaccaggc cgtggactgg ctcatgcctc agcccgcctt caggctgccc | 1920 |
| gccgcccctc cacccatcca gtggactctg ggcgcggcc acaggggacg ggatgaggag | 1980 |
| cgggagggtt ccgccactcc agttttctcc tctgcttctt tgcctccctc agatagaaaa | 2040 |
| cagcccccac tccagtccac tcctgacccc tctcctcaag ggaaggcctt gggtggcccc | 2100 |
| ctctccttct cctagctctg gaggtgctgc tctagggcag ggaattatgg gagaagtggg | 2160 |
| ggcagcccag gcggtttcac gccccacact ttgtacagac cgagaggcca gttgatctgc | 2220 |
| tctgttttat actagtgaca ataaagatta tttttgata caaaaaaaaa aaaaaaaaa | 2280 |
| aaaaa | 2285 |

<210> SEQ ID NO 126
<211> LENGTH: 935
<212> TYPE: DNA
<213> ORGANISM: Homo sapiens

<400> SEQUENCE: 126

```
agtcagaggt cgcgcaggcg ctggtacccc gttggtccgc gcgttgctgc gttgtgaggg      60
gtgtcagctc agtgcatccc aggcagctct tagtgtggag cagtgaactg tgtgtggttc     120
cttctacttg gggatcatgc agagagcttc acgtctgaag agagagctgc acatgttagc     180
cacagagcca cccccaggca tcacatgttg gcaagataaa gaccaaatgg atgacctgcg     240
agctcaaata ttaggtggag ccaacacacc ttatgagaaa ggtgttttta agctagaagt     300
tatcattcct gagaggtacc catttgaacc tcctcagatc cgatttctca ctccaattta     360
tcatccaaac attgattctg ctggaaggat ttgtctggat gttctcaaat gccaccaaa      420 aggtgcttgg agaccatccc tcaacatcgc aactgtgttg acctctattc agctgctcat     480
gtcagaaccc aaccctgatg acccgctcat ggctgacata tcctcagaat ttaaatataa     540
taagccagcc ttcctcaaga atgccagaca gtggacagaa agcatgcaa gacagaaaca      600 aaaggctgat gaggaagaga tgcttgataa tctaccagag gctggtgact ccagagtaca     660
caactcaaca cagaaaagga aggccagtca gctagtaggc atagaaaaga aatttcatcc     720
tgatgtttag gggacttgtc ctggttcatc ttagttaatg tgttctttgc caaggtgatc     780
taagttgcct accttgaatt ttttttttaaa tatatttgat gacataattt ttgtgtagtt    840
tatttatctt gtacatatgt attttgaaat cttttaaacc tgaaaaataa atagtcattt     900
aatgttgaaa aaaaaaaaaa aaaaaaaaaa aaaaa                                935
```

<210> SEQ ID NO 127
<211> LENGTH: 2896
<212> TYPE: DNA
<213> ORGANISM: Homo sapiens

<400> SEQUENCE: 127

```
acgcttgcgc gcgggattta aactgcggcg gtttacgcgg cgttaagact tcgtagggtt      60
agcgaaattg aggtttcttg gtattgcgcg tttctcttcc ttgctgactc tccgaatggc     120
catggactcg tcgcttcagg cccgcctgtt tcccggtctc gctatcaaga tccaacgcag     180
taatggttta attcacagtg ccaatgtaag gactgtgaac ttggagaaat cctgtgtttc     240
agtggaatgg gcagaaggag gtgccacaaa gggcaaagag attgattttg atgatgtggc     300
tgcaataaac ccagaactct tacagcttct tcccttacat ccgaaggaca atctgccctt     360
gcaggaaaat gtaacaatcc agaaacaaaa acggagatcc gtcaactcca aaattcctgc     420
tccaaaagaa agtcttcgaa gccgctccac tcgcatgtcc actgtctcag agcttcgcat     480
cacggctcag gagaatgaca tggaggtgga gctgcctgca gctgcaaact cccgcaagca     540
gttttcagtt cctcctgccc ccactaggcc ttcctgccct gcagtggctg aaataccatt     600
gaggatggtc agcgaggaga tggaagagca agtccattcc atccgaggca gctcttctgc     660
aaaccctgtg aactcagttc ggaggaaatc atgtcttgtg aaggaagtgg aaaaaatgaa     720
gaacaagcga gaagagaaga aggcccagaa ctctgaaatg agaatgaaga gagctcagga     780
gtatgacagt agttttccaa actgggaatt tgcccgaatg attaaagaat tcgggctac      840 tttggaatgt catccactta ctatgactga tcctatcgaa gagcacagaa tatgtgtctg     900
tgttaggaaa cgcccactga ataagcaaga attggccaaa aagaaattg atgtgatttc      960 cattcctagc aagtgtctcc tcttggtaca tgaacccaag ttgaaagtgg acttaacaaa    1020
gtatctggag aaccaagcat tctgctttga ctttgcattt tgatgaaacag cttcgaatga    1080 agttgtctac aggttcacag caaggccact ggtacagaca atctttgaag gtggaaaagc    1140
```

```
aacttgtttt gcatatggcc agacaggaag tggcaagaca catactatgg gcggagacct    1200
ctctgggaaa gcccagaatg catccaaagg gatctatgcc atggcctccc gggacgtctt    1260
cctcctgaag aatcaaccct gctaccggaa gttgggcctg gaagtctatg tgacattctt    1320
cgagatctac aatgggaagc tgtttgacct gctcaacaag aaggccaagc tgcgcgtgct    1380
ggaggacggc aagcaacagg tgcaagtggt ggggctgcag gagcatctgg ttaactctgc    1440
tgatgatgtc atcaagatga tcgacatggg cagcgcctgc agaacctctg gcagacatt     1500 tgccaactcc aattcctccc gctcccacgc gtgcttccaa attattcttc gagctaaagg    1560
gagaatgcat ggcaagttct ctttggtaga tctggcaggg aatgagcgag cgcggacac     1620 ttccagtgct gaccggcaga cccgcatgga gggcgcagaa atcaacaaga gtctcttagc    1680
cctgaaggag tgcatcaggg ccctgggaca gaacaaggct cacacccgt tccgtgagag     1740 caagctgaca caggtgctga gggactcctt cattggggag aactctagga cttgcatgat    1800
tgccacgatc tcaccaggca taagctcctg tgaatatact ttaaacaccc tgagatatgc    1860
agacagggtc aaggagctga gcccccacag tgggcccagt ggagagcagt tgattcaaat    1920
ggaaacagaa gagatggaag cctgctctaa cggggcgctg attccaggca atttatccaa    1980
ggaagaggag gaactgtctt cccagatgtc cagctttaac gaagccatga ctcagatcag    2040
ggagctggag gagaaggcta tggaagagct caaggagatc atacagcaag gaccagactg    2100
gcttgagctc tctgagatga ccgagcagcc agactatgac ctggagacct tgtgaacaa     2160 agcggaatct gctctggccc agcaagccaa gcatttctca gccctgcgag atgtcatcaa    2220
ggccttgcgc ctggccatgc agctggaaga gcaggctagc agacaaataa gcagcaagaa    2280
acggccccag tgacgactgc aaataaaaat ctgtttggtt tgacacccag cctcttccct    2340
ggccctcccc agagaacttt gggtacctgg tgggtctagg cagggtctga gctgggacag    2400
gttctggtaa atgccaagta tgggggcatc tgggcccagg gcagctgggg aggggtcag    2460 agtgacatgg gacactcctt ttctgttcct cagttgtcgc cctcacgaga ggaaggagct    2520
cttagttacc cttttgtgtt gcccttcttt ccatcaaggg gaatgttctc agcatagagc    2580
tttctccgca gcatcctgcc tgcgtggact ggctgctaat ggagagctcc ctggggttgt    2640
cctggctctg gggagagaga cggagccttt agtacagcta tctgctggct ctaaaccttc    2700
tacgcctttg ggccgagcac tgaatgtctt gtactttaaa aaaatgtttc tgagacctct    2760
ttctacttta ctgtctccct agagatccta gaggatccct actgttttct gttttatgtg    2820
tttatacatt gtatgtaaca ataaagagaa aaataaatc agctgtttaa gtgtgtggaa     2880
aaaaaaaaaa aaaaaa                                                    2896
```

<210> SEQ ID NO 128
<211> LENGTH: 2209
<212> TYPE: DNA
<213> ORGANISM: Homo sapiens

<400> SEQUENCE: 128

```
actgcgcgcg tcgtgcgtaa tgacgtcagc gccggcggag aatttcaaat tcgaacggct      60
ttggcgggcc gaggaaggac ctggtgtttt gatgaccgct gtcctgtcta gcagatactt     120
gcacggttta cagaaattcg gtccctgggt cgtgtcagga aactggaaaa aaggtcataa     180
gcatgaagcg cagttcagtt tccagcggtg gtgctggccg cctctccatg caggagttaa     240
gatcccagga tgtaaataaa caaggcctct ataccctca aaccaaagag aaaccaacct      300
ttggaaagtt gagtataaac aaaccgacat ctgaaagaaa agtctcgcta tttggcaaaa     360
```

```
gaactagtgg acatggatcc cggaatagtc aacttggtat attttccagt tctgagaaaa    420
tcaaggaccc gagaccactt aatgacaaag cattcattca gcagtgtatt cgacaactct    480
gtgagtttct tacagaaaat ggttatgcac ataatgtgtc catgaaatct ctacaagctc    540
cctctgttaa agacttcctg aagatcttca catttctta tggcttcctg tgcccctcat     600
acgaacttcc tgacacaaag tttgaagaag aggttccaag aatctttaaa gaccttgggt    660 atcctttgc  actatccaaa agctccatgt acacagtggg ggctcctcat acatggcctc     720
acattgtggc agccttagtt tggctaatag actgcatcaa gatacatact gccatgaaag    780
aaagctcacc tttatttgat gatgggcagc cttggggaga agaaactgaa gatggaatta    840
tgcataataa gttgtttttg gactacacca taaaatgcta tgagagtttt atgagtggtg    900
ccgacagctt tgatgagatg aatgcagagc tgcagtcaaa actgaaggat ttatttaatg    960
tggatgcttt taagctggaa tcattagaag caaaaaacag agcattgaat gaacagattg   1020
caagattgga acaagaaaga gaaaagaac cgaatcgtct agagtcgttg agaaaactga   1080
aggcttcctt acaaggagat gttcaaaagt atcaggcata catgagcaat ttggagtctc   1140
attcagccat tcttgaccag aaattaaatg gtctcaatga ggaaattgct agagtagaac   1200
tagaatgtga aacaataaaa caggagaaca ctcgactaca gaatatcatt gacaaccaga   1260
agtactcagt tgcagacatt gagcgaataa atcatgaaag aaatgaattg cagcagacta   1320
ttaataaatt aaccaaggac ctggaagctg aacaacagaa gttgtggaat gaggagttaa   1380
aatatgccag aggcaaagaa gcgattgaaa cacaattagc agagtatcac aaattggcta   1440
gaaaattaaa acttattcct aaaggtgctg agaattccaa aggttatgac tttgaaatta   1500
agtttaatcc cgaggctggt gccaactgcc ttgtcaaata cagggctcaa gtttatgtac   1560
ctcttaagga actcctgaat gaaactgaag aagaaattaa taaagcccta aataaaaaaa   1620
tgggtttgga ggatacttta gaacaattga atgcaatgat aacagaaagc aagagaagtg   1680
tgagaactct gaaagaagaa gttcaaaagc tggatgatct ttaccaacaa aaaattaagg   1740
aagcagagga gaggatgaa aaatgtgcca gtgagcttga gtccttggag aaacacaagc   1800
acctgctaga aagtactgtt aaccaggggc tcagtgaagc tatgaatgaa ttagatgctg   1860
ttcagcggga ataccaacta gttgtgcaaa ccacgactga agaaagacga aaagtgggaa   1920
ataacttgca acgtctgtta gagatggttg ctacacatgt tgggtctgta gagaaacatc   1980
ttgaggagca gattgctaaa gttgatagag aatatgaaga atgcatgtca gaagatctct   2040
cggaaaatat taaagagatt agagataagt atgaagaaga agctactcta attaagtctt   2100
ctgaagaatg aagataaaat gttgatcatg tatatatatc catagtgaat aaaattgtct   2160
cagtaaagtg taaaaaaaaa aaaaaaaaaa aaaaaaaaaa aaaaaaaa              2209
```

<210> SEQ ID NO 129
<211> LENGTH: 1740
<212> TYPE: DNA
<213> ORGANISM: Homo sapiens

<400> SEQUENCE: 129

```
ctccctcctc tgcaccatga ctacctgcag ccgccagttc acctcctcca gctccatgaa     60
gggctcctgc ggcatcgggg gcggcatcgg gggcggctcc agccgcatct cctccgtcct    120
ggccggaggg tcctgccgcg cccccagcac ctacgggggc ggcctgtctg tctcatcctc    180
ccgcttctcc tctgggggag cctatgggtt ggggggcggc tatggcggtg gcttcagcag    240
```

| | |
|---|---|
| cagcagcagc agctttggta gtggctttgg gggaggatat ggtggtggcc ttggtgctgg | 300 |
| cttgggtggt ggctttggtg gtggctttgc tggtggtgat gggcttctgg tgggcagtga | 360 |
| gaaggtgacc atgcagaacc tcaacgaccg cctggcctcc tacctggaca aggtgcgtgc | 420 |
| tctggaggag gccaacgccg acctggaagt gaagatccgt gactggtacc agaggcagcg | 480 |
| gcctgctgag atcaaagact acagtcccta cttcaagacc attgaggacc tgaggaacaa | 540 |
| gattctcaca gccacagtgg acaatgccaa tgtccttctg cagattgaca atgcccgtct | 600 |
| ggccgcggat gacttccgca ccaagtatga cacagagttg aacctgcgca tgagtgtgga | 660 |
| agccgacatc aatggcctgc gcagggtgct ggacgaactg accctggcca gagctgacct | 720 |
| ggagatgcag attgagagcc tgaaggagga gctggcctac ctgaagaaga ccacgaggga | 780 |
| ggagatgaat gccctgagag ccaggtgggt ggagatgtc aatgtggaga tggacgctgc | 840 |
| acctggcgtg gacctgagcc gcattctgaa cgagatgcgt gaccagtatg agaagatggc | 900 |
| agagaagaac cgcaaggatg ccgaggaatg gttcttcacc aagacagagg agctgaaccg | 960 |
| cgaggtggcc accaacagcg agctggtgca gagcggcaag agcgagatct cggagctccg | 1020 |
| gcgcaccatg cagaacctgg agattgagct gcagtcccag ctcagcatga agcatccct | 1080 |
| ggagaacagc ctggaggaga ccaaaggtcg ctactgcatg cagctggccc agatccagga | 1140 |
| gatgattggc agcgtggagg agcagctggc ccagctccgc tgcgagatgg agcagcagaa | 1200 |
| ccaggagtac aagatcctgc tggacgtgaa gacgcggctg gagcaggaga tcgccaccta | 1260 |
| ccgccgcctg ctggagggcg aggacgccca cctctcctcc tcccagttct cctctggatc | 1320 |
| gcagtcatcc agagatgtga cctcctccag ccgccaaatc cgcaccaagg tcatggatgt | 1380 |
| gcacgatggc aaggtggtgt ccacccacga gcaggtcctt cgcaccaaga actgaggctg | 1440 |
| cccagccccg ctcaggccta ggaggccccc cgtgtggaca cagatcccac tggaagatcc | 1500 |
| cctctcctgc ccaagcactt cacagctgga ccctgcttca ccctcacccc ctcctggcaa | 1560 |
| tcaatacagc ttcattatct gagttgcata aaaaaaaaaa aaaaaaaaaa aaaaaaaaaa | 1620 |
| aaaaaaaaaa aaaaaaaaaa aaaaaaaaaa aaaaaaaaaa aaaaaaaaaa aaaaaaaaaa | 1680 |
| aaaaaaaaaa aaaaaaaaaa aaaaaaaaaa aaaaaaaaaa aaaaaaaaaa aaaaaaaaaa | 1740 |

<210> SEQ ID NO 130
<211> LENGTH: 2895
<212> TYPE: DNA
<213> ORGANISM: Homo sapiens

<400> SEQUENCE: 130

| | |
|---|---|
| ctcttttgca ggggccgttc ctcggggcat gacgctggct cctgcacaga tcctgctcct | 60 |
| ctgtggcctt cctgggctgc cctcccctcc tccgggactg ctctggactg acactgctca | 120 |
| ggttcggatt ccctcaaaga ctttgggaga caagacttgg tcccccttt acaaacaagg | 180 |
| gaacggaggc tctagaactg acttcctgaa aggcttggat ccaaagctcc ctcagttcag | 240 |
| cggccacgtc tatttccctc agacacaggg atccttgaac ctgtgggctg tatctccccg | 300 |
| cggacttgga agaatcccaa gagagtgggg ctcccacagg ctggagtgca atggtgtgat | 360 |
| ctcggctcac tgcaacctcc acctcccagg ttcaagctat tctcctgcct cagcctcctg | 420 |
| agtagctggg attacagatc ctggtggctg tggtcggtaa ttccagcttc gtgctggcta | 480 |
| caggtggatg atgcccacct ggctgccgat gacctctgca ccaagtgagg ctgggtctct | 540 |
| ggagctgccc caggggctgg acaagctgac cctggccggg gccaacctgg agatgcagat | 600 |
| tgagaaccte aaggaggacc tggtctacct gaagaagaac cacaagcagg aaatgaacgt | 660 |

```
cctttgaggt caggtggatg aggatgtcag tgtgaagatg gacactgtgc ctggagtgaa    720
cctgagctgc atcctgaatg agatgcgtga ccaggacaag acattggtgg agaagagctg    780
caaggatgcc gagggctggt tcttcagcat ggtgggtggc cgtgcgtaag caggtgtgta    840
cacgtgtggg cacatgtgct gcatgctggt gcagctggag cactggcaga tccacaggct    900
gtcccagttg gaaggacttt tggaaaccag ttggaccagc ccctcatgtt ttagatgtaa    960
aacgtgaggc tcagagagga ctcaagctca cacagccctt cactgtggcc tgcaaaatag   1020
atccaggtct ctacaagtct ggtcttgggt ttccaccaca gctgtttaca ggatgtgcgt   1080
atttgaatac atatgtatac ccttggcaag cacaggctga gtatctccgg tatcctaggg   1140
acagcaacag gcgcaaaaga ataacaccca gtgcctgtct ttgaggtgct gcagttcagt   1200
aggaaaaaga aatgcaaatg accgcagagc aggctgaatt cctccaagtt ccaatgtggg   1260
tgcagaggct ctctgtgtgc agaaagaggg gctgaactgc gaggtggcca ccaacacaga   1320
ggccctgcag agtggctgga tagagatatg gagctctacg tctctgtgca gaacctgagc   1380
cgtcccagct cagcaagaaa gcatcgctgg agggcagcct ggtggagatg gaggtgtgtt   1440
acaggaccct gccggcccag ctgcaggggc ttaacagaag catggagcag cagctgtgcg   1500
agctctgctg cgacacggag caccaggacc acaagcacag gtccttctgg acgtgaagac   1560
gtggctggag caggagatcg ccacctaccg ccgcttgctg gaggttgagg acgcccagag   1620
gtgatactga cgatgcaggc tggagtctgg ctgaggagcc ttgaatgcca agttaaagcg   1680
tctggactag atcacgtagg caatggggag ccatggaggg atttggagca ggagagtgaa   1740
atgaacatca agagatttta gaacattcac tctggctgca gagggagaaa tggatcagag   1800
gggtcagggc ggggccagag agatgtgtca gggggctgga gcaggagtc tggccagaga   1860
agtcccgtgc ggtggtgggt agtggggcag gggaaggaag gtggtgcacg cagaagagag   1920
gttatagctc aaaacagcgg gactggatgc ctggatctcg gggtaagcat ggctcacagt   1980
caggactcag taagtgtcgg gagaacacat gaaggagcag gcattgatgg ccctgggttt   2040
ctggttctga tgactgtgtg agtggtgaag agcaaggtgg gtggtggttg ggtttgcagt   2100
tgggaagggt gatcaggcct tcagctgaga gtgtcccgga gtctccatgc ttagtcacac   2160
gttgcagctt tttgctcccc ggaaatggtg aagtccatct atagtctaac aacagtctct   2220
cctgctttaa ttgggtctat ttgttgggcc ctctgggtta tggaaaaacc acttgctcag   2280
cttctccttg taaattcctg gtgagtagcc acagagtgcc gccagaccta ctgctgtgct   2340
gtttcttttt cttcttcctg ctgtgctgaa cccctgccct tcattcttg ggcctgcgct   2400
aatttctgtg cattcccaac tgtgatttt caccaattta ggggaacctc ctctgccagg   2460
gcctacttct cccagcagt gcttgcaggt gcctgggctg gctggcatcc ctgggctgat   2520
gggtgcttct ctccctgcag gctggccact cagtactcct tgtccctggc ctcgcagccc   2580
acccgggaag ccacagtgac cagccaccag gtgtgccatc gtgaggaag tccaggttgg   2640
agaggtggtc ttcttctgtg agcaggtcca cttctccacc cactgagacc cctttctgtc   2700
tgcgacagcc ccacctcgag ggccacggca cagccatcag ctccagctcc cagcatgcta   2760
ctgccacgcc ccgagtgtcc gtctgggccc cggtgcatgg cctgttgtct ttctgtatct   2820
actttctgca gcccctcact gaggaggcct cctgggtttg tccagtgcct actattaaag   2880
ctttgctcca agttc                                                   2895

<210> SEQ ID NO 131
```

<211> LENGTH: 2529
<212> TYPE: DNA
<213> ORGANISM: Homo sapiens

<400> SEQUENCE: 131

```
gcatccttttt tgggctgctc acagccccca gcctctatgg tgaagacata cttgctagca      60
gcgtcaccaa cttgctgcca agagatcagt gctgcaaggc aaggttattt ctaactgagc     120
agagcctgcc aggaagaaag cgtttgcacc ccacaccact gtgcaggtgt gaccggtgag     180
ctcacagctg cccccccaggc atgcccagcc cacttaatca ttcacagctc gacagctctc    240
tcgcccagcc cagttctgga agggataaaa aggggggcatc accgttcctg ggtaacagag    300
ccaccttctg cgtcctgctg agctctgttc tctccagcac ctcccaaccc actagtgcct     360
ggttctcttg ctccaccagg aacaagccac catgtctcgc cagtcaagtg tgtccttccg     420
gagcggggggc agtcgtagct tcagcaccgc ctctgccatc accccgtctg tctcccgcac    480
cagcttcacc tccgtgtccc ggtccggggg tggcggtggt ggtggcttcg gcagggtcag     540
ccttgcgggt gcttgtggag tgggtggcta tggcagccgg agcctctaca acctgggggg    600
ctccaagagg atatccatca gcactagagg aggcagcttc aggaaccggt ttggtgctgg     660
tgctggaggc ggctatggct ttggaggtgg tgccggtagt ggatttggtt tcggcggtgg    720
agctggtggt ggcttttggc tcggtggcgg agctggcttt ggaggtggct tcggtggccc    780
tggctttcct gtctgccctc ctggaggtat ccaagaggtc actgtcaacc agagtctcct    840
gactcccctc aacctgcaaa tcgaccccag catccagagg gtgaggaccg aggagcgcga    900
gcagatcaag accctcaaca taagtttgc ctccttcatc gacaaggtgc ggttcctgga     960
gcagcagaac aaggttctgg acaccaagtg gacctgctg caggagcagg gcaccaagac    1020
tgtgaggcag aacctggagc cgttgttcga gcagtacatc aacaacctca ggaggcagct    1080
ggacagcatc gtgggggaac ggggccgcct ggactcagag ctgagaaaca tgcaggacct    1140
ggtggaagac ttcaagaaca gtatgaggat gaaatcaac aagcgtacca ctgctgagaa    1200
tgagtttgtg atgctgaaga aggatgtaga tgctgcctac atgaacaagg tggagctgga    1260
ggccaaggtt gatgcactga tggatgagat taacttcatg aagatgttct ttgatgcgga    1320
gctgtcccag atgcagacgc atgtctctga cacctcagtg gtcctctcca tggacaacaa    1380
ccgcaacctg gacctggata gcatcatcgc tgaggtcaag gcccagtatg aggagattgc    1440
caaccgcagc cggacagaag ccgagtcctg gtatcagacc aagtatgagg agctgcagca    1500
gacagctggc cggcatggcg atgacctccg caacaccaag catgagatca cagagatgaa    1560
ccggatgatc cagaggctga gagccgagat tgacaatgtc aagaaacagt gcgccaatct    1620
gcagaacgcc attgcggatg ccgagcagcg tgggagctg gccctcaagg atgccaggaa    1680
caagctggcc gagctggagg aggccctgca gaaggccaag caggacatgg cccggctgct    1740
gcgtgagtac caggagctca tgaacaccaa gctggccctg gacgtggaga tcgccactta    1800
ccgcaagctg ctgagggcg aggaatgcag actcagtgga gaaggagttg gaccagtcaa    1860
catctctgtt gtcacaagca gtgtttcctc tggatatggc agtggcagtg ctatggcgg    1920
tggcctcggt ggaggtcttg gcggcggcct cggtggaggt cttgccggag gtagcagtgg    1980
aagctactac tccagcagca gtgggggtgt cggcctaggt ggtgggctca gtgtgggggg    2040
ctctggcttc agtgcaagca gtggccgagg gctgggggtg ggctttgca gtggcgggg    2100
tagcagctcc agcgtcaaat ttgtctccac cacctcctcc tcccggaaga gcttcaagag    2160
ctaagaacct gctgcaagtc actgccttcc aagtgcagca acccagccca tggagattgc    2220
```

```
ctcttctagg cagttgctca agccatgttt tatccttttc tggagagtag tctagaccaa    2280
gccaattgca gaaccacatt ctttggttcc caggagagcc ccattcccag ccctggtct     2340 cccgtgccgc agttctatat tctgcttcaa atcagccttc aggtttccca cagcatggcc    2400
cctgctgaca cgagaaccca aagttttccc aaatctaaat catcaaaaca gaatccccac    2460
cccaatccca aattttgttt tggttctaac tacctccaga atgtgttcaa taaaatgctt    2520
ttataatat                                                            2529
```

<210> SEQ ID NO 132  
<211> LENGTH: 6816  
<212> TYPE: DNA  
<213> ORGANISM: Homo sapiens

<400> SEQUENCE: 132

```
ggacggccga gcggcagggc gctcgcgcgc gcccactagt ggccggagga aaggctccc      60 gcggaggccg cgctgcccgc cccctcccct ggggaggctc gcgttcccgc tgctcgcgcc    120
tgcgccgccc gccggcctca ggaacgcgcc ctcttcgccg gcgcgcgccc tcgcagtcac    180
cgccacccac cagctccggc accaacagca gcgccgctgc caccgcccac cttctgccgc    240
cgccaccaca gccaccttct cctcctccgc tgtcctctcc cgtcctcgcc tctgtcgact    300
atcaggtgaa ctttgaacca ggatggctga gccccgccag gagttcgaag tgatggaaga    360
tcacgctggg acgtacgggt tggggacag gaaagatcag gggggctaca ccatgcacca    420
agaccaagag ggtgacacgg acgctggcct gaaagaatct cccctgcaga cccccactga    480
ggacggatct gaggaaccgg gctctgaaac ctctgatgct aagagcactc caacagcgga    540
agatgtgaca gcacccttag tggatgaggg agctcccggc aagcaggctg ccgcgcagcc    600
ccacacggag atcccagaag gaaccacagc tgaagaagca ggcattggag acaccccag     660 cctggaagac gaagctgctg gtcacgtgac ccaagagcct gaaagtggta aggtggtcca    720
ggaaggcttc ctccgagagc caggcccccc aggtctgagc caccagctca tgtccggcat    780
gcctggggct cccctcctgc ctgagggcc cagagaggcc acacgccaac cttcggggac     840
aggacctgag gacacagagg gcggccgcca cgcccctgag ctgctcaagc accagcttct    900
aggagacctg caccaggagg ggccgccgct gaaggggca ggggcaaag agaggccggg      960 gagcaaggag gaggtggatg aagaccgcga cgtcgatgag tcctcccccc aagactcccc   1020 tcccctccaag gcctcccag cccaagatgg gcggcctccc cagacagccg ccagagaagc    1080
caccagcatc ccaggcttcc cagcggaggg tgccatcccc ctccctgtgg atttcctctc    1140
caaagtttcc acagagatcc cagcctcaga gcccgacggg cccagtgtag ggcgggccaa    1200
agggcaggat gcccctctgg agttcacgtt tcacgtggaa atcacaccca acgtgcagaa    1260
ggagcaggcg cactcggagg agcatttggg aagggctgca tttccagggg ccctggaga    1320 ggggccagag gccggggcc cctctttggg agaggacaca aaagaggctg accttccaga     1380
gccctctgaa aagcagcctg ctgctgctcc gcggggaag cccgtcagcc gggtccctca    1440
actcaaagct cgcatggtca gtaaaagcaa agacgggact ggaagcgatg acaaaaaagc    1500
caagacatcc acacgttcct ctgctaaaac cttgaaaaat aggccttgcc ttagccccaa    1560
acaccccact cctggtagct cagaccctct gatccaaccc tccagccctg ctgtgtgccc    1620
agagccacct tcctctccta atacgtctc ttctgtcact tccgaactg gcagttctgg      1680 agcaaaggag atgaaactca ggggggctga tggtaaaacg aagatcgcca caccgcgggg    1740
```

| | |
|---|---|
| agcagcccct ccaggccaga agggccaggc caacgccacc aggattccag caaaaacccc | 1800 |
| gcccgctcca aagacaccac ccagctctgc gactaagcaa gtccagagaa gaccacccc | 1860 |
| tgcagggccc agatctgaga gaggtgaacc tccaaaatca ggggatcgca gcggctacag | 1920 |
| cagccccggc tccccaggca ctcccggcag ccgctcccgc accccgtccc ttccaacccc | 1980 |
| acccacccgg gagcccaaga aggtggcagt ggtccgtact ccacccaagt cgccgtcttc | 2040 |
| cgccaagagc cgcctgcaga cagccccgt gccatgcca gacctgaaga atgtcaagtc | 2100 |
| caagatcggc tccactgaga acctgaagca ccagccggga ggcgggaagg tgcagataat | 2160 |
| taataagaag ctggatctta gcaacgtcca gtccaagtgt ggctcaaagg ataatatcaa | 2220 |
| acacgtcccg ggaggcggca gtgtgcaaat agtctacaaa ccagttgacc tgagcaaggt | 2280 |
| gacctccaag tgtggctcat taggcaacat ccatcataaa ccaggaggtg gccaggtgga | 2340 |
| agtaaaatct gagaagcttg acttcaagga cagagtccag tcgaagattg ggtccctgga | 2400 |
| caatatcacc cacgtccctg gcggaggaaa taaaaagatt gaaacccaca agctgacctt | 2460 |
| ccgcgagaac gccaaagcca agacagacca cggggcggga atcgtgtaca agtcgccagt | 2520 |
| ggtgtctggg gacacgtctc cacggcatct cagcaatgtc tcctccaccg gcagcatcga | 2580 |
| catggtagac tcgccccagc tcgccacgct agctgacgag gtgtctgcct ccctggccaa | 2640 |
| gcagggtttg tgatcaggcc cctggggcgg tcaataattg tggagaggag agaatgagag | 2700 |
| agtgtggaaa aaaaagaat aatgaccggg ccccgccct ctgccccag ctgctcctcg | 2760 |
| cagttcggtt aattggttaa tcacttaacc tgcttttgtc actcggcttt ggctcgggac | 2820 |
| ttcaaaatca gtgatgggag taagagcaaa tttcatcttt ccaaattgat gggtgggcta | 2880 |
| gtaataaaat attaaaaaa aaacattcaa aaacatggcc acatccaaca tttcctcagg | 2940 |
| caattccttt tgattctttt ttcttccccc tccatgtaga agaggagaa ggagaggctc | 3000 |
| tgaaagctgc ttctggggga tttcaaggga ctggggtgc caaccacctc tggccctgtt | 3060 |
| gtggggtgt cacagaggca gtggcagcaa caaaggattt gaaacttggt gtgttcgtgg | 3120 |
| agccacaggc agacgatgtc aaccttgtgt gagtgtgacg ggggttgggg tggggcggga | 3180 |
| ggccacgggg gaggccgagg caggggctgg gcagaggga gaggaagcac aagaagtggg | 3240 |
| agtgggagag gaagccacgt gctggagagt agacatcccc ctccttgccg ctgggagagc | 3300 |
| caaggcctat gccacctgca gcgtctgagc ggccgcctgt ccttggtggc cggggggtggg | 3360 |
| ggcctgctgt gggtcagtgt gccacccctct gcagggcagc ctgtgggaga agggacagcg | 3420 |
| ggtaaaaaga gaaggcaagc tggcaggagg gtggcacttc gtggatgacc tccttagaaa | 3480 |
| agactgacct tgatgtcttg agagcgctgg cctcttcctc cctccctgca gggtagggg | 3540 |
| cctgagttga ggggcttccc tctgctccac agaaaccctg ttttattgag ttctgaaggt | 3600 |
| tggaactgct gccatgattt tggccacttt gcagacctgg gactttaggg ctaaccagtt | 3660 |
| ctctttgtaa ggacttgtgc ctcttgggag acgtccaccc gtttccaagc ctgggccact | 3720 |
| ggcatctctg gagtgtgtgg gggtctggga ggcaggtccc gagcccctg tccttcccac | 3780 |
| ggccactgca gtcaccccgt ctgcgccgct gtgctgttgt ctgccgtgag agcccaatca | 3840 |
| ctgcctatac ccctcatcac acgtcacaat gtcccgaatt cccagcctca cccccttc | 3900 |
| tcagtaatga ccctggttgg ttgcaggagg tacctactcc atactgaggg tgaaattaag | 3960 |
| ggaaggcaaa gtccaggcac aagagtggga ccccagcctc tcactctcag ttccactcat | 4020 |
| ccaactggga ccctcaccac gaatctcatg atctgattcg gttccctgtc tcctcctccc | 4080 |
| gtcacagatg tgagccaggg cactgctcag ctgtgaccct aggtgttct gccttgttga | 4140 |

```
catggagaga gcccttcccc ctgagaaggc ctggccccctt cctgtgctga gcccacagca    4200
gcaggctggg tgtcttggtt gtcagtggtg caccaggat ggaagggcaa ggcacccagg     4260
gcaggcccac agtcccgctg tcccccactt gcacctagc ttgtagctgc caacctccca     4320
gacagcccag cccgctgctc agctccacat gcatagtatc agccctccac acccgacaaa    4380
ggggaacaca ccccttgga aatggttctt ttcccccagt cccagctgga agccatgctg     4440
tctgttctgc tggagcagct gaacatatac atagatgttg ccctgccctc ccatctgca    4500 ccctgttgag ttgtagttgg atttgtctgt ttatgcttgg attcaccaga gtgactatga    4560
tagtgaaaag aaaaaaaaaa aaaaaaagg acgcatgtat cttgaaatgc ttgtaaagag     4620
gtttctaacc caccctcacg aggtgtctct cacccccaca ctgggactcg tgtggcctgt    4680
gtggtgccac cctgctgggg cctcccaagt tttgaaaggc tttcctcagc acctgggacc    4740
caacagagac cagcttctag cagctaagga ggccgttcag ctgtgacgaa ggcctgaagc    4800
acaggattag gactgaagcg atgatgtccc cttccctact tccccttggg gctccctgtg    4860
tcagggcaca gactaggtct tgtggctggt ctggcttgcg gcgcgaggat ggttctctct    4920
ggtcatagcc cgaagtctca tggcagtccc aaaggaggct tacaactcct gcatcacaag    4980
aaaaaggaag ccactgccag ctgggggggat ctgcagctcc cagaagctcc gtgagcctca    5040
gccacccctc agactgggtt cctctccaag ctcgccctct ggaggggcag cgcagcctcc    5100
caccaagggc cctgcgacca cagcagggat tgggatgaat tgcctgtcct ggatctgctc    5160
tagaggccca agctgcctgc ctgaggaagg atgacttgac aagtcaggag acactgttcc    5220
caaagccttg accagagcac ctcagcccgc tgaccttgca caaactccat ctgctgccat    5280
gagaaaaggg aagccgcctt tgcaaaacat tgctgcctaa agaaactcag cagcctcagg    5340
cccaattctg ccacttctgg tttgggtaca gttaaaggca accctgaggg acttggcagt    5400
agaaatccag ggcctcccct ggggctggca gcttcgtgtg cagctagagc tttacctgaa    5460
aggaagtctc tgggcccaga actctccacc aagagcctcc ctgccgttcg ctgagtccca    5520
gcaattctcc taagttgaag ggatctgaga aggagaagga aatgtggggt agatttggtg    5580
gtggttagag atatgccccc ctcattactg ccaacagttt cggctgcatt tcttcacgca    5640
cctcggttcc tcttcctgaa gttcttgtgc cctgctcttc agcaccatgg gccttcttat    5700
acggaaggct ctgggatctc cccccttgtgg ggcaggctct tggggccagc ctaagatcat    5760 ggttttagggt gatcagtgct ggcagataaa ttgaaaaggc acgctggctt gtgatcttaa    5820
atgaggacaa tccccccagg gctgggcact cctccccctcc cctcacttct cccacctgca    5880
gagccagtgt ccttgggtgg gctagatagg atatactgta tgccggctcc ttcaagctgc    5940
tgactcactt tatcaatagt tccatttaaa ttgacttcag tggtgagact gtatcctgtt    6000
tgctattgct tgttgtgcta tggggggagg gggaggaat gtgtaagata gttaacatgg    6060
gcaaagggag atcttgggt gcagcactta aactgcctcg taacccttt catgatttca    6120 accacattgg ctagagggag ggagcagcca cggagttaga ggcccttggg gtttctctt    6180 tccactgaca ggcttttccca ggcagctggc tagttcattc cctcccccagc caggtgcagg    6240 cgtaggaata tggacatctg gttgctttgg cctgctgccc tctttcaggg gtcctaagcc    6300
cacaatcatg cctccctaag accttggcat ccttccctct aagccgttgg cacctctgtg    6360
ccacctctca cactggctcc agacacacag cctgtgcttt tggagctgag atcactcgct    6420
tcaccctcct catctttgtt ctccaagtaa agccacgagg tcggggcgag ggcagaggtg    6480
```

-continued

| | |
|---|---|
| atcacctgcg tgtcccatct acagacctgc agcttcataa aacttctgat ttctcttcag | 6540 |
| ctttgaaaag ggttaccctg ggcactggcc tagagcctca cctcctaata gacttagccc | 6600 |
| catgagtttg ccatgttgag caggactatt tctggcactt gcaagtccca tgatttcttc | 6660 |
| ggtaattctg agggtggggg gagggacatg aaatcatctt agcttagctt tctgtctgtg | 6720 |
| aatgtctata tagtgtattg tgtgttttaa caaatgattt acactgactg ttgctgtaaa | 6780 |
| agtgaatttg gaaataaagt tattactctg attaaa | 6816 |

<210> SEQ ID NO 133
<211> LENGTH: 2372
<212> TYPE: DNA
<213> ORGANISM: Homo sapiens

<400> SEQUENCE: 133

| | |
|---|---|
| gcaccgcgcg agcttggctg cttctggggc ctgtgtggcc ctgtgtgtcg gaaagatgga | 60 |
| gcaagaagcc gagcccgagg ggcggccgcg acccctctga ccgagatcct gctgctttcg | 120 |
| cagccaggag caccgtccct ccccggatta gtgcgtacga gcgccagtg ccctggcccg | 180 |
| gagagtggaa tgatccccga ggcccagggc gtcgtgcttc cgcagtagtc agtccccgtg | 240 |
| aaggaaactg gggagtcttg agggaccccc gactccaagc gcgaaaaccc cggatggtga | 300 |
| ggagcaggca aatgtgcaat accaacatgt ctgtacctac tgatggtgct gtaaccacct | 360 |
| cacagattcc agcttcggaa caagagaccc tggttagacc aaagccattg cttttgaagt | 420 |
| tattaaagtc tgttggtgca caaaagaca cttatactat gaagagagtt cttttttatc | 480 |
| ttggccagta tattatgact aaacgattat atgatgagaa gcaacaacat attgtatatt | 540 |
| gttcaaatga tcttctagga gatttgtttg gcgtgccaag cttctctgtg aaagagcaca | 600 |
| ggaaaatata taccatgatc tacaggaact tggtagtagt caatcagcag gaatcatcgg | 660 |
| actcaggtac atctgtgagt gagaacaggt gtcaccttga aggtgggagt gatcaaaagg | 720 |
| accttgtaca agagcttcag gaagagaaac cttcatcttc acatttggtt tctagaccat | 780 |
| ctacctcatc tagaaggaga gcaattagtg agacagaaga aaattcagat gaattatctg | 840 |
| gtgaacgaca aagaaaacgc cacaaatctg atagtatttc cctttccttt gatgaaagcc | 900 |
| tggctctgtg tgtaataagg gagatatgtt gtgaaagaag cagtagcagt gaatctacag | 960 |
| ggacgccatc gaatccggat cttgatgctg gtgtaagtga acattcaggt gattggttgg | 1020 |
| atcaggattc agtttcagat cagtttagtg tagaatttga agttgaatct ctcgactcag | 1080 |
| aagattatag ccttagtgaa gaaggacaag aactctcaga tgaagatgat gaggtatatc | 1140 |
| aagttactgt gtatcaggca ggggagagtg atacagattc atttgaagaa gatcctgaaa | 1200 |
| tttccttagc tgactattgg aaatgcactt catgcaatga aatgaatccc cccttccat | 1260 |
| cacattgcaa cagatgttgg gcccttcgtg agaattggct tcctgaagat aaagggaaag | 1320 |
| ataaagggga aatctctgag aaagccaaac tggaaaactc aacacaagct gaagagggct | 1380 |
| ttgatgttcc tgattgtaaa aaactatag tgaatgattc cagagagtca tgtgttgagg | 1440 |
| aaaatgatga taaaattaca caagcttcac aatcacaaga aagtgaagac tattctcagc | 1500 |
| catcaacttc tagtagcatt atttatagca gccaagaaga tgtgaaagag tttgaaaggg | 1560 |
| aagaaaccca agacaaagaa gagagtgtgg aatctagttt gccccttaat gccattgaac | 1620 |
| cttgtgtgat ttgtcaaggt cgacctaaaa atggttgcat tgtccatggc aaaacaggac | 1680 |
| atcttatggc ctgctttaca tgtgcaaaga agctaaagaa aaggaataag ccctgcccag | 1740 |
| tatgtagaca accaattcaa atgattgtgc taacttattt cccctagttg acctgtctat | 1800 |

```
aagagaatta tatatttcta actatataac cctaggaatt tagacaacct gaaatttatt    1860
cacatatatc aaagtgagaa aatgcctcaa ttcacataga tttcttctct ttagtataat    1920
tgacctactt tggtagtgga atagtgaata cttactataa tttgacttga atatgtagct    1980
catcctttac accaactcct aatttttaaat aatttctact ctgtcttaaa tgagaagtac   2040 ttggttttt tttttcttaaa tatgtatatg acatttaaat gtaacttatt attttttttg   2100
agaccgagtc ttgctctgtt acccaggctg gagtgcagtg ggtgatcttg gctcactgca    2160
agctctgccc tccccgggtt cgcaccattc tcctgcctca gcctcccaat tagcttggcc    2220
tacagtcatc tgccaccaca cctggctaat ttttttgtact tttagtagag acagggtttc   2280
accgtgttag ccaggatggt ctcgatctcc tgacctcgtg atccgcccac ctcggcctcc    2340
caaagtgctg ggattacagg catgagccac cg                                  2372

<210> SEQ ID NO 134
<211> LENGTH: 2486
<212> TYPE: DNA
<213> ORGANISM: Homo sapiens

<400> SEQUENCE: 134
gagatttgat tcccttggcg ggcggaagcg gccacaaccc ggcgatcgaa aagattctta     60
ggaacgccgt accagccgcg tctctcagga cagcaggccc ctgtccttct gtcgggcgcc    120
gctcagccgt gccctccgcc cctcaggttc ttttctaat tccaaataaa cttgcaagag    180
gactatgaaa gattatgatg aacttctcaa atattatgaa ttacatgaaa ctattgggac    240
aggtggcttt gcaaaggtca aacttgcctg ccatatcctt actggagaga tggtagctat    300
aaaaatcatg gataaaaaca cactagggag tgatttgccc cggatcaaaa cggagattga    360
ggccttgaag aacctgagac atcagcatat atgtcaactc taccatgtgc tagagacagc    420
caacaaaata ttcatggttc ttgagtactg ccctggagga gagctgtttg actatataat    480
ttcccaggat cgcctgtcag aagaggagac ccgggttgtc ttccgtcaga tagtatctgc    540
tgttgcttat gtgcacagcc agggctatgc tcacagggac ctcaagccag aaaatttgct    600
gtttgatgaa tatcataaat taaagctgat tgactttggt ctctgtgcaa acccaaggg    660 taacaaggat taccatctac agacatgctg tgggagtctg gcttatgcag cacctgagtt    720
aatacaaggc aaatcatatc ttggatcaga ggcagatgtt tggagcatgg gcatactgtt    780
atatgttctt atgtgtggat ttctaccatt tgatgatgat aatgtaatgg ctttatacaa    840
gaagattatg agaggaaaat atgatgttcc caagtggctc tctcccagta gcattctgct    900
tcttcaacaa atgctgcagg tggacccaaa gaaacggatt tctatgaaaa atctattgaa    960
ccatccctgg atcatgcaag attacaacta tcctgttgag tggcaaagca agaatccttt   1020
tattcacctc gatgatgatt gcgtaacaga actttctgta catcacagaa acaacaggca   1080
aacaatggag gatttaattt cactgtggca gtatgatcac ctcacggcta cctatcttct   1140
gcttctagcc aagaaggctc ggggaaaacc agttcgtttta aggctttctt ctttctcctg   1200
tggacaagcc agtgctaccc cattcacaga catcaagtca ataattggag gtctggaaga   1260
tgtgaccgca agtgataaaa attatgtggc gggattaata gactatgatt ggtgtgaaga   1320
tgatttatca acaggtgctg ctactccccg aacatcacag tttaccaagt actggacaga   1380
atcaaatggg gtggaatcta aatcattaac tccagcctta tgcagaacac ctgcaaataa   1440
attaaagaac aaagaaaatg tatatactcc taagtctgct gtaaagaatg aagagtactt   1500
```

```
tatgtttcct gagccaaaga ctccagttaa taagaaccag cataagagag aaatactcac    1560
tacgccaaat cgttacacta caccctcaaa agctagaaac cagtgcctga aagaaactcc    1620
aattaaaata ccagtaaatt caacaggaac agacaagtta atgacaggtg tcattagccc    1680
tgagaggcgg tgccgctcag tggaattgga tctcaaccaa gcacatatgg aggagactcc    1740
aaaaagaaag ggagccaaag tgtttgggag ccttgaaagg gggttggata aggttatcac    1800
tgtgctcacc aggagcaaaa ggaagggttc tgccagagac gggcccagaa gactaaagct    1860
tcactataac gtgactacaa ctagattagt gaatccagat caactgttga atgaaataat    1920
gtctattctt ccaaagaagc atgttgactt tgtacaaaag ggttatacac tgaagtgtca    1980
aacacagtca gattttggga aagtgacaat gcaatttgaa ttagaagtgt gccagcttca    2040
aaaacccgat gtggtgggta tcaggaggca gcggcttaag ggcgatgcct gggtttacaa    2100
aagattagtg gaagacatcc tatctagctg caaggtataa ttgatggatt cttccatcct    2160
gccggatgag tgtgggtgtg atacagccta cataaagact gttatgatcg ctttgatttt    2220
aaagttcatt ggaactacca acttgtttct aaagagctat cttaagacca atatctcttt    2280
gtttttaaac aaaagatatt attttgtgta tgaatctaaa tcaagcccat ctgtcattat    2340
gttactgtct tttttaatca tgtggttttg tatattaata attgttgact ttcttagatt    2400
cacttccata tgtgaatgta agctcttaac tatgtctctt tgtaatgtgt aatttctttc    2460
tgaaataaaa ccatttgtga atatag                                        2486

<210> SEQ ID NO 135
<211> LENGTH: 1140
<212> TYPE: DNA
<213> ORGANISM: Homo sapiens
<220> FEATURE:
<221> NAME/KEY: misc_feature
<222> LOCATION: (1140)..(1140)
<223> OTHER INFORMATION: n is a, c, g, or t

<400> SEQUENCE: 135
gcagcggagg agcccagtcc acgatggccc ggtccctggt gtgccttggt gtcatcatct      60
tgctgtctgc cttctccgga cctggtgtca ggggtggtcc tatgcccaag ctggctgacc     120
ggaagctgtg tgcggaccag gagtgcagcc accctatctc catggctgtg gcccttcagg     180
actacatggc ccccgactgc cgattcctga ccattcaccg gggccaagtg gtgtatgtct     240
tctccaagct gaagggccgt gggcggctct tctggggagg cagcgttcag ggagattact     300
atggagatct ggctgctcgc ctgggctatt tccccagtag cattgtccga gaggaccaga     360
ccctgaaacc tggcaaagtc gatgtgaaga cagacaaatg ggatttctac tgccagtgag     420
ctcagcctac cgctggccct gccgtttccc ctccttgggt ttatgcaaat acaatcagcc     480
cagtgcaaaa aaaaaaaaaa aaaaaaaaa cttcggagaa gagatagcaa caaaaggccg     540
cttgtgtgaa ggcgccaaaa gttttcgccc aagagacctt cggcctcccc cagggcgcgc     600
gcaaaggcgc cttgttttga caacctcttg acaaccggga gggctaccg cccggagacc     660 cctgtggtgg acccccggg caacccggtg tgacagggta ctcacccca cggctttgtc     720 gggggtccca ccaaaggccc caagaggct cttcaaggc actattcctt gttgtagacc     780
ttgtgtgtgc cacaggcgcc aaagaaacct cggggggcta acaaacgcac gtgcttggca     840
gctccgagaa ggctctctcc cacccgaggg gtggacgcaa caggggggaat gggccatcat     900 attgttgccc ccggtgggca ccaactcttt ttcccccata gagaggcctt agcacactat     960
gtggggcacg ttattgccgc ctagagaaac cgagcgccag aaaatttcga aggggggggc    1020
```

| | |
|---|---:|
| gcttctcatc attttgcgca aaaccccctt gtgggagtat gccccgaact cctctggaac | 1080 |
| acacaagcga cacttgcgcg gggtctgcaa aaaacctcct gttgggaagc cggcttcacn | 1140 |

<210> SEQ ID NO 136
<211> LENGTH: 12507
<212> TYPE: DNA
<213> ORGANISM: Homo sapiens

<400> SEQUENCE: 136

| | |
|---|---:|
| taccgggcgg aggtgagcgc ggcgccggct cctcctgcgg cggactttgg gtgcgacttg | 60 |
| acgagcggtg gttcgacaag tggccttgcg ggccggatcg tcccagtgga agagttgtaa | 120 |
| atttgcttct ggccttcccc tacggattat acctggcctt cccctacgga ttatactcaa | 180 |
| cttactgttt agaaaatgtg gcccacgaga cgcctggtta ctatcaaaag gagcggggtc | 240 |
| gacggtcccc actttcccct gagcctcagc acctgcttgt ttggaagggg tattgaatgt | 300 |
| gacatccgta tccagcttcc tgttgtgtca aaacaacatt gcaaaattga aatccatgag | 360 |
| caggaggcaa tattacataa tttcagttcc acaaatccaa cacaagtaaa tgggtctgtt | 420 |
| attgatgagc ctgtacggct aaaacatgga gatgtaataa ctattattga tcgttccttc | 480 |
| aggtatgaaa atgaaagtct tcagaatgga aggaagtcaa ctgaatttcc aagaaaaata | 540 |
| cgtgaacagg agccagcacg tcgtgtctca agatctagct tctcttctga ccctgatgag | 600 |
| aaagctcaag attccaaggc ctattcaaaa atcactgaag gaaaagtttc aggaaatcct | 660 |
| caggtacata tcaagaatgt caaagaagac agtaccgcag atgactcaaa agacagtgtt | 720 |
| gctcagggaa caactaatgt tcattcctca gaacatgctg gacgtaatgg cagaaatgca | 780 |
| gctgatccca tttctgggga ttttaaagaa atttccagcg ttaaattagt gagccgttat | 840 |
| ggagaattga agtctgttcc cactacacaa tgtcttgaca atagcaaaaa aaatgaatct | 900 |
| ccctttttgga agctttatga gtcagtgaag aaagagttgg atgtaaaatc acaaaaagaa | 960 |
| aatgtcctac agtattgtag aaaatctgga ttacaaactg attacgcaac agagaaagaa | 1020 |
| agtgctgatg gtttacaggg ggagacccaa ctgttggtct cgcgtaagtc aagaccaaaa | 1080 |
| tctggtggga gcggccacgc tgtggcagag cctgcttcac ctgaacaaga gcttgaccag | 1140 |
| aacaagggga agggaagaga cgtggagtct gttcagactc ccagcaaggc tgtgggcgcc | 1200 |
| agctttcctc tctatgagcc ggctaaaatg aagacccctg tacaatattc acagcaacaa | 1260 |
| aattctccac aaaaacataa gaacaaagac ctgtatacta ctggtagaag agaatctgtg | 1320 |
| aatctgggta aaagtgaagg cttcaaggct ggtgataaaa ctcttactcc caggaagctt | 1380 |
| tcaactagaa atcgaacacc agctaaagtt gaagatgcag ctgactctgc cactaagcca | 1440 |
| gaaaatctct cttccaaaac cagaggaagt attcctacga atgtggaagt tctgcctacg | 1500 |
| gaaactgaaa ttcacaatga gccattttta actctgtggc tcactcaagt tgagaggaag | 1560 |
| atccaaaagg attccctcag caagcctgag aaattgggca ctacagctgg acagatgtgc | 1620 |
| tctgggttac ctggtcttag ttcagttgat atcaacaact ttggtgattc cattaatgag | 1680 |
| agtgagggaa tacctttgaa aagaaggcgt gtgtcctttg gtgggcacct aagacctgaa | 1740 |
| ctatttgatg aaaacttgcc tcctaatacg cctctcaaaa gggagaagc cccaaccaaa | 1800 |
| agaaagtctc tggtaatgca cactccacct gtcctgaaga aaatcatcaa ggaacagcct | 1860 |
| caaccatcag gaaaacaaga gtcaggttca gaaatccatg tggaagtgaa ggcacaaagc | 1920 |
| ttggttataa gccctccagc tcctagtcct aggaaaactc cagttgccag tgatcaacgc | 1980 |

```
cgtaggtcct gcaaaacagc ccctgcttcc agcagcaaat ctcagacaga ggttcctaag    2040
agaggaggga gaaagagtgg caacctgcct tcaaagagag tgtctatcag ccgaagtcaa    2100
catgatattt tacagatgat atgttccaaa agaagaagtg gtgcttcgga agcaaatctg    2160
attgttgcaa aatcatgggc agatgtagta aaacttggtg caaaacaaac acaaactaaa    2220
gtcataaaac atggtcctca aaggtcaatg aacaaaaggc aaagaagacc tgctactcca    2280
aagaagcctg tgggcgaagt tcacagtcaa tttagtacag gccacgcaaa ctctccttgt    2340
accataataa tagggaaagc tcatactgaa aaagtacatg tgcctgctcg accctacaga    2400
gtgctcaaca acttcatttc caaccaaaaa atggactttta aggaagatct ttcaggaata    2460
gctgaaatgt tcaagacccc agtgaaggag caaccgcagt tgacaagcac atgtcacatc    2520
gctatttcaa attcagagaa tttgcttgga aaacagtttc aaggaactga ttcaggagaa    2580
gaacctctgc tccccacctc agagagtttt ggaggaaatg tgttcttcag tgcacagaat    2640
gcagcaaaac agccatctga taaatgctct gcaagccctc ccttaagacg gcagtgtatt    2700
agagaaaatg gaaacgtagc aaaaacgccc aggaacacct acaaaatgac ttctctggag    2760
acaaaaactt cagatactga gacagagcct tcaaaaacag tatccactgc aaacaggtca    2820
ggaaggtcta cagagttcag gaatatacag aagctacctg tggaaagtaa gagtgaagaa    2880
acaaatacag aaattgttga gtgcatccta aaaagaggtc agaaggcaac actactacaa    2940
caaaggagag aaggagagat gaaggaaata gaaagacctt ttgagacata taggaaaat     3000 attgaattaa aagaaaacga tgaaaagatg aaagcaatga agagatcaag aacttggggg    3060
cagaaatgtg caccaatgtc tgacctgaca gacctcaaga gcttgcctga tacagaactc    3120
atgaaagaca cggcacgtgg ccagaatctc ctccaaaccc aagatcatgc caaggcacca    3180
aagagtgaga aaggcaaaat cactaaaatg ccctgccagt cattcaaacc agaaccaata    3240
aacaccccaa cacacacaaa acaacagttg aaggcatccc tggggaaagt aggtgtgaaa    3300
gaagagctcc tagcagtcgg caagttcaca cggacgtcag gggagaccac gcacacgcac    3360
agagagccag caggagatgg caagagcatc agaacgttta aggagtctcc aaagcagatc    3420
ctggacccag cagcccgtgt aactggaatg aagaagtggc caagaacgcc taaggaagag    3480
gcccagtcac tagaagacct ggctggcttc aaagagctct tccagacacc aggtccctct    3540
gaggaatcaa tgactgatga gaaaactacc aaaatagcct gcaaatctcc accaccagaa    3600
tcagtggaca ctccaacaag cacaaagcaa tggcctaaga gaagtctcag gaaagcagat    3660
gtagaggaag aattcttagc actcaggaaa ctaacaccat cagcagggaa agccatgctt    3720
acgcccaaac cagcaggagg tgatgagaaa gacattaaag catttatggg aactccagtg    3780
cagaaactgg acctggcagg aactttacct ggcagcaaaa gacagctaca gactcctaag    3840
gaaaaggccc aggctctaga agacctggct ggctttaaag agctcttcca gactcctggt    3900
cacaccgagg aattagtggc tgctggtaaa accactaaaa tacccctgcga ctctccacag    3960 tcagacccag tggacacccc aacaagcaca aagcaacgac ccaagagaag tatcaggaaa    4020
gcagatgtag agggagaact cttagcgtgc aggaatctaa tgccatcagc aggcaaagcc    4080
atgcacacgc ctaaaccatc agtaggtgaa gagaaagaca tcatcatatt tgtgggaact    4140
ccagtgcaga aactggacct gacagagaac ttaaccggca gcaagagacg gccacaaact    4200
cctaaggaag aggcccaggc tctggaagac ctgactggct ttaaagagct cttccagacc    4260
cctggtcata ctgaagaagc agtggctgct ggcaaaacta ctaaaatgcc ctgcgaatct    4320
tctccaccag aatcagcaga cacccccaaca agcacaagaa ggcagcccaa gacacctttg    4380
```

```
gagaaaaggg acgtacagaa ggagctctca gccctgaaga agctcacaca gacatcaggg    4440
gaaaccacac acacagataa agtaccagga ggtgaggata aaagcatcaa cgcgtttagg    4500
gaaactgcaa aacagaaact ggacccagca gcaagtgtaa ctggtagcaa gaggcaccca    4560
aaaactaagg aaaaggccca acccctagaa gacctggctg gcttgaaaga gctcttccag    4620
acaccagtat gcactgacaa gcccacgact cacgagaaaa ctaccaaaat agcctgcaga    4680
tcacaaccag acccagtgga cacaccaaca agctccaagc cacagtccaa gagaagtctc    4740
aggaaagtgg acgtagaaga agaattcttc gcactcagga aacgaacacc atcagcaggc    4800
aaagccatgc acacacccaa accagcagta agtggtgaga aaaacatcta cgcatttatg    4860
ggaactccag tgcagaaact ggacctgaca gagaacttaa ctggcagcaa gagacggcta    4920
caaactccta aggaaaaggc ccaggctcta gaagacctgg ctggctttaa agagctcttc    4980
cagacacgag gtcacactga ggaatcaatg actaacgata aaactgccaa agtagcctgc    5040
aaatcttcac aaccagaccc agacaaaaac ccagcaagct ccaagcgacg gctcaagaca    5100
tccctgggga agtgggcgt gaaagaagag ctcctagcag ttggcaagct cacacagaca    5160
tcaggagaga ctacacacac acacacagag ccaacaggag atggtaagag catgaaagca    5220
tttatggagt ctccaaagca gatcttagac tcagcagcaa gtctaactgg cagcaagagg    5280
cagctgagaa ctcctaaggg aaagtctgaa gtccctgaag acctggccgg cttcatcgag    5340
ctcttccaga caccaagtca cactaaggaa tcaatgacta acgaaaaaac taccaaagta    5400
tcctacagag cttcacagcc agacctagtg gacaccccaa caagctccaa gccacagccc    5460
aagagaagtc tcaggaaagc agacactgaa gaagaatttt tagcatttag gaaacaaacg    5520
ccatcagcag gcaaagccat gcacacaccc aaaccagcag taggtgaaga gaaagacatc    5580
aacacgtttt tgggaactcc agtgcagaaa ctggaccagc caggaaattt acctggcagc    5640
aatagacggc tacaaactcg taaggaaaag gcccaggctc tagaagaact gactggcttc    5700
agagagcttt tccagacacc atgcactgat aaccccacga ctgatgagaa aactaccaaa    5760
aaaatactct gcaaatctcc gcaatcagac ccagcggaca ccccaacaaa cacaaagcaa    5820
cggcccaaga gaagcctcaa gaaagcagac gtagaggaag aattttttagc attcaggaaa    5880 ctaacaccat cagcaggcaa agccatgcac acgcctaaag cagcagtagg tgaagagaaa    5940
gacatcaaca catttgtggg gactccagtg agaaactgg acctgctagg aaatttacct    6000
ggcagcaaga gacggccaca aactcctaaa gaaaaggcca aggctctaga agatctggct    6060
ggcttcaaag agctcttcca gacaccaggt cacactgagg aatcaatgac cgatgacaaa    6120
atcacagaag tatcctgcaa atctccacaa ccagacccag tcaaaacccc aacaagctcc    6180
aagcaacgac tcaagatatc cttggggaaa gtaggtgtga aagaagaggt cctaccagtc    6240
ggcaagctca cacagacgtc agggaagacc acacagacac acagagagac agcaggagat    6300
ggaaagagca tcaaagcgtt taaggaatct gcaaagcaga tgctggaccc agcaaactat    6360
ggaactggga tggagaggtg gccaagaaca cctaaggaag aggcccaatc actagaagac    6420
ctggccggct tcaaagagct cttccagaca ccagaccaca ctgaggaatc aacaactgat    6480
gacaaaacta ccaaaatagc ctgcaaatct ccaccaccag aatcaatgga cactccaaca    6540
agcacaagga ggcggcccaa aacacctttg ggaaaaggg atatagtgga agagctctca    6600
gccctgaagc agctcacaca gaccacacac acagacaaag taccaggaga tgaggataaa    6660
ggcatcaacg tgttcaggga aactgcaaaa cagaaactgg acccagcagc aagtgtaact    6720
```

-continued

```
ggtagcaaga ggcagccaag aactcctaag ggaaaagccc aaccccctaga agacttggct    6780 ggcttgaaag agctcttcca gacaccaata tgcactgaca agcccacgac tcatgagaaa    6840
actaccaaaa tagcctgcag atctccacaa ccagacccag tgggtacccc aacaatcttc    6900
aagccacagt ccaagagaag tctcaggaaa gcagacgtag aggaagaatc cttagcactc    6960
aggaaacgaa caccatcagt agggaaagct atggacacac ccaaaccagc aggaggtgat    7020
gagaaagaca tgaaagcatt tatgggaact ccagtgcaga aattggacct gccaggaaat    7080
ttacctggca gcaaaagatg gccacaaact cctaaggaaa aggcccaggc tctagaagac    7140
ctggctggct tcaaagagct cttccagaca ccaggcactg acaagcccac gactgatgag    7200
aaaactacca aaatagcctg caaatctcca caaccagacc cagtggacac cccagcaagc    7260
acaaagcaac ggcccaagag aaacctcagg aaagcagacg tagaggaaga attttttagca    7320 ctcaggaaac gaacaccatc agcaggcaaa gccatggaca caccaaaacc agcagtaagt    7380
gatgagaaaa atatcaacac atttgtggaa actccagtgc agaaactgga cctgctagga    7440
aatttacctg gcagcaagag acagccacag actcctaagg aaaaggctga ggctctagag    7500
gacctggttg gcttcaaaga actcttccag acaccaggtc acactgagga atcaatgact    7560
gatgacaaaa tcacagaagt atcctgtaaa tctccacagc cagagtcatt caaaacctca    7620
agaagctcca agcaaaggct caagataccc ctggtgaaag tggacatgaa agaagagccc    7680
ctagcagtca gcaagctcac acggacatca ggggagacta cgcaaacaca cacagagcca    7740
acaggagata gtaagagcat caaagcgttt aaggagtctc caaagcagat cctggaccca    7800
gcagcaagtg taactggtag caggaggcag ctgagaactc gtaaggaaaa ggcccgtgct    7860
ctagaagacc tggttgactt caaagagctc ttctcagcac aggtcacac tgaagagtca    7920 atgactattg caaaaacac aaaaattccc tgcaaatctc ccccaccaga actaacagac    7980
actgccacga gcacaaagag atgccccaag acacgtccca ggaaagaagt aaaagaggag    8040
ctctcagcag ttgagaggct cacgcaaaca tcagggcaaa gcacacacac acacaaagaa    8100
ccagcaagcg gtgatgaggg catcaaagta ttgaagcaac gtgcaaagaa gaaaccaaac    8160
ccagtagaag aggaacccag caggagaagg ccaagagcac taaggaaaaa ggcccaaccc    8220
ctggaagacc tggccggctt cacagagctc tctgaaacat caggtcacac tcaggaatca    8280
ctgactgctg gcaaagccac taaaataccc tgcgaatctc ccccactaga agtggtagac    8340
accacagcaa gcacaaagag gcatctcagg acacgtgtgc agaaggtaca agtaaaagaa    8400
gagccttcag cagtcaagtt cacacaaaca tcagggaaa ccacggatgc agacaaagaa    8460
ccagcaggtg aagataaagg catcaaagca ttgaaggaat ctgcaaaaca gacaccggct    8520
ccagcagcaa gtgtaactgg cagcaggaga cggccaagag cacccaggga agtgcccaa    8580 gccatagaag acctagctgg cttcaaagac ccagcagcag gtcacactga agaatcaatg    8640
actgatgaca aaaccactaa aatacccctgc aaatcatcac cagaactaga agacaccgca    8700
acaagctcaa agagacggcc caggacacgt gcccagaaag tagaagtgaa ggaggagctg    8760
ttagcagttg gcaagctcac acaaaacctca ggggagacca cgcacaccga caaagagccg    8820
gtaggtgagg gcaaaggcac gaaagcattt aagcaaacctg caaagcggaa gctgacgca    8880 gaagatgtaa ttggcagcag gagacagcca agagcaccta aggaaaggc caacccctg    8940 gaagatctgg ccagcttcca agagctctct caaacaccag gccacactga ggaactggca    9000
aatggtgctg ctgatagctt tacaagcgct ccaaaagcaaa cacctgacag tggaaaacct    9060
ctaaaaatat ccagaagagt tcttcgggcc cctaaagtag aacccgtggg agacgtggta    9120
```

```
agcaccagag accctgtaaa atcacaaagc aaaagcaaca cttccctgcc cccactgccc    9180
ttcaagaggg gaggtggcaa agatggaagc gtcacgggaa ccaagaggct gcgctgcatg    9240
ccagcaccag aggaaattgt ggaggagctg ccagccagca agaagcagag ggttgctccc    9300
agggcaagag gcaaatcatc cgaacccgtg gtcatcatga agagaagttt gaggacttct    9360
gcaaaaagaa ttgaacctgc ggaagagctg aacagcaacg acatgaaaac caacaaagag    9420
gaacacaaat tacaagactc ggtccctgaa aataagggaa tatccctgcg ctccagacgc    9480
caaaataaga ctgaggcaga acagcaaata actgaggtct ttgtattagc agaaagaata    9540
gaaataaaca gaaatgaaaa gaagcccatg aagacctccc cagagatgga cattcagaat    9600
ccagatgatg gagcccggaa acccatacct agagacaaag tcactgagaa caaaaggtgc    9660
ttgaggtctg ctagacagaa tgagagctcc cagcctaagg tggcagagga gagcggaggg    9720
cagaagagtg cgaaggttct catgcagaat cagaaaggga aaggagaagc aggaaattca    9780
gactccatgt gcctgagatc aagaaagaca aaaagccagc ctgcagcaag cactttggag    9840
agcaaatctg tgcagagagt aacgcggagt gtcaagaggt gtgcagaaaa tccaaagaag    9900
gctgaggaca atgtgtgtgt caagaaaata agaaccagaa gtcatagggc cagtgaagat    9960
atttgacaga aaaatcgaac tgggaaaaat ataataaagt tagttttgtg ataagttcta   10020 gtgcagttttt tgtcataaat tacaagtgaa ttctgtaagt aaggctgtca gtctgcttaa   10080
gggaagaaaa ctttggatttt gctgggtctg aatcggcttc ataaactcca ctgggagcac   10140
tgctgggctc ctggactgag aatagttgaa caccgggggc tttgtgaagg agtctgggcc   10200
aaggtttgcc ctcagctttg cagaatgaag ccttgaggtc tgtcaccacc cacagccacc   10260
ctacagcagc cttaactgtg acacttgcca cactgtgtcg tcgtttgttt gcctatgtcc   10320
tccagggcac ggtggcagga caactatcc tcgtctgtcc caacactgag caggcactcg   10380
gtaaacacga atgaatggat gagcgcacgg atgaatggag cttacaagat ctgtctttcc   10440
aatggccggg ggcatttggt ccccaaatta aggctattgg acatctgcac aggacagtcc   10500
tatttttgat gtccttttcct ttctgaaaat aaagttttgt gctttggaga atgactcgtg   10560
agcacatctt tagggaccaa gagtgacttt ctgtaaggag tgactcgtgg cttgccttgg   10620
tctcttggga atacttttct aactagggtt gctctcacct gagacattct ccacccgcgg   10680
aatctcaggg tcccaggctg tgggccatca cgacctcaaa ctggctccta atctccagct   10740
ttcctgtcat tgaaagcttc ggaagtttac tggctctgct cccgcctgtt ttctttctga   10800
ctctatctgg cagcccgatg ccacccagta caggaagtga caccagtact ctgtaaagca   10860
tcatcatcct tggagagact gagcactcag caccttcagc cacgatttca ggatcgcttc   10920
cttgtgagcc gctgcctccg aaatctcctt tgaagcccag acatctttct ccagcttcag   10980
acttgtagat ataactcgtt catcttcatt tactttccac tttgcccct gtcctctctg   11040 tgttccccaa atcagagaat agcccgccat cccccaggtc acctgtctgg attcctcccc   11100
attcacccac cttgccaggt gcaggtgagg atggtgcacc agacagggta gctgtccccc   11160
aaaatgtgcc ctgtgcgggc agtgccctgt ctccacgttt gtttcccag tgtctggcgg   11220 ggagccaggt gacatcataa atacttgctg aatgaatgca gaaatcagcg gtactgactt   11280
gtactatatt ggctgccatg atagggttct cacagcgtca tccatgatcg taagggagaa   11340
tgacattctg cttgagggag ggaatagaaa ggggcaggga ggggacatct gagggcttca   11400
cagggctgca aagggtacag ggattgcacc agggcagaac aggggagggt gttcaaggaa   11460
```

| | |
|---|---|
| gagtggctct tagcagaggc actttggaag gtgtgaggca taaatgcttc cttctacgta | 11520 |
| ggccaacctc aaaactttca gtaggaatgt tgctatgatc aagttgttct aacactttag | 11580 |
| acttagtagt aattatgaac ctcacataga aaaatttcat ccagccatat gcctgtggag | 11640 |
| tggaatattc tgtttagtag aaaaatcctt tagagttcag ctctaaccag aaatcttgct | 11700 |
| gaagtatgtc agcaccttt ctcaccctgg taagtacagt atttcaagag cacgctaagg | 11760 |
| gtggttttca ttttacaggg ctgttgatga tgggttaaaa atgttcattt aagggctacc | 11820 |
| cccgtgttta atagatgaac accacttcta cacaaccctc cttggtactg ggggagggag | 11880 |
| agatctgaca aatactgccc attccctag gctgactgga tttgagaaca aatacccacc | 11940 |
| catttccacc atggtatggt aacttctctg agcttcagtt tccaagtgaa tttccatgta | 12000 |
| ataggacatt cccattaaat acaagctgtt tttacttttt cgcctcccag ggcctgtggg | 12060 |
| atctggtccc ccagcctctc ttgggctttc ttacactaac tctgtaccta ccatctcctg | 12120 |
| cctcccttag gcaggcacct ccaaccacca cacactccct gctgttttcc ctgcctggaa | 12180 |
| ctttccctcc tgccccacca agatcatttc atccagtcct gagctcagct taagggaggc | 12240 |
| ttcttgcctg tgggttccct caccccatg cctgtcctcc aggctggggc aggttcttag | 12300 |
| tttgcctgga attgttctgt acctctttgt agcacgtagt gttgtggaaa ctaagccact | 12360 |
| aattgagttt ctggctcccc tcctggggtt gtaagttttg ttcattcatg agggccgact | 12420 |
| gcatttcctg gttactctat cccagtgacc agccacagga gatgtccaat aaagtatgtg | 12480 |
| atgaaatggt cttaaaaaaa aaaaaaa | 12507 |

<210> SEQ ID NO 137
<211> LENGTH: 3771
<212> TYPE: DNA
<213> ORGANISM: Homo sapiens

<400> SEQUENCE: 137

| | |
|---|---|
| gcgccgggac gtggccagtt gcccgcctgc cccggagagc caggcgctaa ccagccgctc | 60 |
| tgcgccccgc gccctgcttg cccccattat ccagccttgc cccggcgccc tgacctgacg | 120 |
| ccctggcctg acgccctgct tcgtcgcctc ctttctctcc caggtgctgg accagggact | 180 |
| gagcgtcccc cggagagggt ccggtgtgac cccgacaaga agcagaaatg gggaagaaac | 240 |
| tggatctttc caagctcact gatgaagagg cccagcatgt cttggaagtt gttcaacgag | 300 |
| attttgacct ccgaaggaaa gaagaggaac ggctagaggc gttgaagggc aagattaaga | 360 |
| aggaaagctc caagagggag ctgctttccg acactgccca tctgaacgag acccactgcg | 420 |
| cccgctgcct gcagccctac cagctgcttg tgaatagcaa aaggcagtgc ctggaatgtg | 480 |
| gcctcttcac ctgcaaaagc tgtggccgcg tccacccgga ggagcagggc tggatctgtg | 540 |
| accctgcca tctggccaga gtcgtgaaga tcggctcact ggagtggtac tatgagcatg | 600 |
| tgaaagcccg cttcaagagg ttcggaagtg ccaaggtcat ccggtccctc cacgggcggc | 660 |
| tgcagggtgg agctgggcct gaactgatat ctgaagagag aagtgagac agcgaccaga | 720 |
| cagatgagga tggagaacct ggctcagagg cccaggccca ggcccagccc tttggcagca | 780 |
| aaaaaaagcg cctcctctcc gtccacgact tcgacttcga gggagactca gatgactcca | 840 |
| ctcagcctca aggtcactcc ctgcacctgt cctcagtccc tgaggccagg acagcccac | 900 |
| agtccctcac agatgagtcc tgctcagaga aggcagcccc tcacaaggct gagggcctgg | 960 |
| aggaggctga tactggggcc tctgggtgcc actcccatcc ggaagagcag ccgaccagca | 1020 |
| tctcaccttc cagacacggc gccctggctg agctctgccc gcctggaggc tcccacagga | 1080 |

-continued

```
tggccctggg gactgctgct gcactcgggt cgaatgtcat caggaatgag cagctgcccc    1140
tgcagtactt ggccgatgtg gacacctctg atgaggaaag catccgggct cacgtgatgg    1200
cctcccacca ttccaagcgg agaggccggg cgtcttctga gagtcagatc tttgagctga    1260
ataagcatat ttcagctgtg gaatgcctgc tgacctacct ggagaacaca gttgtgcctc    1320
ccttggccaa gggtctaggt gctggagtgc gcacggaggc cgatgtagag gaggaggccc    1380
tgaggaggaa gctggaggag ctgaccagca acgtcagtga ccaggagacc cgtccgagg     1440 aggaggaagc caaggacgaa aaggcagagc ccaacaggga caaatcagtt gggcctctcc    1500
cccaggcgga cccggaggtg ggcacggctg cccatcaaac caacagacag gaaaaaagcc    1560
cccaggaccc tggggacccc gtccagtaca acaggaccac agatgaggag ctgtcagagc    1620
tggaggacag agtggcagtg acggcctcag aagtccagca ggcagagagc gaggtttcag    1680
acattgaatc caggattgca gccctgaggg ccgcagggct cacggtgaag ccctcgggaa    1740
agccccggag gaagtcaaac ctcccgatat ttctccctcg agtggctggg aaacttggca    1800
agagaccaga ggacccaaat gcagaccctt caagtgaggc caaggcaatg gctgtgccct    1860
atcttctgag aagaaagttc agtaattccc tgaaaagtca aggtaaagat gatgattctt    1920
ttgatcggaa atcagtgtac cgaggctcgc tgacacagag aaaccccaac gcgaggaaag    1980
gaatggccag ccacaccttc gcgaaacctg tggtggccca ccagtcctaa cgggacagga    2040
cagagagaca gagcagccct gcactgtttt ccctccacca cagccatcct gtccctcatt    2100
ggctctgtgc tttccactat acacagtcac cgtcccaatg agaaacaaga aggagcaccc    2160
tccacatgga ctcccacctg caagtggaca gcgacattca gtcctgcact gctcacctgg    2220
gtttactgat gactcctggc tgccccacca tcctctctga tctgtgagaa acagctaagc    2280
tgctgtgact tcccttagg acaatgttgt gtaaatcttt gaaggacaca ccgaagacct     2340
ttatactgtg atctttacc cctttcactc ttggctttct tatgttgctt tcatgaatgg     2400
aatggaaaaa agatgactca gttaaggcac cagccatatg tgtattcttg atggtctata    2460
tcggggtgtg agcagatgtt tgcgtatttc ttgtgggtgt gactggatat tagacatccg    2520
gacaagtgac tgaactaatg atctgctgaa taatgaagga ggaatagaca ccccagtccc    2580
caccctacgt gcacccgctc tgcaagttcc catgtgatct gtagaccagg gaaattaca    2640 ctgcggtcaa gggcagagcc tgcacatgac agcaagtgag catttgatag atgctcagat    2700
gctagtgcag agagcctgct gggagacgaa gagacagcag gcagagctcc agatgggcaa    2760
ggaagaggct tggttctagc ctggctctgc ccctcactgc agtggatcca gtggggcaga    2820
ggacagaggg tcacaaccaa tgagggatgt ctgccaagga tggggtgca gaggccacag     2880 gagtcagctt gccactcgcc cattggttac atagatgatc tctcagacag gctgggactc    2940
agagttattt cctagtatcg gtgtgcccca tccagtttta agtggagccc tccaagactc    3000
tccagagctg cctttgaaca tcctaacagt aatcacatct caccctccct gaggttcact    3060
ttagacagga cccaatggct gcactgcctt tgtcagaggg ggtgctgaga ggagtggctt    3120
cttttagaat caaacagtag agacaagagt caagccttgt gtcttcaagc attgaccaag    3180
ttaagtgttt ccttccctct ctcaataaga cacttccagg agcttttccaa tctctcactt    3240 aaaactaagg tttgaatctc aaagtgttgc tgggaggctg atactcctgc aacttcagga    3300
gacctgtgag cacacattag cagctgtttc tctgactcct tgtggcatca gataaaaacg    3360 tgggagttttt tccatataat tcccagcctt acttataaat tctattcttt gaaaaaatta   3420
```

| | |
|---|---|
| ttcaggctag gtaaggtggc tcataccaat aatcccagcc ctttgagagg ccaaggtggg | 3480 |
| agaattgctt gaggccagga gtttgagacc tcctgggcaa catagtgaga tcccatctct | 3540 |
| acaaaaaaca aaacaaaaaa attacccaag catgatggta tatgcctgta gtcgtaccta | 3600 |
| cttacttagg aggctgaggc aggaggatca cttgagccct ggaggttggg gctgcagtga | 3660 |
| gccatgatcg catcactata ctcgagcctg gcaacagag tgagaccttg tctcttaaaa | 3720 |
| aaattaataa taaataaatg aaaataattc ttcagaaaaa aaaaaaaaa a | 3771 |

<210> SEQ ID NO 138
<211> LENGTH: 2240
<212> TYPE: DNA
<213> ORGANISM: Homo sapiens

<400> SEQUENCE: 138

| | |
|---|---|
| aagcccagca gccccggggc ggatggctcc ggccgcctgg ctccgcagcg cggccgcgcg | 60 |
| cgccctcctg ccccgatgc tgctgctgct gctccagccg ccgccgctgc tggcccgggc | 120 |
| tctgccgccg gacgcccacc acctccatgc cgagaggagg gggccacagc cctggcatgc | 180 |
| agccctgccc agtagcccgg cacctgcccc tgccacgcag gaagcccccc ggcctgccag | 240 |
| cagcctcagg cctccccgct gtggcgtgcc cgacccatct gatgggctga gtgcccgcaa | 300 |
| ccgacagaag aggttcgtgc tttctggcgg gcgctgggag aagacggacc tcacctacag | 360 |
| gatccttcgg ttcccatggc agttggtgca ggagcaggtg cggcagacga tggcagaggc | 420 |
| cctaaaggta tggagcgatg tgacgccact cacctttact gaggtgcacg agggccgtgc | 480 |
| tgacatcatg atcgacttcg ccaggtactg catggggac gacctgccgt ttgatgggcc | 540 |
| tgggggcatc ctggcccatg ccttcttccc caagactcac cgagaagggg atgtccactt | 600 |
| cgactatgat gagacctgga ctatcgggga tgaccaggc acagacctgc tgcaggtggc | 660 |
| agcccatgaa tttggccacg tgctggggct gcagcacaca acagcagcca aggccctgat | 720 |
| gtccgccttc tacaccttc gctacccact gagtctcagc ccagatgact gcaggggcgt | 780 |
| tcaaccccta tatggccagc cctggcccac tgtcacctcc aggaccccag ccctgggccc | 840 |
| ccaggctggg atagacacca atgagattgc accgctggag ccagacgccc cgccagatgc | 900 |
| ctgtgaggcc tcctttgacg cggtctccac catccgaggc gagctctttt tcttcaaagc | 960 |
| gggctttgtg tggcgcctcc gtggggggcca gctgcagccc ggctacccag cattggcctc | 1020 |
| tcgccactgg caggactgc ccagccctgt ggacgctgcc ttcgaggatg cccagggcca | 1080 |
| catttggttc ttccaaggtg ctcagtactg ggtgtacgac ggtgaaaagc cagtcctggg | 1140 |
| ccccgcaccc ctcaccgagc tgggcctggt gaggttcccg gtccatgctg ccttggtctg | 1200 |
| gggtcccgag aagaacaaga tctacttctt ccgaggcagg gactactggc gtttccaccc | 1260 |
| cagcacccgg cgtgtagaca gtcccgtgcc ccgcagggcc actgactgga gagggtgcc | 1320 |
| ctctgagatc gacgctgcct tccaggatgc tgatggctat gcctacttcc tgcgcggccg | 1380 |
| cctctactgg aagtttgacc ctgtgaaggt gaaggctctg gaaggcttcc ccgtctcgt | 1440 |
| gggtcctgac ttctttggct gtgccgagcc tgccaacact ttcctctgac catggcttgg | 1500 |
| atgccctcag gggtgctgac ccctgccagg ccacgaatat caggctagag acccatggcc | 1560 |
| atctttgtgg ctgtgggcac caggcatggg actgagccca tgtctcctca ggggatggg | 1620 |
| gtggggtaca accaccatga caactgccgg gagggccacg caggtcgtgg tcacctgcca | 1680 |
| gcgactgtct cagactgggc agggaggctt tggcatgact taagaggaag ggcagtcttg | 1740 |
| ggcccgctat gcaggtcctg gcaaacctgg ctgccctgtc tccatccctg tccctcaggg | 1800 |

```
tagcaccatg gcaggactgg gggaactgga gtgtccttgc tgtatccctg ttgtgaggtt    1860
ccttccaggg gctggcactg aagcaagggt gctgggaccc catggccttc agccctggct    1920
gagcaactgg gctgtagggc agggccactt cctgaggtca ggtcttggta ggtgcctgca    1980
tctgtctgcc ttctggctga caatcctgga aatctgttct ccagaatcca ggccaaaaag    2040
ttcacagtca aatggggagg ggtattcttc atgcaggaga ccccaggccc tggaggctgc    2100
aacatacctc aatcctgtcc caggccggat cctcctgaag cccttttcgc agcactgcta    2160
tcctccaaag ccattgtaaa tgtgtgtaca gtgtgtataa accttcttct tcttttttttt   2220 tttttaaact gaggattgtc                                                2240

<210> SEQ ID NO 139
<211> LENGTH: 3167
<212> TYPE: DNA
<213> ORGANISM: Homo sapiens

<400> SEQUENCE: 139
tagcagcaca caagggttcg tgtttgtgga accaggtagc ttccttcaga gctgacattt      60
gcccacagcc agcctggccc agccccatac caccagccct ggcgctctgg ggcgtgaggt     120
gccttttctg cccccctgct ctagggcagg tggaaatcac ccatggtggg tctacatctg     180
atagaagcat cttatagttc tgcttctgga ccagaccatc ctgggttttt ctctgttctg     240
ctgaagggtt ccctccacgt gtccatcacc tcggtgaact cttgggagac ctgggaagat     300
gctggcctca cctctcgcct ctcctttccc tcattgtgct gccaccatcc ttctcacaca     360
ggctctccag ggagagctgg gcaggatggg atcttcctgg gttcccacct tgctccgtgc     420 ccctctcac tgttcctgaa gtgtggccac ggactgcctt gttttctgga aagtcccaag      480 tctgaccat gactgagcag cattctcggc tatctgccac ctgtctgggg ctcctggccc      540
ctcttagact cccctctccc ttctgttttcc cccgagcccc tgacttggac ctgcaggtg     600 gggagaggga tgggacgaga acctgtgctg gggccaaagg tcgcactggg ggaaggtgga    660
gccagggcag cagagtgcct ggcgtcggcc cctatcctgt cactagttcc cccgttctgg    720 ccctggcag gtttgtaacc ccagatcaga agtactccat ggacaacact ccccacacgc     780 caacccgtt caagaacgcc ctggagaagt acggacccct gaagcccctg gtacgtggtg    840
tggtcactgc cgtggatctc tgcacagtgg gatcccttcg gttcatccaa ccatgttcag     900
tccacaggac ccttccctct gaggtctcat ttgattcttt ctcctgagaa gatgcagaga    960
tcctgataat ataaatgggg aagctgaggc tgctcttgt cacttcctcc gactgctcct    1020
gagcacctga gtttgcaagc acgcgccggc tggtgctaga gacatggtgg tatcccgtga    1080
cactcagcct caggatgggg agactgatg tgaaatacaa ataacttaaa cactttcagg    1140
caaagataag cactgggcct agttcagaga agtggcaaat tgctactctg gcctgtctct    1200
gaccaactcc cagttctcta cagagcacgg gaaagcccct cggggacgtc tttcctgcag    1260
tgtgcaggct gcccttctcc cctgctcttc ccagttgatg ggatggttgt gttttctcta    1320
tgaaaaaagg agttggcacc ttgggctttc tgaaacacac aggtgtttta gaaatcagtg    1380
gagggtgaga gaaaggcatg gttgtggagg cactggactg tgaacaaggt ctgcagcggg    1440 tcccctgct gtctctctct actgcatgga gcctcctatg aagcccaagg tggctggggg     1500
ctgaggctcc cttgggcctg ccatggaact gattctgagt caagcagact ttccacggac    1560
catgctacat gagccgaggt gaggcactag ttagtgctcc tttcctgttg cagtgggaat    1620
```

| | |
|---|---:|
| ttggctcctc tgtactaaaa tatctgcatg ctctccaaac aggtgtgagg gcaaatcaca | 1680 |
| tgaccttggc agctgtaatt aaagtttgtg ggggcttttc ggatgactta tgaggagtgg | 1740 |
| ctgtgattcg cacctttcac tcttagtagc actcgccctc cctgttctc tgttgcctga | 1800 |
| agctggagag gtccttggaa ccccgaggcc tgagaaaggg aaatggggttt gagagccccc | 1860 |
| attagtgtgg aacaaagggt tgagtgagcc tgggctttga gctgtcgggg tcctaattca | 1920 |
| gcagctgtgt gactgtgtgc caggctgttg atctctgagc ttctgtttct acctgcttaa | 1980 |
| aatgacggtt actgcacagg gctgtgtgag ggttacagtg cgtctctggg ctgctcccag | 2040 |
| ccatggcagg cccctgggaa tcaaggtcat cagctgcttg tccaaggcag cagttagtgg | 2100 |
| ttgtgaatgg tgcgtgtgag atctgcatcc tggcgtcagg cctccttcct gccttaccca | 2160 |
| ggacagccca gttgcagctg ggttggtccc acagtcccac acacacacag cccgagtgtg | 2220 |
| gtgcctcacg tgggctgccc cgtgcctacc cacagccaca gaccccgcac ctggaggagg | 2280 |
| acttgaagga ggtgctgcgt tctgaggctg gcatcgaact catcatcgag gacgacatca | 2340 |
| ggcccgagaa gcagaagagg aagcctgggc tgcggcggag ccccatcaag aaagtccgga | 2400 |
| agtctctggc tcttgacatt gtggatgagg atgtgaagct gatgatgtcc acactgccca | 2460 |
| agtctctatc cttgccgaca actgcccctt caaactcttc cagcctcacc ctgtcaggta | 2520 |
| tcaaagaaga caacagcttg ctcaaccagg gcttcttgca ggccaagccc gagaaggcag | 2580 |
| cagtggccca gaagccccga agccacttca cgacacctgc ccctatgtcc agtgcctgga | 2640 |
| agacggtggc ctgcgggggg accagggacc agcttttcat gcaggagaaa gcccggcagc | 2700 |
| tcctgggccg cctgaagccc agccacacat ctcggaccct catcttgtcc tgaggtgttg | 2760 |
| agggtgtcac gagcccattc acatgtttac aggggttgtg ggggcagagg gggtctgtga | 2820 |
| atctgagagt cattcaggtg acctcctgca gggagccttc tgccaccagc ccctccccag | 2880 |
| actctcaggt ggaggcaaca gggccatgtg ctgccctgtt gccgagccca gctgtgggcg | 2940 |
| gctcctggtg ctaacaacaa agttccactt ccaggtctgc ctggttcccc ccccaaggcc | 3000 |
| acagggagct ccgtcagctt ctcccaagcc cacgtcaggc ctggcctcat ctcagaccct | 3060 |
| gcttaggatg ggggatgtgg ccaggggtgc tcctgtgctc accctctctt ggtgcatttt | 3120 |
| tttggaagaa taaaattgcc tctctctttg aaaaaaaaaa aaaaaaa | 3167 |

<210> SEQ ID NO 140
<211> LENGTH: 2379
<212> TYPE: DNA
<213> ORGANISM: Homo sapiens

<400> SEQUENCE: 140

| | |
|---|---:|
| gacccccgag ctgtgctgct cgcggccgcc accgccgggc cccggccgtc cctggctccc | 60 |
| ctcctgcctc gagaagggca gggcttctca gaggcttggc ggggaaaaga acggagggag | 120 |
| ggatcgcgct gagtataaaa gccggttttc ggggctttat ctaactcgct gtagtaattc | 180 |
| cagcgagagg cagaggggagc gagcgggcgg ccggctaggg tggaagagcc gggcgagcag | 240 |
| agctgcgctg cgggcgtcct gggaagggag atccggagcg aatagggggc ttcgcctctg | 300 |
| gcccagccct cccgctgatc ccccagccag cggtccgcaa ccttgccgc atccacgaaa | 360 |
| cttttgcccat agcagcgggc gggcactttg cactggaact acaacacccc gagcaaggac | 420 |
| gcgactctcc cgacgcgggg aggctattct gcccatttgg ggacacttcc ccgccgctgc | 480 |
| caggacccgc ttctctgaaa ggctctcctt gcagctgctt agacgctgga ttttttttcgg | 540 |
| gtagtggaaa accagcagcc tcccgcgacg atgcccctca acgttagctt caccaacagg | 600 |

```
aactatgacc tcgactacga ctcggtgcag ccgtatttct actgcgacga ggaggagaac      660
ttctaccagc agcagcagca gagcgagctg cagcccccgg cgcccagcga ggatatctgg      720
aagaaattcg agctgctgcc caccccgccc ctgtccccta gccgccgctc cgggctctgc      780
tcgccctcct acgttgcggt cacacccttc tccttcggg gagacaacga cggcggtggc       840
gggagcttct ccacggccga ccagctggag atggtgaccg agctgctggg aggagacatg      900
gtgaaccaga gtttcatctg cgacccggac gacgagacct tcatcaaaaa catcatcatc     960
caggactgta tgtggagcgg cttctcggcc gccgccaagc tcgtctcaga gaagctggcc     1020
tcctaccagg ctgcgcgcaa agacagcggc agcccgaacc cgcccgcgg ccacagcgtc      1080 tgctccacct ccagcttgta cctgcaggat ctgagcgccg ccgcctcaga gtgcatcgac     1140
ccctcggtgg tcttcccta ccctctcaac gacagcagct cgcccaagtc ctgcgcctcg      1200
caagactcca gcgccttctc tccgtcctcg gattctctgc tctcctcgac ggagtcctcc     1260
ccgcagggca gccccgagcc cctggtgctc catgaggaga ccgcccac caccagcagc       1320 gactctgagg aggaacaaga agatgaggaa gaaatcgatg ttgtttctgt ggaaaagagg     1380
caggctcctg gcaaaaggtc agagtctgga tcaccttctg ctggaggcca cagcaaacct    1440
cctcacagcc cactggtcct caagaggtgc cacgtctcca cacatcagca caactacgca    1500
gcgcctccct ccactcggaa ggactatcct gctgccaaga gggtcaagtt ggacagtgtc    1560
agagtcctga cacagatcag caacaaccga aaatgcacca gccccaggtc ctcggacacc    1620
gaggagaatg tcaagaggcg aacacacaac gtcttggagc gccagaggag gaacgagcta    1680
aaacggagct ttttttgccct gcgtgaccag atcccggagt tggaaaacaa tgaaaaggcc    1740
cccaaggtag ttatccttaa aaaagccaca gcatacatcc tgtccgtcca agcagaggag    1800
caaaagctca tttctgaaga ggacttgttg cggaaacgac gagaacagtt gaaacacaaa    1860
cttgaacagc tacggaactc ttgtgcgtaa ggaaaagtaa ggaaaacgat tccttctaac    1920
agaaatgtcc tgagcaatca cctatgaact tgtttcaaat gcatgatcaa atgcaacctc    1980
acaaccttgg ctgagtcttg agactgaaag attttagccat aatgtaaact gcctcaaatt    2040
ggactttggg cataaaagaa cttttttatg cttaccatct ttttttttc tttaacagat     2100 ttgtatttaa gaattgtttt taaaaaattt taagatttac acaatgtttc tctgtaaata    2160
ttgccattaa atgtaaataa ctttaataaa acgtttatag cagttacaca gaatttcaat    2220
cctagtatat agtacctagt attataggta ctataaaccc taattttttt tatttaagta    2280
cattttgctt tttaaagttg atttttttct attgttttta gaaaaaataa aataactggc    2340
aaatatatca ttgagccaaa tcttaaaaaa aaaaaaaaa                            2379
```

<210> SEQ ID NO 141
<211> LENGTH: 1799
<212> TYPE: DNA
<213> ORGANISM: Homo sapiens

<400> SEQUENCE: 141

```
gtgggaggat tgcattcagt ctagttcctg gttgccggct gaaataacct gctctccaaa      60
atgtccacaa aagtgactta agtcaggttc ccccaaacca gacaccaaga caagaatcca     120
tgtgtgtgtg actgaaggaa gtgctgggag agccccagct gcagcctgga tgtgaactgc     180
aactccaaag tgtgtccaga ctcaaggcaa gggcactagg cttttccagac ctcctactaa    240 gtcattgatc cagcactgcc ctgccaggac ataaatccct ggcacctctt gctctctgca    300
```

| | |
|---|---:|
| aaggagggca aagcagcttc aggagcccctt gggagtcctc caaagagagt ctagggtaca | 360 |
| ggtccgaaag tagaagaaca cagaaggcag gccaggggca ctgtgagatg gtaaaagaga | 420 |
| tctgaaggga tccagaattc aagccaggaa gaagcagcaa tctgtcttct ggattaaaac | 480 |
| tgaagatcaa cctactttca acttactaag aaaggggatc atggacattg aagcatatct | 540 |
| tgaaagaatt ggctataaga agtctaggaa caaattggac ttggaaacat taactgatat | 600 |
| tcttcaacac cagatccgag ctgttccctt tgagaacctt aacatccatt gtggggatgc | 660 |
| catggactta ggcttagagg ccattttga tcaagttgtg agaagaaatc ggggtggatg | 720 |
| gtgtctccag gtcaatcatc ttctgtactg ggctctgacc actattggtt ttgagaccac | 780 |
| gatgttggga gggtatgttt acagcactcc agccaaaaaa tacagcactg gcatgattca | 840 |
| ccttctcctg caggtgacca ttgatggcag gaactacatt gtcgatgctg ggtttggacg | 900 |
| ctcataccag atgtggcagc tctggagtt aatttctggg aaggatcagc tcaggtgcc | 960 |
| ttgtgtcttc cgtttgacgg aagagaatgg attctggtat ctagaccaaa tcagaaggga | 1020 |
| acagtacatt ccaaatgaag aatttcttca ttctgatctc ctagaagaca gcaaataccg | 1080 |
| aaaaatctac tcctttactc ttaagcctcg aacaattgaa gattttgagt ctatgaatac | 1140 |
| ataccctgca acatctccat catctgtgtt tactagtaaa tcattttgtt ccttgcagac | 1200 |
| cccagatggg gttcactgtt tggtgggctt caccctcacc cataggagat tcaattataa | 1260 |
| ggacaataca gatctaatag agttcaagac tctgagtgag gaagaaatag aaaaagtgct | 1320 |
| gaaaaatata tttaatattt ccttgcagag aaagcttgtg cccaaacatg gtgatagatt | 1380 |
| ttttactatt tagaataagg agtaaaaacaa tcttgtctat tgtcatcca gctcaccagt | 1440 |
| tatcaactga cgacctatca tgtatcttct gtaccttac cttattttga agaaaatcct | 1500 |
| agacatcaaa tcatttcacc tataaaaatg tcatcatata taattaaaca gcttttttaaa | 1560 |
| gaaacataac cacaaacctt ttcaaataat aataataata ataataataa atgtcttta | 1620 |
| aagatggcct gtggttatct tggaaattgg tgatttatgc tagaaagctt ttaatgttgg | 1680 |
| tttattgttg aattcctaga aaagttttat gggtagatga gtaaataaaa tattgtaaaa | 1740 |
| aaacttattg tctataaagt atattaaaac attgttggct aatataaaaa aaaaaaaaa | 1799 |

<210> SEQ ID NO 142
<211> LENGTH: 1644
<212> TYPE: DNA
<213> ORGANISM: Homo sapiens

<400> SEQUENCE: 142

| | |
|---|---:|
| gcgcgcgggt ttcgttgacc cgcggcgttc acgggaattg ttcgctttag tgccggcgcc | 60 |
| atggggtcgg agctgatcgg gcgcctagcc ccgcgcctgg gcctcgccga gcccgacatg | 120 |
| ctgaggaaag cagaggagta cttgcgcctg tcccgggtga agtgtgtcgg cctctccgca | 180 |
| cgcaccacgg agaccagcag tgcagtcatg tgcctggacc ttgcagcttc ctggatgaag | 240 |
| tgccccttgg acagggctta tttaattaaa ctttctggtt tgaacaagga gacatatcag | 300 |
| agctgtctta aatcttttga gtgtttactg ggcctgaatt caaatattgg aataagagac | 360 |
| ctagctgtac agtttagctg tatagaagca gtgaacatgg cttcaaagat actaaaaagc | 420 |
| tatgagtcca gtcttcccca gacacagcaa gtggatcttg acttatccag gccacttttc | 480 |
| acttctgctg cactgctttc agcatgcaag attctaaagc tgaaagtgga taaaaacaaa | 540 |
| atggtagcca catccggtgt aaaaaaagct atatttgatc gactgtgtaa acaactagag | 600 |
| aagattggac agcaggtcga cagagaacct ggagatgtag ctactccacc acggaagaga | 660 |

```
aagaagatag tggttgaagc cccagcaaag gaaatggaga aggtagagga gatgccacat      720
aaaccacaga aagatgaaga tctgacacag gattatgaag aatggaaaag aaaaattttg      780
gaaaatgctg ccagtgctca aaaggctaca gcagagtgat ttcagcttcc aaactggtat      840
acattccaaa ctgatagtac attgccatct ccaggaagac ttgacggctt tgggattttg      900
tttaaacttt tataataagg atcctaagac tgttgccttt aaatagcaaa gcagcctacc      960
tggaggctaa gtctgggcag tgggctggcc cctggtgtga gcattagacc agccacagtg     1020
cctgattggt atagccttat gtgctttcct acaaaatgga attggaggcc gggcgcagtg     1080
gctcacgcct gtaatcccag cactttggga ggccaaggtg ggtggatcac ctgaggtcag     1140
gagctcgaga ccagcctggc caacatggtg aaaccccatc tctactaaaa atacaaaaat     1200
tagccaggtg tgatggtgca tgcctgtaat cccagctcct cagtaggctg agacaggagc     1260
atcacttgaa cgtgggaggc agaggttgca gtgagccgag attgcaccac cgcactccag     1320
cctgggtgac agagcgagac ttatctcata aataaataga tagatactcc agcctgggtg     1380
acagagcgag acttatagat agatagatag atagatggat agatagatag atagatagat     1440
agatagataa acgaattggg agccatttg  ctttaagtga atggcagtcc cttgtcttat     1500
tcagaatata aaattcagtc tgaatggcat cttacagatt ttacttcaat ttttgtgtac     1560 ggtattttt  atttgactaa atcaatatat tgtacagcct aagttaataa atgttattta     1620
tatatgcaaa aaaaaaaaa  aaaa                                           1644

<210> SEQ ID NO 143
<211> LENGTH: 13037
<212> TYPE: DNA
<213> ORGANISM: Homo sapiens

<400> SEQUENCE: 143
agtccacagc tgtcactaat cggggtaagc cttgttgtat ttgtgcgtgt gggtggcatt       60
ctcaatgaga actagcttca cttgtcattt gagtgaaatc tacaacccga ggcggctagt      120
gctcccgcac tactgggatc tgagatcttc ggagatgact gtcgcccgca gtacggagcc      180
agcagaagtc cgacccttcc tgggaatggg ctgtaccgag aggtccgact agccccaggg      240
ttttagtgag ggggcagtgg aactcagcga gggactgaga gcttcacagc atgcacgagt      300
ttgatgccag agaaaagtc  gggagataaa ggagccgcgt gtcactaaat tgccgtcgca      360
gccgcagcca ctcaagtgcc ggacttgtga gtactctgcg tctccagtcc tcggacagaa      420
gttggagaac tctcttggag aactccccga gttaggagac gagatctcct aacaattact      480 acttttttctt gcgctcccca cttgccgctc gctgggacaa cgacagcca  cagttcccct      540 gacgacagga tggaggccaa gggcaggagc tgaccagcgc cgcccctccc cgcccccgac      600
ccaggaggtg gagatccctc cggtccagcc acattcaaca cccactttct cctccctctg      660
cccctatatt cccgaaaccc cctcctcctt cccttttccc tcctcctgga gacggggag       720 gagaaaaggg gagtccagtc gtcatgactg agctgaaggc aaagggtccc cgggctcccc      780
acgtggcggg cggcccgccc tcccccgagg tcggatcccc actgctgtgt cgcccagccg      840
caggtccgtt cccggggagc cagacctcgg acaccttgcc tgaagtttcg gccataccta      900 tctcccctgga cgggctactc ttccctcggc cctgccaggg acaggacccc tccgacgaaa      960
agacgcagga ccagcagtcg ctgtcggacg tggaggcgc  atattccaga gctgaagcta     1020
caaggggtgc tggaggcagc agttctagtc ccccagaaaa ggacagcgga ctgctggaca     1080
```

```
gtgtcttgga cactctgttg gcgccctcag gtcccgggca gagccaaccc agccctcccg    1140
cctgcgaggt caccagctct tggtgcctgt ttggccccga acttcccgaa gatccaccgg    1200
ctgcccccgc cacccagcgg gtgttgtccc cgctcatgag ccggtccggg tgcaaggttg    1260
gagacagctc cgggacggca gctgcccata aagtgctgcc ccggggcctg tcaccagccc    1320
ggcagctgct gctcccggcc tctgagagcc ctcactggtc cggggcccca gtgaagccgt    1380
ctccgcaggc cgctgcggtg gaggttgagg aggaggatgg ctctgagtcc gaggagtctg    1440
cgggtccgct tctgaagggc aaacctcggg ctctgggtgg cgcggcggct ggaggaggag    1500
ccgcggctgt cccgccgggg gcggcagcag gaggcgtcgc cctggtcccc aaggaagatt    1560
cccgcttctc agcgcccagg gtcgccctgg tggagcagga cgcgccgatg gcgcccgggc    1620 gctcccccgct ggccaccacg gtgatggatt tcatccacgt gcctatcctg cctctcaatc    1680
acgccttatt ggcagcccgc actcggcagc tgctggaaga cgaaagttac gacggcgggg    1740
ccggggctgc cagcgccttt gccccgccgc ggagttcacc ctgtgcctcg tccaccccgg    1800
tcgctgtagg cgacttcccc gactgcgcgt acccgcccga cgccgagccc aaggacgacg    1860
cgtaccctct ctatagcgac ttccagccgc ccgctctaaa gataaaggag gaggaggaag    1920
gcgcggaggc ctccgcgcgc tccccgcgtt cctaccttgt ggccggtgcc aaccccgcag    1980
ccttcccgga tttcccgttg gggccaccgc cccgctgcc gccgcgagcg accccatcca    2040
gacccgggga agcggcggtg acggccgcac ccgccagtgc ctcagtctcg tctgcgtcct    2100
cctcggggtc gaccctggag tgcatcctgt acaaagcgga gggcgcgccg cccagcagg     2160 gcccgttcgc gccgccgccc tgcaaggcgc cgggcgcgag cggctgcctg ctcccgcggg    2220
acggcctgcc ctccacctcc gcctctgccg ccgccgccgg ggcggccccc gcgctctacc    2280
ctgcactcgg cctcaacggg ctcccgcagc tcggctacca ggccgccgtg ctcaaggagg    2340
gcctgccgca ggtctacccg ccctatctca actacctgag gccggattca gaagccagcc    2400
agagcccaca atacagcttc gagtcattac ctcagaagat ttgtttaatc tgtggggatg    2460
aagcatcagg ctgtcattat ggtgtcctta cctgtgggag ctgtaaggtc ttctttaaga    2520
gggcaatgga agggcagcac aactacttat gtgctggaag aaatgactgc atcgttgata    2580
aaatccgcag aaaaaactgc ccagcatgtc gccttagaaa gtgctgtcag gctggcatgg    2640
tccttggagg tcgaaaattt aaaaagttca ataaagtcag agttgtgaga gcactggata    2700
ctgttgctct cccacagcca gtgggcgttc caaatgaaag ccaagcccta agccagagat    2760 tcacttttc accaggtcaa gacatacagt tgattccacc actgatcaac ctgttaatga    2820
gcattgaacc agatgtgatc tatgcaggac atgacaacac aaaacctgac acctccagtt    2880
ctttgctgac aagtcttaat caactaggcg agaggcaact tctttcagta gtcaagtggt    2940
ctaaatcatt gccaggtttt cgaaacttac atattgatga ccagataact ctcattcagt    3000
attcttggat gagcttaatg gtgtttggtc taggatggag atcctacaaa cacgtcagtg    3060
ggcagatgct gtattttgca cctgatctaa tactaaatga acagcggatg aaagaatcat    3120
cattctattc attatgcctt accatgtggc agatcccaca ggagtttgtc aagcttcaag    3180
ttagccaaga agagttcctc tgtatgaaag tattgttact tcttaataca attcctttgg    3240
aagggctacg aagtcaaacc cagtttgagg agatgaggtc aagctacatt agagagctca    3300
tcaaggcaat ggtttgagg caaaaggag ttgtgtcgag ctcacagcgt ttctatcaac    3360
ttacaaaact tcttgataac ttgcatgatc ttgtcaaaca acttcatctg tactgcttga    3420
atacatttat ccagtcccgg gcactgagtg ttgaatttcc agaaatgatg tctgaagtta    3480
```

```
ttgctgcaca attacccaag atattggcag ggatggtgaa acccttctc  tttcataaaa   3540
agtgaatgtc atcttttct  tttaaagaat taaattttgt ggtatgtctt tttgttttgg   3600
tcaggattat gaggtcttga gttttataa  tgttcttctg aaagccttac atttataaca   3660
tcatagtgtg taaatttaaa agaaaaattg tgaggttcta attattttct tttataaagt   3720
ataattagaa tgtttaactg ttttgtttac ccatattttc ttgaagaatt tacaagattg   3780
aaaaagtact aaaattgtta aagtaaacta tcttatccat attatttcat accatgtagg   3840
tgaggatttt taacttttgc atctaacaaa tcatcgactt aagagaaaaa atcttacatg   3900
taataacaca aagctattat atgttatttc taggtaactc cctttgtgtc aattatattt   3960
ccaaaaatga acctttaaaa tggtatgcaa aattttgtct atatatattt gtgtgaggag   4020
gaaattcata actttcctca gattttcaaa agtattttta atgcaaaaaa tgtagaaaga   4080
gtttaaaacc actaaaatag attgatgttc ttcaaactag gcaaacaac  tcatatgtta   4140
agaccatttt ccagattgga aacacaaatc tcttaggaag ttaataagta gattcatatc   4200
attatgcaaa tagtattgtg ggttttgtag gttttttaaa taacctttt  tggggagaga   4260
attgtcctct aatgaggtat tgcgagtgga cataagaaat cagaagatta tggcctaact   4320
gtactcctta ccaactgtgg catgctgaaa gttagtcact cttactgatt ctcaattctc   4380
tcacctttga aagtagtaaa atatcttcc  tgccaattgc tcctttgggt cagagcttat   4440
taacatcttt tcaaatcaaa ggaaagaaga aagggagagg aggaggaggg aggtatcaat   4500
tcacatacct ttctcctctt tatcctccac tatcatgaat tcatattatg tttcagccat   4560
gcaaatcttt ttaccatgaa atttcttcca gaattttccc cctttgacac aaattccatg   4620
catgtttcaa ccttcgagac tcagccaaat gtcattctg  taaaatcttc cctgagtctt   4680
ccaagcagta atttgccttc tcctagagtt tacctgccat tttgtgcaca tttgagttac   4740
agtagcatgt tattttacaa ttgtgactct cctgggagtc tgggagccat ataaagtggt   4800
caatagtgtt tgctgactga gagttgaatg acatttctc  tctgtcttgg tattactgta   4860
gatttcgatc attctttggt tacatttctg catatttctg tacccatgac tttatcactt   4920
tcttctccca tgctttatct ccatcaatta tcttcattac ttttaaattt tccacctttg   4980
cttcctactt tgtgagatct ctcccttac  tgactataac atagaagaat agaagtgtat   5040
tttatgtgtc ttaaggacaa tactttagat tccttgttct aagttttaa  actgaatgaa   5100
tggaatatta tttctctccc taagcaaaat tccacaaaac aattatttct tatgtttatg   5160
tagccttaaa ttgttttgta ctgtaaacct cagcataaaa actttcttca tttctaattt   5220
cattcaacaa atattgattg aatacctggt attagcacaa gaaaaatgtg ctaataagcc   5280
ttatgagaat ttggagctga agaaagacat ataactcagg aaagttacag tccagtagta   5340
ggtataaatt acagtgcctg ataaataggc attttaatat ttgtacactc aacgtatact   5400
aggtaggtgc aaaacattta catataattt tactgatacc catgcagcac aaaggtacta   5460
actttaaata ttaaataaca cctttatgtg tcagtaattc atttgcatta aatcttattg   5520
aaaaggcttt caatatattt tccccacaaa tgtcatccca agaaaaaagt attttttaaca  5580
tctcccaaat ataatagtta caggaaatct acctctgtga gagtgacacc tctcagaatg   5640
aactgtgtga cacaagaaaa tgaatgtagg tctatccaaa aaaaccccca agaaacaaaa   5700
acaatattat tagccccttta tgcttaagtg atggactcag ggaacagttg atgttgtgat   5760
cattttatta tctgattctt gttactttga attaaaccaa tattttgatg atataaatca   5820
```

```
tttccaccag catatattta atttccataa aactttaaa attttctaat ttcactcaac   5880
tatgagggaa tagaatgtgg tggccacagg tttggctttt gttaaaatgt ttgatatctt   5940
cgatgttgat ctctgtctgc aatgtagatg tctaaacact aggatttaat atttaaggct   6000
aagctttaaa aataaagtac cttttaaaa agaatatggc ttcaccaaat ggaaaatacc   6060
taatttctaa atcttttct ctacaaagtc ctatctacta atgtctccat tactatttag   6120
tcatcataac cattatcttc attttacatg tcgtgttctt tctggtagct ctaaaatgac   6180
actaaatcat aagaagacag gttacatatc aggaaatact tgaaggttac tgaaatagat   6240
tcttgagtta atgaaaatat tttctgtaaa aaggtttgaa aagccatttg agtctaaagc   6300
attatacctc cattatcagt agttatgtga caattgtgtg tgtgtttaat gtttaaagat   6360
gtggcacttt ttaataaggc aatgctatgc tattttttcc catttaacat taagataatt   6420
tattgctata cagatgatat ggaaatatga tgaacaatat tttttttgcc aaaactatgc   6480
cttgtaagta gccatggaat gtcaacctgt aacttaaatt atccacagat agtcatgtgt   6540
ttgatgatgg gcactgtgga gataactgac ataggactgt gccccccttc tctgccactt   6600
actagctgga tgagattaag caagtcattt aactgctctg attaaacctg cctttcccaa   6660
gtgctttgta atgaatagaa atggaaacca aaaaaaacgt atacaggcct tcagaaatag   6720
taattgctac tattttgttt tcattaagcc atagttctgg ctataatttt atcaaactca   6780
ccagctatat tctacagtga aagcaggatt ctagaaagtc tcactgtttt atttatgtca   6840
ccatgtgcta tgatatattt ggttgaattc atttgaaatt agggctggaa gtattcaagt   6900
aatttcttct gctgaaaaaa tacagtgttt tgagtttagg gcctgtttta tcaaagttct   6960
aaagagccta tcactcttcc attgtagaca tttaaaata atgacactga ttttaacatt   7020
tttaagtgtc tttttagaac agagagcctg actagaacac agcccctcca aaaacccatg   7080
ctcaaattat ttttactatg gcagcaattc cacaaagggaa acaatgggt ttagaaatta   7140
caatgaagtc atcaacccaa aaaacatccc tatccctaag aaggttatga tataaaatgc   7200
ccacaagaaa tctatgtctg ctttaatctg tcttttattg ctttggaagg atggctatta   7260
catttttagt ttttgctgtg aatacctgag cagtttctct catccatact tatccttcac   7320
acatcagaag tcaggataga atatgaatca ttttaaaaac ttttacaact ccagagccat   7380
gtgcataaga agcattcaaa acttgccaaa acatacattt tttttcaaat ttaaagatac   7440
tctattttg tattcaatag ctcaacaact gtggtcccca ctgataaagt gaagtggaca   7500
aggagacaag taatggcata agtttgttt tcccaaagta tgcctgttca atagccattg   7560
gatgtgggaa atttctacat ctcttaaaat tttacagaaa atacatagcc agatagtcta   7620
gcaaaagttc accaagtcct aaattgctta tccttacttc actaagtcat gaaatcatt   7680
taatgaaaag aacatcacct aggttttgtg gtttctttt ttcttattca tggctgagtg   7740
aaaacaacaa tctctgtttc tccctagcat ctgtggacta tttaatgtac cattattcca   7800
cactctatgg tccttactaa atacaaaatt gaacaaaaag cagtaaaaca actgactctt   7860
cacccatatt ataaaatata atccaagcca gattagtcaa catccataag atgaatccaa   7920
gctgaactgg gcctagatta ttgagttcag gttggatcac atccctattt attaataaac   7980
ttaggaaaga aggccttaca gaccatcagt tagctggagc taatagaacc tacacttcta   8040
aagttcggcc tagaatcaat gtggccttaa aagctgaaaa gaagcaggaa agaacagttt   8100
tcttcaataa tttgtccacc ctgtcactgg agaaaatta agaatttggg ggtgttggta   8160
gtaagttaaa cacagcagct gttcatggca gaaattattc aatacatacc ttctctgaat   8220
```

```
atcctataac caaagcaaag aaaaacacca aggggtttgt tctcctcctt ggagttgacc     8280
tcattccaag gcagagctca ggtcacaggc acaggggctg cgcccaagct tgtccgcagc     8340
cttatgcagc tgtggagtct ggaagactgt tgcaggactg ctggcctagt cccagaatgt     8400
cagcctcatt ttcgatttac tggctcttgt tgctgtatgt catgctgacc ttattgttaa     8460
acacaggttt gtttgctttt tttccactca tggagacatg ggagaggcat tattttaag     8520 ctggttgaaa gctttaaccg ataaagcatt tttagagaaa tgtgaatcag gcagctaaga     8580
aagcatactc tgtccattac ggtaaagaaa atgcacagat tattaactct gcagtgtggc     8640
attagtgtcc tggtcaatat tcggatagat atgaataaaa tatttaaatg gtattgtaaa     8700 tagtttcag gacatatgct atagcttatt tttattatct tttgaaattg ctcttaatac     8760
atcaaatcct gatgtattca atttatcaga tataaattat tctaaatgaa gcccagttaa     8820 atgttttgt cttgtcagtt atatgttaag tttctgatct cttttgtctat gacgtttact     8880 aatctgcatt tttactgtta tgaattattt tagacagcag tggtttcaag cttttttgcca     8940 ctaaaaatac cttttatttt ctcctccccc agaaaagtct ataccttgaa gtatctatcc     9000
accaaactgt acttctatta agaaatagtt attgtgtttt cttaatgttt tgttattcaa     9060
agacatatca atgaaagctg ctgagcagca tgaataacaa ttatatccac acagatttga     9120
tatattttgt gcagccttaa cttgatagta taaaatgtca ttgcttttta aataatagtt     9180
agtcaatgga cttctatcat agctttccta aactaggtta agatccagag ctttggggtc     9240
ataatatatt acatacaatt aagttatctt tttctaaggg cttttaaaatt catgagaata     9300 accaaaaaag gtatgtggag agttaataca aacataccat attcttgttg aaacagagat     9360
gtggctctgc ttgttctcca taaggtagaa atactttcca gaatttgcct aaactagtaa     9420
gccctgaatt tgctatgatt agggatagga agagattttc acatggcaga ctttagaatt     9480
cttcacttta gccagtaaag tatctccttt tgatcttagt attctgtgta ttttaacttt     9540
tctgagttgt gcatgtttat aagaaaaatc agcacaaagg gtttaagtta aagccttttt     9600
actgaaattt gaaagaaaca gaagaaaata tcaaagttct ttgtattttg agaggattaa     9660
atatgattta caaaagttac atggagggct ctctaaaaca ttaaattaat tatttttgt     9720 tgaaaagtct tactttaggc atcattttat tcctcagcaa ctagctgtga agcctttact     9780
gtgctgtatg ccagtcactc tgctagattg tggagattac cagtgttccc gtcttctccg     9840
agcttagagt tggatgggga ataaagacag gtaaacagat agctacaata ttgtactgtg     9900
aatgcttatg ctggaggaag tacagggaac tattggagca cctaagagga gcacctacct     9960
tgaatttagg ggttagcaga ggcatcctga aaaagtcaa agctaagcca caatctataa     10020
gcagtttagg aattagcaga acgtgcgtgg tgaggagatg ccaaaggcaa gaagagaaga     10080
gtattccaaa caggagggat tccaaagaga gaagagtatc ccaaacaaca tttgcacaaa     10140
cctgatgggg agagagaatg tggggtgggg atggatgatg agactgaaga agaaagccag     10200
gtctagataa tcagtggcct tgtacaccat gttaaagagt gtagacttga ttctgttgta     10260
aacaggaaag cagcacaatt catatgaata ttttagaaga ctcccactgg aatatggaga     10320
ataaagttgg agatgactaa tcctggaagc agggagaaca ttttgagga agttgcacta     10380 ttttggtgaa aatgatgatc ataaacatga agaattgtag gtgatcatga cctcctctct     10440
aattttccag aagggttttg gaagatataa cataggaaca ttgacaggac tgacgaaagg     10500
agatgaaata caccatataa attgtcaaac acaaggccag atgtctaatt attttgctta     10560
```

```
tgtgttgaaa ttacaaattt ttcatcagga aaccaaaaac tacaaaactt agttttccca   10620
agtcccagaa ttctatctgt ccaaacaatc tgtaccactc cacctatatc cctacctttg   10680
catgtctgtc caacctcaaa gtccaggtct atacacacgg gtaagactag agcagttcaa   10740
gtttcagaaa atgagaaaga ggaactgagt tgtgctgaac ccatacaaaa taaacacatt   10800
ctttgtatag attcttggaa cctcgagagg aattcaccta actcataggt atttgatggt   10860
atgaatccat ggctgggctc ggcttttaaa aagccttatc tgggattcct tctatggaac   10920
caagttccat caaagcccat ttaaaagcct acattaaaaa caaaattctt gctgcattgt   10980
atacaaataa tgatgtcatg atcaaataat cagatgccat tatcaagtgg aattacaaaa   11040
tggtataccc actccaaaaa aaaaaaaaaa gctaaattct cagtagaaca ttgtgacttc   11100
atgagccctc cacagccttg gagctgagga gggagcactg gtgagcagta ggttgaagag   11160
aaaacttggc gcttaataat ctatccatgt ttttttcatct aaaagagcct tcttttttgga   11220 ttaccttatt caatttccat caaggaaatt gttagttcca ctaaccagac agcagctggg   11280
aaggcagaag cttactgtat gtacatggta gctgtgggaa ggaggtttct ttctccaggt   11340
cctcactggc catacaccag tcccttgtta gttatgcctg gtcatagacc cccgttgcta   11400
tcatctcata tttaagtctt tggcttgtga atttatctat tctttcagct tcagcactgc   11460
agagtgctgg gactttgcta acttccattt cttgctggct tagcacattc ctcataggcc   11520
cagctctttt ctcatctggc cctgctgtgg agtcaccttg cccctcagg agagccatgg   11580 cttaccactg cctgctaagc ctccactcag ctgccaccac actaaatcca agcttctcta   11640
agatgttgca gactttacag gcaagcataa aaggcttgat cttcctggac ttcccttttac   11700 ttgtctgaat ctcacctcct tcaactttca gtctcagaat gtaggcattt gtcctctttg   11760
ccctacatct tccttcttct gaatcatgaa agcctctcac ttcctcttgc tatgtgctgg   11820
aggcttctgt caggttttag aatgagttct catctagtcc tagtagcttt tgatgcttaa   11880 gtccacctttaaggatacc tttgagattt agaccatgtt tttcgcttga gaagccctta   11940
atctccagac ttgcctttct gtggatttca aagaccaact gaggaagtca aaagctgaat   12000
gttgactttc tttgaacatt tccgctataa caattccaat tctcctcaga gcaatatgcc   12060
tgcctccaac tgaccaggag aaaggtccag tgccaaagag aaaaacacaa agattaatta   12120
tttcagttga gcacatactt tcaaagtggt ttgggtattc atatgaggtt ttctgtcaag   12180
agggtgagac tcttcatcta tccatgtgtg cctgacagtt ctcctggcac tggctggtaa   12240
cagatgcaaa actgtaaaaa ttaagtgatc atgtatttta acgatatcat cacatactta   12300
ttttctatgt aatgttttaa atttccccta acatactttg actgttttgc acatggtaga   12360
tattcacatt ttttttgtgtt gaagttgatg caatcttcaa agttatctac cccgttgctt   12420
attagtaaaa ctagtgttaa tacttggcaa gagatgcagg gaatctttct catgactcac   12480
gccctattta gttattaatg ctactaccct atttttgagta agtagtaggt ccctaagtac   12540
attgtccaga gttatacttt taaagatatt tagccccata tacttcttga atctaaagtc   12600
atacaccttg ctcctcattt ctgagtggga aagacatttg agagtatgtt gacaattgtt   12660
ctgaaggttt ttgccaagaa ggtgaaactg tcctttcatc tgtgtatgcc tggggctggg   12720
tccctggcag tgatggggtg acaatgcaaa gctgtaaaaa ctaggtgcta gtgggcacct   12780
aatatcatca tcatatactt attttcaagc taatatgcaa aatcccatct ctgttttttaa   12840 actaagtgta gatttcagag aaaatatttt gtggttcaca taagaaaaca gtctactcag   12900
cttgacaagt gttttatgtt aaattggctg gtggtttgaa atgaatcatc ttcacataat   12960
```

```
gttttcttta aaaatattgt gaatttaact ctaattcttg ttattctgtg tgataataaa    13020
gaataaacta atttcta                                                  13037

<210> SEQ ID NO 144
<211> LENGTH: 3180
<212> TYPE: DNA
<213> ORGANISM: Homo sapiens

<400> SEQUENCE: 144
attctatgct gcagcctaag catcattcct cttctcttct tagtggagat aaaattaccc      60
actgctctcc ttacatttac tttgtccata tttgctccta tgctctaggc tcgtgcacaa     120
caaacacagt gtgggccctt accctagaag ccaacttctc atgacctttc tctatctcca     180
gaatccatgc agtgggaatg aaggtaaaag aaggttttca tgggatccag ctgagagctc     240 tacgggaaa atggatctga ggagccatgt gctccatctc tttttatttta caggtagaga     300 ctaggggtat agagtgaggt gaattaccgc agtgacccac acattgttgg cagacctagg     360
attagaactc tgtcttcctg gttcccagct tggtgctttt gaaagcatac ttgctgcttt     420
cttaccggcc tggtgtctgc cactttggga cagagtgtgg acttgctcac ctgccccatt     480
tcttagggat tctcattctg tgtttgagca agaatattct tattctggaa agaaccacat     540
accacaggat tctgggtgag cataaggaag attgtcttgg ggatctgact tagctcacgt     600
atagtggcta tgatgaattc agtgtcttat tttttgcata tgtatatttt tagtctaata     660
ttgcctgggt gtctgagcaa gtctagatga atttaattgc tctcatttt ccctgcccc     720 tcttcctttg gtctctcttt taggaaatgt ttttctttca acattcgttt cattcattat     780
ttactcattc ggccaaccaa catttattga gtgccttccc tgtatcaggg acaggggctt     840
acaaagtaga atttgatccc acctctgccc tcagtagctc agtgtctaat ggaggtagtg     900
atgttcatta agcgtcgcca gatactgtgc taggtgctgt gcctgttctc tctcgcttgt     960
tcctcacaca cttgagaagg ccgaagctga ttcatagctt ggaaggcagg ggccttggat    1020
ttgaacccag gcctgaccaa tggcagaacc tatcagatgt gtggacagat gacattgcct    1080
ttctttcttt ggatatatca aaatcagcca gcaggcagga actcccattt tgagcaagca    1140
atgtgcagga atgatagggt atacagagag gaacaggaga tggcccctga cttccagcat    1200
gtgtctgatg gacatccagg ctgcaggcat catggtgctg tctagagaga tgagccaggt    1260
gcccagagcc catgggccaa tgctgcccctt tcttgagcat gccaaacaaa gcggttggtg    1320
tgttagaggc acagtctcct ccactctaag taaaaatcag catgagtcct agcccacatt    1380
tccctagtga gtacaccaaa gatatctatg aactggcagt catcagtgac ttcctaaggt    1440 tccgaaatg catctcttac tcaggagtaa gcaatgatgt gcctgcggct ttacgagttc    1500
tcacagaatg actttctgga cccaaatgtt ttttctgctt caggactgtg aaggccttat    1560
tgttcgctct gccaccaagg tgaccgctga tgtcatcaac gcagctgaga actccaggt    1620 ggtgggcagg gctggcacag gtgtggacaa tgtggatctg gaggccgcaa caaggaaggg    1680
catcttggtt atgaacaccc ccaatgggaa cagcctcagt gccgcagaac tcacttgtgg    1740
aatgatcatg tgcctggcca ggcagattcc ccaggcgacg gcttcgatga aggacggcaa    1800
atgggagcgg aagaagttca tgggaacaga gctgaatgga aagaccctgg gaattcttgg    1860
cctgggcagg attgggagag aggtagctac ccggatgcag tcctttggga tgaagactat    1920
agggtatgac cccatcattt ccccagaggt ctcggcctcc tttggtgttc agcagctgcc    1980
```

| | |
|---|---|
| cctggaggag atctggcctc tctgtgattt catcactgtg cacactcctc tcctgccctc | 2040 |
| cacgacaggc ttgctgaatg acaacacctt tgcccagtgc aagaaggggg tgcgtgtggt | 2100 |
| gaactgtgcc cgtggaggga tcgtggacga aggcgccctg ctccgggccc tgcagtctgg | 2160 |
| ccagtgtgcc ggggctgcac tggacgtgtt tacggaagag ccgccacggg accgggcctt | 2220 |
| ggtggaccat gagaatgtca tcagctgtcc ccacctgggt gccagcacca aggaggctca | 2280 |
| gagccgctgt ggggaggaaa ttgctgttca gttcgtggac atggtgaagg ggaaatctct | 2340 |
| cacgggggtt gtgaatgccc aggcccttac cagtgccttc tctccacaca ccaagccttg | 2400 |
| gattggtctg gcagaagctc tggggacact gatgcgagcc tgggctgggt cccccaaagg | 2460 |
| gaccatccag gtgataacac agggaacatc cctgaagaat gctgggaact gcctaagccc | 2520 |
| cgcagtcatt gtcggcctcc tgaaagaggc ttccaagcag gcggatgtga acttggtgaa | 2580 |
| cgctaagctg ctggtgaaag aggctggcct caatgtcacc acctcccaca gccctgctgc | 2640 |
| accaggggg caaggcttcg gggaatgcct cctggccgtg gccctggcag gcgcccctta | 2700 |
| ccaggctgtg ggcttggtcc aaggcactac acctgtactg caggggctca atggagctgt | 2760 |
| cttcaggcca gaagtgcctc tccgcaggga cctgcccctg ctcctattcc ggactcagac | 2820 |
| ctctgacccct gcaatgctgc ctaccatgat tggcctcctg gcagaggcag gcgtgcggct | 2880 |
| gctgtcctac cagacttcac tggtgtcaga tggggagacc tggcacgtca tgggcatctc | 2940 |
| ctccttgctg cccagcctgg aagcgtggaa gcagcatgtg actgaagcct tccagttcca | 3000 |
| cttctaacct tggagctcac tggtccctgc ctctggggct tttctgaaga aacccaccca | 3060 |
| ctgtgatcaa tagggagaga aaatccacat tcttgggctg aacgcgagcc tctgacactg | 3120 |
| cttacactgc actctgaccc tgtagtacag caataaccgt ctaataaaga gcctaccccc | 3180 |

<210> SEQ ID NO 145
<211> LENGTH: 1301
<212> TYPE: DNA
<213> ORGANISM: Homo sapiens
<220> FEATURE:
<221> NAME/KEY: misc_feature
<222> LOCATION: (1301)..(1301)
<223> OTHER INFORMATION: n is a, c, g, or t

<400> SEQUENCE: 145

| | |
|---|---|
| caaacaaaaa cagccaagct tttctgccaa aaagatgact gagaagactg ttaaagcaaa | 60 |
| aagctctgtt cctgcctcag atgatgccta tccagaaata gaaaaattct ttcccttcaa | 120 |
| tcctctagac tttgagagtt ttgacctgcc tgaagagcac cagattgcgc acctcccctt | 180 |
| gagtggagtg cctctcatga tccttgacga ggagagagag cttgaaaagc tgtttcagct | 240 |
| gggcccccct tcacctgtga agatgccctc tccaccatgg gaatccaatc tgttgcagtc | 300 |
| tccttcaagc attctgtcga ccctggatgt tgaattgcca cctgtttgct gtgacataga | 360 |
| tatttaaatt tcttagtgct tcagagtctg tgtgtatttg tattaataaa gcattcttta | 420 |
| acagaaaaaa aaaaaaaaa aaaaaaaaa aaaaaaaaa aaaaaaaaa agggggggga | 480 |
| gacacaaaaa gaattcccca agagggggcc acaagataat cagaggatat cacacaagat | 540 |
| ctctcggcgc accaacgacg ggggcccaa ataaggaga gacccagaat cacaacagcc | 600 |
| aagacacggt ggacacgacg gaaacaaaca cacagcccag acacggggc aaacacgcgc | 660 |
| gcacaccgcg gacaccatgg gacaaagcag acaccaccca caaacaaca ccgcggaggg | 720 |
| ggaagaacaa caaaacaagt gcgcaaacag aacacaacca cagaaagaga aaattaaaa | 780 |
| cggcccccaa gacggcgaca acacaacaaa acaaccacta cagagcgctc aacagccgag | 840 |

| | |
|---|---|
| taaaaacaca acaacggaca actaacacac aaaggaatga aacaaagcgg ggccacacac | 900 |
| cgacaccgga aatccggcga acaactcaca ccgagcgagg gtcccagaca acaaatacac | 960 |
| agacaacgaa accgagaaac aagaccagca agacgagcag gcaaaagaca aacaagacag | 1020 |
| aggagacgac gacgaacgca aaggacaaga ggacacaacg acgcgaggag cgagagcgag | 1080 |
| aggaagagac aacaaaaaga cacaaaagaa caacaagcaa gcagcgaaga acgacacaca | 1140 |
| accacacgag acagcaggag cagaggcgga gaaaacacaa cgagcaagcc aagaccaaga | 1200 |
| gaggagaaca aaataaaaaa atacgagagc aggcggacga gagcacgaga cgaacagaca | 1260 |
| aacgggaatc agaagcataa cgatccgcga cgcgaacaac n | 1301 |

<210> SEQ ID NO 146
<211> LENGTH: 3203
<212> TYPE: DNA
<213> ORGANISM: Homo sapiens

<400> SEQUENCE: 146

| | |
|---|---|
| gtgcaccctg tcccagccgt cctgtcctgg ctgctcgctc tgcttcgctg cgcctccact | 60 |
| atgctctccc tccgtgtccc gctcgcgccc atcacggacc cgcagcagct gcagctctcg | 120 |
| ccgctgaagg ggctcagctt ggtcgacaag gagaacacgc cgccggccct gagcgggacc | 180 |
| cgcgtcctgg ccagcaagac cgcgaggagg atcttccagg agaaaacccc cgccgctttg | 240 |
| tcatcttccc catcgagtac catgatatct ggcagatgta taagaaggca gaggcttcct | 300 |
| tttggaccgc cgaggaggtg gacctctcca aggacattca gcactgggaa tccctgaaac | 360 |
| ccgaggagag atattttata tcccatgttc tggctttctt tgcagcaagc gatggcatag | 420 |
| taaatgaaaa cttggtggag cgatttagcc aagaagttca gattacagaa gcccgctgtt | 480 |
| tctatggctt ccaaattgcc atggaaaaca tacattctga aatgtatagt cttcttattg | 540 |
| acacttacat aaaagatccc aaagaaaggg aatttctctt caatgccatt gaaacgatgc | 600 |
| cttgtgtcaa gaagaaggca gactgggcct tgcgctggat tggggacaaa gaggctacct | 660 |
| atggtgaacg tgttgtagcc tttgctgcag tggaaggcat tttcttttcc ggttcttttg | 720 |
| cgtcgatatt ctggctcaag aaacgaggac tgatgcctgg cctcacattt tctaatgaac | 780 |
| ttattagcag agatgagggt ttacactgtg attttgcttg cctgatgttc aaacacctgg | 840 |
| tacacaaacc atcggaggag agagtaagag aaataattat caatgctgtt cggatagaac | 900 |
| aggagttcct cactgaggcc ttgcctgtga agctcattgg gatgaattgc actctaatga | 960 |
| agcaatacat tgagtttgtg gcagacagac ttatgctgga actgggtttt agcaaggttt | 1020 |
| tcagagtaga gaacccattt gactttatgg agaatatttc actggaagga aagactaact | 1080 |
| tctttgagaa gagagtaggc gagtatcaga ggatgggagt gatgtcaagt ccaacagaga | 1140 |
| attcttttac cttggatgct gacttctaaa tgaactgaag atgtgcccct acttggctga | 1200 |
| tttttttttt tccatctcat aagaaaaatc agctgaagtg ttaccaacta gccacaccat | 1260 |
| gaattgtccg taatgttcat taacagcatc tttaaaactg tgtagctacc tcacaaccag | 1320 |
| tcctgtctgt ttatagtgct ggtagtatca ccttttgcca gaaggcctgg ctggctgtga | 1380 |
| cttaccatag cagtgacaat ggcagtcttg gcttaaagt gaggggtgac cctttagtga | 1440 |
| gcttagcaca gcgggattaa acagtccttt aaccagcaca gccagttaaa agatgcagcc | 1500 |
| tcactgcttc aacgcagatt ttaatgttta cttaaatata aacctggcac tttacaaaca | 1560 |
| aataaacatt gtttgtactc acaaggcgat aatagcttga tttatttggt ttctacacca | 1620 |

| | | | |
|---|---|---|---|
| aatacattct | cctgaccact | aatgggagcc | aattcacaat tcactaagtg actaaagtaa | 1680 |
| gttaaacttg | tgtagactaa | gcatgtaatt | tttaagtttt attttaatga attaaaatat | 1740 |
| ttgttaacca | actttaaagt | cagtcctgtg | tatacctaga tattagtcag ttggtgccag | 1800 |
| atagaagaca | ggttgtgttt | ttatcctgtg | gcttgtgtag tgtcctggga ttctctgccc | 1860 |
| cctctgagta | gagtgttgtg | ggataaagga | atctctcagg gcaaggagct tcttaagtta | 1920 |
| aatcactaga | aatttagggg | tgatctgggc | cttcatatgt gtgagaagcc gtttcatttt | 1980 |
| atttctcact | gtattttcct | caacgtctgg | ttgatgagaa aaaattcttg aagagttttc | 2040 |
| atatgtggga | gctaaggtag | tattgtaaaa | tttcaagtca tccttaaaca aaatgatcca | 2100 |
| cctaagatct | tgcccctgtt | aagtggtgaa | atcaactaga ggtggttcct acaagttgtt | 2160 |
| cattctagtt | ttgtttggtg | taagtaggtt | gtgtgagtta attcatttat atttactatg | 2220 |
| tctgttaaat | cagaaatttt | ttattatcta | tgttcttcta gattttacct gtagttcata | 2280 |
| cttcagtcac | ccagtgtctt | attctggcat | tgtctaaatc tgagcattgt ctaggggat | 2340 |
| cttaaacttt | agtaggaaac | catgagctgt | taatacagtt tccattcaaa tattaatttc | 2400 |
| agaatgaaac | ataatttttt | tttttttttt | ttgagatgga gtctcgctct gttgcccagg | 2460 |
| ctggagtgca | gtggcgcgat | tttggctcac | tgtaacctcc atctcctggg ttcaagcaat | 2520 |
| tctcctgtct | cagcctccct | agtagctggg | actgcaggta tgtgctacca cacctggcta | 2580 |
| attttttgtat | ttttagtaga | gatggagttt | caccatattg gtcaggctgg tcttgaactc | 2640 |
| ctgacctcag | gtgatccacc | cacctcggcc | tcccaaagtg ctgggattgc aggcgtgata | 2700 |
| aacaaatatt | cttaataggg | ctactttgaa | ttaatctgcc tttatgtttg ggagaagaaa | 2760 |
| gctgagacat | tgcatgaaag | atgatgagag | ataaatgttg atcttttggc cccatttgtt | 2820 |
| aattgtattc | agtatttgaa | cgtcgtcctg | tttattgtta gttttcttca tcatttattg | 2880 |
| tatagacaat | ttttaaatct | ctgtaatatg | atacattttc ctatcttta agttattgtt | 2940 |
| acctaaagtt | aatccagatt | atatggtcct | tatatgtgta caacattaaa atgaaaggct | 3000 |
| ttgtcttgca | ttgtgaggta | caggcggaag | ttggaatcag gttttaggat tctgtctctc | 3060 |
| attagctgaa | taatgtgagg | attaacttct | gccagctcag accatttcct aatcagttga | 3120 |
| aagggaaaca | agtatttcag | tctcaaaatt | gaataatgca caagtcttaa gtgattaaaa | 3180 |
| taaaactgtt | cttatgtcag | ttt | | 3203 |

<210> SEQ ID NO 147
<211> LENGTH: 4482
<212> TYPE: DNA
<213> ORGANISM: Homo sapiens

<400> SEQUENCE: 147

| | | | |
|---|---|---|---|
| agcgggggca | ctccagccct | gcagcctccg | gagtcagtgc cgcgcgcccg ccgcccgcg | 60 |
| ccttcctgct | cgccgcacct | ccgggagccg | gggcgcaccc agcccgcagc gccgcctccc | 120 |
| cgcccgcgcc | gcctccgacc | gcaggccgag | ggccgccact ggccgggggg accgggcagc | 180 |
| agcttgcggc | cgcggagccg | ggcaacgctg | gggactgcgc cttttgtccc cggaggtccc | 240 |
| tggaagtttg | cggcaggacg | cgcgcgggga | ggcggcggag gcagcccga cgtcgcggag | 300 |
| aacagggcgc | agagccggca | tgggcatcgg | gcgcagcgag gggggccgcc gcggggcagc | 360 |
| cctgggcgtg | ctgctggcgc | tggcgcggc | gcttctggcc gtgggctcgg ccagcgagta | 420 |
| cgactacgtg | agcttccagt | cggacatcgg | cccgtaccag agcggcgct tctacaccaa | 480 |
| gccacctcag | tgcgtggaca | tccccgcgga | cctgcggctg tgccacaacg tgggctacaa | 540 |

```
gaagatggtg ctgcccaacc tgctggagca cgagaccatg gcggaggtga agcagcaggc    600
cagcagctgg gtgcccctgc tcaacaagaa ctgccacgcc ggcacccagg tcttcctctg    660
ctcgctcttc gcgcccgtct gcctggaccg gcccatctac ccgtgtcgct ggctctgcga    720
ggccgtgcgc gactcgtgcg agccggtcat gcagttcttc ggcttctact ggcccgagat    780
gcttaagtgt gacaagttcc ccgagggga cgtctgcatc gccatgacgc cgcccaatgc    840
caccgaagcc tccaagcccc aaggcacaac ggtgtgtcct ccctgtgaca acagttgaa    900 atctgaggcc atcattgaac atctctgtgc cagcgagttt gcactgagga tgaaaataaa    960
agaagtgaaa aagaaaatg gcgacaagaa gattgtcccc aagaagaaga agcccctgaa   1020
gttggggccc atcaagaaga aggacctgaa gaagcttgtg ctgtacctga agaatggggc   1080
tgactgtccc tgccaccagc tggacaacct cagccaccac ttcctcatca tgggccgcaa   1140
ggtgaagagc cagtacttgc tgacggccat ccacaagtgg gacaagaaaa acaaggagtt   1200
caaaaacttc atgaagaaaa tgaaaaacca tgagtgcccc acctttcagt ccgtgtttaa   1260
gtgattctcc cggggcagg gtggggaggg agcctcgggt ggggtgggag cggggggac   1320 agtgccccgg gaacccggtg ggtcacacac acgcactgcg cctgtcagta gtggacattt   1380
aatccagtcg gcttgttctt gcagcattcc cgctcccttc cctccatagc cacgctccaa   1440
accccagggt agccatggcc gggtaaagca agggccattt agattaggaa ggttttaag   1500 atccgcaatg tggagcagca gccactgcac aggaggaggt gacaaaccat ttccaacagc   1560
aacacagcca ctaaaacaca aaaggggga ttgggcggaa agtgagagcc agcagcaaaa   1620
actacatttt gcaacttgtt ggtgtggatc tattggctga tctatgcctt tcaactagaa   1680
aattctaatg attggcaagt cacgttgttt tcaggtccag agtagtttct ttctgtctgc   1740
tttaaatgga aacagactca taccacactt acaattaagg tcaagcccag aaagtgataa   1800
gtgcagggag gaaaagtgca agtccattat gtaatagtga cagcaaaggg accaggggag   1860
aggcattgcc ttctctgccc acagtctttc cgtgtgattg tctttgaatc tgaatcagcc   1920
agtctcagat gccccaaagt ttcggttcct atgagcccgg ggcatgatct gatccccaag   1980
acatgtggag gggcagcctg tgcctgcctt tgtgtcagaa aaaggaaacc acagtgagcc   2040
tgagagagac ggcgattttc gggctgagaa ggcagtagtt ttcaaaacac atagttaaaa   2100
aagaaacaaa tgaaaaaaat tttagaacag tccagcaaat tgctagtcag ggtgaattgt   2160
gaaattgggt gaagagctta cgattctaat ctcatgtttt ttcctttca catttttaaa   2220 agaacaatga caaacaccca cttatttttc aaggttttaa aacagtctac attgagcatt   2280
tgaaaggtgt gctagaacaa ggtctcctga tccgtccgag gctgcttccc agaggagcag   2340
ctctccccag gcatttgcca agggaggcgg atttccctgg tagtgtagct gtgtggcttt   2400
ccttcctgaa gagtccgtgg ttgccctaga acctaacacc cctagcaaa actcacagag   2460 ctttccgttt ttttcttcc tgtaaagaaa catttccttt gaacttgatt gcctatggat   2520
caaagaaatt cagaacagcc tgcctgtccc cccgcacttt ttacatatat ttgtttcatt   2580
tctgcagatg gaaagttgac atgggtgggg tgtccccatc cagcgagaga gtttaaaaag   2640
caaaacatct ctgcagtttt tcccaagtgc cctgagatac ttcccaaagc ccttatgttt   2700
aatcagcgat gtatataagc cagttcactt agacaacttt acccttcttg tccaatgtac   2760
aggaagtagt tctaaaaaaa atgcatatta atttcttccc ccaaagccgg attcttaatt   2820
ctctgcaaca ctttgaggac atttatgatt gtccctctgg gccaatgctt atacccagtg   2880
```

```
aggatgctgc agtgaggctg taaagtggcc cctgcggcc ctagcctgac ccggaggaaa    2940
ggatggtaga ttctgttaac tcttgaagac tccagtatga aaatcagcat gcccgcctag    3000
ttacctaccg gagagttatc ctgataaatt aacctctcac agttagtgat cctgtccttt    3060 taacacctttt tttgtggggt tctctctgac ctttcatcgt aaagtgctgg ggaccttaag   3120
tgatttgcct gtaattttgg atgattaaaa aatgtgtata tatattagct aattagaaat    3180
attctacttc tctgttgtca aactgaaatt cagagcaagt tcctgagtgc gtggatctgg    3240
gtcttagttc tggttgattc actcaagagt tcagtgctca tacgtatctg ctcattttga    3300
caaagtgcct catgcaaccg ggccctctct ctgcggcaga gtccttagtg gaggggttta    3360
cctggaacat tagtagttac cacagaatac ggaagagcag gtgactgtgc tgtgcagctc    3420
tctaaatggg aattctcagg taggaagcaa cagcttcaga aagagctcaa aataaattgg    3480
aaatgtgaat cgcagctgtg ggttttacca ccgtctgtct cagagtccca ggaccttgag    3540
tgtcattagt tactttattg aaggttttag acccatagca gctttgtctc tgtcacatca    3600
gcaatttcag aaccaaaagg gaggctctct gtaggcacag agctgcacta tcacgagcct    3660 ttgttttttct ccacaaagta tctaacaaaa ccaatgtgca gactgattgg cctggtcatt    3720
ggtctccgag agaggaggtt tgcctgtgat ttcctaatta tcgctagggc caaggtggga    3780
tttgtaaagc tttacaataa tcattctgga tagagtcctg ggaggtcctt ggcagaactc    3840
agttaaatct ttgaagaata tttgtagtta tcttagaaga tagcatggga ggtgaggatt    3900
ccaaaaacat tttattttta aaatatcctg tgtaacactt ggctcttggt acctgtgggt    3960
tagcatcaag ttctccccag ggtagaattc aatcagagct ccagtttgca tttggatgtg    4020
taaattacag taatcccatt tcccaaacct aaaatctgtt tttctcatca gactctgagt    4080
aactggttgc tgtgtcataa cttcatagat gcaggaggct caggtgatct gtttgagcag    4140
agcaccctag gcagcctgca gggaataaca tactggccgt tctgacctgt tgccagcaga    4200
tacacaggac atggatgaaa ttcccgtttc ctctagtttc ttcctgtagt actcctcttt    4260
tagatcctaa gtctcttaca aaagctttga atactgtgaa aatgttttac attccatttc    4320
atttgtgttg ttttttttaac tgcatttttac cagatgttttt gatgttatcg cttatgttaa    4380
tagtaattcc cgtacgtgtt catttttattt tcatgctttt tcagccatgt atcaatattc    4440
acttgactaa aatcactcaa ttaatcaaaa aaaaaaaaa aa                         4482

<210> SEQ ID NO 148
<211> LENGTH: 3637
<212> TYPE: DNA
<213> ORGANISM: Homo sapiens

<400> SEQUENCE: 148
agtcctgggc gaaggggggcg gtggttcccc gcggcgctgc gcgcggcggt aattagtgat      60
tgtcttccag cttcgcgaag gctagggggcg cggctgccgg gtggctgcgc ggcgctgccc     120
ccggaccgag gggcagccaa cccaatgaaa ccaccgcgtg ttcgcgcctg gtagagattt     180
ctcgaagaca ccagtgggcc cgttccgagc cctctggacc gcccgtgtgg aaccaaacct     240
gcgcgcgtgg ccgggccgtg ggacaacgag gccgcggaga cgaaggcgca atggcgagga     300
agttatctgt aatcttgatc ctgaccttttg ccctctctgt cacaaatccc cttcatgaac     360
taaaagcagc tgctttcccc cagaccactg agaaaattag tccgaattgg gaatctggca     420
ttaatgttga cttggcaatt tccacacggc aatatcatct acaacagctt ttctaccgct     480
atggagaaaa taattctttg tcagttgaag ggttcagaaa attacttcaa aatataggca     540
```

```
tagataagat taaaagaatc catatacacc atgaccacga ccatcactca gaccacgagc    600
atcactcaga ccatgagcgt cactcagacc atgagcatca ctcagaccac gagcatcact    660
ctgaccatga tcatcactct caccataatc atgctgcttc tggtaaaaat aagcgaaaag    720
ctctttgccc agaccatgac tcagatagtt caggtaaaga tcctagaaac agccagggga    780
aaggagctca ccgaccagaa catgccagtg gtagaaggaa tgtcaaggac agtgttagtg    840
ctagtgaagt gacctcaact gtgtacaaca ctgtctctga aggaactcac tttctagaga    900
caatagagac tccaagacct ggaaaactct tccccaaaga tgtaagcagc tccactccac    960
ccagtgtcac atcaaagagc cgggtgagcc ggctggctgg taggaaaaca aatgaatctg   1020
tgagtgagcc ccgaaaaggc tttatgtatt ccagaaacac aaatgaaaat cctcaggagt   1080
gtttcaatgc atcaaagcta ctgacatctc atggcatggg catccaggtt ccgctgaatg   1140
caacagagtt caactatctc tgtccagcca tcatcaacca aattgatgct agatcttgtc   1200
tgattcatac aagtgaaaag aaggctgaaa tccctccaaa gacctattca ttacaaatag   1260
cctgggttgg tggttttata gccatttcca tcatcagttt cctgtctctg ctggggttta   1320
tcttagtgcc tctcatgaat cgggtgtttt caaatttct cctgagtttc cttgtggcac   1380
tggccgttgg gactttgagt ggtgatgctt ttttacacct tcttccacat tctcatgcaa   1440
gtcaccacca tagtcatagc catgaagaac cagcaatgga aatgaaaaga ggaccacttt   1500
tcagtcatct gtcttctcaa aacatagaag aaagtgccta ttttgattcc acgtggaagg   1560
gtctaacagc tctaggaggc ctgtatttca tgtttcttgt tgaacatgtc ctcacattga   1620
tcaaacaatt taaagataag aagaaaaaga atcagaagaa acctgaaaat gatgatgatg   1680
tggagattaa gaagcagttg tccaagtatg aatctcaact ttcaacaaat gaggagaaag   1740
tagatacaga tgatcgaact gaaggctatt tacgagcaga ctcacaagag ccctcccact   1800
ttgattctca gcagcctgca gtcttggaag aagaagaggt catgatagct catgctcatc   1860
cacaggaagt ctacaatgaa tatgtaccca gagggtgcaa gaataaatgc cattcacatt   1920
tccacgatac actcggccag tcagacgatc tcattcacca ccatcatgac taccatcata   1980
ttctccatca tcaccaccac caaaaccacc atcctcacag tcacagccag cgctactctc   2040
gggaggagct gaaagatgcc ggcgtcgcca ctctggcctg gatggtgata atgggtgatg   2100
gcctgcacaa tttcagcgat ggcctagcaa ttggtgctgc ttttactgaa gcttatcaa    2160 gtggtttaag tacttctgtt gctgtgttct gtcatgagtt gcctcatgaa ttaggtgact   2220
ttgctgttct actaaaggct ggcatgaccg ttaagcaggc tgtcctttat aatgcattgt   2280
cagccatgct ggcgtatctt ggaatggcaa caggaatttt cattggtcat tatgctgaaa   2340
atgtttctat gtggatattt gcacttactg ctggcttatt catgtatgtt gctctggttg   2400
atatggtacc tgaaatgctg cacaatgatg ctagtgacca tggatgtagc cgctggggt    2460 atttctttt acagaatgct gggatgcttt tgggttttgg aattatgtta cttatttcca   2520
tatttgaaca taaaatcgtg tttcgtataa atttctagtt aaggtttaaa tgctagagta   2580
gcttaaaaag ttgtcatagt ttcagtaggt cataggagag tgagtttgta tgctgtacta   2640
tgcagcgttt aaagttagtg ggttttgtga tttttgtatt gaatattgct gtctgttaca   2700
aagtcagtta aaggtacgtt ttaatattta agttattcta tcttggagat aaaatctgta   2760
tgtgcaattc accggtatta ccagtttatt atgtaaacaa gagatttggc atgacatgtt   2820
ctgtatgttt cagggaaaaa tgtctttaat gcttttcaa gaactaacac agttattcct   2880
```

| | |
|---|---|
| atactggatt ttaggtctct gaagaactgc tggtgtttag gaataagaat gtgcatgaag | 2940 |
| cctaaaatac caagaaagct tatactgaat ttaagcaaag aaataaagga gaaaagagaa | 3000 |
| gaatctgaga attggggagg catagattct tataaaaatc acaaaatttg ttgtaaatta | 3060 |
| gaggggagaa atttagaatt aagtataaaa aggcagaatt agtatagagt acattcatta | 3120 |
| aacattttg tcaggattat ttcccgtaaa aacgtagtga gcacttttca tatactaatt | 3180 |
| tagttgtaca tttaactttg tataatacag aaatctaaat atatttaatg aattcaagca | 3240 |
| atatatcact tgaccaagaa attggaattt caaaatgttc gtgcgggtat ataccagatg | 3300 |
| agtacagtga gtagttttat gtatcaccag actgggttat tgccaagtta tatatccacca | 3360 |
| aaagctgtat gactggatgt tctggttacc tggtttacaa aattatcaga gtagtaaaac | 3420 |
| tttgatatat atgaggatat taaaactaca ctaagtatca tttgattcga ttcagaaagt | 3480 |
| actttgatat ctctcagtgc ttcagtgcta tcattgtgag caattgtctt ttatatacgg | 3540 |
| tactgtagcc atactaggcc tgtctgtggc attctctaga tgtttctttt ttacacaata | 3600 |
| aattccttat atcagcttga aaaaaaaaaa aaaaaaa | 3637 |

<210> SEQ ID NO 149
<211> LENGTH: 2208
<212> TYPE: DNA
<213> ORGANISM: Homo sapiens

<400> SEQUENCE: 149

| | |
|---|---|
| aacgcacttg gcgcgcggcg cgggctgcag acggctgcga ggcgctgggc acaggtgtcc | 60 |
| tgatggcaaa tttcaagggc cacgcgcttc cagggagttt cttcctgatc attgggctgt | 120 |
| gttggtcagt gaagtacccg ctgaagtact ttagccacac gcggaagaac agcccactac | 180 |
| attactatca gcgtctcgag atcgtcgaag ccgcaattag gactttgttt tccgtcactg | 240 |
| ggatcctggc agagcagttt gttccggatg ggccccacct gcacctctac catgagaacc | 300 |
| actggataaa gttaatgaat tggcagcaca gcaccatgta cctattcttt gcagtctcag | 360 |
| gaattgttga catgctcacc tatctggtca gccacgttcc cttggggtg gacagactgg | 420 |
| ttatggctgt ggcagtattc atggaaggtt tcctcttcta ctaccacgtc cacaaccggc | 480 |
| ctccgctgga ccagcacatc cactcactcc tgctgtatgc tctgttcgga gggtgtgtta | 540 |
| gtatctccct agaggtgatc ttccgggacc acattgtgct ggaactttc cgaaccagtc | 600 |
| tcatcattct tcagggaacc tggttctggc agattgggtt tgtgctgttc ccacctttg | 660 |
| gaacacccga atgggaccag aaggatgatg ccaacctcat gttcatcacc atgtgcttct | 720 |
| gctggcacta cctggctgcc ctcagcattg tggccgtcaa ctattctctt gtttactgcc | 780 |
| ttttgactcg gatgaagaga cacggaaggg gagaaatcat tggaattcag aagctgaatt | 840 |
| cagatgacac ttaccagacc gccctcttga gtggctcaga tgaggaatga gccgagatgc | 900 |
| ggagggcgca gatgtcccac tgcacagctg aatgaatgg agttcatccc ctccacctga | 960 |
| atgcctgctg tggtctgatc ttaagggtct atatatttgc acctcctcat tcaacacagg | 1020 |
| gctggaggtt ctacaacagg aaatcaggcc tacagcatcc tgtgtatctt gcagttggga | 1080 |
| tttttaaaca tactataaag tctgtgttgg tatagtaccc ttcataagga aaatgaagt | 1140 |
| aatgcctata agtagcaggc ctttgtgcct cagtgtcaag agaaatcaag agatgctaaa | 1200 |
| agctttacaa tggaagtggc ctcatggatg aatccggggt atgagcccag gagaacgtgc | 1260 |
| tgcttttggt aacttatccc ttttctctt aagaaagcag gtactttctt attagaaata | 1320 |
| tgttagaatg tgtaagcaaa cgacagtgcc tttagaatta caattctaac ttacatattt | 1380 |

-continued

```
tttgaaagta aaataattca caagctttgg tattttaaaa ttattgttaa acatatcata    1440
actaatcata ccagggtact gcaataccac tgtttataag tgacaaaatt aggccaaagg    1500
tgattttttt ttaaatcagg aagctggtta ctggctctac tgagagttgg agccctgatg    1560
ttctgattct tcaaagtcac cctaaaagaa gatctgacag gaaagctgta taatgagata    1620
gaaaaacgtc aggtatggaa ggctttcagt tttaatatgg ctgaaagcaa aggataacga    1680
attcagaatt agtaatgtaa aatcttgata ccctaatctt gcttctggat ctgttctttt    1740
tttaaaaaaa cttccttcac cgcgcctata atcctagcac tttgggaggc cgaggcaggc    1800
agatcacggg gtcaggagat caagaccatc ctggctaaca tggtgaaacc ccgtctctac    1860
tgaaaataca aaaaattagc cgggtgtggt ggcgggcgcc tgtagttcca gctactcggg    1920
aggctgaggc aagagaatgg catgaacccg gtagggagc ttgcagtgag cccagatcat     1980
gccactgtac tccagcctag gtgacagagc aagactctgt ctcaaaaaca agcaaacaga    2040
cttccttcaa caaatattta ttaaatatcc actttgcaac agcactgaaa tggctgtaag    2100
gactcctgag atatgtgtcc agcaaggagt ttacagtcaa acaggagaga catgcctgta    2160
gttacatcca gtgtgatggg tgctgagagg caagtacaaa ccacgatg                 2208
```

<210> SEQ ID NO 150
<211> LENGTH: 1678
<212> TYPE: DNA
<213> ORGANISM: Homo sapiens
<220> FEATURE:
<221> NAME/KEY: misc_feature
<222> LOCATION: (523)..(523)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (961)..(961)
<223> OTHER INFORMATION: n is a, c, g, or t
<220> FEATURE:
<221> NAME/KEY: misc_feature
<222> LOCATION: (1021)..(1021)
<223> OTHER INFORMATION: n is a, c, g, or t
<220> FEATURE:
<221> NAME/KEY: misc_feature
<222> LOCATION: (1066)..(1066)
<223> OTHER INFORMATION: n is a, c, g, or t
<220> FEATURE:
<221> NAME/KEY: misc_feature
<222> LOCATION: (1069)..(1069)
<223> OTHER INFORMATION: n is a, c, g, or t
<220> FEATURE:
<221> NAME/KEY: misc_feature
<222> LOCATION: (1194)..(1194)
<223> OTHER INFORMATION: n is a, c, g, or t
<220> FEATURE:
<221> NAME/KEY: misc_feature
<222> LOCATION: (1202)..(1202)
<223> OTHER INFORMATION: n is a, c, g, or t
<220> FEATURE:
<221> NAME/KEY: misc_feature
<222> LOCATION: (1287)..(1287)
<223> OTHER INFORMATION: n is a, c, g, or t
<220> FEATURE:
<221> NAME/KEY: misc_feature
<222> LOCATION: (1472)..(1472)
<223> OTHER INFORMATION: n is a, c, g, or t

<400> SEQUENCE: 150

```
tcccgccgcg ccacttcgcc tgcctccgtc ccccgcccgc cgcgccatgc ctgtggccgg      60
```

```
ctcggagctg ccgcgccggc ccttgccccc cgccgcacag gagcgggacg ccgagccgcg      120
tccgccgcac ggggagctgc agtacctggg gcagatccaa cacatcctcc gctgcggcgt      180
caggaaggac gcccgcccgg gcaccggtac cctgccggta ttcggcatgc aggcgcgcta      240
cagcctgaga gatgaattcc ctctgctgac aaccaaacgt gtgttctgga acggtgcttc      300
ggaggagctg ctgtggctta tcaagggatc cacaaacgct atagacctgt cttccccggc      360
agcgaaaatc tcgggatgcc actggatccc gacactctct ggacaccctg ggattctcca      420
ccagagaaga acgcgacttg ggcccagttt gtggctctca gcggaggcct cctgtggcag      480
aatacataca tttccaatca gatcacttcc cggacacgga ccntgaccag cctgccaaaa      540
agtggatttc cccccacccc agaacccanc ccctgacgca cagaaaccaa cccattcgtt      600
gttgccgcct tgcgaacccc aaccagaatc tctcccccct ggccggcgcg cctgccgctg      660
ccaatgcccc tatggcggcc tcttggcccg caccttccaa ttggtcgccc tgcgcaacca      720
gcgagaaaac actggcccgc ccgtctcccc ccgctccgc ctaccccact taatgcgcct      780
ccgtggcatg acgcacgcgt ttggtgtccg ccgccgtctc atgtccgcgc ggtgtggacc      840
cccttttctc tcgcggcaca tccccctat tcccttgccc tttggggggc accccctcta      900
gacccgcgct tctcttctcg tccggtgggg gacattggtt tgcctgccgc ggcggggggcg      960 ntaaaaataa aaacagcctg ttagcccggc ccagtacccc ccccggccg gggccgcctt     1020 ncgtttgcat ttatacccca acccataaag ccgcgcccct ttagcnccnt aacttttgtg     1080
gtgtggcctc ccccctttt cccggggagc agcaacggac atctgtacac taatgctggc     1140
cccgaccttt cccaaaaacc ccccgcccgt gtcccgtata aatttggtgc caanccctgac     1200 gngttctccc ccgccctcgc cccgttggcc gcccgtttaa agccccccg gtggttgcgc     1260 cgcccaacga gtccacctat agttaantcc accaacaccc ccacctttc ctccccgccg     1320 catcttcccc acgtacccc ttttgtcgcg agatggccac tccccccccc ctgtttgttt     1380
aaaacaacga gaatggtgct gccaacgctg gtcttttccc ccccccggacc gcgaccgcca     1440 gggggaatac gtaccataag cccccgcgcc cnccttttt ccccccctccc cgccaatcaa     1500 gatccgccgt ccattagacg tattattttt cccgcgatac acgaaaaaac agggccgccc     1560
atttataact aaaattcccgt cgccgccgcg cggatatgtt tcccaaaata ccacccccc      1620 ccccccattt tctttgcccc caactcctgc gcaccggtgt tcaccagcct cgcgccgc      1678
```

<210> SEQ ID NO 151
<211> LENGTH: 1611
<212> TYPE: DNA
<213> ORGANISM: Homo sapiens

<400> SEQUENCE: 151

```
ggacgcgtgg gtcgacccac gcgtccggac ccacgcgtcc ggtcgtgttc tccgagttcc       60
tgtctctctg ccaacgccgc ccggatggct tcccaaaacc gcgacccagc cgccactagc      120
gtcgccgccg cccgtaaagg agctgagccg agcgggggcg ccgcccgggg tccggtgggc      180
aaaaggctac agcaggagct gatgaccctc atggtgagtg attaagtgcc cagaaccccca      240 gccttccatc caattttcag tagcctcctt ttttccgtca gctttttttgc tagacatagg      300 ggtaatgtaa tttgctccct cctgggaaag aagttcatac accccaccta caccatttct      360
tccagcagtc cctcctccca attccatccc ccacacgaa gttatctcga acacttccct      420
gaagtcatac aagaccctcc ctatccagtg tgtccctact tcctagcccc aaccaagctt      480
tacccacacc caactccccg cccttcttgg tatttctagc ctatgaattt ggttgcttta      540
```

```
ttttggatca gagtgatgag attaagggga ggctgggcgc ggtagctcac accttataat    600
cccaaagtgc tgggattaca ggcgtgagcc accgcgcccg gccagcaact aatattctaa    660
ttgaactaaa gcacaggatg ccaatttaca atccttagac caaagagtca ctgatgtctc    720
caccagataa gaggaaagca tcaggctagg catagtggct cacacctgta atctcagcac    780
tttgggaggc tgaggcaggc agatcacatg agcccaggag tttgagactg gcctgggcaa    840
catggtgaaa ccctgtctct aaaataaaaa ctaaactaaa aaaactttt aaaaaggcag     900 tggggagcat cagaaccagc tcaacagttt gtctactgtc cggtcccaga gaaactcaag    960
attctagcaa gccccttgtg tggggcttgg gttgggacat gaggctgctg ctggagctta   1020
ctctgcaact gtttctccaa atgccaggta tatgaagacc tgaggtataa gctctcgcta   1080
gagttcccca gtggctaccc ttacaatgcg cccacagtga agttcctcac gccctgctat   1140
caccccaacg tggacaccca gggtaacata tgcctggaca tcctgaagga aaagtggtct   1200
gccctgtatg atgtcaggac cattctgctc tccatccaga gccttctagg agaacccaac   1260
attgatagtc ccttgaacac acatgctgcc gagctctgga aaaacccac agcttttaag    1320 aagtacctgc aagaaaccta ctcaaagcag gtcaccagcc aggagccctg acccaggctg   1380
cccagcctgt ccttgtgtcg tcttttttaat ttttccttag atggtctgtc cttttgtga   1440 tttctgtata ggactcttta tcttgagctg tggtattttt gttttgtttt tgtctttaa    1500 attaagcctc ggttgagccc ttgtatatta aataaatgca tttttgtcct tttttaaaaa   1560
aaaaataaaa aaaaaaaaaa aaaaaaaaaa aaaaaaaaaa aaaaaaaaaa a            1611
```

METHOD FOR PREDICTING RESPONSE TO BREAST CANCER THERAPEUTIC AGENTS AND METHOD OF TREATMENT OF BREAST CANCER

CROSS-REFERENCE TO RELATED APPLICATIONS

This application is a continuation of U.S. patent application Ser. No. 14/962,864, filed Dec. 8, 2015, now U.S. Pat. No. 10,196,693, which claims the benefit of the following U.S. Provisional Applications, the entire disclosures of which are incorporated herein by reference: No. 62/091,195, filed Dec. 12, 2014; No. 62/142,504, filed Apr. 3, 2015; and No. 62/167,110, filed May 27, 2015.

SEQUENCE LISTING

The instant application contains a Sequence Listing which has been submitted in ASCII format via EFS-Web and is hereby incorporated by reference in its entirety. Said ASCII copy, created on Dec. 4, 2015, is named 212181_0001_00_WO_SeqListing_ST25 and is 262,467 bytes in size.

FIELD OF THE INVENTION

The field relates to breast cancer therapy.

BACKGROUND OF THE INVENTION

Breast cancer is considered a genetically heterogeneous and biologically diverse disease. The long-recognized clinical and phenotypic differences have been shown to correlate with differences in gene expression. Previous studies of breast tumors have identified five distinct subtypes of breast carcinomas that are associated with different clinical outcomes: luminal A (estrogen receptor (ER)+); luminal B (ER+); HER2 overexpressing; normal breast-like; and basal-like. See, Perou et al. *Nature,* 406(6797):747-52 (2000); Sorlie et al. *PNAS,* 98(19):10869-74 (2001).

Analysis of breast cancer biopsy and surgical specimens typically includes an assessment of nuclear and cell surface receptors (ER, PgR, and HER2), gene amplification of HER2 (if HER2 analysis by immunohistochemistry(IHC) is not definitive), and other prognostic tests such as microvessel invasion and proliferation markers. Endocrine therapies that target ER signaling pathways for ER+ disease and HER2-targeted therapies for HER2+ disease play a critical role in the treatment of most patients with breast cancer. However, little progress has been made in identifying effective targeted therapies for patients whose disease lacks these receptors, i.e., the so-called "triple negative" breast cancers or "TNBC", and nonselective cytotoxic chemotherapy remains the primary therapeutic option.

The androgen receptor (AR) is the most commonly expressed nuclear hormone receptor in breast cancer, though its functional role in initiating or driving malignancy is not yet well understood. In a study of 3093 breast cancers, AR expression (10% or more nuclear staining by IHC) was observed in 77% of invasive breast tumors and across all molecular phenotypes (Collins et al., *Mod Pathol* 2011; 24(7):924-931). However, androgen receptor levels are not routinely assessed, since they have not been shown to predict responses to currently used therapies.

The use of AR inhibitors has been proposed as part of a therapeutic regimen for the treatment of breast cancer. See, e.g., Garay and Park, *Am. J. Cancer Res.* 2012; 2(4):434-445. Interest has been generated recently in the treatment of TNBC. Lack of expression of all three of estrogen receptor, progesterone receptor and HER2 predicts non-response to available endocrine (tamoxifen, aromatase inhibitors) and anti-HER2 (trastuzumab) targeted therapies. From 10 to 35% of such TNBC tumors express androgen receptor (Ogawa et al., *Int J. Clin, Oncol.* 2008; 13:431435). AR-targeted therapies may prove to be a valuable treatment for a large proportion of breast cancers, including triple negative cancers.

Despite the interest in androgen receptor signaling inhibition as a modality for the treatment of breast cancer, and in the treatment of TNBC in particular, there remains a need for predicting whether the individual patient will be responsive in advance of therapy. A test to predict the likelihood of whether or not a particular patient will respond to a therapy that inhibits androgen receptor signaling, and TNBC patients in particular, would be a valuable tool in planning patient treatment.

SUMMARY OF THE INVENTION

In one embodiment, provided is a method of screening a treatment for triple negative breast cancer comprising the use of an androgen receptor inhibitor, the method comprising assaying a biological sample obtained from a subject to determine whether the biological sample obtained from the subject is classified as basal-like subtype or another subtype. If the biological sample is classified as other than a basal-like subtype, the breast cancer treatment comprising an androgen receptor inhibitor is more likely to be effective than if the sample were classified as basal-like subtype.

Also provided is a method of screening for the likelihood of the effectiveness of a treatment for triple negative breast cancer comprising an androgen receptor inhibitor, in a subject in need of such treatment. The method comprises:
  assaying a biological sample obtained from the subject to determine whether the biological sample is classified as a basal-like subtype or another subtype; and
  wherein if the biological sample is classified as other than a basal-like subtype, the breast cancer treatment comprising an androgen receptor inhibitor is more likely to be effective than if the sample were classified as basal-like subtype.

Also provided is a method of classifying a biological sample from a subject as an indicator of the likelihood of the effectiveness of a treatment of the patient for triple negative breast cancer, said treatment comprising an androgen receptor inhibitor, the method comprising:
  assaying a biological sample obtained from the subject to determine whether the biological sample is classified as a basal-like subtype or another subtype; and
  wherein the biological sample classified as other than basal-like subtype indicates that the breast cancer treatment comprising an androgen receptor inhibitor is more likely to be effective than if the sample were classified as basal-like subtype.

In certain embodiments of the screening and classifying methods (collectively "the aforementioned methods"), assaying the biological sample to determine whether the biological sample is classified as a basal-like subtype or another subtype is performed by detecting the expression of the set of intrinsic genes listed in Table 1.

In certain embodiments of the aforementioned methods, the Basal Centroid classifier score of the sample is determined from the expression of the set of intrinsic genes listed in Table 1.

In one embodiment of the aforementioned methods, if the Basal Centroid classifier score is less than or equal to 0.9, the breast cancer treatment comprising an androgen receptor inhibitor is determined to be likely more effective in treating the subject than if the Basal Centroid classifier score is greater than 0.9. In another embodiment, if the Basal Centroid classifier score is less than or equal to 0.6, the breast cancer treatment comprising an androgen receptor inhibitor is determined to be likely more effective in treating the subject than if the Basal Centroid classifier score is greater than 0.6. In another embodiment, if the Basal Centroid classifier score is in the range from 0.2 to 0.8, the breast cancer treatment comprising an androgen receptor inhibitor is likely to be effective in treating the subject. In another embodiment, if the Basal Centroid classifier score is in the range from 0.4 to 0.7, the breast cancer treatment comprising an androgen receptor inhibitor is likely to be effective in treating the subject.

In certain embodiments of the aforementioned methods, the Basal Centroid classifier score and the Luminal A Centroid classifier score of the sample are determined from the expression of the set of intrinsic genes listed in Table 1. The methods further comprises calculating a Weighted Basal and Luminal A classifier score from the Basal Centroid classifier score and the Luminal A Centroid classifier score according to the following equation:

Weighted Basal and Luminal A classifier score=−0.25(Basal Centroid classifier score)+0.27(Luminal A Centroid classifier score)

wherein if the Weighted Basal and Luminal A classifier score is greater than −0.3, the breast cancer treatment comprising an androgen receptor inhibitor is more likely to be effective in the subject than if the Weighted Basal and Luminal A classifier score is less than or equal to −0.3. In another embodiment, if the Weighted Basal and Luminal A classifier score is greater than −0.2, the breast cancer treatment comprising an androgen receptor inhibitor is more likely to be effective in the subject than if the Weighted Basal and Luminal A classifier score is less than or equal to −0.2. In another embodiment, if the Weighted Basal and Luminal A classifier score is greater than −0.25, the breast cancer treatment comprising an androgen receptor inhibitor is more likely to be effective in the subject than if the Weighted Basal and Luminal A classifier score is less than or equal to −0.25.

In some embodiments, the equation for determining the Weighted Basal and Luminal A classifier score takes the form:

Weighted Basal and Luminal A classifier score=−0.2468275(Basal Centroid classifier score)+0.2667110(Luminal A Centroid classifier score)

In certain embodiments of the aforementioned methods, the breast cancer is characterized by the presence of androgen receptor-positive tumor cells.

In certain embodiments of the aforementioned methods, the biological sample is selected from the group consisting of a cell, tissue and bodily fluid. In certain embodiments, the body fluid is selected from the group consisting of blood, lymph, urine, saliva, fluid from ductal lavage and nipple aspirate. In some embodiments, the tissue is obtained from a biopsy.

In any of the aforementioned methods, an assay to determine the androgen receptor status of the cells of the sample, i.e. AR-positive vs. AR-negative, may be carried out.

Also provided is a method of treating triple negative breast cancer in a subject, said subject having a breast cancer comprising breast cancer cells that have been classified as other than basal-like subtype, said method comprising administering a breast cancer treatment to the subject comprising an androgen receptor inhibitor, thereby treating the triple negative breast cancer in the subject.

In one embodiment of the treatment method, the breast cancer cells of the subject are characterized by a Basal Centroid classifier score of less than or equal to 0.9, determined from the expression by said cells of the set of intrinsic genes listed in Table 1. In another embodiment of the treatment method, the breast cancer cells of the subject are characterized by a Basal Centroid classifier score of less than or equal to 0.6. In another embodiment of the treatment method, the breast cancer cells of the subject are characterized by a Basal Centroid classifier score in the range from 0.2 to 0.8. In another embodiment of the treatment method, the breast cancer cells of the subject are characterized by a Basal Centroid classifier score in the range from 0.4 to 0.7.

In another embodiment of the treatment method, the breast cancer cells of the subject are characterized by Weighted Basal and Luminal A classifier score greater than −0.3. In another embodiment of the treatment method, the breast cancer cells of the subject are characterized by a Weighted Basal and Luminal A classifier score greater than −0.2. In another embodiment of the treatment method, the breast cancer cells of the subject are characterized by a Weighted Basal and Luminal A classifier score greater than −0.25.

Also provided is a triple negative breast cancer treatment comprising an androgen receptor inhibitor for use in the treatment of a triple negative breast cancer in a subject in need thereof, wherein said method of treatment comprises: (a) assaying a biological sample from the subject to determine whether the biological sample is classified as basal-like subtype or another subtype; and (b) administering said triple negative breast cancer treatment to the subject if the biological sample is classified as other than basal-like subtype.

Also provided is a therapeutic agent for triple negative breast cancer therapy or treatment for use in a subject in need thereof, wherein said agent is an androgen receptor inhibitor, comprising: (a) assaying a biological sample from the subject to determine whether the biological sample is classified as basal-like subtype or another subtype; and (b) administering said agent to the subject if the biological sample is classified as other than basal-like subtype.

Also provided is an androgen receptor inhibitor for use in the treatment of a triple negative breast cancer in a subject wherein a biological sample from the subject has been assayed to determine whether sample is classified as basal-like subtype or another subtype.

Also provided is a method of treating triple negative breast cancer in a subject in need of such treatment comprising: (a) assaying the biological sample to determine whether the biological sample is classified as a basal-like subtype or another subtype; and (b) if the biological sample is classified as other than a basal-like subtype, administering a breast cancer treatment to the subject comprising an androgen receptor inhibitor, thereby treating the breast cancer in the subject.

In certain embodiments of the aforementioned methods of treatment, treatments and androgen receptor inhibitors for use in treatment, assaying the biological sample to determine whether the biological sample is classified as a basal-like subtype or another subtype is performed by detecting the expression of the intrinsic genes listed in Table 1.

In certain embodiments of the aforementioned methods of treatment, treatments and androgen receptor inhibitors for use in treatment, assaying the biological sample comprises determining the Basal Centroid classifier score of the sample from the expression of the set of intrinsic genes listed in Table 1, wherein the breast cancer treatment is administered if the Basal Centroid classifier score is less than or equal to 0.9. In one embodiment, the breast cancer treatment is administered if the Basal Centroid classifier score is less than or equal to 0.6. In one embodiment, the breast cancer treatment is administered if the Basal Centroid classifier score is in the range from 0.2 to 0.8. In another embodiment, the breast cancer treatment is administered if the Basal Centroid classifier score is in the range from 0.4 to 0.7.

In certain embodiments of the aforementioned methods of treatment, treatments and androgen receptor inhibitors for use in treatment, assaying the biological sample comprises determining the Basal Centroid classifier score and the Luminal A Centroid classifier score of the sample from the expression of the set of intrinsic genes listed in Table 1, and calculating a Weighted Basal and Luminal A classifier score, wherein the breast cancer treatment is administered to the subject if the Weighted Basal and Luminal A classifier score greater than −0.3. In one embodiment, the breast cancer treatment is administered if the Weighted Basal and Luminal A classifier score is greater than —0.2. In another embodiment, the breast cancer treatment is administered if the Weighted Basal and Luminal A classifier score is greater than −0.25.

In certain embodiments of the aforementioned methods of treatment, treatments and androgen receptor inhibitors for use in treatment, the breast cancer of the subject is further characterized by the presence of androgen receptor-positive tumor cells.

In embodiments of the aforementioned methods of treatment, treatments and androgen receptor inhibitors for use in treatment, the androgen receptor inhibitor is selected from the group consisting of enzalutamide, bicalutamide, flutamide, nilutamide, ARN509, ketoconazole, abiraterone acetate, VN/124-1 (TOK-001), orteronel (TAK-700), finasteride, galeterone, cyproterone acetate, andarine and combinations thereof. The list of androgen receptor inhibitor is exemplary and not meant to be limiting.

In certain embodiments, the androgen receptor inhibitor is enzalutamide. In once such embodiment, enzalutamide is orally administered once daily at a dose of 160 mg. In some embodiments, enzalutamide is administered as a single capsule comprising 160 mg enzalutamide. In other embodiments, enzalutamide is administered as four capsules, each capsule comprising 40 mg enzalutamide.

In embodiments of the aforementioned methods of treatment, treatments and androgen receptor inhibitors for use in treatment, the breast cancer treatment comprising an androgen receptor inhibitor further comprises one or more other anti-cancer agents that is not an androgen receptor inhibitor. Such other anti-cancer agents that are not androgen receptor inhibitors may be selected from the group consisting of cyclophosphamide, fluorouracil, 5-fluorouracil, methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, and combinations thereof. The list of other anti-cancer agents is exemplary and not meant to be limiting.

In one embodiment, the non-AR inhibitor anticancer agent is paclitaxel. In another embodiment, the AR inhibitor is enzalutamide and the non-AR inhibitor anticancer agent is paclitaxel.

In certain embodiments, the treatment method comprises a step of testing the subject to determine whether the subject has a breast cancer comprising breast cancer cells that are other than basal-like subtype.

In certain embodiments, the treatment method comprises a step of testing the subject to determine the Basal Centroid classifier score of breast cancer cells of the subject.

In certain embodiments, the treatment method comprises a step of testing the subject to determine the Weighted Basal and Luminal A classifier score of breast cancer cells of the subject.

In some embodiments of the aforementioned methods of treatment, treatments and androgen receptor inhibitors for use in treatment, the subject has received zero or one rounds of prior treatment with an anti-cancer agent, other than an androgen receptor inhibitor, for treatment of triple negative breast cancer.

In embodiments of the aforementioned screening methods, classifying methods, treatment methods, treatments, and androgen receptor inhibitors for use in treatment, the biological sample may be selected from the group consisting of a cell, tissue and bodily fluid In certain embodiments, the body fluid is selected from the group consisting of blood, lymph, urine, saliva, fluid from ductal lavage and nipple aspirate. In some embodiments, the tissue is obtained from a biopsy.

In any of the aforementioned screening methods, classifying methods, treatment methods, treatments, and androgen receptor inhibitors for use in treatment, an assay to determine the androgen receptor status of the cells of the sample, i.e. AR-positive vs. AR-negative, may be carried out.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

DEFINITIONS

The articles "a" and "an" are used herein to refer to one or to more than one (i.e. to at least one) of the grammatical object of the article. By way of example, "an element" means one element or more than one elements.

"About" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

"Androgen receptor inhibitor" means a compound or molecule that directly or indirectly inhibits the androgen receptor (AR) signaling pathway. In one embodiment, direct inhibitors of the AR receptor include enzalutamide, bicalutamide (Casodex), flutamide, nilutamide, ARN509 and the like. In another embodiment, indirect inhibitors of AR include Cyp 17 inhibitors such as ketoconazole, abiraterone acetate, VN/124-1 (TOK-001), orteronel (TAK-700) and the like. In another embodiment, AR inhibitors include finasteride, galeterone, cyproterone acetate, and andarine, and the like.

By "detecting expression" is intended determining the quantity or presence of an RNA transcript or its expression product of an intrinsic gene.

By "inhibit" or other forms of inhibit means to hinder or restrain a particular characteristic. It is understood that this is typically in relation to some standard or expected value, in other words it is relative, but that it is not always necessary for the standard or relative value.

As used throughout, by a "subject" is meant an individual, typically a mammal or fowl. Mammals can include, for example, domesticated animals (e.g., cat or dog), livestock (e.g., cattle, horses, pigs, sheep, goats, etc.), laboratory animals (e.g., mouse, rabbit, rat, guinea pig, etc.) and primates. Preferably, the mammal is a human being.

"Triple negative breast cancer" or "TNBC" refers to any breast cancer that does not express the genes for estrogen receptor (ER), progesterone receptor (PR) and Her2/neu. The term includes primary epithelial TNBCs, as well as TNBC that involved with other tumors. The cancer can include a triple negative carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. TNBC can also include any stage of triple negative breast cancer, and can include breast neoplasms having histologic and ultrastructual heterogeneity (e.g., mixed cell types).

"A TNBC treatment comprising androgen receptor inhibitor" is a TNBC treatment that includes administration of an androgen receptor inhibitor. The treatment may include other anti-cancer or chemotherapeutic agents.

A subject "in need of" treatment for TNBC is a subject having TNBC or presenting with one or more symptoms of TNBC, or a subject having an increased risk of developing TNBC relative to the population at large. Preferably, a subject "in need" of treatment for TNBC is a subject who is afflicted with TNBC.

As used herein, "therapeutically effective amount" or "therapeutically effective dose" refers to an agent, compound, material, or composition containing a compound that is at least sufficient to produce a therapeutic effect. An effective amount is the quantity of a therapeutic agent necessary for preventing, curing, ameliorating, arresting or partially arresting a symptom of a disease or disorder.

"Treating" or "treatment" does not mean a complete cure. It means that the symptoms of the underlying disease are reduced, and/or that one or more of the underlying cellular, physiological, or biochemical causes or mechanisms causing the symptoms are reduced. It is understood that reduced, as used in this context, means relative to the state of the disease, including the molecular state of the disease, not just the physiological state of the disease.

Weighted Basal and Luminal A classifier score=− 0.2468275(Basal Centroid classifier score)+ 0.2667110(Luminal A Centroid classifier score).

Figure 14A:
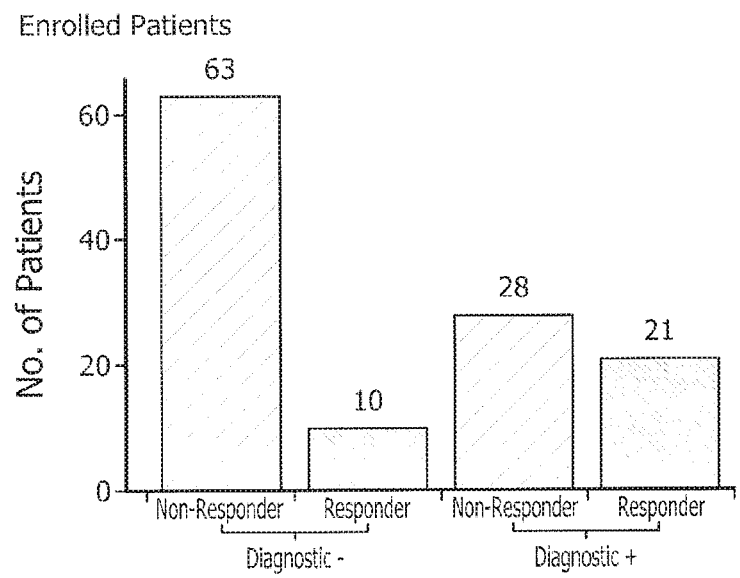
FIGS. 14A-14D comprise the results of patient responses in the clinical trial of the drug enzalutamide for the treatment of TNBC. Gene expression analysis was carried out on patient breast tumor samples using PAM50 intrinsic gene set of Table 1. The Spearman rank correlation to the Basal-like gene expression centroid was evaluated for each sample and assigned as the "Basal Centroid classifier score". The Spearman rank correlation to the Luminal A gene expression centroid was evaluated for each sample and assigned as the "Luminal A classifier score". A Weighted Basal and Luminal A classifier score of the patient samples was determined from the following formula.
Figure 14B:
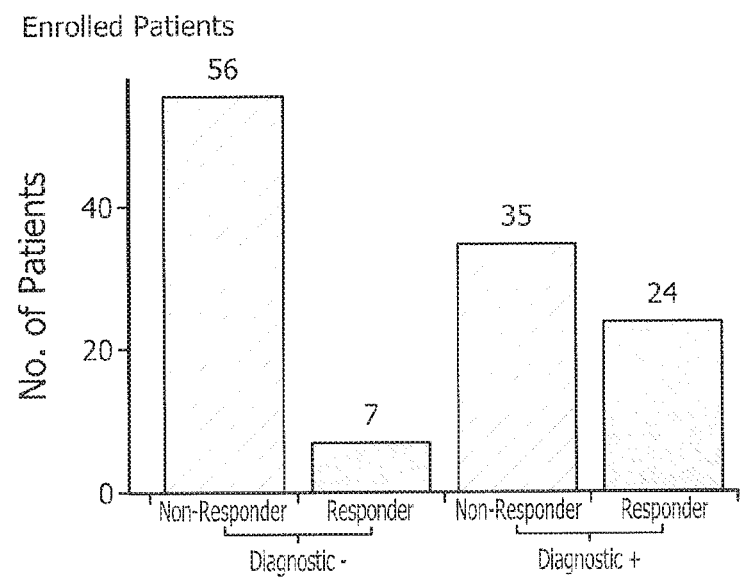
Figure 14C:
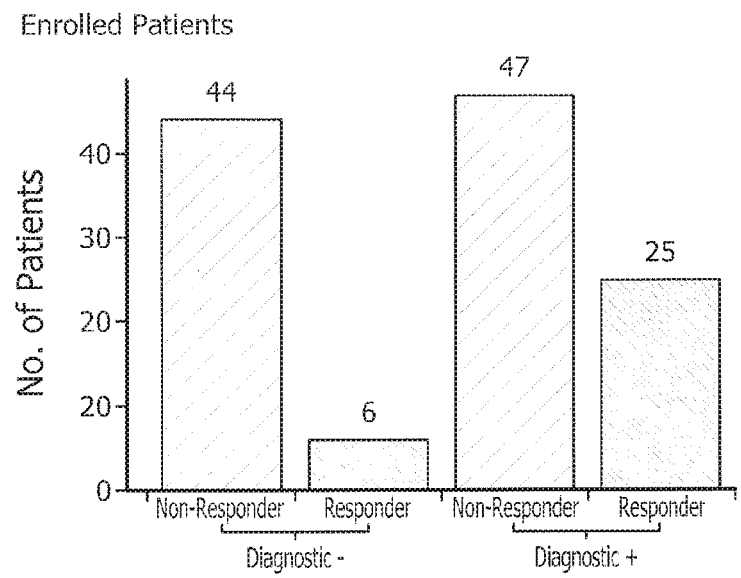
Figure 14D:
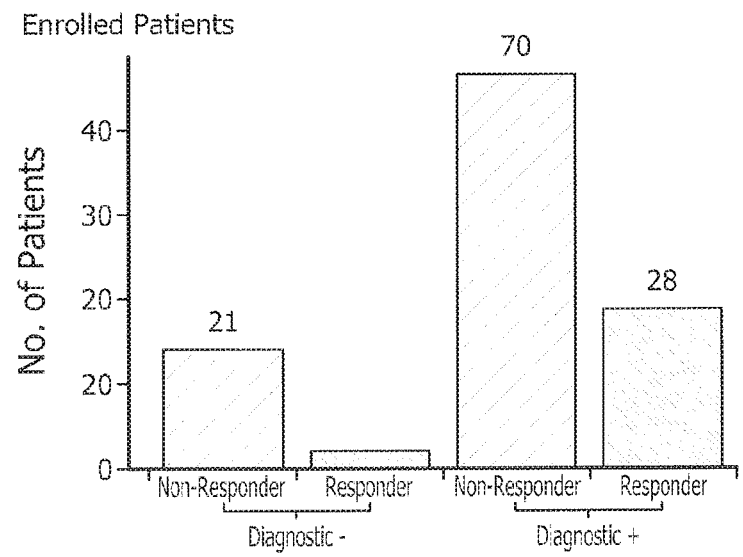

The enzalutamide response/non-response data was analyzed using Weighted Basal and Luminal A classifier score cut-offs of >−2 (FIG. 14A), >−25 (FIG. 14B), >−3 (FIG. 14C) and >−35 (FIG. 14D). The data is set forth in FIG. 14A-14D. In each figure, "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.

Figure 15:
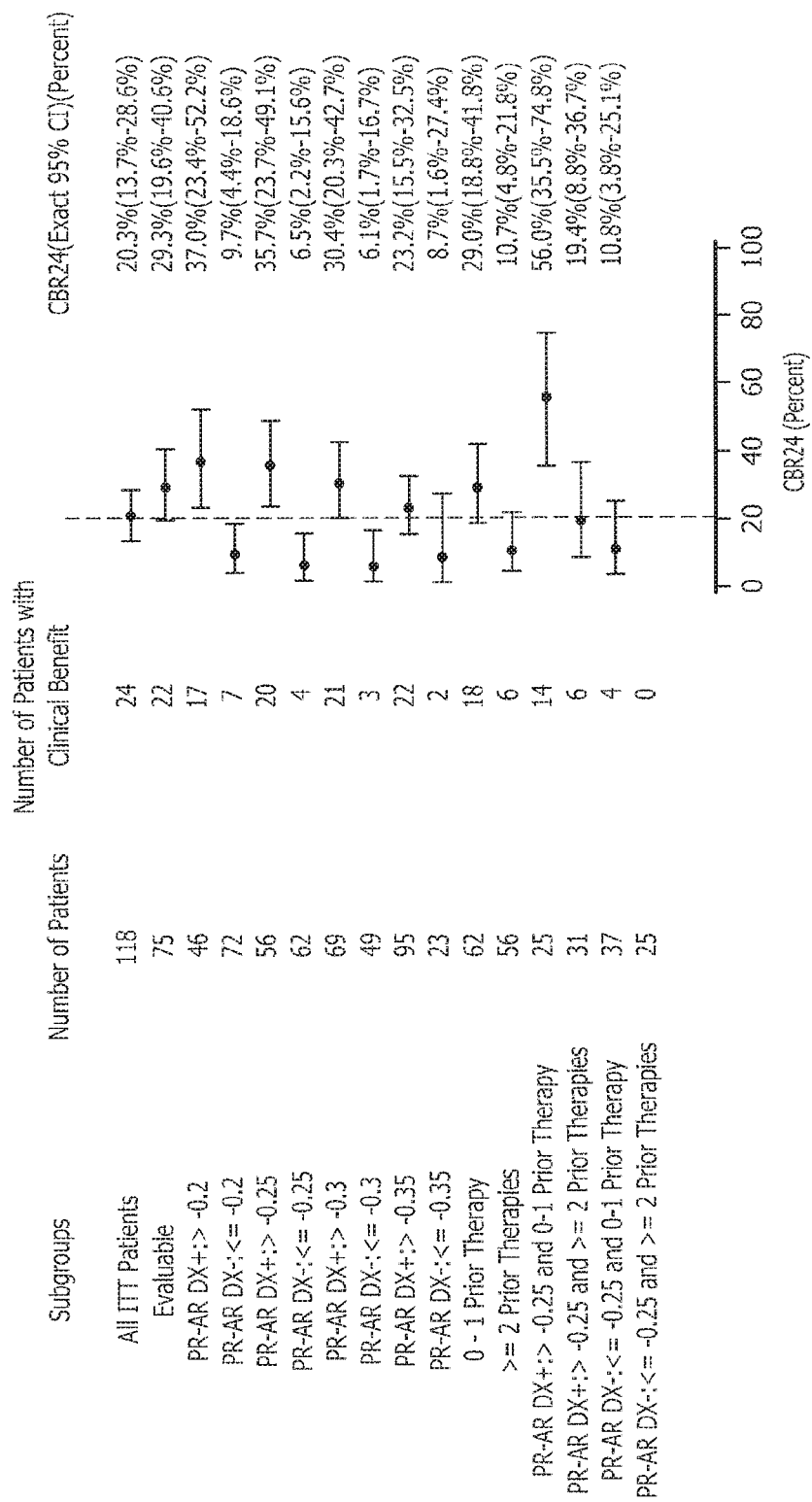

FIG. 15 comprises a representation of the response to enzalutamide of various patient subgroups treated with enzalutamide in the clinical trial. Response is shown in terms of Clinical Benefit Rate at ≥24 weeks (CBR24). The subgroups include Intent-To-Treat (ITT) patients; Evaluable Patients; patients whose breast tumor tissue was classified as a non-Basal like subtype by the PAM50 subtype classifier (PAM50 non-basal); patients whose tumors were classified as Basal-like subtype (PAM50 basal); and patients whose breast tumor tissue samples were analyzed to by applying the indicated cut-offs of >−2, −>25, >−3, and >−35 to the Weighted Basal and Luminal A classifier score. "PR-AR DX −" signifies patients whose samples did not meet the indicated threshold cut-off. "PR-AR DX +" signifies patients whose samples did meet the indicated threshold cut-off. Also shown are response data (applying a Weighted Basal and Luminal A classifier score cut-off of >−25) for samples from patients in the study receiving enzalutamide therapy after having received from zero to one prior therapies for treatment of TNBC with a drug other than an androgen receptor inhibitor ("and 0-1 prior therapy") or after having received two or more prior therapies for treatment of TNBC with a drug other than an androgen receptor inhibitor ("and >=2 prior therapies").

Figure 16:
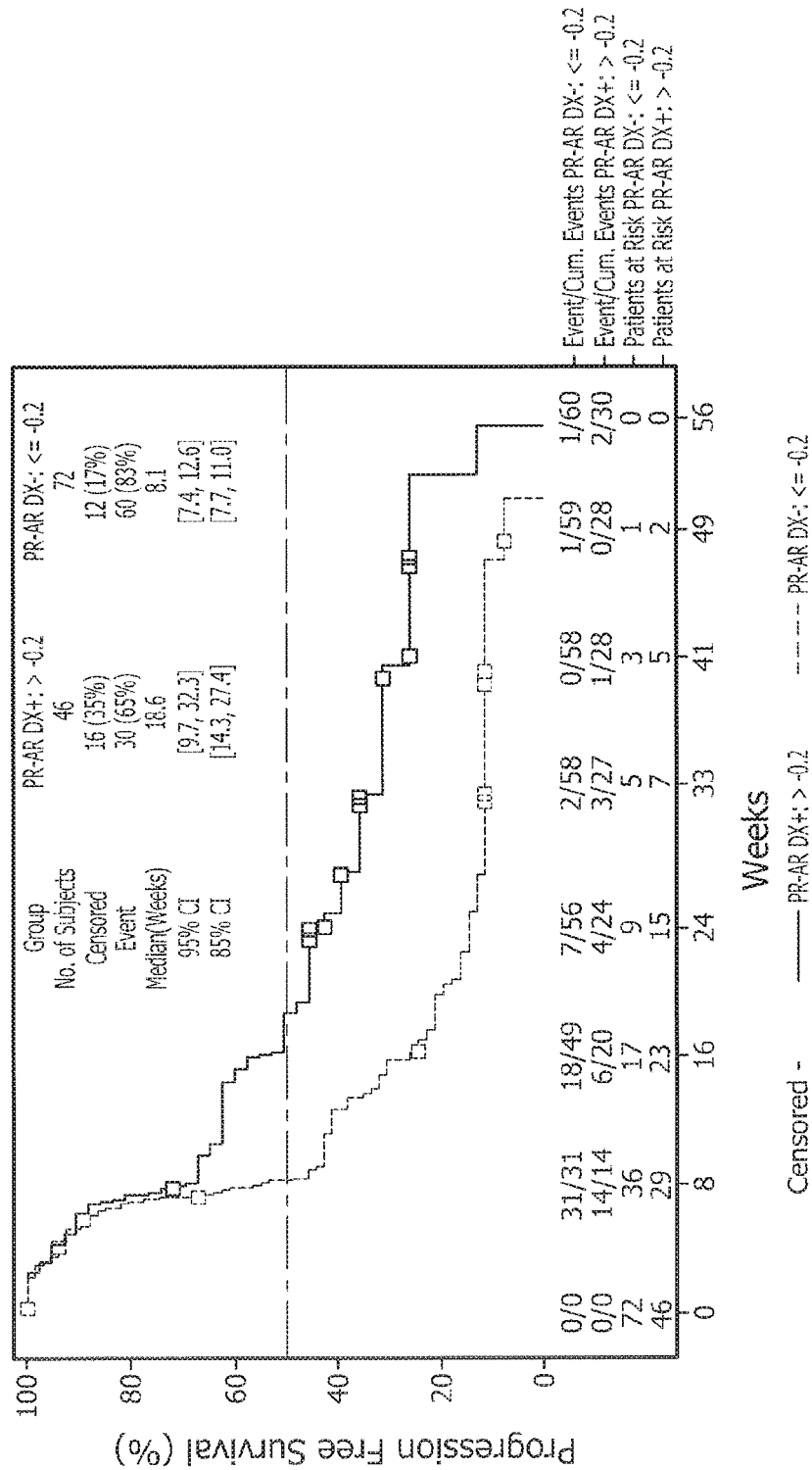

FIG. 16 is a Kaplan-Meier plot showing progression-free survival of patients treated with enzalutamide as a function of time to 56 weeks. The curves correspond to patients that were identified as meeting the signature condition of a Weighted Basal and Luminal A classifier score of greater than −0.2 ("PR-AR DX+: >−0.2", top curve) versus a classifier score of less than or equal to −0.2 ("PR-AR DX−: <=−0.2", bottom curve).

Figure 17:
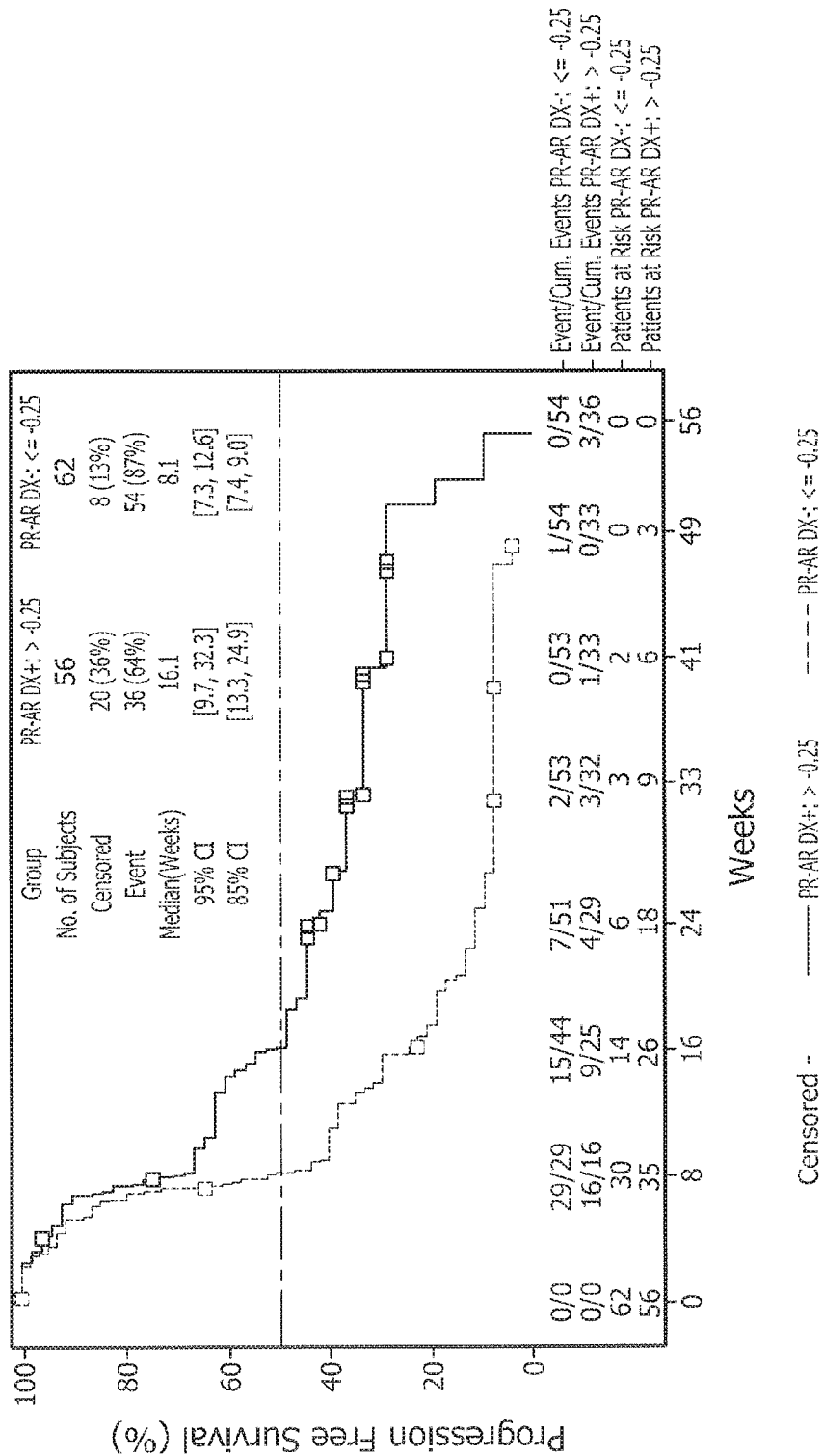

FIG. 17 is a Kaplan-Meier plot showing progression-free survival of patients treated with enzalutamide as a function of time to 56 weeks. The curves correspond to patients that were identified as meeting the signature condition of a Weighted Basal and Luminal A classifier score of greater than −0.25 ("PR-AR DX+: >−0.25", top curve) versus a classifier score of less than or equal to −0.25 ("PR-AR DX−: <=−0.25", bottom curve).

Figure 18:
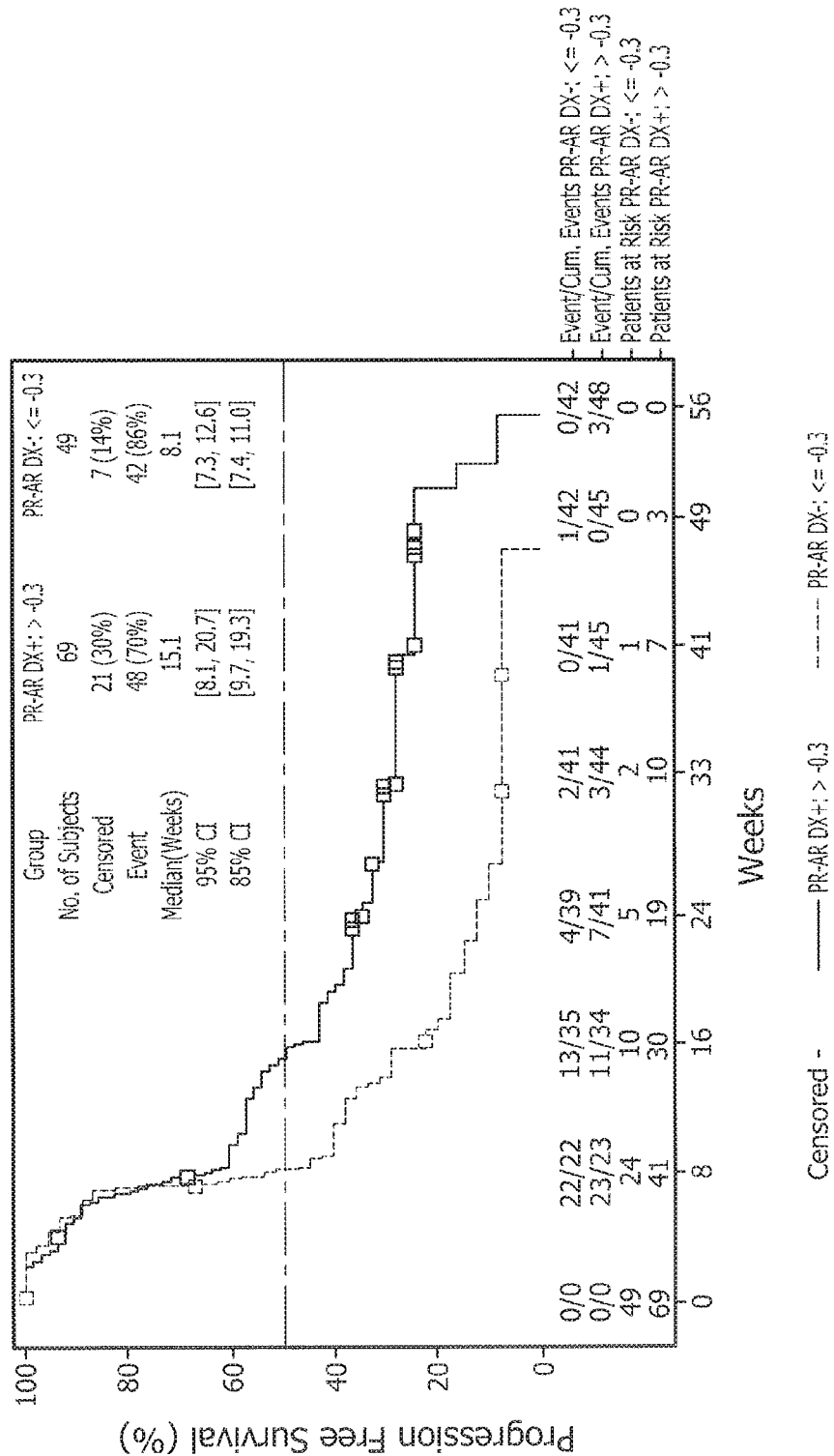

FIG. 18 is a Kaplan-Meier plot showing progression-free survival of patients treated with enzalutamide as a function of time to 56 weeks. The curves correspond to patients that were identified as meeting the signature condition of a Weighted Basal and Luminal A classifier score of greater than −0.3 ("PR-AR DX+: >−0.3", top curve) versus a classifier score of less than or equal to −0.30 ("PR-AR DX−: <=−0.3", bottom curve).

Figure 19:
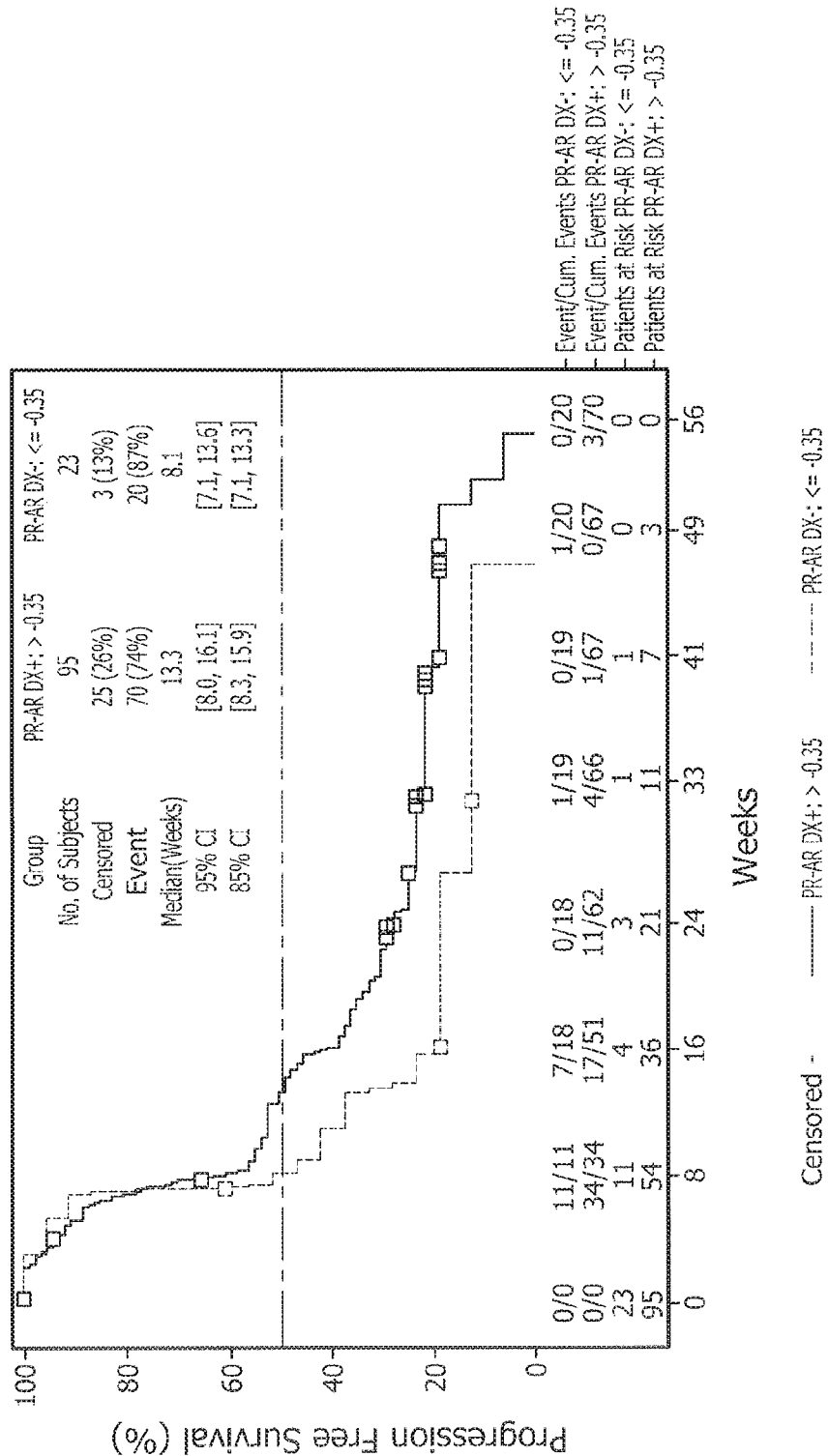

FIG. 19 is a Kaplan-Meier plot showing progression-free survival of patients treated with enzalutamide as a function of time to 56 weeks. The curves correspond to patients that were identified as meeting the signature condition of a Weighted Basal and Luminal A classifier score of greater than −0.35 ("PR-AR DX+: >−0.35", top curve) versus a classifier score of less than or equal to −0.35 ("PR-AR DX−: <=−0.35", bottom curve).

Figure 20:
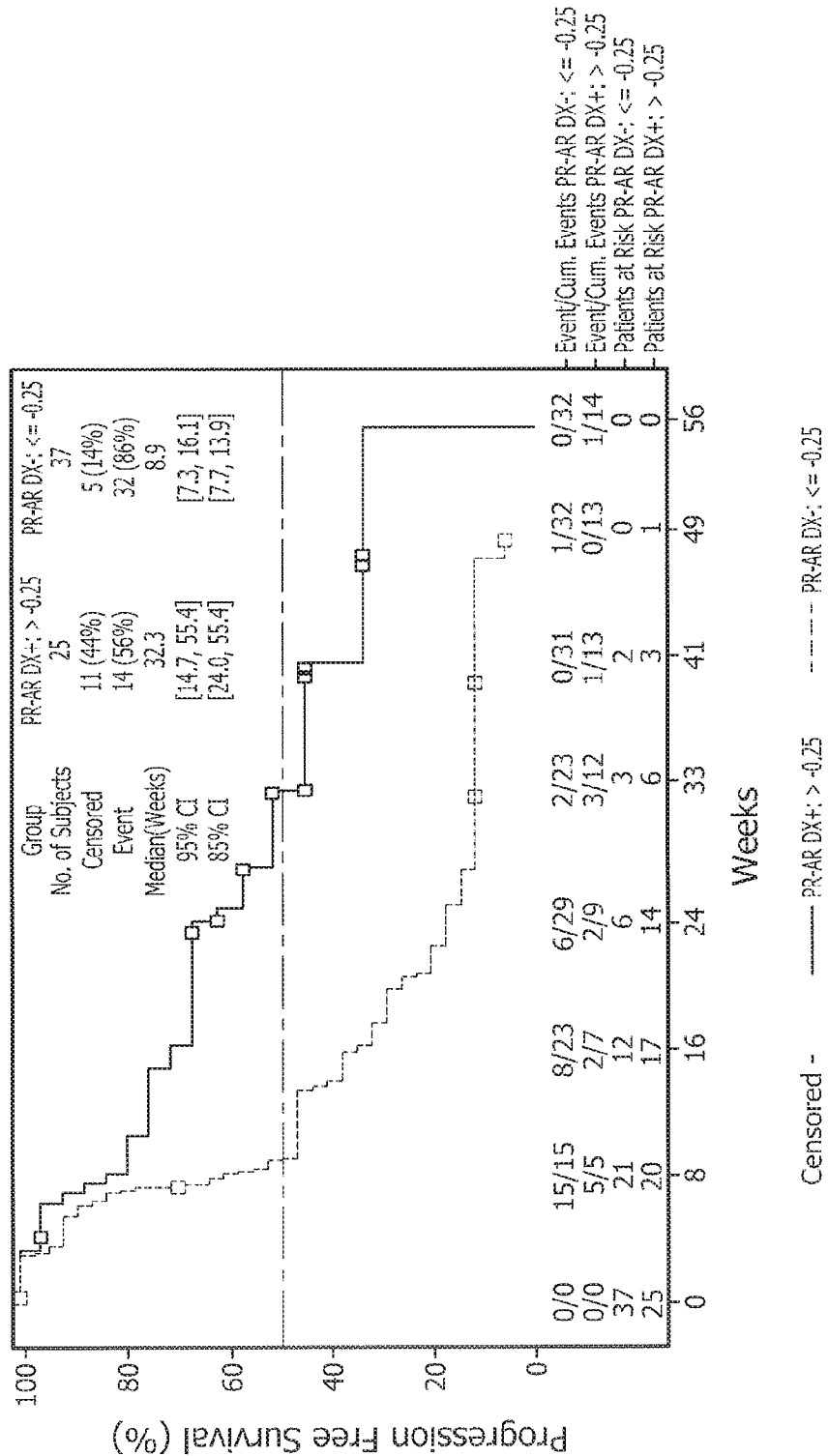

FIG. 20 is a Kaplan-Meier plot showing progression-free survival of patients treated with enzalutamide after receiving from zero to one prior therapies for treatment of TNBC with a drug other than an androgen receptor inhibitor. The curves correspond to patients that were identified as meeting the signature condition of a Weighted Basal and Luminal A classifier score of greater than −0.25 ("PR-AR DX+: >−0.25", top curve) versus a classifier score of less than or equal to −0.25 ("PR-AR DX−: <=−0.25", bottom curve).

Figure 21A:
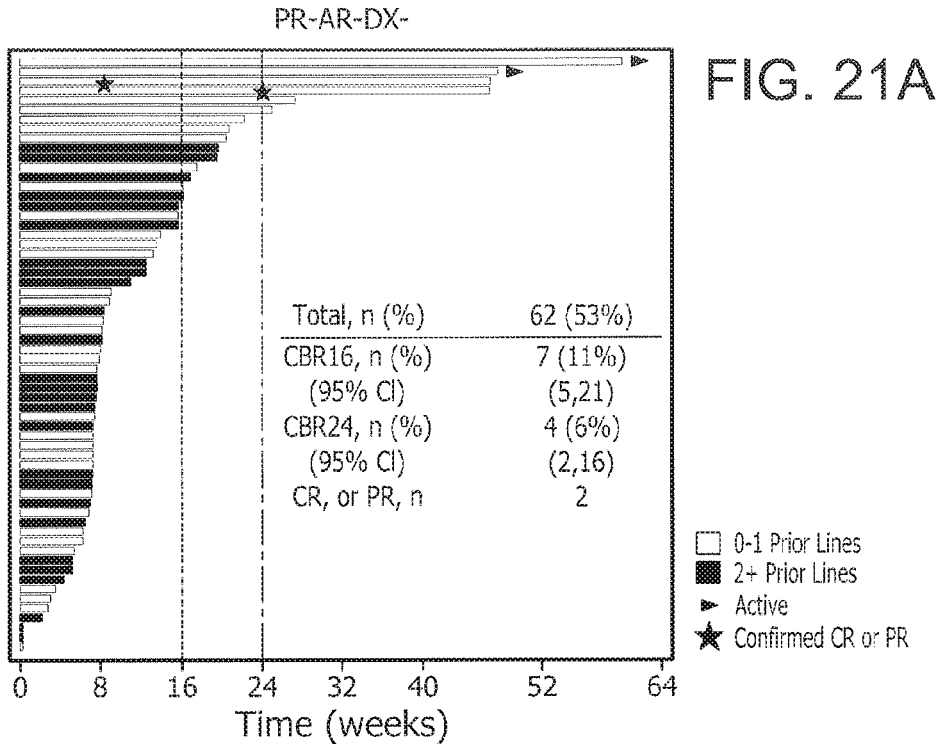
Figure 21B:
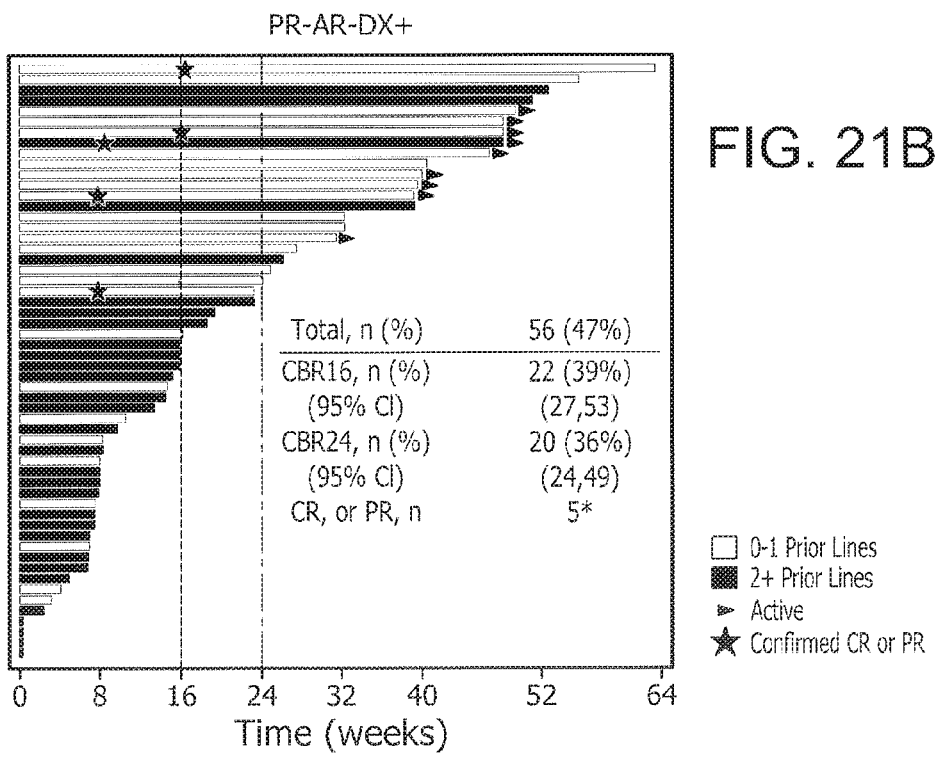

FIGS. 21A and 21B comprise graphs of the effect of the novel prognostic signature utilizing a Weighted Basal and Luminal A classifier score cut-off of >−0.25 as a predictor of response to AR inhibitor therapy in patients receiving zero or one (0-1 Prior Lines) or two or more (2+ Prior Lines) prior therapies for treatment of TNBC with a drug other than an androgen receptor inhibitor. The 56 patients of FIG. 21B were identified as meeting the signature condition of a Weighted Basal and Luminal A classifier score of greater than −0.25 The 62 study patients identified by a classifier score of less than or equal to −0.25 are identified in FIG. 21A. Each bar in the figures represents a single patient. Patient bars marked with a triangle ("Active") are active in the study. Patient bars marked with a star signify complete response (CR) or partial response (PR).

Figure 22A:
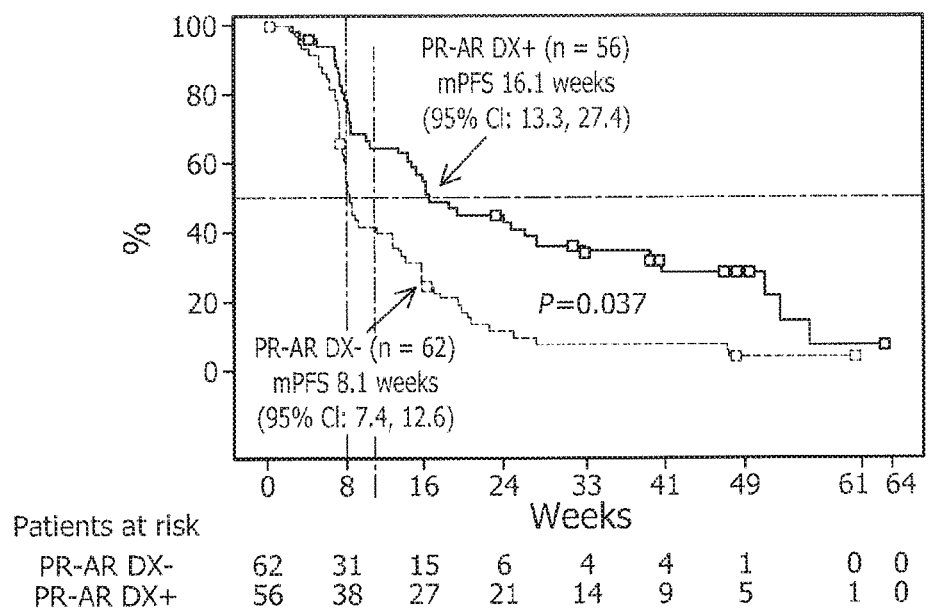
Figure 22B:
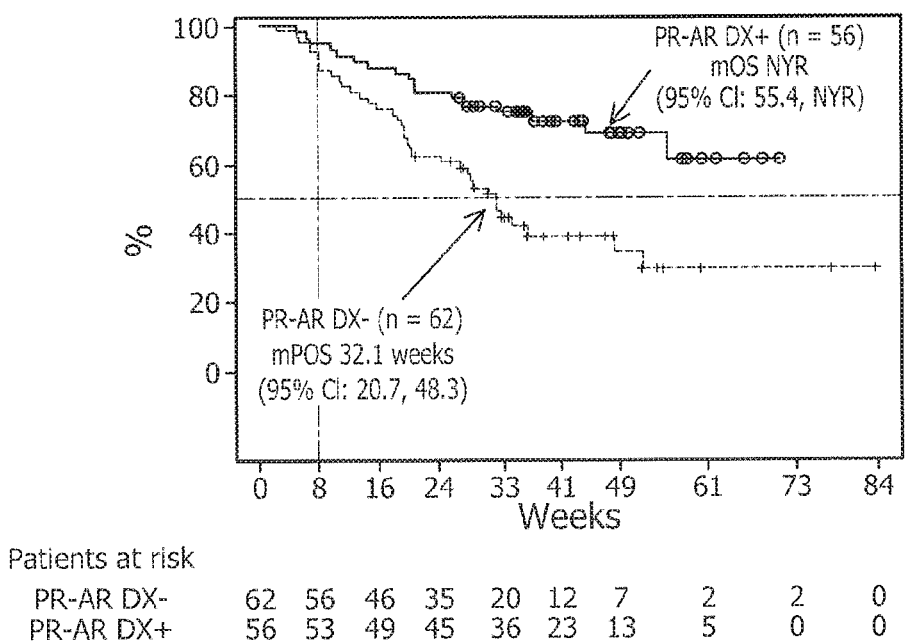

FIGS. 22A and 22B comprise Kaplan-Meier plots respectively showing median progression-free survival (FIG. 22A) (mPFS) and overall survival (mOS) of patients treated with enzalutamide as a function of time. The curves correspond to patients that were identified as meeting the signature condition of a Weighted Basal and Luminal A classifier score of greater than −0.25 ("PR-AR DX+", top curves) versus a classifier score of less than or equal to −0.25 ("PR-AR DX−", bottom curves). FIG. 22A: mPFS=16.1 weeks for patients meeting signature condition; mPFS=8.1 weeks for patients not meeting signature condition. FIG. 22B: mOS=NYR (not yet reached) at 84 weeks for patients meeting signature condition; mOS=32.1 weeks for patients not meeting signature condition.

Figure 23:
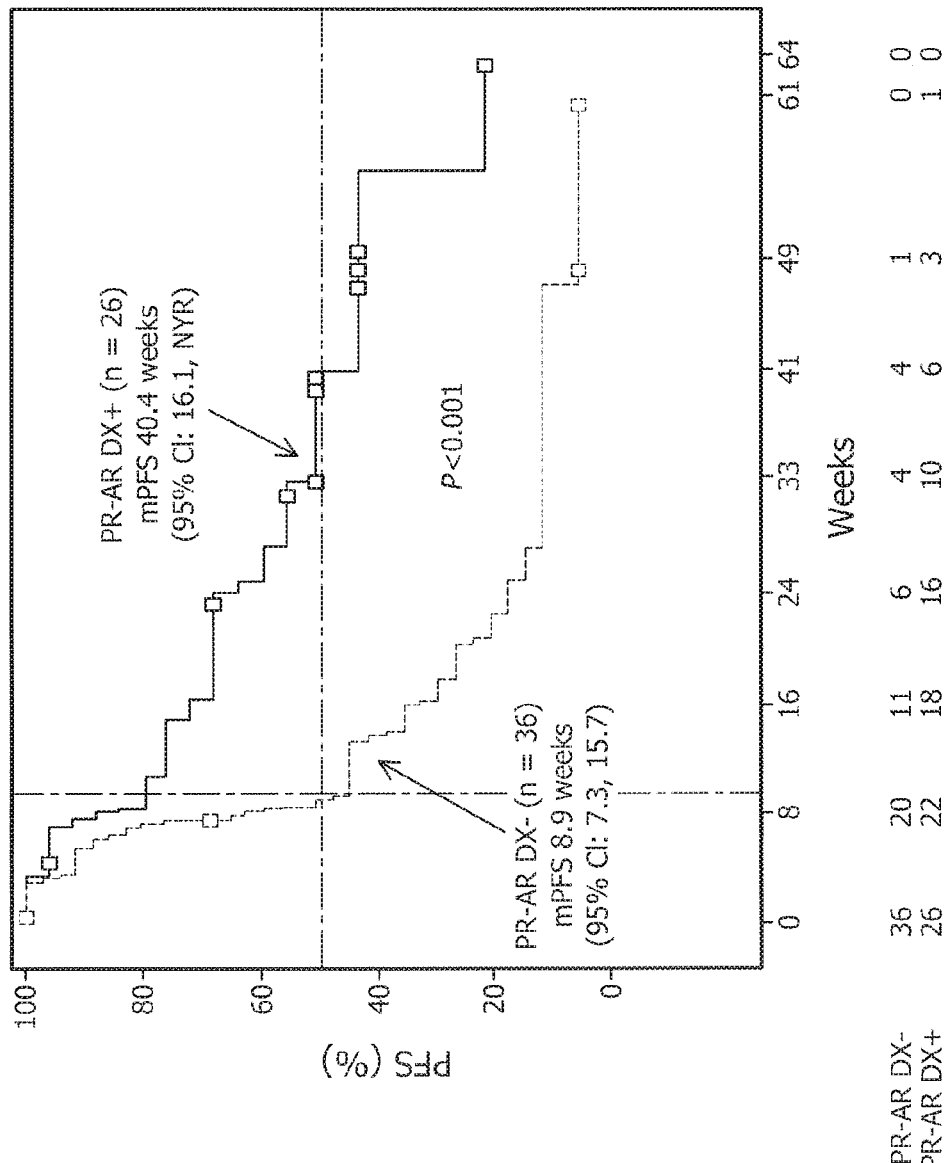

FIG. 23 is a Kaplan-Meier plot showing progression-free survival of patients treated with enzalutamide after receiving from zero to one prior therapies for treatment of TNBC with a drug other than an androgen receptor inhibitor. The curves correspond to patients that were identified as meeting the signature condition of a Weighted Basal and Luminal A classifier score of greater than −0.25 ("PR-AR DX+: >−0.25", top curve) versus a classifier score of less than or equal to −0.25 ("PR-AR DX−: <=−0.25", bottom curve). The data represents a continuation of the study of FIG. 20, taken beyond the 56 week interval of FIGS. 20 to 64 weeks in FIG. 23. In FIG. 23, mPFS=40.4 weeks for patients meeting signature condition; mPFS=8.9 weeks for patients not meeting signature condition. "NYR" means "not yet reached" in the statement of the 95% confidence interval (CI) for the data represented by patients meeting the signature condition in FIG. 23.

Figure 24A:
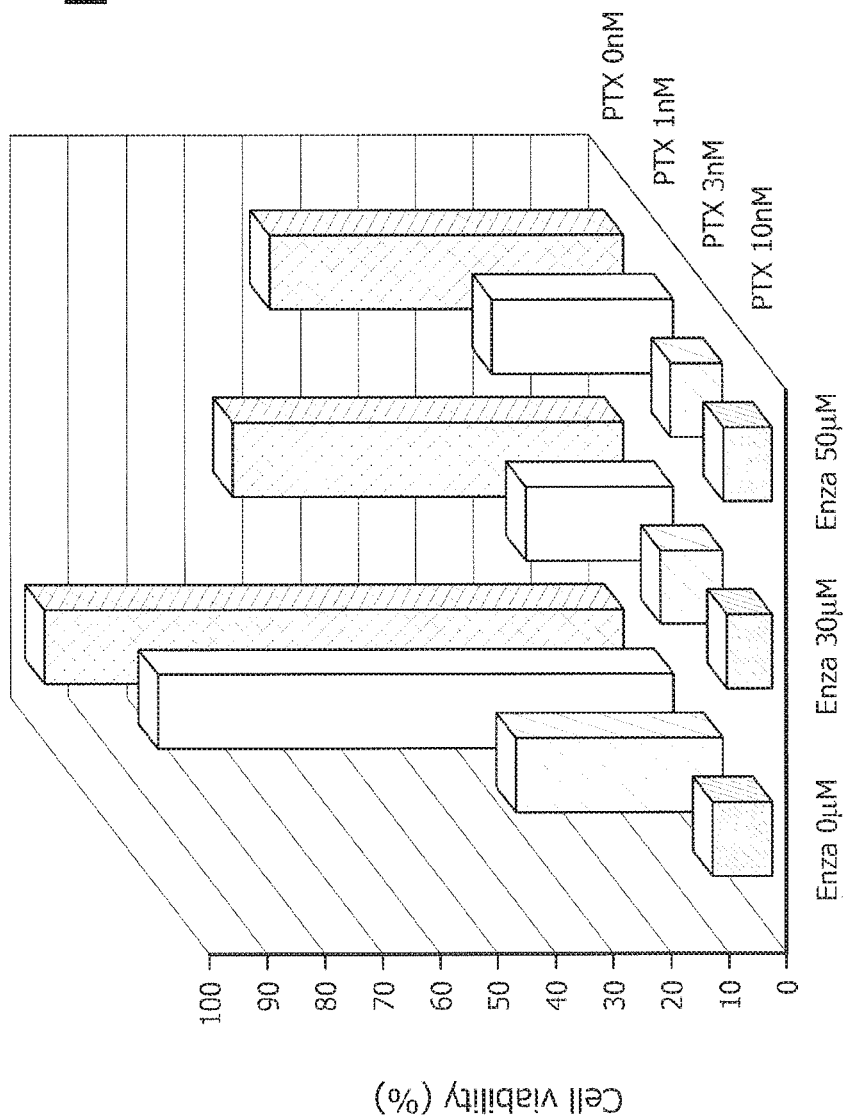
Figure 24B:
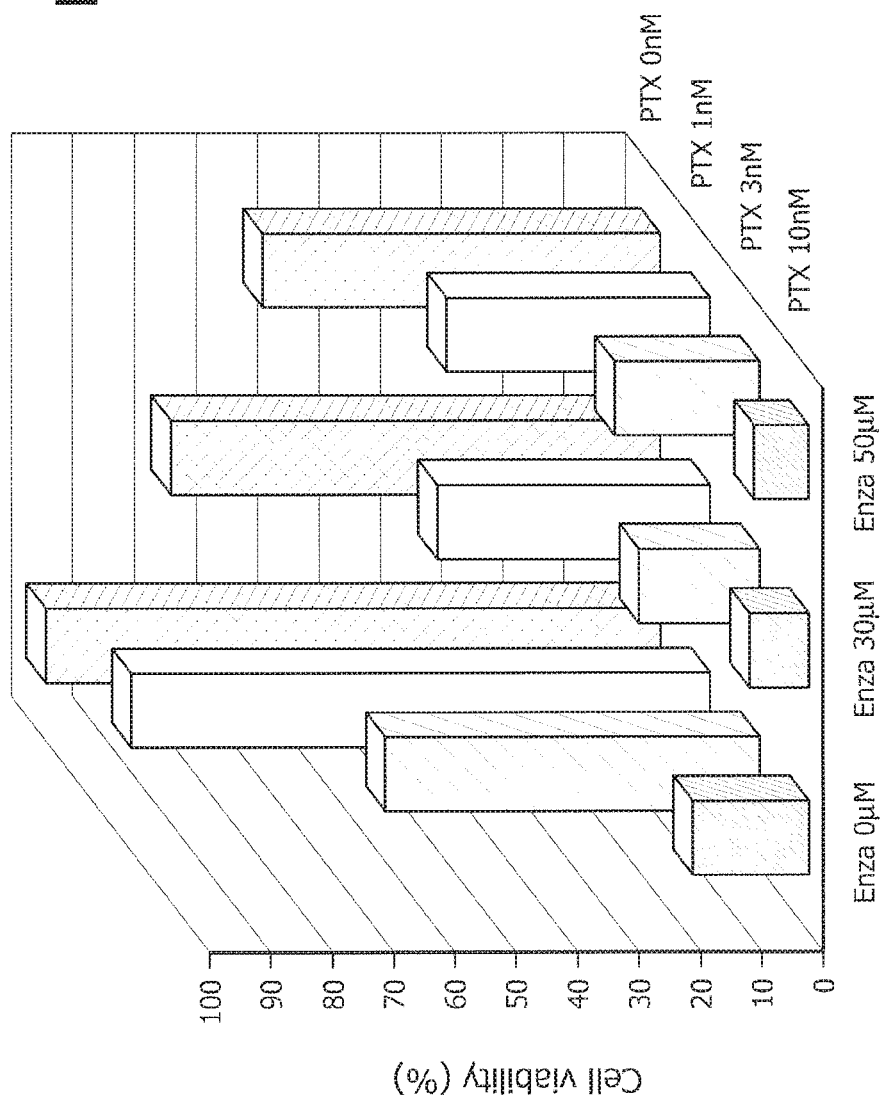
Figure 24C:
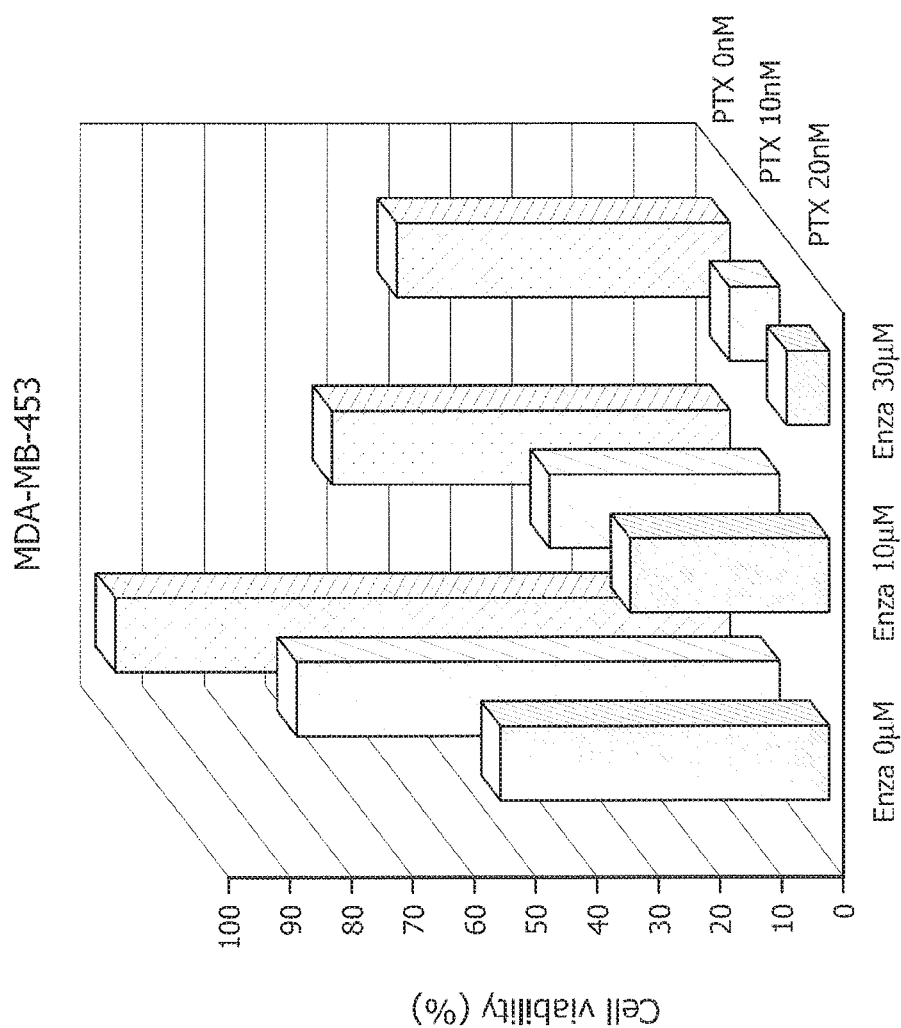

FIGS. 24A, 24B and 24C show the viability of TNBC cell lines BT549, MDA-MB-436 and MDA-MB-453, respectively, when treated with the indicated concentrations of enzalutamide (Enza), paclitaxel (PTX) or combinations thereof. Mean values are presented for each cell line (n=5).

Figure 25B:
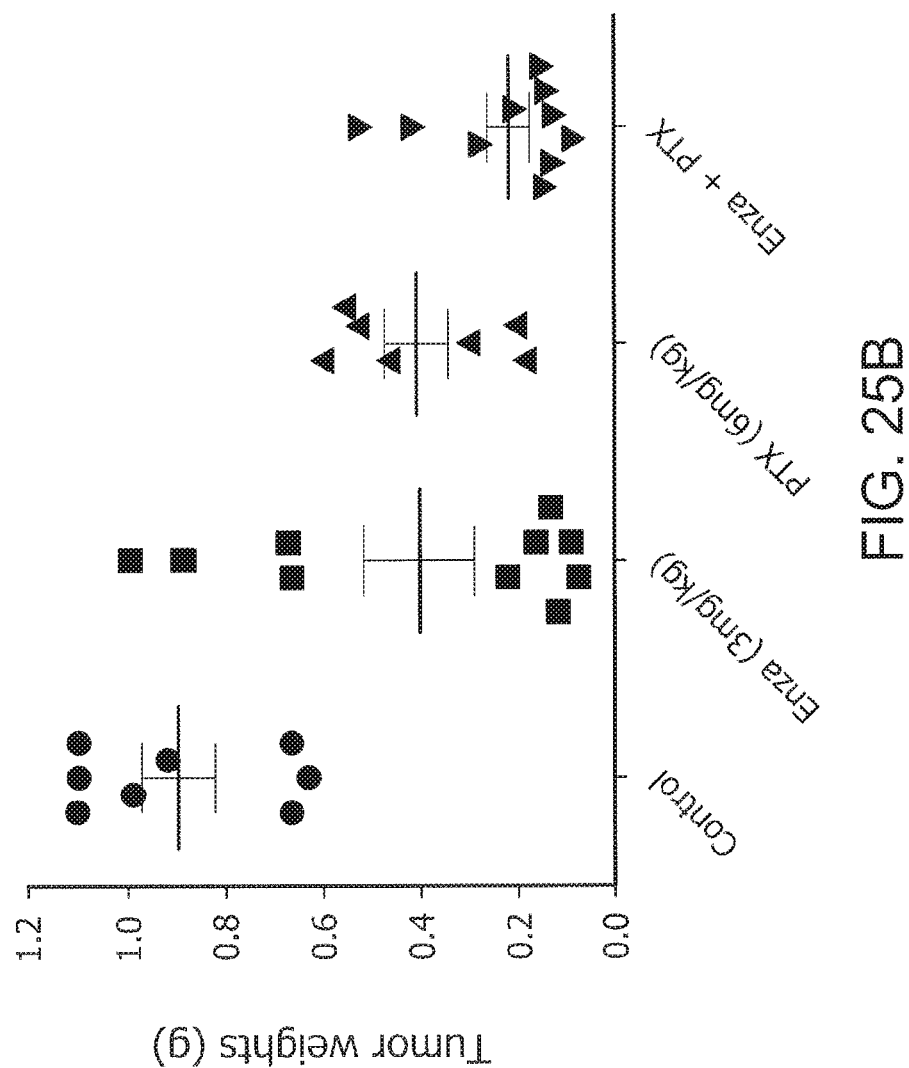

FIGS. 25A and 25B show the growth of tumors induced in NOD-SCID mice transplanted with cells of the TNBC cell line MDA-MB-453 following (i) oral gavage (PO) with enzalutamide (Enza) at 3 mg/kg/day (n=10), (ii) paclitaxel (PTX) at 6 mg/kg QMWF (IP) (n=7), or (iii) the combination of (i) and (ii) (n=10). Tumor volume was measured on the days indicated in FIG. 25A. Data points in FIG. 25A represent the average tumor volume for each group, and error bars reflect the SEM of the data. Tumor weights in FIG. 25B were determined at day 35.

DETAILED DESCRIPTION OF THE INVENTION

The present invention provides a method of treating TNBC in subjects afflicted with TNBC in which breast cancer cells of the TNBC-afflicted subject are characterized by a score derived from the expression by those cells of a certain set of intrinsic genes described more particularly below. The present invention also provides a method of assessing whether a TNBC treatment comprising an AR inhibitor is recommended (will likely be effective) for administration as a course of therapy for a patient afflicted with TNBC. Thus, the present invention provides in one embodiment a method of evaluating a treatment for triple negative breast cancer comprising the use of an androgen receptor inhibitor, the method comprising assaying a biological sample obtained from a subject to determine whether the biological sample obtained from the subject is classified as basal-like subtype or another subtype. If the biological sample is classified as other than a basal-like subtype, the breast cancer treatment comprising an androgen receptor inhibitor is more likely to be effective than if the sample were classified as basal-like subtype. Thus, the present invention provides in one embodiment a method of treating triple negative breast cancer in a subject having a cancer comprising breast cancer cells that have been previously classified as other than basal-like subtype. The method comprises administering a breast cancer treatment to the subject comprising an androgen receptor inhibitor, thereby treating the triple negative breast cancer in the subject.

The present invention further provides a method of treating TNBC by determining whether a TNBC patient should receive a treatment including AR inhibitor therapy, and then administering the optimal AR inhibitor treatment to the patient based on that determination. While the studies referenced herein were conducted on patient samples comprising tumor tissue staining positive by immunohistochemistry (IHC) for the AR receptor, the scope of the present invention is not so limited to the treatment and prognosis of AR(+) TNBC.

Studies of breast tumors based upon intrinsic gene analysis have identified five distinct subtypes of breast carcinomas: Luminal A (LumA), Luminal B (LumB), HER2-enriched (Her-2-E), Basal-like, and Normal-like (Perou et al. *Nature*, 406(6797):747-52 (2000); Sorlie et al. *PNAS*, 98(19):10869-74 (2001)). The HER2-enriched subtype may be referred to herein by "HER2", it being understood that the latter also means the HER2-enriched subtype. The Basal-like subtype may be referred to herein as "Basal", it being understood that the latter also means the Basal-like subtype. A breast cancer sample or cell is thus "classified" by assigning the cell or sample to an aforementioned subtype. A breast cancer sample or cell can also be considered "classified" in negative terms, i.e., a cell or sample may be classified as "non-Basal" or "other than Basal" upon determination that the cell or sample is of the LumA, LumB, HER2, or Normal-like sub-type.

We have unexpectedly found that the presence of the basal-like subtype is indicative of a likelihood of clinical non-response in TNBC to treatment with an AR inhibitor. We have found that a Basal Centroid classifier score of less than or equal to 0.9 is indicative of a likelihood of clinical response to an AR inhibitor. We have also unexpectedly found that an empirically determined weighted score based upon Basal-like and Luminal A subtype analysis conducted on biological samples from TNBC patients is indicative of a likelihood of clinical response to treatment with an AR inhibitor. Thus, in one embodiment, an assay is thus performed on a biological sample from a patient suffering from TNBC to determine the breast cancer subtype. In another embodiment, an assay is performed on a biological sample from a patient suffering from TNBC to determine the Basal Centroid classifier score, or both the Basal Centroid classifier score and the Luminal A classifier score.

The assay for determining whether the biological sample is classified as a subtype other than a basal-like subtype can comprise an assay for determining the presence of a basal-like subtype; a negative result indicates a non-basal subtype. Any assay capable of identifying the presence of a basal-like subtype may be utilized for this purpose. With approximately 70-90% of triple-negative carcinomas revealed to be basal-like breast carcinomas (Bertucci et al., *Int. J. Cancer* 2008, 123, 236-240; Wang et al,. *Eur. J. Clin. Invest.* 2008, 38, 438-446), the tripe negative phenotype has been used as a surrogate for the basal-like subtype. However, studies have shown that triple-negative and basal-like breast tumors are not synonymous. See, e.g., Choo and Nielsen, *Cancers* 2010, 2,1040-1065. Thus, care must be exercised in selecting an assay for identifying the basal-like subtype.

Recently, an assay for basal-like subtype has been announced that relies on the following profile which has been found to be characteristic of the basal-like subtype: ER negative, HER2 negative, and cytokeratin 5/6 and/or HER1 positive. A panel of four antibodies (ER, HER1, HER2, and cytokeratin 5/6) has thus been proposed as an immunohistochemical profile for identifying breast basal-like tumors (Nielsen et al., *Clinical Cancer Research* 2014; 10:5367-5374).

The Basal-like and Luminal A subtype analysis is performed by means of a gene expression assay which utilizes expression of intrinsic genes as classifier genes for breast cancer classification. Intrinsic genes, as described in Perou et al. (2000) *Nature* 406:747-752, are statistically selected to have low variation in expression between biological sample replicates from the same individual and high variation in expression across samples from different individuals. The present invention utilizes the PAM50 gene expression assay (Parker et al. *J Clin Oncol.*, 27(8):1160-7 (2009) and U.S. Patent Application Publication No. 2011/0145176, both incorporated herein, by reference, in their entireties). The PAM50 gene expression assay can be used to identify intrinsic subtypes of breast cancer (Luminal A, Luminal B, HER2-enriched, Basal-like, and Normal-like) from standard biological samples, such as formalin fixed paraffin embedded tumor tissue. The PAM50 gene expression classifier is a supervised, centroid-based prediction method to classify breast cancers into one of the five aforesaid molecular subtypes using a 50-gene intrinsic gene signature.

As described in Parker et al. and in U.S. Patent Application Publication No. 2011/0145176, as well as in U.S. Patent application Publication No. 2013/0004482, the PAM50 gene expression assay method utilizes a supervised algorithm to classify subject samples according to breast cancer intrinsic subtype. This algorithm, referred to herein as the "PAM50 classification model" or "PAM50 classifier" is based on the gene expression profile of a defined subset of 50 intrinsic genes that has been identified for classifying breast cancer intrinsic subtypes. The subset of genes, along with primers specific for their detection, is provided in Table 1 of U.S. Patent Application Publication No. 2013/0004482 and reproduced below as Table 1 of this disclosure. Select sequences of the same 50 intrinsic genes are set forth in Table 2 below. The entire disclosure of Publication No. 2013/0004482, is incorporated herein by reference.

The detection and estimation of the expression of the set of 50 subtype predictor genes of Table 1 is performed by any suitable means.

The PAM50 gene expression classifier operates by using a supervised prediction algorithm developed based on the profiles of objectively-selected prototype samples for "training" the algorithm. The samples are selected and subtyped using an expanded intrinsic gene set according to the methods disclosed in U.S. Patent Publication No. 2009/0299640, the entire disclosure of which is incorporated herein by reference. After stratifying the training samples according to subtype, a centroid-based prediction algorithm is used to construct centroids for each molecular subtype based on the expression profile of the intrinsic gene set described in Table 1. The centroid is the average gene expression for each gene in each subtype (or "class") divided by the within-class standard deviation for that gene. Nearest centroid classification takes the gene expression profile of a new sample, and compares it to each of these class centroids. Subtype prediction is done by calculating the Spearman's rank correlation of each test case to the five centroids of the PAM50 subtypes, and assigning a sample to a subtype based on the nearest centroid.

According to one embodiment, which does not necessarily involve assigning the patient sample to a PAM50 subtype, the Spearman rank correlation to the basal-like gene expression centroid is determined. The Spearman rank correlation between the sample and the basal-like centroid is assigned as the "Basal Centroid classifier score". The Spearman rank correlation to the Luminal A gene expression centroid is determined. The Spearman rank correlation between the sample and the Luminal A centroid is assigned as the "Luminal A Centroid classifier score". Methods for utilizing the PAM50-based signature to provide a Basal Centroid classifier score and a Luminal A Centroid classifier score are known to those skilled in the art. See, for example, U.S. Patent Application Publication No. 2009/0299640;

Parker et al., J Clin. Oncol., 27(8):1160-7 (2009); U.S. Patent Application Publication No. 2011/0145176. Also see, for example, Prat et al., *British Journal of Cancer*, (2014) 111, 1532-1541, incorporated herein by reference.

We have found, as demonstrated by the clinical trial of TNBC patients treated with the AR inhibitor enzalutamide, that a Basal Centroid classifier score of less than or equal to 0.9 is indicative of a likelihood of clinical response to an AR inhibitor. In some embodiments, a Basal Centroid classifier scores of less than or equal to 0.9, from 0.2 to 0.8, from 0.4 to 0.7 are used to predict the likelihood of clinical response to an AR inhibitor. In one embodiment, a Basal Centroid classifier score of less than or equal to 0.6 is used to predict the likelihood of clinical response to an AR inhibitor.

We have further found that the Basal Centroid classifier score and Luminal A Centroid classifier score, when combined subject to certain empirically defined weighting factors, provides a score ("Weighted Basal and Luminal A classifier score") that can be used to further predict responsiveness to androgen receptor inhibitor therapy in an individual TNBC patient. The Weighted Basal and Luminal A classifier score is determined from the following equation:

Weighted Basal and Luminal A classifier score=−0.25(Basal Centroid classifier score)+0.27(Luminal A Centroid classifier score).

In some embodiments, the equation for determining the Weighted Basal and Luminal A classifier score takes the form:

Weighted Basal and Luminal A classifier score=−0.2468275(Basal Centroid classifier score)+0.2667110(Luminal A Centroid classifier score).

As demonstrated by the clinical trial of TNBC patients treated with the AR inhibitor enzalutamide, if the Weighted Basal and Luminal A classifier score is greater than −0.3, the patient is identified as one likely responsive to AR inhibitor therapy. Alternatively, if the Weighted Basal and Luminal A classifier score is greater than −0.2, the patient may also be identified as one likely responsive to AR inhibitor therapy. Increased accuracy is obtained by selecting −0.25 as the cut-off for predicting responsiveness to AR inhibitor therapy. Thus, in a preferred embodiment, if the Weighted Basal and Luminal A classifier score is greater than −0.25, the patient is identified as one likely responsive to AR inhibitor therapy. If the TNBC patient is identified through determination of the Weighted Basal and Luminal A classifier score as one who is likely responsive to AR inhibitor therapy for TNBC, an appropriate AR inhibitor therapy may then be administered to treat the TNBC condition in the patient.

The utility of the Weighted Basal and Luminal A classifier score for predicting patient response to AR inhibitor therapy is illustrated in FIGS. 14A-14D and FIG. 15. The figures comprise a representation of the response to enzalutamide of various TNBC patient subgroups treated with enzalutamide in the clinical trial. Patient responsiveness to enzalutamide therapy was correlated with Weighted Basal and Luminal A classifier score, applying a series of cut-offs of >'10.2 (FIG. 14A), >−0.25 (FIG. 14B), >−0.3 (FIG. 14C), and >−0.35 (FIG. 14D) to the Weighted Basal and Luminal A classifier score. "Diagnostic −" in FIGS. 14A-D and "PR-AR DX −" in FIG. 15 signify patients whose samples did not meet the indicated Weighted Basal and Luminal A classifier score threshold cut-off. "Diagnostic +" in FIGS. 14A-14D and "PR-AR DX +" in FIG. 15 signify patients whose samples did meet the indicated threshold cut-off. As is apparent from a consideration of the data, a Weighted Basal and Luminal A classifier score of greater than −0.25 provided the highest level of accuracy in predicting TNBC patient responsiveness to enzalutamide therapy, with the criteria of greater than −0.2, or greater than −0.3, also providing acceptable results.

The correlation between patient response and Weighted Basal and Luminal A classifier score is further illustrated in the Kaplan-Meier plot of FIGS. 16-19, showing progression-free survival of TNBC patients treated with enzalutamide, as a function of time to 56 weeks. The curves in FIG. 16 correspond to patients that were identified as meeting the signature condition of a Weighted Basal and Luminal A classifier score of greater than −0.2 ("PR-AR DX+: >−0.2", top curve) versus a classifier score of less than or equal to −0.2 ("PR-AR DX−: <=−0.2", bottom curve). FIGS. 17, 18 and 19 are similar to FIG. 16, where the signature conditions of greater than −0.25 (FIG. 17), greater than −0.3 (FIG. 18) and greater than −0.35 (FIG. 19) were imposed. It may be appreciated that the magnitude of the vertical separation between the respective curves on each individual plot is a measure of the accuracy of correlation between patient Weighted Basal and Luminal A classifier score and progression-free survival. On this basis, it may be further appreciated from a comparison of FIGS. 16-19 that applying the criterion of a Weighted Basal and Luminal A classifier score greater than −0.25 (FIG. 17) provides the most accuracy in correlating Weighted Basal and Luminal A classifier score to TNBC patient responsiveness to enzalutamide therapy, with the criteria of greater than −0.2 (FIG. 16) or greater than −0.3 (FIG. 18) also provided acceptable results.

It was also found that the novel Weighted Basal and Luminal A classifier score as a predictor of responsiveness to AR inhibitor therapy for TNBC achieves even greater accuracy in patients who have either received no prior TNBC therapy, or have received no more than one round of prior TNBC therapy. As may be appreciated from a comparison of FIG. 20 and FIG. 17, imposing the criterion of a Weighted Basal and Luminal A classifier score of greater than −0.25 in the zero to 1 prior therapy patient group (FIG. 20), versus the larger group of all trial patients (FIG. 17), resulted in increased accuracy in identifying patients responsive to enzalutamide therapy, as evidenced by the greater vertical separation between the curves in FIG. 20, versus the vertical separation of the curves in FIG. 17. The trend is further observed in FIG. 23, in which the progression-free survival time in the study subjects of FIG. 20 is shown beyond the 56 weeks in FIG. 20, to 64 weeks in FIG. 23.

This result is also illustrated in FIGS. 21A and 21B, showing the extent of time on treatment without progression of disease (progression-free survival) for 56 patients that were identified as meeting the signature condition of a Weighted Basal and Luminal A classifier score of greater than −0.25 (FIG. 21B) versus 62 patients identified by a classifier score of less than or equal to −0.25 (FIG. 21A). Each bar represents a patient. Patients received either zero or one prior TNBC therapy before enzalutamide treatment (0-1 Prior Lines) with a drug other than an androgen receptor inhibitor, or two or more prior therapies (2+ Prior Lines) with a drug other than an androgen receptor inhibitor. Patient bars marked with a triangle ("Active") are active in the study. Patient bars marked with a star signify complete response (CR) or partial response (PR). The best time on treatment without disease progression is apparent in responder patients who received one or no prior lines of therapy (FIG. 21B).

The correlation between patient response and Weighted Basal and Luminal A classifier score is further illustrated in the Kaplan-Meier plots of FIGS. 22A and 22B, comparing the endpoints of median progression-free survival (mPFS) (FIG. 22A) and median overall survival (mOS) (FIG. 22B) of study patients. The curves in FIGS. 22A and 22B correspond to patients that were identified as meeting the signature condition of a Weighted Basal and Luminal A classifier score of greater than −0.25 ("PR-AR DX+", top curves) versus a classifier score of less than or equal to −0.25 ("PR-AR DX−", bottom curves). The results thus show that the Weighted Basal and Luminal A classifier of greater than −0.25 score correlates with overall survival, in addition to progression-free survival. The patients not meeting the prognostic signature condition were characterized by a median progression-free survival of 8.1 weeks and median overall survival of 32.1 weeks. In contrast, patients meeting the prognostic signature condition were characterized by a median progression-free survival of 16.1 weeks and median overall survival not yet reached (mOS NYR) at 84 weeks.

Gene Expression Detection

As the first step in determining the Basal Centroid Classifier Score or Weighted Basal and Luminal A classifier score of a TNBC patient, gene expression detection of the genes of the intrinsic gene set of Table 1 is carried out on patient samples by any method for determining the quantity or presence of an RNA transcript or its expression product of an intrinsic gene. Such methods are described in U.S. Patent Application Publication Nos. 2009/0299640 and 2013/0004482, incorporated herein by reference. They include, for example means, methods based on hybridization analysis of polynucleotides, methods based on sequencing of polynucleotides, immunohistochemistry methods, and proteomics-based methods. The methods generally detect expression products (e.g., mRNA) of the intrinsic genes listed in Table 1.

RNA sequencing as a method for assaying gene expression may be utilized in one embodiment. The assay for gene expression of the intrinsic gene set can also be performed by other technologies used to evaluate gene expression/quantification, including but not limited to real-time PCR, microarrays, microfluidic gene expression, and targeted gene sequencing. Such methods include, for example, hybridization analysis of polynucleotides, methods based on sequencing of polynucleotides, immunohistochemistry methods, and proteomics-based methods. PCR-based methods, such as reverse transcription PCR (RT-PCR) (Weis et al., *TIG* 8:263-64, 1992), and array-based methods such as microarray (Schena et al., *Science* 270:467-70, 1995) may be used.

General methods for RNA extraction are well known in the art and are disclosed in standard textbooks of molecular biology, including Ausubel et al., ed., *Current Protocols in Molecular Biology*, John Wiley & Sons, New York 1987-1999. Methods for RNA extraction from paraffin embedded tissues are disclosed, for example, in Rupp and Locker, *Lab Invest.* 56:A67, (1987); and De Andres et al., *Biotechniques* 18:42-44, (1995). Isolated RNA can be used in hybridization or amplification assays that include, but are not limited to, PCR analyses and probe arrays. Intrinsic gene expression product level determination in a sample may also involve nucleic acid amplification, for example, by RT-PCR (U.S. Pat. No. 4,683,202), ligase chain reaction, self-sustained sequence replication, transcriptional amplification, rolling circle replication, and other methods utilizing nucleic acid amplification method, followed by the detection of the amplified molecules using techniques well known to those of skill in the art.

Microarrays may be used for expression profiling. Each array includes a reproducible pattern of capture probes attached to a solid support. Labeled RNA or DNA is hybridized to complementary probes on the array and then detected by laser scanning Hybridization intensities for each probe on the array are determined and converted to a quantitative value representing relative gene expression levels. See, for example, U.S. Pat. Nos. 6,040,138, 5,800,992 and 6,020,135, 6,033,860, and 6,344,316. High-density oligonucleotide arrays are particularly useful for determining the gene expression profile for a large number of RNAs in a sample.

Total RNA for analysis of the intrinsic gene set may be isolated from a biological sample, such as a tumor. If the source of RNA is a primary tumor, RNA (e.g., mRNA) can be extracted, for example, from frozen or archived paraffin-embedded and fixed (e.g., formalin-fixed) tissue samples (e.g., pathologist-guided tissue core samples).

Gene Analysis and Data Processing

Patient sample gene expression data from the intrinsic gene set may be pre-processed by known techniques to achieve sequence data alignment, data normalization and mean centering of data, for example. Methods of normalization include, for example, (i) global normalization that uses all genes on the array; (ii) housekeeping genes normalization that uses constantly expressed housekeeping/invariant genes; and (iii) internal controls normalization that uses known amount of exogenous control genes added during hybridization (Quackenbush *Nat. Genet.* 32 (Suppl.), 496-501 (2002)). Gene count estimates can also be normalized to a fixed quartile, such as a fixed upper quartile. The resulting normalized gene expression estimates may then be adjusted such that the median expression value of each gene is equivalent to the median of a known subset, such as a gene subset from TNBC patients.

According to one embodiment, patient sample expression data for processing by the PAM50 classifier is first pre-processed by alignment and data centering techniques. RNA-sequence data is first aligned to Human (Homo sapiens) genome sequence hg19 (https://genome.ucsc.edu/cgi-bin/hgGateway?db=hg19) (http://www.ncbi.nlm.nih.gov/assembly/GCF_000001405.25/) using, for example, MapSplice (Nucleic Acids Res. 2010 October; 38(18):e178. doi: 10.1093/nar/gkq622). Gene and isoform level counts may be estimated, for example, using RNA-Seq by Expectation-Maximization (RSEM) (deweylab.biostat.wisc.edu/rsem/). Gene count estimates are normalized to a fixed upper quartile. The resulting normalized gene expression estimates may then be adjusted such that the median expression value of each gene is equivalent to the median of the triple negative subset of the TCGA RNA-seq data reported in "Comprehensive Molecular Portraits of Human Breast Tumors", *The Cancer Genome Atlas Network, Nature* 490, 61-70 (Oct. 4, 2012) (www.nature.com/nature/journal/v490/n7418/full/nature11412.html.

Following pre-processing, the patient sample expression data from the PAM50 gene array is processed according to the known techniques for processing intrinsic gene set data. Complete instructions for processing of patient sample gene expression data from the PAM50 intrinsic gene set is described in detail in at least the following, and will not be detailed herein except by way of summary: Parker et al. J Clin Oncol., 27(8):1160-7 (2009); U.S. Patent Application Publication No. 2011/0145176; and U.S. Patent Application Publication No. 2013/0004482. (U.S. Patent Application Publication No. 2013/0004482 describes the application of the PAM50 classifier for screening breast cancer subjects' possible responsiveness to anthracycline therapy relying on, inter alia, classification of the patient tumor into the HER2 subtype by the PAM50 classifier.) The Spearman rank correlation to the basal-like gene expression centroid is determined. The Spearman rank correlation between the sample and the basal-like centroid is assigned as the Basal Centroid classifier score. The Spearman rank correlation to the Luminal A gene expression centroid is determined. The Spearman rank correlation between the sample and the Luminal A centroid is assigned as the Luminal A Centroid classifier score. The Basal Centroid classifier score and Luminal A Centroid classifier score so determined are then inserted into the equation, Weighted Basal and Luminal A classifier score=−0.25(Basal Centroid classifier score)+0.27(Luminal A Centroid classifier score)

to provide the Weighted Basal and Luminal A classifier score for the patient sample.

Samples

Samples for analysis of intrinsic subtype classification may comprise a biological sample comprising a cancer cell or tissue, such as a breast tissue sample or a primary breast tumor tissue sample. In some embodiments, the biological sample comprises breast tissue or cells. By "biological sample" is intended any sampling of cells, tissues, or bodily fluids in which expression of an intrinsic gene can be detected. Examples of such biological samples include, but are not limited to, biopsies and smears. Bodily fluids useful in the present disclosure include blood, lymph, urine, saliva, nipple aspirates, fluid from ductal lavage, gynecological fluids, or any other bodily secretion or derivative thereof. Blood can include whole blood, plasma, serum, or any derivative of blood. In some embodiments, the biological sample includes breast cells, and may particularly comprise breast tissue from a biopsy, such as a breast tumor tissue sample. Biological samples may be obtained from a subject by a variety of techniques including, for example, by scraping or swabbing an area, by using a needle to aspirate cells or bodily fluids, or by removing a tissue sample (i.e., biopsy). Methods for collecting various biological samples are well known in the art. In some embodiments, a breast tissue sample is obtained by, for example, fine needle aspiration biopsy, core needle biopsy, or excisional biopsy. In another embodiment, fluid is obtained by ductal lavage. A thin catheter is inserted into the natural opening of the milk duct. A saline solution is then infused through the catheter to rinse the duct, which loosens cells from the duct lining. The solution containing the loosened cells is withdrawn through the catheter and biopsied. Fixative and staining solutions may be applied to the cells or tissues for preserving the specimen and for facilitating examination. In one embodiment, the biological sample is a formalin-fixed, paraffin-embedded breast tissue sample, particularly a primary breast tumor sample. In various embodiments, the tissue sample is obtained from a pathologist-guided tissue core sample.

Therapeutic Agents

Androgen receptor inhibitors directly or indirectly inhibit the androgen receptor (AR) signaling pathway. In one embodiment, direct inhibitors of the AR receptor include enzalutamide, bicalutamide (Casodex), flutamide, nilutamide, ARN509, and the like. In another embodiment, indirect inhibitors of AR include Cyp 17 inhibitors such as ketoconazole, abiraterone acetate, VN/124-1 (TOK-001), orteronel (TAK-700) and the like. In another embodiment, AR inhibitors include finasteride, galeterone, cyproterone acetate, and andarine, and the like. The antigen receptor inhibitor may result in complete or partial inhibition of the biological activity of the androgen receptor.

In a preferred embodiment, the AR inhibitor is enzalutamide (Xtandi®), which has the systematic (IUPAC) name 4-(3-(4-cyano-3-(trifluoromethyl)phenyl)-5,5-dimethyl-4-oxo-2-thioxoimidazolidin-1-yl)-2-fluoro-N-methylbenzamide, directly binds the androgen receptor (AR) and has three sites of activity. It inhibits binding of androgens to AR, inhibits nuclear translocation of AR, and inhibits AR-mediated DNA binding.

In certain embodiments, the breast cancer treatment comprising an androgen receptor inhibitor further comprises one or more other anti-cancer agents that is not an androgen receptor inhibitor. Such non-AR inhibitor anticancer agents that may also be administered to patients in conjunction with AR inhibitor therapy include, for example, cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, or combinations thereof.

In one embodiment, the non-AR inhibitor anticancer agent is paclitaxel. In one embodiment, the AR inhibitor is enzalutamide and the non-AR inhibitor anticancer agent is paclitaxel. As described hereinafter, it has been found that the combination of enzalutamide and paclitaxel results in enhanced cytotoxicity in tumor cells that are positive for the prognostic marker consisting of a Weighted Basal and Luminal A classifier score of greater than −0.25.

A therapeutically effective amount of one or more AR inhibitors is administered to the subject according to the present invention, to treat TNBC utilizing dosing and treatment regimens that are typically employed when administering AR inhibitors in the treatment of cancer. The AR inhibitor can be administered in the breast cancer treatments described herein, by the routes by which such agents are typically administered. A representative regimen for one such AR inhibitor, enzalutamide, is 160 mg/day orally, once daily. The dosage form may comprise, for example, a capsule. The daily dose may be administered, for example, in the form of a capsule comprising 160 mg enzalutamide. In another embodiment, four capsules, each comprising 40 mg enzalutamide, are administered. Lower or higher doses may be utilized. The non-AR inhibitor agents are administered according to well-known dosages and treatment regimens for such agents as used in the treatment of breast cancer.

TABLE 1

PAM50 Intrinsic Gene List

| Gene | Genbank Accession No. | Forward Primer | SEQ ID NO: | Reverse Primer | SEQ ID NO: |
|---|---|---|---|---|---|
| ACTR3B | NM_020445 NM_001040135 | AAAGATTCCTG GGACCTGA | 1 | TGGGGCAGTTCT GTATTACTTC | 51 |
| ANLN | NM_018685 | ACAGCCACTTTC AGAAGCAAG | 2 | CGATGGTTTTGT ACAAGATTCTC | 52 |
| BAG1 | NM_004323 | CTGGAAGAGTT GAATAAAGAGC | 3 | GCAAATCCTTGG GCAGA | 53 |
| BCL2 | NM_000633 | TACCTGAACCG GCACCTG | 4 | GCCGTACAGTTC CACAAAGG | 54 |
| BIRC5 | NM_001012271 | GCACAAAGCCA TTCTAAGTC | 5 | GACGCTTCCTAT CACTCTATTC | 55 |
| BKVRA | BX647539 | GCTGGCTGAGC AGAAAG | 6 | TTCCTCCATCAA GAGTTCAACA | 56 |
| CCNB1 | NM_031966 | CTTTCGCCTGAG CCTATTT | 7 | GGGCACATCCAG ATGTTT | 57 |
| CCNE1 | BC035498 | GGCCAAAATCG ACAGGAC | 8 | GGGTCTGCACAG ACTGCAT | 58 |
| CDC20 | BG256659 | CTGTCTGAGTGC CGTGGAT | 9 | TCCTTGTAATGG GGAGACCA | 59 |
| CDC6 | NM 001254 | GTAAATCACCTT CTGAGCCT | 10 | ACTTGGGATATG TGAATAAGACC | 60 |
| CDCA1 | NM 031423 | GGAGGCGGAAG AAACCAG | 11 | GGGGAAAGACA AAGTTTCCA | 61 |
| CDH3 | BC041846 | GACAAGGAGAA TCAAAAGATCA GC | 12 | ACTGTCTGGGTC CATGGCTA | 62 |
| CENPF | NM_016343 | GTGGCAGCAGA TCACAA | 13 | GGATTTCGTGGT GGGTTC | 63 |
| CEP55 | AB091343 | CCTCACGAATT GCTGAACTT | 14 | CCACAGTCTGTG ATAAACGG | 64 |
| CXXC5 | BC006428 | CATGAAATAGT GCATAGTTTGCC | 15 | CCATCAACATTC TCTTTATGAACG | 65 |
| EGFR | NM_005228 | ACACAGAATCT ATACCCACCAG AGT | 16 | ATCAACTCCCAA ACGGTCAC | 66 |
| ERBB2 | NM_001005862 | GCTGGCTCTCAC ACTGATAG | 17 | GCCCTTACACAT CGGAGAAC | 67 |
| ESR1 | NM_001122742 | GCAGGGAGAGG AGTTTGT | 18 | GACTTCAGGGTG CTGGAC | 68 |
| EXO1 | NM_130398 | CCCATCCATGTG AGGAAGTATAA | 19 | TGTGAAGCCAGC AATATGTATC | 69 |
| FGFR4 | AB209631 | CTTCTTGGACCT TGGCG | 20 | TATTGGGAGGCA GGAGGTTTA | 70 |
| FOXA1 | NM_004496 | GCTACTACGCA GACACG | 21 | CTGAGTTCATGT TGCTGACC | 71 |
| FOXC1 | NM_001453 | GATGTTCGAGT CACAGAGG | 22 | GACAGCTACTAT TCCCGTT | 72 |
| GPR160 | AJ249248 | TTCGGCTGGAA GGAACC | 23 | TATGTGAGTAAG CTCGGAGAC | 73 |
| GRB7 | NM_005310 | CGTGGCAGATG TGAACGA | 24 | AGTGGGCATCCC GTAGA | 74 |

TABLE 1-continued

PAM50 Intrinsic Gene List

| Gene | Genbank Accession No. | Forward Primer | SEQ ID NO: | Reverse Primer | SEQ ID NO: |
|---|---|---|---|---|---|
| HSPC150 (UBE2T) | NM_014176 | GGAGATCCGTCAACTCCAAA | 25 | AGTGGACATGCGAGTGGAG | 75 |
| KIF2C | NM_006845 | TGGGTCGTGTCAGGAAAC | 26 | CACCGCTGGAAACTGAAC | 76 |
| KNTC2 | NM_006101 | CGCAGTCATCCAGAGATGTG | 27 | CGTGCACATCCATGACCTT | 77 |
| KRT14 | BC042437 | ACTCAGTACAAGAAAGAACCG | 28 | GAGGAGATGACCTTGCC | 78 |
| KRT17 | AK095281 | GTTGGACCAGTCAACATCTCTG | 29 | GCCATAGCCACTGCCACT | 79 |
| KRT5 | M21389 | TGTGGCTCATTAGGCAAC | 30 | CTTCGACTGGACTCTGT | 80 |
| MAPT | NM_001123066 | GACTCCAAGCGCGAAAAC | 31 | CAGACATGTTGGTATTGCACATT | 81 |
| MDM2 | M92424 | CCAACAAAATATTCATGGTTCTTG | 32 | AGGCGATCCTGGGAAATTAT | 82 |
| MELK | NM_014791 | CCAGTAGCATTGTCCGAG | 33 | CCCATTTGTCTGTCTTCAC | 83 |
| MIA | BG765502 | GTCTCTGGTAATGCACACT | 34 | CTGATGGTTGAGGCTGTT | 84 |
| MK167 | NM_002417 | GTGGAATGCCTGCTGACC | 35 | CGCACTCCAGCACCTAGAC | 85 |
| MLPH | NM_024101 | AGGGGTGCCCTCTGAGAT | 36 | TCACAGGGTCAAACTTCCAGT | 86 |
| MMP11 | NM_005940 | CGAGATCGCCAAGATGTT | 37 | GATGGTAGAGTTCCAGTGATT | 87 |
| MYBL2 | BX647151 | AGGCGAACACACAACGTC | 38 | TCTGGTCACGCAGGGCAA | 88 |
| MYC | NM_002467 | AGCCTCGAACAATTGAAGA | 39 | ACACAGATGATGGAGATGTC | 89 |
| NAT1 | BC013732 | ATCGACTGTGTAAACAACTAGAGAAGA | 40 | AGTAGCTACATCTCCAGGTTCTCTG | 90 |
| ORC6L | NM_014321 | TTTAAGAGGGCAATGGAAGG | 41 | CGGATTTTATCAACGATGCAG | 91 |
| PGR | NM_000926 | TGCCGCAGAACTCACTTG | 42 | CATTTGCCGTCCTTCATCG | 92 |
| PHGDH | AK093306 | CCTCAGATGATGCCTATCCA | 43 | GCAGGTCAAAACTCTCAAAG | 93 |
| PTTG1 | BE904476 | CAGCAAGCGATGGCATAGT | 44 | AGCGGGCTTCTGTAATCTGA | 94 |
| RRM2 | AK123010 | AATGCCACCGAAGCCTC | 45 | GCCTCAGATTTCAACTCGT | 95 |
| SFRP1 | BC036503 | TCGAACTGAAGGCTATTTACGAG | 46 | CTGCTGAGAATCAAAGTGGGA | 96 |
| SLC39A6 | NM_012319 | GTCGAAGCCGCAATTAGG | 47 | GGAACAAACTGCTCTGCCA | 97 |
| TMEM45B | AK098106 | CAAACGTGTGTTCTGGAAGG | 48 | ACAGCTCTTTAGCATTTGTGGA | 98 |

TABLE 1-continued

PAM50 Intrinsic Gene List

| Gene | Genbank Accession No. | Forward Primer | SEQ ID NO: | Reverse Primer | SEQ ID NO: |
|---|---|---|---|---|---|
| TYMS | BQ056428 | TGCCCTGTATGATGTCAGGA | 49 | GGGACTATCAATGTTGGGTTCTC | 99 |
| UBE2C | BC032677 | GTGAGGGGTGTCAGCTCAGT | 50 | CACACAGTTCACTGCTCCACA | 100 |

TABLE 2

PAM50 Intrinsic Gene Sequences

| Gene | Genbank Accession No. | SEQ ID NO: |
|---|---|---|
| ACTR3B | NM_020445 | 101 |
|  | NM_001040135 | 102 |
| ANLN | NM_018685 | 103 |
| BAG1 | NM_004323 | 104 |
| BCL2 | NM_000633 | 105 |
| BIRC5 | NM_001012271 | 106 |
| BKVRA | BX647539 | 107 |
| CCNB1 | NM_031966 | 108 |
| CCNE1 | BC035498 | 109 |
| CDC20 | BG256659 | 110 |
| CDC6 | NM_001254 | 111 |
| CDCA1 | NM_031423 | 112 |
| CDH3 | BC041846 | 113 |
| CENPF | NM_016343 | 114 |
| CEP55 | AB091343 | 115 |
| CXXC5 | BC006428 | 116 |
| EGFR | NM_005228 | 117 |
| ERBB2 | NM_001005862 | 118 |
| ESR1 | NM_001122742 | 119 |
| EXO1 | NM_130398 | 120 |
| FGFR4 | AB209631 | 121 |
| FOXA1 | NM_004496 | 122 |
| FOXC1 | NM_001453 | 123 |
| GPR160 | AJ249248 | 124 |
| GRB7 | NM_005310 | 125 |
| HSPC150 (UBE2T) | NM_014176 | 126 |
| KIF2C | NM_006845 | 127 |
| KNTC2 | NM_006101 | 128 |
| KRT14 | BC042437 | 129 |
| KRT17 | AK095281 | 130 |
| KRT5 | M21389 | 131 |
| MAPT | NM_001123066 | 132 |
| MDM2 | M92424 | 133 |
| MELK | NM_014791 | 134 |
| MIA | BG765502 | 135 |
| MKI67 | NM_002417 | 136 |
| MLPH | NM_024101 | 137 |
| MMP11 | NM_005940 | 138 |
| MYBL2 | BX647151 | 139 |
| MYC | NM_002467 | 140 |
| NAT1 | BC013732 | 141 |
| ORC6L | NM_014321 | 142 |
| PGR | NM_000926 | 143 |
| PHGDH | AK093306 | 144 |
| PTTG1 | BE904476 | 145 |
| RRM2 | AK123010 | 146 |
| SFRP1 | BC036503 | 147 |
| SLC39A6 | NM_012319 | 148 |
| TMEM45B | AK098106 | 149 |
| TYMS | BQ056428 | 150 |
| UBE2C | BC032677 | 151 |

The practice of the invention is illustrated by the following non-limiting examples.

EXAMPLES

Example 1

Clinical Study Protocol

A clinical trial was conducted to determine clinical benefit of enzalutamide treatment in patients whose tumors are androgen receptor-positive (AR+) and triple-negative. In this study, AR+ is defined as any nuclear AR staining by immunohistochemistry (IHC) and TNBC is defined as <1% staining by IHC for estrogen receptor (ER) and progesterone receptor (PgR), 0 or 1+ by IHC for human epidermal growth factor receptor 2 (HER2), or negative for HER2 amplification by in situ hybridization (ISH) for 2+ IHC disease. AR staining was carried out by IHC with two different antibodies each of which were individually optimized on breast cancer tissue. Enzalutamide (160 mg/day) was administered as four 40 mg soft gelatin capsules orally once daily with or without food. Patients received enzalutamide until disease progression per Response Evaluation Criteria in Solid Tumors version 1.1 (RECIST 1.1) was documented unless treatment was discontinued due to other reasons specified in the trial protocol. The study periods included prescreening (patients could sign consent to submit to tissue for testing for AR expression at any time in their disease course); screening (28 days before first dose of study drug); treatment (day 1 through discontinuation); safety follow-up (approximately 30 days after the last dose of study drug or before initiation of a new antitumor treatment, whichever occurs first); and long-term follow-up (assessment of subsequent breast cancer therapies and survival status every 3 to 6 months after treatment discontinuation). Objective response—complete response (CR) or partial response (PR)—was determined by investigators according to the RECIST 1.1.

The trial was a Simon 2-stage study where a minimum benefit was required in a pre-defined patient population prior to expanding the study to a larger size. In Stage 1, 42 patients enrolled into the study to obtain the pre-defined 26 Evaluable patients. The requisite clinical benefit to proceed to Stage 2 was observed in Stage 1 and an additional 76 patients were enrolled for a total of 118 patients overall. Patients who received prior treatment with an androgen receptor signaling inhibitor, who had central nervous system (CNS) metastases were excluded; there was no limit to number of prior therapies, and patients with patients measurable disease or bone-only nonmeasurable disease were eligible. Clinical Benefit Rate at 16 weeks (CBR16) was defined as the proportion of Evaluable Patients with a best response of complete remission (CR), partial response (PR) or stable disease (SD) ≥16 weeks (CBR16). The Clinical Benefit Rate at ≥24 weeks (CBR16) was also assessed.

In Stage 1, 42 patients were enrolled to get 26 Evaluable Patients (n=26). Evaluable patients were those who had both AR staining in ≥10% of tumor and at least 1 post-baseline tumor assessment. The Intent-To-Treat (ITT) population (n=42 in Stage 1) was defined as all enrolled patients who had centrally assessed AR+ TNBC and received at least 1 dose of study drug. Twenty-six (62%) of 42 ITT patients were Evaluable, while 16 of 42 were not Evaluable. Of the 16 not meeting the criteria for Evaluable, 10 had AR expression below 10%; 6 had AR expression ≥10% but did not have a post-baseline assessment (2 were discovered to have CNS metastases shortly after study entry and were withdrawn from treatment prior to having a post-baseline tumor assessment). More than 50% of the patients received enzalutamide as their first or second line of therapy, while >30% had ≥3 prior regimens before receiving enzalutamide.

Intrinsic Gene Expression Analysis

Human breast tumors from TNBC patients were obtained from the aforementioned clinical study of enzalutamide, an AR antagonist. The patient breast cancer tissue was stained for AR expression. The patient staining was graded by a pathologist on both the staining intensity (3+, 2+ and 1+) as well as the percentage of tumor cells stained as given in the standard operating procedure. AR staining was evaluated both in the nucleus and cytoplasm.

RNA-seq data utilized in this study were pre-processed as follows. The RNA-seq data was aligned to Human (Homo sapiens) genome sequence hg19 from the Human Genome Browser—hg19 Assembly created by the Genome Bioinformatics Group of UC Santa Cruz (genome.ucsc.edu/cgi-bin/hgGateway?db=hg19) (www.ncbi.nlm.nih.gov/assembly/GCF_000001405.25/) using MapSplice (Nucleic Acids Res. 2010 October; 38(18):e178. doi: 10.1093/nar/gkq622). Gene and isoform level counts were estimated using RNA-Seq by Expectation-Maximization (RSEM) (deweylab.biostat.wisc.edu/rsem/). Gene count estimates were normalized to a fixed upper quartile. The resulting normalized gene expression estimates were adjusted such that the median expression value of each gene was equivalent to the median of the triple negative subset of the TCGA RNA-seq data reported in "Comprehensive Molecular Portraits of Human Breast Tumors", The Cancer Genome Atlas Network, Nature 490, 61-70 (Oct. 4, 2012) (www.nature.com/nature/journal/v490/n7418/full/nature11412.html).

Intrinsic subtype classification was performed into the LumA, LumB, Basal, HER2 and Normal groups using the PAM50 classification model as described in Parker et al. J Clin Oncol., 27(8):1160-7 (2009). The intrinsic subtype classification was carried out on genomic data obtained from RNA sequencing of RNA obtained from formalin fixed, paraffin embedded tissue collected from subjects' breast tumors. The data was pre-processed as indicated above. Subtype classification was performed on a "Training and Test" set and a further "Validation" set. The Training and Test set consisted of 122 patient samples out of which 42 patients were from the pre-screened population but not enrolled in the study and 80 patients samples were from the enrolled population in the clinical study. The Validation set consisted of 55 patient samples which had 15 patients from the pre-screened population not enrolled on the study and 40 samples from the enrolled population.

The data was analyzed according to the known methods for analyzing PAM50 intrinsic gene set data, as described by Parker et al. et al., supra. Essentially, the detection and estimation of the expression of the set of 50 subtype predictor genes of Table 1 from patient tumor samples was carried out. The expression profile of the set of 50 subtype predictor genes by the described method that provides Basal-like, HER2, LumA, LumB and Normal subtype classifications was analyzed. The Spearman correlation was calculated for each sample and PAM50 centroid. These values were used as continuous estimates of distance or similarity of a sample to each centroid. The subtype of each sample was assigned as the closest (largest positive correlation) centroid. The underlying measures of correlation to each subtype were used to classify a sample as one of 4 tumor subtypes (Basal-like, HER2, LumA and LumB) or Normal-like.

Further, the Spearman rank correlation to the Basal-like gene expression centroid was evaluated. The Spearman rank correlation between the sample and the Basal-like centroid was assigned as the "Basal Centroid classifier score". The Spearman rank correlation to the Luminal A gene expression centroid was evaluated. The Spearman rank correlation between the sample and the Luminal A centroid was assigned as the "Luminal A classifier score".

Figure 1:
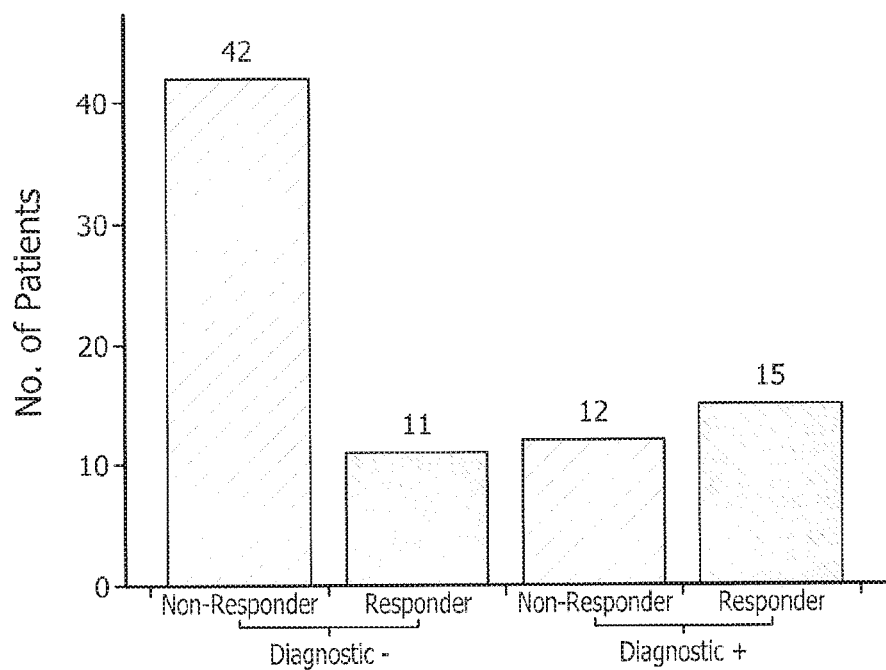
FIG. 1 is a graph of the results from some of the patients enrolled into either the prescreening or screening period of a clinical trial evaluating enzalutamide in patients whose TNBC also expressed AR. "Diagnostic −" represents patients having the Basal-like subtype, as determined by PAM50 gene breast cancer subtype classification. "Diagnostic +" represents the patients with Her2, LumA, LumB or Normal subtypes. Patients were scored as "Responder" or "Non-Responder" to the enzalutamide therapy according to the criteria set forth in Example 1.

In the enrolled patients (Intent-To-Treat (ITT) population, Basal-like subtype generally correlated with non-response to enzalutamide therapy, while existence of one of the other subtypes generally correlated with response to enzalutamide therapy. See FIG. 1, wherein "Diagnostic −" represents the Basal-like subtype patients and "Diagnostic +" represents the patients with Her2, LumA, LumB or Normal subtypes. Thus, a PAM50 gene expression classifier result indicating a non-Basal-like tumor type is a marker for predicting responsiveness to enzalutamide therapy in TNBC.

Example 2

The results of the clinical study of Example 1 were further analyzed utilizing the patient Basal Centroid classifier scores. The therapeutic response data was evaluated imposing a series of threshold cut-offs on the Basal Centroid classifier score. The enzalutamide response/non-response data was analyzed using Basal Centroid classifier score cut-offs of 0.2, 0.3, 0.4, 0.5, 0.6, 0.65, 0.7, 0.8 and 0.9. The data is set forth in FIGS. 2A/B through 10A/B. In each figure, "Diagnostic +" represents patients whose samples met the indicated prognostic signature comprising the indicted threshold cut-off. "Diagnostic −" represents patients whose samples did not meet the indicated threshold cut-off.

| | FIG. | | | | | | | | |
|---|---|---|---|---|---|---|---|---|---|
| | 2A/B | 3A/B | 4A/B | 5A/B | 6A/B | 7A/B | 8A/B | 9A/B | 10A/B |
| Basal Centroid classifier score | 0.2 | 0.3 | 0.4 | 0.5 | 0.6 | 0.65 | 0.7 | 0.8 | 0.9 |

Figure 2A:
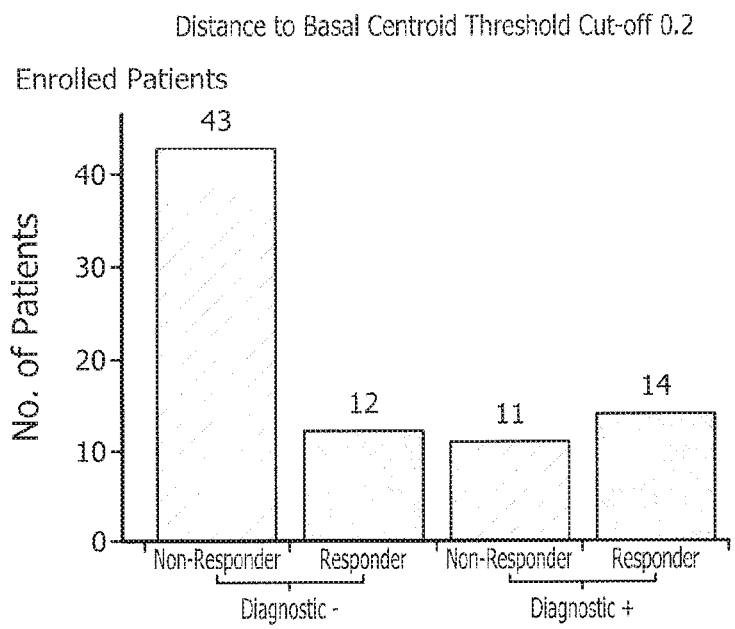
FIGS. 2A and 2B are graphs of results of the same TNBC clinical trial in which patient gene expression classifier scores for the Basal-like subtype were correlated with patient response. A threshold cut-off of 0.2 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 2B:
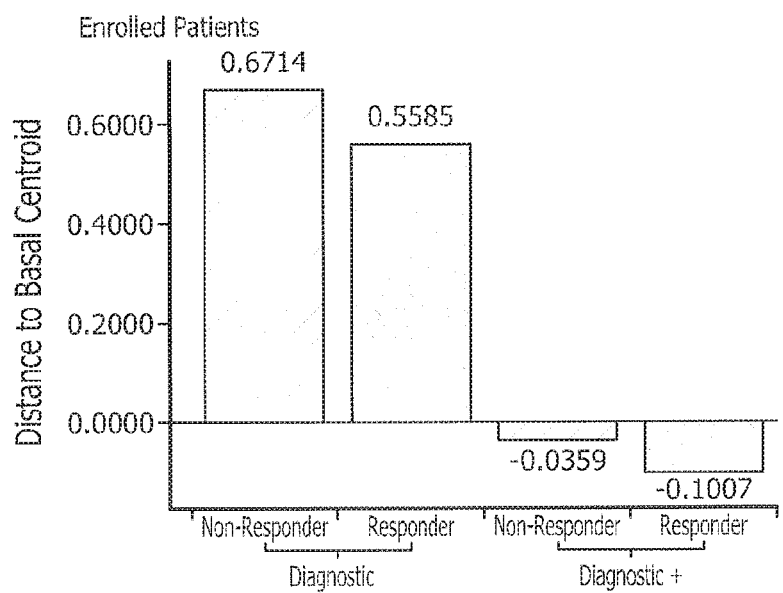
Figure 3A:
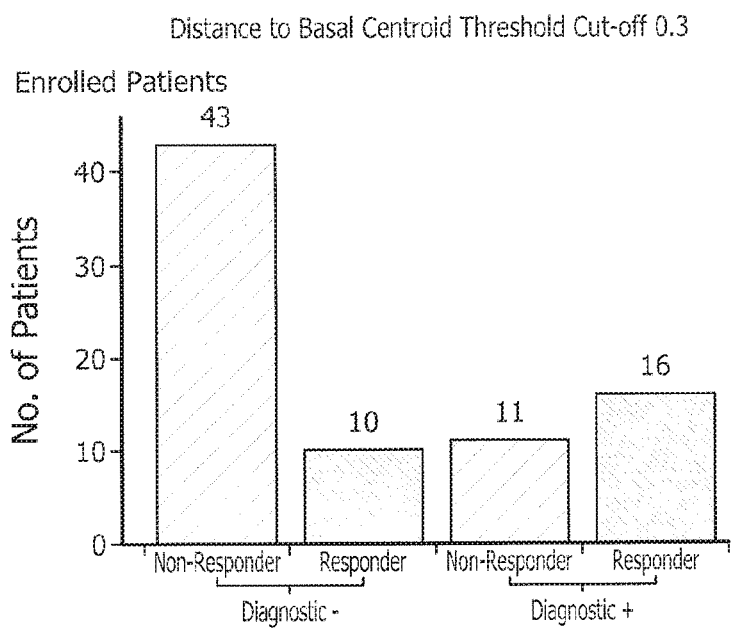
FIGS. 3A and 3B are graphs of results of the same TNBC clinical trial in which patient gene expression classifier scores for the Basal-like subtype were correlated with patient response. A threshold cut-off of 0.3 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 3B:
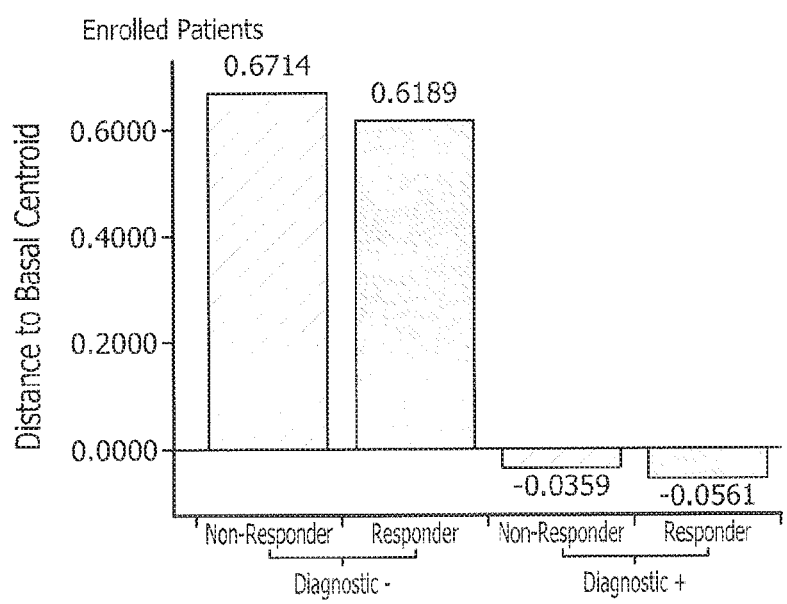
Figure 4A:
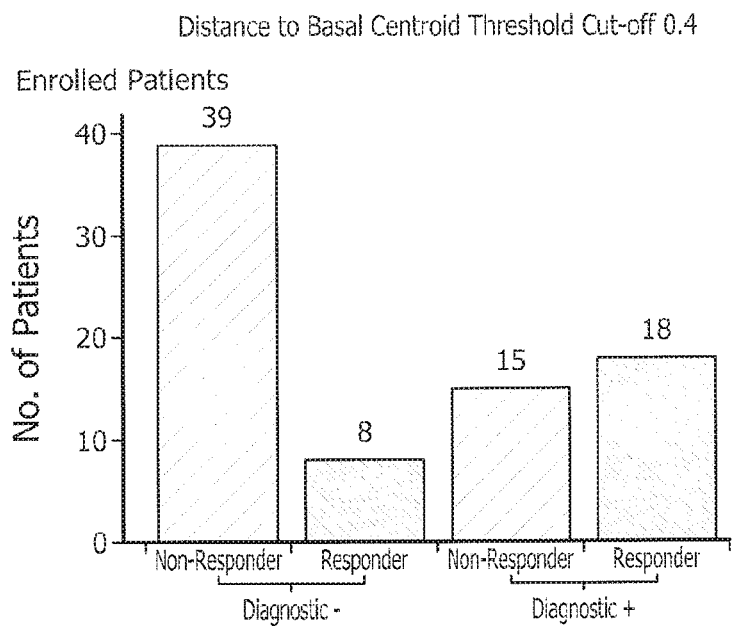
FIGS. 4A and 4B are graphs of results of the same TNBC clinical trial in which patient gene expression classifier scores for the Basal-like subtype were correlated with patient response. A threshold cut-off of 0.4 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 4B:
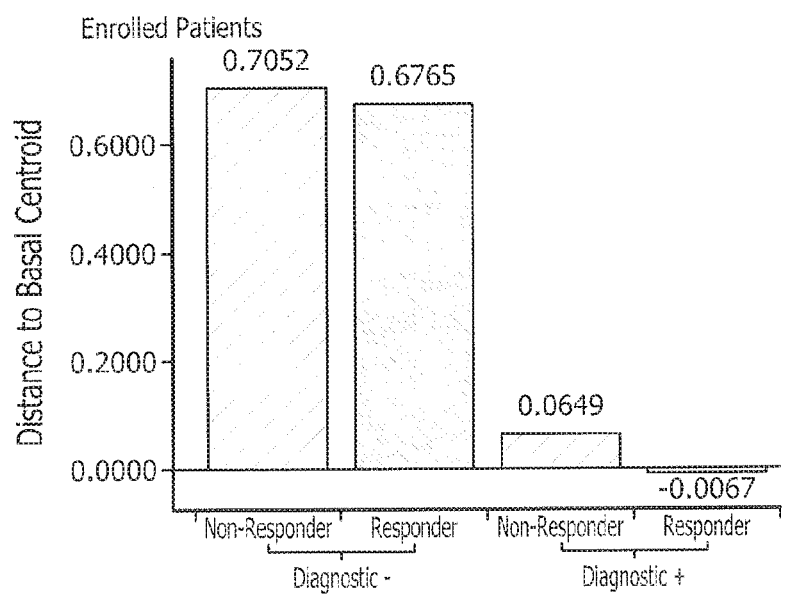
Figure 5A:
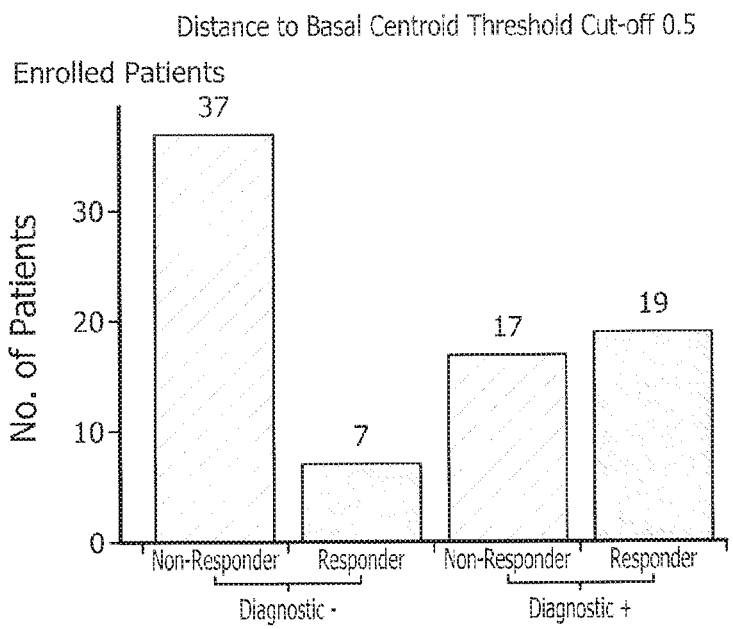
FIGS. 5A and 5B are graphs of results of the same TNBC clinical trial in which patient gene expression classifier scores for the Basal-like subtype were correlated with patient response. A threshold cut-off of 0.5 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 5B:
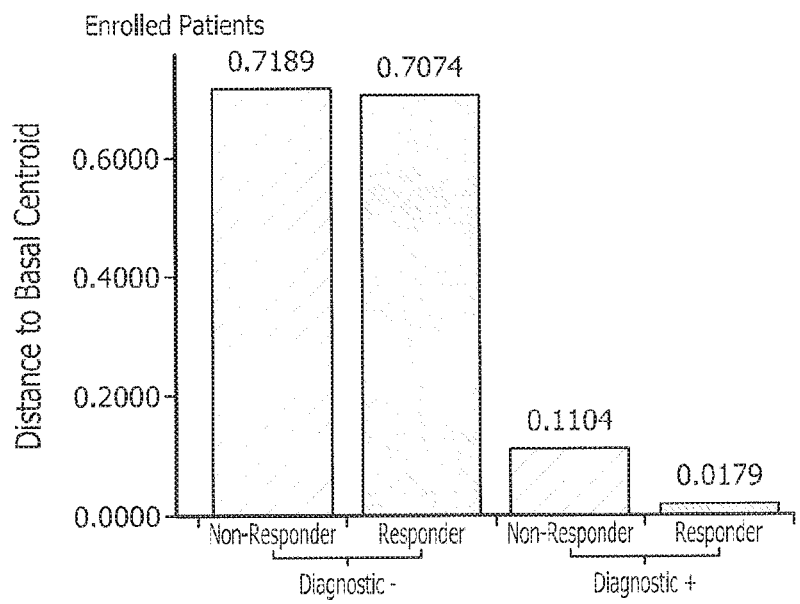
Figure 6A:
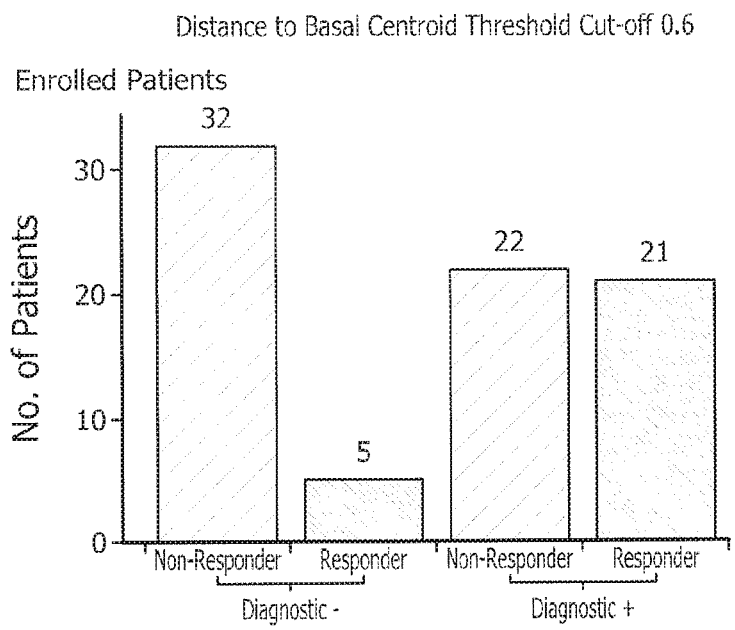
FIGS. 6A and 6B are graphs of results of the same TNBC clinical trial in which patient gene expression classifier scores for the Basal-like subtype were correlated with patient response. A threshold cut-off of 0.6 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 6B:
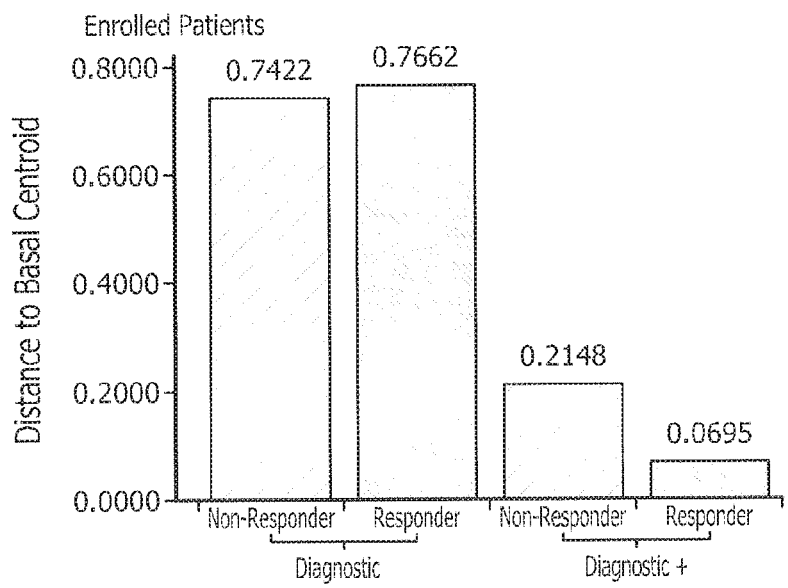
Figure 7A:
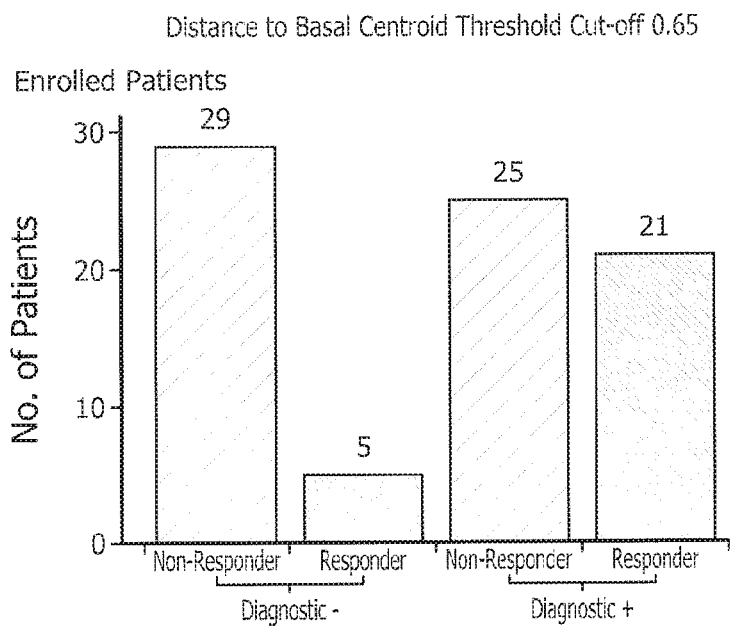
FIGS. 7A and 7B are graphs of results of the same TNBC clinical trial in which patient gene expression classifier scores for the Basal-like subtype were correlated with patient response. A threshold cut-off of 0.65 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 7B:
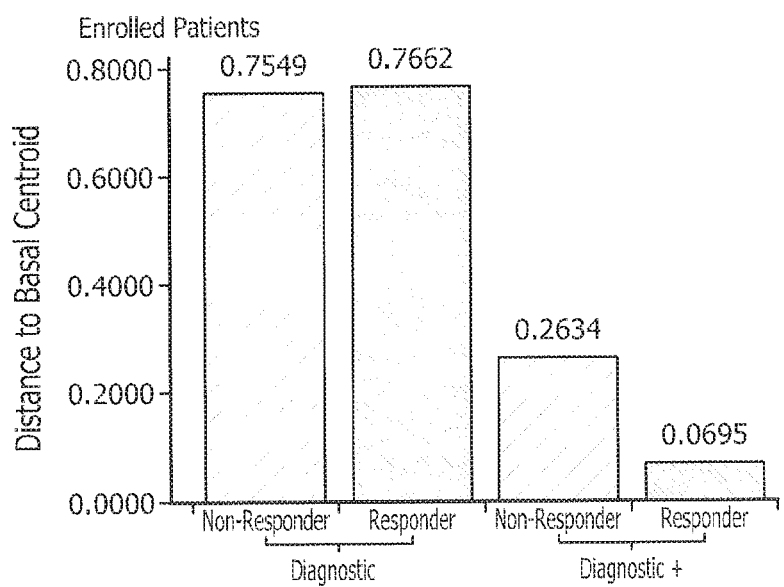
Figure 8A:
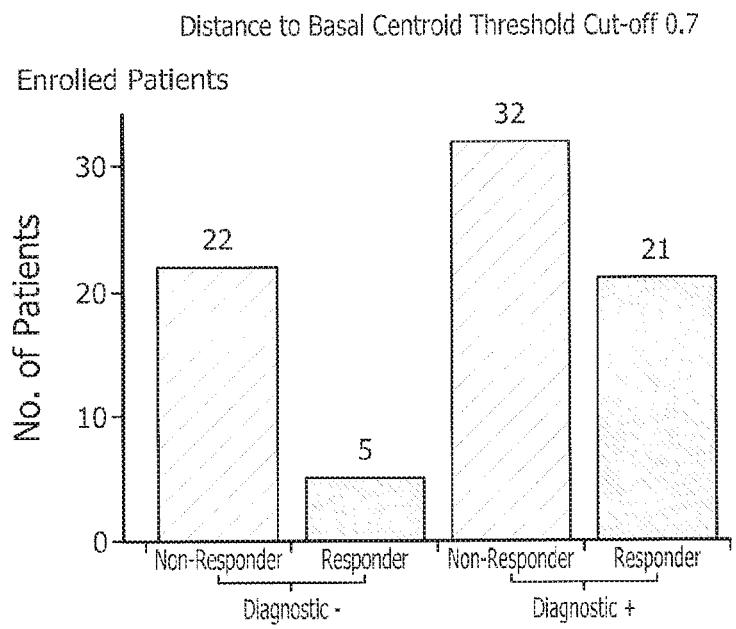
FIGS. 8A and 8B are graphs of results of the same TNBC clinical trial in which patient gene expression classifier scores for the Basal-like subtype were correlated with patient response. A threshold cut-off of 0.7 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 8B:
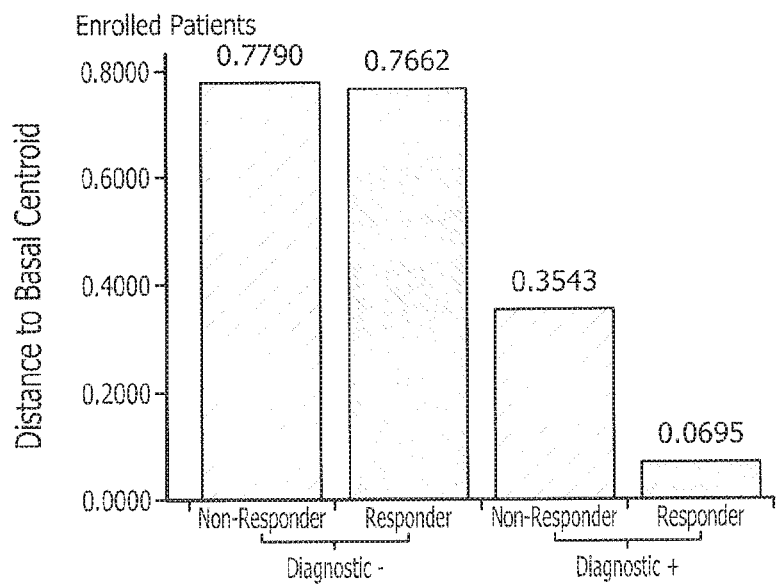
Figure 9A:
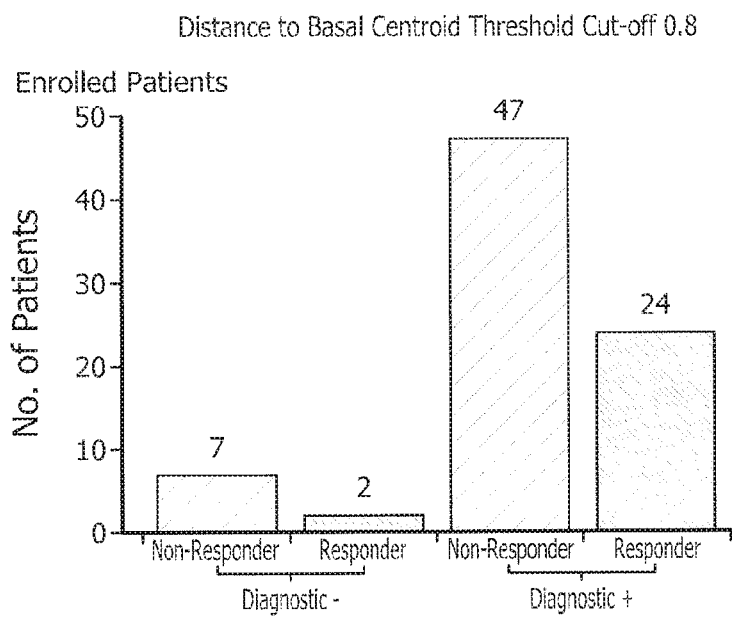
FIGS. 9A and 9B are graphs of results of the same TNBC clinical trial in which patient gene expression classifier scores for the Basal-like subtype were correlated with patient response. A threshold cut-off of 0.8 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 9B:
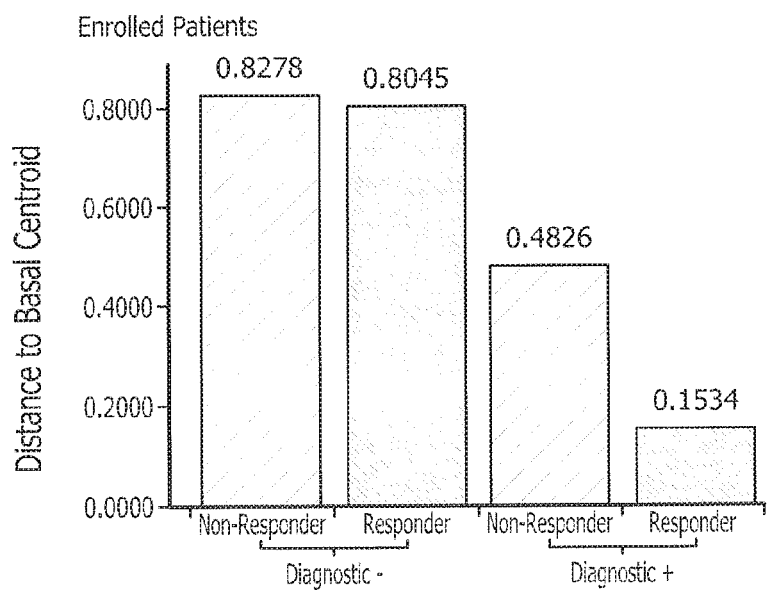
Figure 10A:
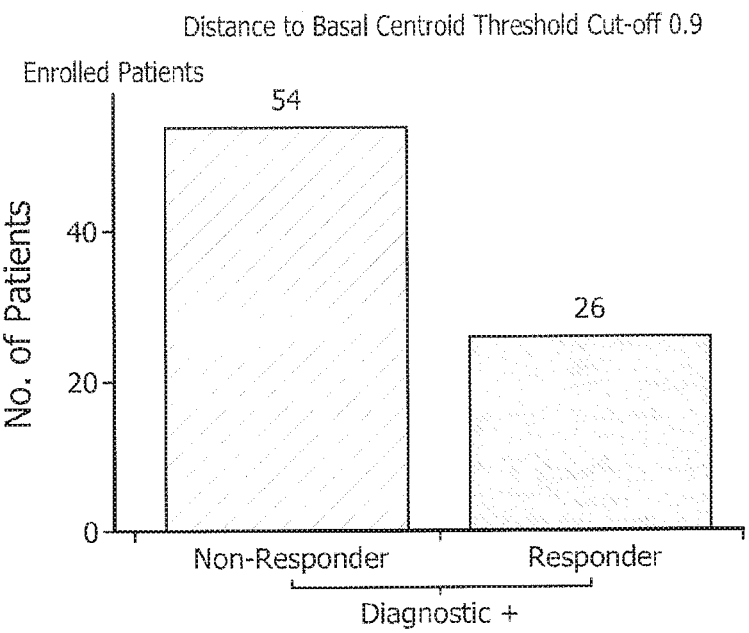
FIGS. 10A and 10B are graphs of results of the same TNBC clinical trial in which patient gene expression classifier scores for the Basal-like subtype were correlated with patient response. A threshold cut-off of 0.9 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 10B:
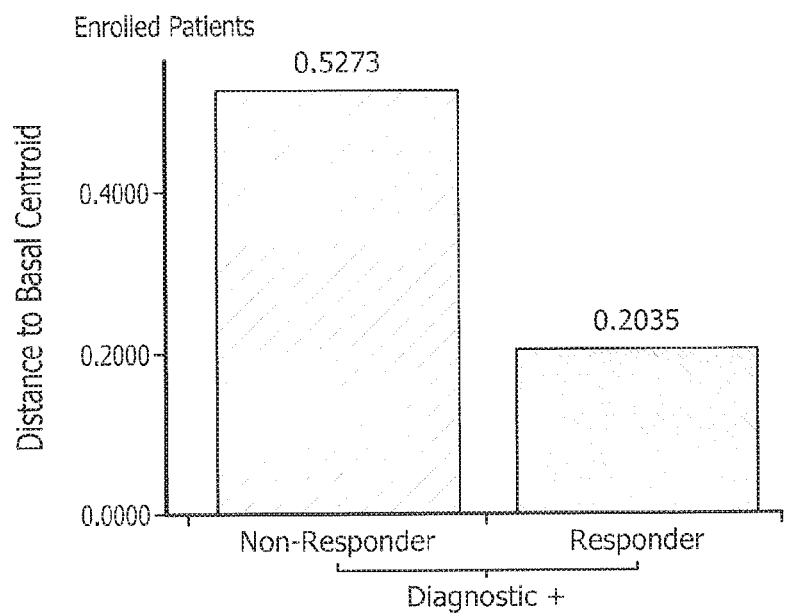

As shown in FIGS. 2A/B-10A/B, a target Basal Centroid classifier score of 0.6 or less for defining Dx+ and Dx− patients best correlated with response to enzalutamide therapy, while defining the Dx+ and Dx− based upon scores from 0.2 to 0.9 enriched the predictive value somewhat less. Thus, defining the population of responders and non-responders upon a Basal Centroid classifier cutoff score that is in the range of 0.2-0.9 is a further basis for predicting responsiveness to enzalutamide therapy in TNBC, with a sample's Basal Centroid classifier score of 0.6 or less being a preferred embodiment for a marker to predict responsiveness. As shown in FIG. 6A, defining Dx+ and Dx− pursuant to a relative Basal Centroid classifier score of 0.6 resulted in a prediction that yielded a large Diagnostic + population with most responders in the Diagnostic + population and high non-responders in the Diagnostic − population.

Example 3

Figure 11:
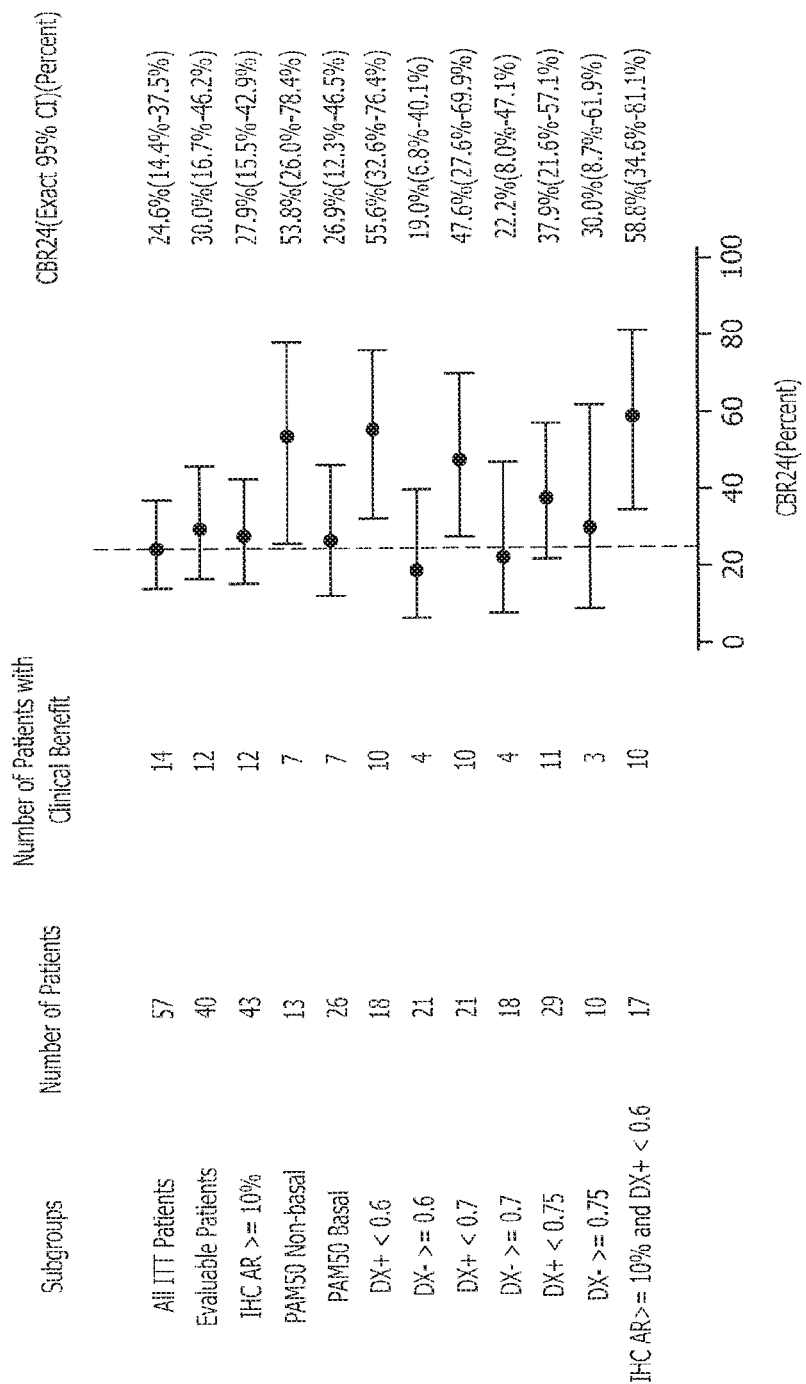
FIG. 11 comprises a representation of the response to enzalutamide of various patient subgroups treated with enzalutamide in the clinical trial. Response is shown in terms of Clinical Benefit Rate at ≥24 weeks (CBR24). The subgroups include Intent-To-Treat (ITT) patients; Evaluable Patients; patients with breast tumor tissue which was AR staining ≥10% (IHC AR >=10%); patients whose breast tumor tissue was classified as a non-Basal like subtype by the PAM50 subtype classifier (PAM50 non-basal); patients whose tumors were classified as Basal-like subtype (PAM50 basal); and patient samples analyzed by applying the indicated cut-offs of <0.6, ≥0.6, <0.7, ≥0.7, <0.75 and ≥0.75, from patient Basal Centroid classifier scores. "DX −" signifies patients whose samples did not meet the indicated threshold cut-off. "DX +" signifies patients whose samples did meet the indicated threshold cut-off. Also shown in in FIG. 11 are data for the combined criteria IHC AR >=10% and DX+<0.6.

The results of the clinical study of Example 1 are further analyzed and summarized in FIG. 11, showing the response of various patient subgroups to enzalutamide therapy in terms of Clinical Benefit Rate at ≥24 weeks (CBR24). The subgroups include all Intent-To-Treat (ITT) patients; Evaluable Patients; patients with breast tumor tissue which was AR staining ≥10% (IHC AR >=10%); patients whose breast tumor tissue was classified as a non-Basal like subtype by the PAM50 subtype classifier (PAM50 non-basal); patients whose tumors were classified as Basal like subtype (PAM50 basal); and patient samples analyzed by applying the indicated cut-offs of <0.6, ≥0.6, <0.7, ≥0.7, <0.75≥0.75 to the Basal Centroid classifier score. "DX −" signifies patients whose samples did not meet the indicated threshold cut-off. "DX +" signifies patients whose samples did meet the indicated threshold cut-off. Also shown in in FIG. 11 are data for the samples satisfying the combined criteria IHC AR >=10% and DX+<0.6, that is the sample met the criteria of (i) staining for AR of more than 10% and (ii) a PAM50 gene expression Basal Centroid classifier scoreof 0.6 or less.

Example 4

Figure 12:
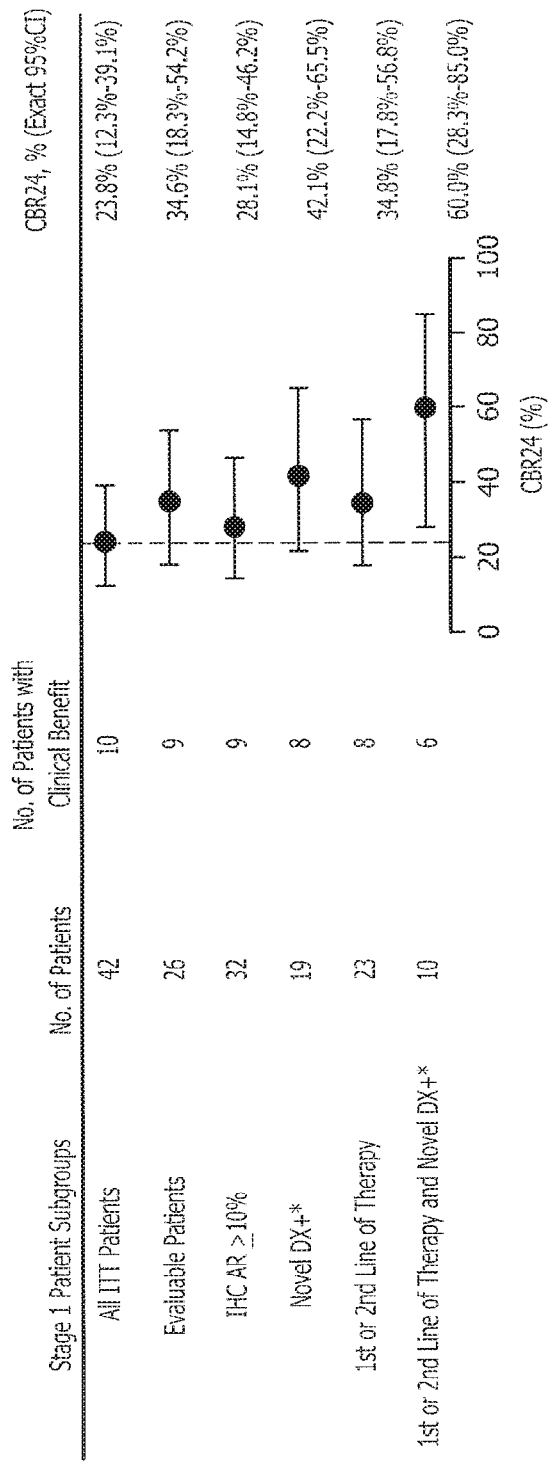
FIG. 12 is a further representation of the response to enzalutamide of various patient subgroups treated with enzalutamide in the clinical trial. Response is shown in terms of Clinical Benefit Rate at ≥24 weeks (CBR24). The subgroups include Intent-To-Treat (ITT) patients; Evaluable Patients; patients with breast tumor tissue which was AR staining ≥10% (IHC AR >=10%); and patients in which the enzalutamide therapy is administered as the first (1st line) or second (2nd line) of therapy. The subgroups further include a subgroup of patient samples analyzed by applying a <0.6 cut-off to Basal Centroid classifier scores ("Novel DX+"), and a subgroup comprising samples from 1st and 2nd line therapy, applying the <0.6 cut-off to Basal Centroid classifier scores.

The results of the clinical study of Example 1 are further analyzed and summarized in FIG. 12, showing the response of various patient subgroups to enzalutamide therapy in terms of Clinical Benefit Rate at ≥24 weeks (CBR24). The subgroups include all Intent-To-Treat (ITT) patients; Evaluable Patients; patients with breast tumor tissue which was AR staining ≥10% (IHC AR >=10%); and patients in which the enzalutamide therapy is the sole (1st line) or second (2nd line) of therapy. The subgroups further include subgroup of patient samples analyzed by applying a <0.6 Basal Centroid classifier score cut-off ("Novel DX+,"), and a subgroup comprising samples from 1st and 2nd line therapy, applying the <0.6 cut-off. A CBR of 42% using the prognostic Basal Centroid classifier score of <0.6 (and 60% when used in a group comprising both 1st line and 2nd line patients) exceeds typical benchmarks for predicting responsiveness to therapy in TNBC and is on a par with the predictive ability of models used to predict response to hormonal agent therapy in ER+/PgR+ breast cancer.

Example 5

Figure 13:
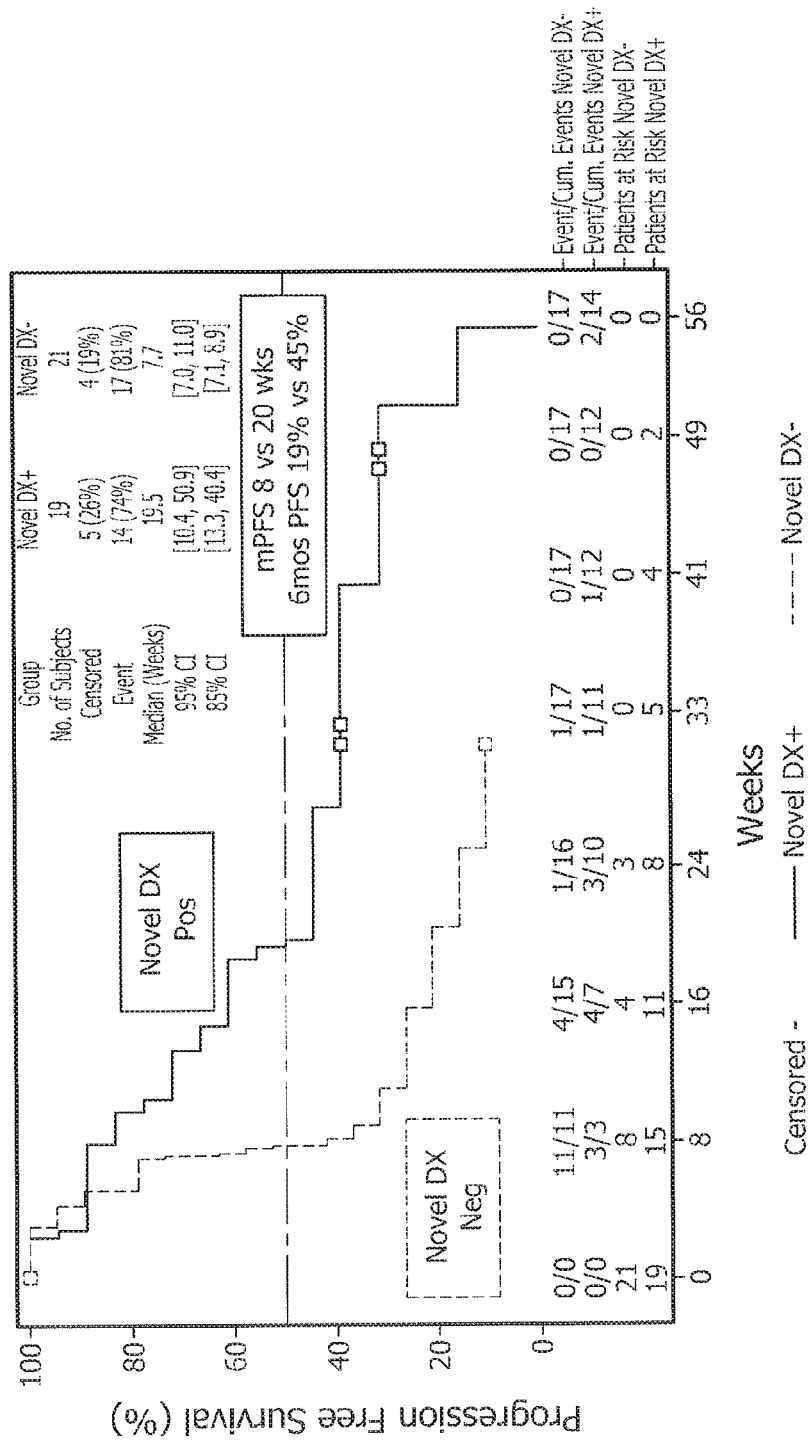
FIG. 13 is a Kaplan-Meier plot showing median progression-free survival (MPS) of patients treated with enzalutamide as a function of time. The curves correspond to patients that were identified as meeting the novel prognostic signature condition of a Basal Centroid classifier score of <0.6 ("Novel DX Pos") versus patients who did not meet the definition ("Novel DX Neg").

The effect of the novel prognostic signature utilizing a Basal Centroid classifier score of <0.6 as a predictor of response to AR inhibitor therapy is further illustrated in FIG. 13 with respect to patient progression-free survival time to 56 weeks. The results demonstrate a prolonged progression-free survival in patients that were identified as meeting the novel prognostic signature condition of a Basal Centroid classifier score of <0.6 ("Novel DX Pos") versus patients having a ≥0.6 distance score ("Novel DX Neg").

Example 6

The results of the clinical study of Example 1 were further analyzed utilizing the patient Basal Centroid classifier and Luminal A classifier scores. The classifier scores and response data were analyzed. As a result of analysis, a Weighted Basal and Luminal A classifier score was empirically devised that predicted responsiveness to androgen receptor inhibitor therapy in the clinical trial. The Weighted Basal and Luminal A classifier score of patient samples was determined from the following formula:

Weighted Basal and Luminal A classifier score=−0.2468275(Basal Centroid classifier score)+0.2667110(Luminal A Centroid classifier score).

The therapeutic response data was then evaluated imposing a series of threshold cut-offs on the Weighted Basal and Luminal A classifier score. Specifically, the enzalutamide response/non-response data was analyzed using Weighted Basal and Luminal A classifier score cut-offs of greater than −0.2, greater than −0.25, greater than −0.3 and greater than −0.35. The data is set forth in FIGS. 14A (>−0.2), 14B (>−0.25), 14C (>−0.3), and 14D (>−0.35). In each figure, "Diagnostic +" represents patients whose samples met the indicated prognostic signature comprising the indicted threshold cut-off. "Diagnostic −" represents patients whose samples did not meet the indicated threshold cut-off.

As shown in FIGS. 14A-14D, selecting a criterion of a Weighted Basal and Luminal A classifier of greater than x, with x in the range of −0.2 to −0.3, best correlated with response to enzalutamide therapy, with the criterion of a score of greater than −0.25 being optimal. Thus, defining the population of responders and non-responders based upon a Weighted Basal and Luminal A classifier score that is greater than −0.2, or greater than −0.3 is a basis for predicting responsiveness to enzalutamide therapy in TNBC, with a Weighted Basal and Luminal A classifier score of greater than −0.25 being a preferred embodiment of a criterion for predicting responsiveness.

Example 7

The results of the clinical study of Example 1 are further analyzed and summarized in FIG. 15, showing the response of various patient subgroups to enzalutamide therapy in terms of Clinical Benefit Rate at ≥24 weeks (CBR24). The subgroups include all Intent-To-Treat (ITT) patients; Evaluable Patients; patients whose breast tumor tissue samples were analyzed by applying the indicated cut-offs of >−0.2, >−0.25, >−0.3, and >−0.35, to the Weighted Basal and Luminal A classifier score. "PR-AR DX −" signifies patients whose samples did not meet the indicated threshold cut-off. "PR-AR DX +" signifies patients whose samples did meet the indicated threshold cut-off. Thus, for example, "PR-AR DX + >−0.25" indicates the patients whose samples met the criterion of a Weighted Basal and Luminal A classifier score greater than −0.25.

Also shown in in FIG. 15 are data for samples from patients in the study receiving enzalutamide therapy (i) after having received from zero to one prior therapies for treatment of TNBC with a drug other than an androgen receptor inhibitor ("and 0-1 prior therapy") or (ii) after having received two or more prior therapies for treatment of TNBC with a drug other than an androgen receptor inhibitor ("and >=2 prior therapies"). A Weighted Basal and Luminal A classifier score cut-off of >−0.25 was applied to these patient samples.

Example 8

The effect of the novel prognostic signature utilizing a Weighted Basal and Luminal A classifier score cut-off of >−0.2 as a predictor of response to AR inhibitor therapy is further illustrated in FIG. 16 with respect to patient progression-free survival time to 56 weeks. The results demonstrate a prolonged progression-free survival in patients that were identified as meeting the prognostic signature condition of a Weighted Basal and Luminal A classifier score of greater than −0.2 ("PR-AR DX+: >—0.2", top curve) versus a classifier score of less than or equal to −0.2 ("PR-AR DX−: <=−0.2", bottom curve).

Example 9

The effect of the novel prognostic signature utilizing a Weighted Basal and Luminal A classifier score cut-off of >−0.25 as a predictor of response to AR inhibitor therapy is further illustrated in FIG. 17 with respect to patient progression-free survival time to 56 weeks. The results demonstrate a prolonged progression-free survival in patients that were identified as meeting the prognostic signature condition of a Weighted Basal and Luminal A classifier score of greater than −0.25 ("PR-AR DX+: >−0.25", top curve) versus less than or equal to −0.25 ("PR-AR DX−: <=−0.25", bottom curve).

Example 10

The effect of the novel prognostic signature utilizing a Weighted Basal and Luminal A classifier score cut-off of >−0.3 as a predictor of response to AR inhibitor therapy is further illustrated in FIG. 18 with respect to patient progression-free survival time to 56 weeks. The results demonstrate a prolonged progression-free survival in patients that were identified as meeting the prognostic signature condition of a Weighted Basal and Luminal A classifier score of greater than −0.3 ("PR-AR DX+: >−0.3", top curve) versus a classifier score of less than or equal to −0.3 ("PR-AR DX−: <=−0.3", bottom curve).

Example 11

The effect of the novel prognostic signature utilizing a Weighted Basal and Luminal A classifier score cut-off of >−0.35 as a predictor of response to AR inhibitor therapy is further illustrated in FIG. 19 with respect to patient progression-free survival time to 56 weeks. The results demonstrate a prolonged progression-free survival in patients that were identified as meeting the prognostic signature condition of a Weighted Basal and Luminal A classifier score of greater than −0.35 ("PR-AR DX+: >−0.35", top curve) versus less than or equal to −0.35 ("PR-AR DX−: <=−0.35", bottom curve).

Example 12

The effect of the novel prognostic signature utilizing a Weighted Basal and Luminal A classifier score cut-off of >−0.25 as a predictor of response to AR inhibitor therapy is further illustrated in FIG. 20 with respect to patient progression-free survival time to 56 weeks, in patients receiving from zero to one prior therapies for treatment of TNBC with a drug other than an androgen receptor inhibitor. The results demonstrate a prolonged progression-free survival in patients that were identified as meeting the prognostic signature condition of a Weighted Basal and Luminal A classifier score of greater than −0.25 ("PR-AR DX+: >−0.25", top curve) versus less than or equal to −0.25 ("PR-AR DX−: <=−0.25", bottom curve). It may be appreciated from a comparison of FIGS. 17 and 20, that the −0.25 cut-off was able to identify a longer duration of progression-free survival that characterized the zero to 1 prior therapy group (FIG. 20) versus the shorter duration of progression-free survival that characterized the population of all study patients (FIG. 17).

The effect of the novel prognostic signature utilizing a Weighted Basal and Luminal A classifier score cut-off of >−0.25 as a predictor of response to AR inhibitor therapy in patients receiving from zero to one prior therapies for treatment of TNBC with a drug other than an androgen receptor inhibitor is further shown in FIG. 23. FIG. 23 is similar to FIG. 20, except that the progression-free survival time in the study is determined beyond the 56 weeks in FIG. 20 to 64 weeks in FIG. 23.

Example 13

The effect of the novel prognostic signature utilizing a Weighted Basal and Luminal A classifier score cut-off of >−0.25 as a predictor of response to AR inhibitor therapy is further illustrated in FIGS. 21A and 21B, with respect to time on treatment without progression of patients receiving zero or one (0-1 Prior Lines), or two or more (2+ Prior Lines), prior therapies for treatment of TNBC with a drug other than an androgen receptor inhibitor. The 56 patients that were identified as meeting the signature condition of a Weighted Basal and Luminal A classifier score of greater than −0.25 are represented in FIG. 21B. The 62 study patients identified by a classifier score of less than or equal to −0.25 are identified in FIG. 21A. Each bar in the figures represents a single patient. The best time on treatment without disease progression is apparent in responder patients who received one or no prior lines of therapy (FIG. 21B). Patient bars marked with a triangle ("Active") are active on study. Patient bars marked with a star signify complete response (CR) or partial response (PR).

Example 14

The effect of the novel prognostic signature utilizing a Weighted Basal and Luminal A classifier score cut-off of >−0.25 as a predictor of response to AR inhibitor therapy is further illustrated in FIGS. 22A and 22B with respect to patient progression-free survival time to 64 weeks (FIG. 22A) and overall survival to 84 weeks (FIG. 22B). The results of FIG. 22A demonstrate a prolonged progression-free survival in patients that were identified as meeting the prognostic signature condition of a Weighted Basal and Luminal A classifier score of greater than −0.25 ("PR-AR DX+: >−0.25", top curve) versus less than or equal to −0.25 ("PR-AR DX−: <=−0.25", bottom curve). The results of FIG. 22B demonstrate a prolonged overall survival in patients that were identified as meeting the prognostic signature condition of a Weighted Basal and Luminal A classifier score of greater than −0.25 ("PR-AR DX+: >−0.25", top curve) versus less than or equal to −0.25 ("PR-AR DX−: <=−0.25", bottom curve). The patients not meeting the prognostic signature condition were characterized by a median progression-free survival of 8.1 weeks and median overall survival of 32.1 weeks. In contrast, patients meeting the prognostic signature condition were characterized by a median progression-free survival of 16.1 weeks and median overall survival not yet reached at 84 weeks.

Example 15

A Phase II clinical trial of the androgen receptor antagonist bicalutamide has been reported. Ayca et al., "Phase II Trial of Bicalutamide in Patients with Androgen Receptor Positive, Hormone Receptor Negative Metastatic Breast Cancer", *Clin Cancer Res* 19: 5505-5512 (Oct. 1, 2013). The trial was designed to study the effect of bicalutamide in treating metastatic breast cancer that is AR-positive, estrogen receptor (ER)-negative, and progesterone receptor (PgR)-negative.

Briefly, as described by Ayca et al., tumors from 452 patients with ER-negative/PgR-negative advanced breast cancer were tested centrally for AR by immunohistochemistry (IHC) (>10% nuclear staining considered positive). See Ayca et al., p. 5506 for additional eligibility criteria. If either the primary or a metastatic site was positive, patients were eligible to receive the AR antagonist bicalutamide at a dose of 150 mg daily. Twenty-eight patients were treated on study. Bicalutamide 150 mg was administered orally on a continuous daily schedule. Patients were treated until disease progression or unacceptable adverse events. A maximum of 2 dose reductions for grade ≥3 toxicity were allowed (100 and 50 mg). A maximum of 2 weeks was permitted for treatment delays due to toxicity. Two patients who initiated bicalutamide were removed from study, leaving 26 study participants with AR(+) ER/PgR(−) metastatic breast cancer. Five patients had stable disease >6 months (number of cycles completed: 6, 8, 10+, 13, 57+) as their best response on treatment. There were no confirmed complete or partial responses yielding a clinical benefit rate of 19% (95% CI, 7%-39%) in the target population (n=26). In an intention-to-treat analysis, a CBR of 18% (95% CI, 6%-37%) was observed. See Ayca et al., p. 5507.

Twenty-one of the 26 bicalutamide-treated study patients were determined to also be HER-2 negative, i.e., twenty-one patients had breast cancers that were triple negative (Her-2 (−), ER (−) and PgR(−)). Following the study, patient tumor samples from the twenty-one TNBC patients that received bicalutamide therapy were subjected to intrinsic subtype classification into the Luminal A, Luminal B, Basal-like, HER2-enriched and Normal-like groups using the PAM50 classification model. Each subtype score for each sample is listed in Table 3. Also set forth in Table 3 is the Weighted Basal and Luminal A classifier score of each sample. Based on the results obtained in Example 6 from the clinical trial of the AR-receptor antagonist enzalutamide, a greater than −0.25 Weighted Basal and Luminal A classifier score ("PR-AR DX+>−0.25") indicates that such patients are more likely to respond to the bicalutamide treatment than patients with a Weighted Basal and Luminal A classifier score of less than or equal to −0.25. Eight patients satisfied this criterion, and are designated in Table 3 as having a likely positive ("POS") prognosis on bicalutamide treatment. Each of the 21 patient samples displayed a confidence level of 1, except for sample No. 16, which had a confidence level of 0.99.

TABLE 3

| No. | Basal Score | Her2 Score | LumA Score | LumB Score | Normal Score | Weighted Basal/LumA Score | Prognosis |
|-----|-------------|------------|------------|------------|--------------|---------------------------|-----------|
| 1 | 0.542569 | −0.02857 | −0.59846 | 0.242161 | −0.25186 | −0.29354 | NEG |
| 2 | 0.405618 | −0.17714 | −0.11635 | −0.30343 | 0.296423 | −0.13115 | POS |
| 3 | 0.509628 | 0.038367 | −0.3915 | −0.20711 | 0.059208 | −0.23021 | POS |
| 4 | 0.753469 | 0.003025 | −0.59088 | −0.28912 | 0.055078 | −0.34357 | NEG |
| 5 | 0.766146 | −0.00543 | −0.69729 | −0.08581 | −0.07851 | −0.37508 | NEG |
| 6 | 0.638896 | −0.34665 | −0.22439 | −0.54103 | 0.447779 | −0.21755 | POS |
| 7 | 0.75078 | 0.112509 | −0.7188 | −0.01945 | −0.11001 | −0.37702 | NEG |
| 8 | 0.795342 | 0.039808 | −0.66511 | −0.22968 | 0.052293 | −0.37371 | NEG |
| 9 | 0.793421 | −0.06708 | −0.59818 | −0.372 | 0.158127 | −0.35538 | NEG |
| 10 | 0.699496 | −0.23275 | −0.43616 | −0.26617 | 0.192221 | −0.28898 | NEG |
| 11 | 0.634478 | −0.15333 | −0.33906 | −0.49273 | 0.304298 | −0.24704 | POS |
| 12 | 0.729556 | −0.15188 | −0.48984 | −0.35529 | 0.206531 | −0.31072 | NEG |
| 13 | 0.721104 | 0.015222 | −0.66387 | −0.074 | −0.03558 | −0.35505 | NEG |
| 14 | 0.747419 | −0.26098 | −0.42406 | −0.40687 | 0.255414 | −0.29758 | NEG |
| 15 | 0.702089 | −0.04 | −0.53719 | −0.25522 | 0.095414 | −0.31657 | NEG |
| 16 | 0.161104 | −0.10146 | −0.01647 | −0.29834 | 0.383721 | −0.04416 | POS |
| 17 | 0.571477 | −0.12826 | −0.27549 | −0.34146 | 0.260024 | −0.21453 | POS |
| 18 | 0.399184 | −0.03741 | −0.21268 | −0.22113 | 0.090708 | −0.15525 | POS |
| 19 | 0.622089 | −0.18588 | −0.31313 | −0.58329 | 0.431741 | −0.23706 | POS |
| 20 | 0.752797 | −0.13546 | −0.55064 | −0.40072 | 0.161008 | −0.33267 | NEG |
| 21 | 0.736567 | −0.1346 | −0.58339 | −0.24216 | 0.082737 | −0.3374 | NEG |

Example 16

The following study demonstrates the enhanced antitumor effect of the combination of enzalutamide plus paclitaxel in cells positive for the prognostic marker of a Weighted Basal and Luminal A classifier score greater than −0.25.

Triple negative breast cancer cell lines BT549, MDA-MB-436, MDA-MB-453 were selected for study. Messenger RNA datasets for the cell lines were down-loaded from the Cancer Cell Line Encyclopedia (CCLE) database. The Weighted Basal and Luminal A classifier score for each cell line was determined from the downloaded datasets. Applying a Weighted Basal and Luminal A classifier score of >−0.25 as a prognostic marker for responsiveness to AR inhibitor therapy, it was determined that MDA-MB-453, but not BT549 and MDA-MB-436, satisfied this criterion.

Cells were maintained in 10% FBS supplemented growth media. Viability assays were performed in 10% FBS, and measured by CellTiter-Glo reagent according to the manufacturer's protocol (Promega). To determine molecular effects of enzalutamide alone or in combination with paclitaxel on androgen receptor signaling, cells (BT549, MDA-MB-436 or MDA-MB-453) were seeded on day one in 10% FBS. The cells were treated with enzalutamide or paclitaxel or the combination in 2% charcoal-stripped serum and were stimulated with 10 nM DHT for 4 hours. Cell fractionation was isolated for cytosolic and nuclear fractions. Protein expression levels were determined using a Western blotting method. The $IC_{50}$ for enzalutamide or paclitaxel for each cell line is shown in Table 4. Mean values are presented for each cell line (n=3). The prognostic marker-positive MDA-MB- 453 cells exhibited greater sensitivity to enzalutamide compared to the prognostic marker-negative BT549 and MDA-MB-463 cells.

TABLE 4

| Cell Line | Enzalutamide IC$_{50}$ (μM) | Paclitaxel IC$_{50}$ (nM) |
|---|---|---|
| BT549 | 57.0 | 2.8 |
| MDA-MB-436 | 73.0 | 6.7 |
| MDA-MB-453 | 22.7 | 20.7 |

Viability of the cells was measured in the presence of the concentrations of enzalutamide (Enza) and paclitaxel (PTX) in FIGS. 24A-C. Mean values are presented for each cell line (n=5). In the prognostic marker-positive MDA-MB-453 cell line, the combination of enzalutamide plus paclitaxel resulted in enhanced cytotoxicity. See FIG. 24C.

Example 17

To generate a mouse xenograft model, 5- to 6-week-old female NOD-SCID mice were injected orthotopically into the mammary gland with 6.0×10$^6$ MDA-MB-453 cells. DHT (10.5 mg in a 60-day release pellet) or control pellets were implanted into animals. When tumor size reached ~100 mm$^3$, mice were treated by (i) oral gavage (PO) with enzalutamide ("Enza") at 3 mg/kg/day (n=10), (ii) paclitaxel ("PTX") at 6 mg/kg QMWF (IP) (n=7), or (iii) the combination of (i) and (ii) (n=10). A control group of mice (n=8) was treated with vehicle (0.5% Methocel solution). Tumor size was measured by caliper. Tumor weights were determined at day 35. The results are shown in FIG. 25A (tumor volume vs. time) and FIG. 25B (tumor weight). Data points in FIG. 25A represent the average tumor volume for each group, and error bars reflect the SEM of the data. The student T-Test was used to calculate p values: FIG. 25A: control v. enzalutamide, 0.007; control v. paclitaxel, 0.0007; enzalutamide vs. enzalutamide plus paclitaxel, 0.074; paclitaxel vs. enzalutamide plus paclitaxel, 0.013. FIG. 25B: control v. enzalutamide, 0.001; control v. paclitaxel, 0.0001; enzalutamide vs. enzalutamide plus paclitaxel, 0.08; paclitaxel vs. enzalutamide plus paclitaxel, 0.017. The data demonstrates that the combination of enzalutamide plus paclitaxel results in enhanced antitumor effect compared to either drug alone.

Representative tumors from each treated group were selected to perform immunohistochemistry against AR, Ki67 or p-AKT. Immunohistochemistry staining for Ki67 or AKT phosphorylation was significantly reduced in the enzalutamide plus paclitaxel tumors compared to the enzalutamide or paclitaxel single treated group (data not shown).

The disclosures of each and every patent, patent application, and publication cited herein are hereby incorporated herein by reference in their entirety. One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

The invention claimed is:

1. A method of treating triple negative breast cancer (TNBC) in a subject, the subject having a breast cancer comprising breast cancer cells that have been classified as basal-like subtype or another sub-type, the method comprising:
testing the subject to determine a Basal Centroid classifier score of breast cancer cells of the subject; and
administering a breast cancer treatment to the subject comprising an androgen receptor inhibitor, thereby treating the triple negative breast cancer in the subject;
wherein the Basal Centroid classifier score is determined for the breast cancer cells of the subject from the expression by the cells of a set of intrinsic genes listed in Table 1 using the PAM50 classifier; and
wherein the breast cancer cells of the subject are characterized by the Basal Centroid classifier score of 0.4 to 0.7.

2. The method according to claim 1, wherein the breast cancer cells of the subject are characterized by the Basal Centroid classifier score of 0.4 to 0.6.

3. The method according to claim 1, wherein the breast cancer of the subject is characterized by the presence of androgen receptor-positive tumor cells.

4. The method according to claim 1, wherein the androgen receptor inhibitor is selected from the group consisting of enzalutamide, bicalutamide, flutamide, nilutamide, ARN509, ketoconazole, abiraterone acetate, VN/124-1 (TOK-001), orteronel (TAK-700), finasteride, galeterone, cyproterone acetate, andarine, and combinations thereof.

5. The method according to claim 4, wherein the androgen receptor inhibitor is enzalutamide.

6. The method according to claim 2, wherein the androgen receptor inhibitor is enzalutamide.

7. The method according to claim 5, wherein the enzalutamide is orally administered once daily at a dose of 160 mg.

8. The method according to claim 7, wherein the enzalutamide is administered as a single capsule comprising 160 mg enzalutamide.

9. The method according to claim 7, wherein the enzalutamide is administered as four capsules, each capsule comprising 40 mg enzalutamide.

10. The method according to claim 1, wherein the breast cancer treatment comprising an androgen receptor inhibitor further comprises one or more other anti-cancer agents that is not an androgen receptor inhibitor.

11. The method according to claim 10, wherein the other anti-cancer agent that is not an androgen receptor inhibitor is selected from the group consisting of cyclophosphamide, fluorouracil, 5-fluorouracil, methotrexate, thiotepa, carboplatin, cisplatin, a taxane, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserelin, goserelin, megestrol acetate, risedronate, pamidronate, ibandronate, alendronate, denosumab, zoledronate, trastuzumab, tykerb, bevacizumab, and combinations thereof.

12. The method according to claim 11, wherein the other anti-cancer agent that is not an androgen receptor inhibitor is paclitaxel.

13. The method according to claim 1, further comprising a step of testing the subject to determine whether the subject has a breast cancer comprising breast cancer cells that are other than basal-like subtype.

14. The method according to claim 1, wherein the subject has received zero rounds or one round of prior treatment with an anti-cancer agent, other than an androgen receptor inhibitor, for treatment of triple negative breast cancer.

15. A method of treating triple negative breast cancer in a subject in need of such treatment comprising:
(a) providing a biological sample from the subject;
(b) assaying the biological sample to determine whether the biological sample is classified as a basal-like subtype or another subtype, wherein a Basal Centroid classifier score of breast cancer cells is determined for the breast cancer cells of the subject from the expression by said cells of a set of intrinsic genes listed in Table 1 using the PAM50 classifier, and wherein the breast cancer cells of the subject are characterized by the Basal Centroid classifier score of 0.4 to 0.7; and
(c) if the biological sample is classified as the other than a basal-like subtype, administering a breast cancer treatment to the subject comprising an androgen receptor inhibitor, thereby treating the breast cancer in the subject.

16. The method according to claim 15, wherein the breast cancer treatment is administered if the Basal Centroid classifier score is 0.4 to 0.6.

17. The method according to claim 15, wherein the breast cancer of the subject is characterized by the presence of androgen receptor-positive tumor cells.

18. The method according to claim 15, wherein the androgen receptor inhibitor is selected from the group consisting of enzalutamide, bicalutamide, flutamide, nilutamide, ARN509, ketoconazole, abiraterone acetate, VN/124-1 (TOK-001), orteronel (TAK-700), finasteride, galeterone, cyproterone acetate, andarine, and combinations thereof.

19. The method according to claim 16, wherein the androgen receptor inhibitor is enzalutamide.

20. The method according to claim 18, wherein the androgen receptor inhibitor is enzalutamide.

21. The method according to claim 19, wherein the enzalutamide is orally administered once daily at a dose of 160 mg.

22. The method according to claim 21, wherein the enzalutamide is administered as a single capsule comprising 160 mg enzalutamide.

23. The method according to claim 21, wherein the enzalutamide is administered as four capsules, each capsule comprising 40 mg enzalutamide.

24. The method according to claim 15, wherein the breast cancer treatment comprising an androgen receptor inhibitor further comprises one or more other anti-cancer agents that is not an androgen receptor inhibitor.

25. The method according to claim 24, wherein the other anti-cancer agent that is not an androgen receptor inhibitor is selected from the group consisting of cyclophosphamide, fluorouracil, 5-fluorouracil, methotrexate, thiotepa, carboplatin, cisplatin, a taxane, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserelin, goserelin, megestrol acetate, risedronate, pamidronate, ibandronate, alendronate, denosumab, zoledronate, trastuzumab, tykerb, bevacizumab, and combinations thereof.

26. The method according to claim 25, wherein the other anti-cancer agent that is not an androgen receptor inhibitor is paclitaxel.

27. The method according to claim 15, wherein the biological sample is selected from the group consisting of a cell, a tissue, and a bodily fluid.

28. The method according to claim 26, wherein the biological sample comprises breast tissue or breast cells.

29. The method of claim 28, wherein the tissue is obtained from a biopsy.

30. The method of claim 26, wherein the bodily fluid is selected from the group consisting of blood, lymph, urine, saliva, fluid from ductal lavage, and nipple aspirate.

31. The method according to claim 15, wherein the subject has received zero rounds or one round of prior treatment with an anti-cancer agent, other than an androgen receptor inhibitor, for treatment of triple negative breast cancer.

32. The method according to claim 1, wherein detecting the expression of the set of intrinsic genes listed in Table 1 using the PAM50 classifier is conducted by RNA sequencing.

33. The method according to claim 15, wherein detecting the expression of the set of intrinsic genes listed in Table 1 using the PAM50 classifier is conducted by RNA sequencing.

34. The method according to claim 1, wherein prior to determining the Basal centroid classifier score, the sample expression data is normalized and adjusted such that the median expression value of each gene in Table 1 is equivalent to the median of a known subset from TNBC patients.

35. The method according to claim 25, wherein prior to determining the Basal centroid classifier score, the sample expression data is normalized and adjusted such that a median expression value of each gene in Table 1 is equivalent to a median of a known subset from TNBC patients.

36. The method according to claim 5, wherein (i) detecting the expression of the set of intrinsic genes listed in Table 1 is conducted by RNA sequencing;
(ii) aligning the resulting biological sample expression data to human genome sequence hg19; (iii) estimating gene and isoform level counts using RNA sequencing by expectations maximization; (iv) normalizing gene level counts estimates to a fixed upper quartile; and (v) adjusting the resulting normalized gene expression estimates such that a median expression value of each gene of Table 1 is equivalent to a median of the triple negative subset of TCGA RNA sequence data.

37. The method according to claim 15, wherein (i) detecting the expression of the set of intrinsic genes listed in Table 1 is conducted by RNA sequencing;
(ii) aligning the resulting biological sample expression data to human genome sequence hg19; (iii) estimating gene and isoform level counts using RNA sequencing by expectations maximization; (iv) normalizing gene level counts estimates to a fixed upper quartile; and (v) adjusting the resulting normalized gene expression estimates such that a median expression value of each gene of Table 1 is equivalent to a median of the triple negative subset of TCGA RNA sequence data.

\* \* \* \* \*